US007144901B2

(12) United States Patent
Ohmoto et al.

(10) Patent No.: US 7,144,901 B2
(45) Date of Patent: Dec. 5, 2006

(54) OXADIAZOLE DERIVATIVES AND DRUGS CONTAINING THESE DERIVATIVES AS THE ACTIVE INGREDIENT

(75) Inventors: Kazuyuki Ohmoto, Osaka (JP); Iori Itagaki, Nagano (JP)

(73) Assignee: ONO Pharmaceutical Co.,Ltd., Osaka (JP)

( * ) Notice: Subject to any disclaimer, the term of this patent is extended or adjusted under 35 U.S.C. 154(b) by 413 days.

(21) Appl. No.: 10/148,612

(22) PCT Filed: Dec. 1, 2000

(86) PCT No.: PCT/JP00/08514

§ 371 (c)(1),
(2), (4) Date: Aug. 21, 2002

(87) PCT Pub. No.: WO01/44214

PCT Pub. Date: Jun. 21, 2001

(65) Prior Publication Data

US 2003/0166573 A1 Sep. 4, 2003

(30) Foreign Application Priority Data

Dec. 3, 1999 (JP) ................................ 11/344389

(51) Int. Cl.
*A61K 31/4245* (2006.01)
*C07D 271/113* (2006.01)

(52) U.S. Cl. ...................................... 514/364; 548/144

(58) Field of Classification Search ................ 548/144; 514/364

See application file for complete search history.

(56) References Cited

U.S. PATENT DOCUMENTS

2004/0204368 A1* 10/2004 Ohmoto

FOREIGN PATENT DOCUMENTS

| | | | |
|---|---|---|---|
| EP | 1 234 821 | A1 | 8/2002 |
| EP | 1 254 901 | A1 | 11/2002 |
| WO | WO 99/54317 | A1 | 10/1999 |
| WO | WO 00/01666 | | 1/2000 |

OTHER PUBLICATIONS

Todd L. Graybill, et al., "Synthesis and Evaluation of Diacylhydrazines as Inhibitors of the Interleukin-1β Converting Enzyme (ICE)," Bioorganic & Medicinal Chemistry Letters, 1995, pp. 1197-1202, vol. 5, No. 11.

* cited by examiner

*Primary Examiner*—Kamal A. Saeed
*Assistant Examiner*—Rebecca Anderson
(74) *Attorney, Agent, or Firm*—Sughrue Mion, PLLC

(57) ABSTRACT

An oxadiazole derivative of formula (I) and a non-toxic salt thereof,

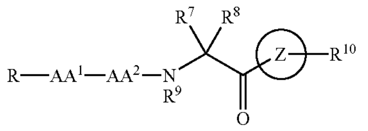

(I)

wherein R is hydrogen, alkyl, CycA, etc.; $AA^1$ is a single bond, amino acid residue, etc.; $AA^2$ is a single bond, amino acid residue, etc.; $R^7$ and $R^8$ are hydrogen, alkyl, etc.; $R^9$ is hydrogen, alkyl, etc. $R^{10}$ is hydrogen, alkyl, etc.).

6 Claims, No Drawings

OXADIAZOLE DERIVATIVES AND DRUGS CONTAINING THESE DERIVATIVES AS THE ACTIVE INGREDIENT

This application is a 371 of PCT/JP00/08514 filed Dec. 1, 2000.

TECHNICAL FIELD

The present invention relates to an oxadiazole derivative.

Specifically, the present invention relates to;

1) an oxadiazole derivative of formula (I), (I)

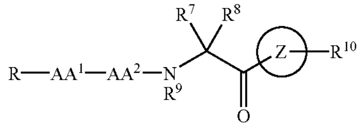

wherein all symbols have the same meanings as hereafter, and a non-toxic salt thereof, 2) a method for the preparation thereof and 3) a pharmaceutical agent comprising the oxadiazole derivative and non-toxic salt thereof as active ingredient.

BACKGROUND

Cysteine protease is a generic name of proteases which have a cysteine residue in the activity center and catalyze protein degradation thereat. In animal cells, a large number of cysteine proteases are known; for example, cathepsin family, calpain family, caspase-1, etc. Cysteine protease exists in various kinds of cells extensively and plays a basic and essential role in the homeostasis, such as conversion (processing) of precursor protein into its active form and degradation of proteins which have become out of use, etc. Until now, its physiological effects are being vigorously studied, and as the studies progress and characteristics of the enzymes are revealed, cysteine protease came to be taken as a cause of really various kinds of diseases.

It is revealed that cathepsin S (See J. Immunol., 161, 2731 (1998)) and cathepsin L (See J. Exp. Med., 183, 1331 (1996)) play a role in processing of major histocompatibility antigen class-II in antigen presenting cells which play an important role in the early stage of immune responses. In an experimental inflammatory response model induced by antigens, a specific inhibitor of cathepsin S showed an inhibitory effect (see J. Clin. Invest., 101, 2351 (1998)). It is also reported that in a leishmania-infected immune response model cathepsin B inhibitor inhibited an immune response and by means of this effect it inhibited the proliferation of protozoans (See J. Immunol., 161, 2120 (1998)). In vitro, a result is given that a calpain inhibitor and a cysteine protease inhibitor E-64 inhibited apoptosis which is induced by stimuli on T cell receptors (see J. Exp. Med., 178, 1693 (1993)). Therefore, it is conceivable that cysteine protease is much concerned with the progress of immune responses.

It is speculated that caspase-1 or a cysteine protease similar thereto occupies an important position in the mechanism of cell death including apoptosis. Therefore it is expected for a cysteine protease inhibitor to be used as an agent for the prophylaxis and/or treatment of those diseases concerning apoptosis, such as infectious diseases, deterioration or sthenia of immune function and brain function, tumors, etc. Diseases concerning apoptosis are, acquired immune deficiency syndrome (AIDS), AIDS-related complex (ARC), adult T cell leukemia, hairy cell leukemia, spondylopathy, respiratory apparatus disorder, arthitis, HIV or HTLV-1 related diseases such as uveitis, virus-related diseases such as hepatitis C, cancer, collagenosis (systemic lupus erythematosus, rheumatoid arthritis, etc.), autoimmune diseases (ulcerative colitis, Sjögren's syndrome, primary biliary cirrhosis, spontaneous thrombocytopenic purpura, autoimmune hemolytic anemia, myasthenia gravis, insulin dependent (type I) diabetes, etc.), diseases accompanied by thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type C, A, B, F, etc.) or hepatitis medicamentosus and cirrhosis, dementia (Alzheimer's diseases, Alzheimer's senile dementia, etc.), cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.

Moreover, caspase-1 is concerned with various inflammatory diseases and those diseases caused by immune disorders, by means of interleukin-1β (IL-1β) production. A lot of diseases are shown to be involved with caspase-1 including inflammatory diseases and autoimmune diseases listed below; inflammatory bowel diseases such as ulcerative colitis, insulin-dependent (type-I) diabetes, autoimmune thyroid diseases, infectious diseases, rejection of an organ transplantation, graft versus host diseases, psoriasis, periodontitis (above, see N. Eng. J. Med., 328, 106 (1993)), pancreatitis (see J. Interferon Cytokine Res., 17, 113 (1997)), hepatitis (see J. Leuko. Biol., 58, 90 (1995)), glomerulonephritis (see Kidney Int., 47, 1303 (1995)), endocarditis (see Infect. Immun., 64, 1638 (1996)), myocarditis (see Br. Heart J., 7, 561 (1995)), systemic lupus erythematosus (see Br. J. Rheumatol., 34, 107 (1995)), Hashimoto's diseases (see Autoimmunity, 16, 141 (1993)), etc.), etc. Experimentally, it is reported that in liver injury model induced by lipopolysaccharide and D-galactosamine, a caspase-1 inhibitor depressed the symptoms, and it is expected that a caspase inhibitor shows an effect in sepsis, ischemic reperfusion and hepatitis gravis (see Am. J. Respir. Crit. Care Med., 159, 1308 (1999)).

It is also shown that cysteine protease is concerned with rheumatoid arthritis. IL-1β is shown to be concerned with this disease (see Arthritis Rheum., 39, 1092 (1996)), and in addition, as autoantibody toward calpastatin (endogenous calpain inhibitor) was found in the serum of the patients, it is considered that increase of calpain activity leads to the cause of diseases.

It is also known that cysteine protease causes a disease symptom by decomposing various proteins which compose the organism.

It is reported that cathepsin B plays a role in decomposing muscular protein in the chronic phase of sepsis (see J. Clin. Invest., 97, 1610 (1996)), and in decomposing muscular protein in myodystrophy model (see Biochem. J., 288, 643 (1992)). And it is also reported that calpain decomposes the myocyte cells protein of myodystrophy patients (see J. Biol. Chem., 270, 10909 (1995)).

In the ischemic reperfusion model, a result is given that calpain causes degeneration of brain tissues by means of degradation of protein kinase C-β (see J. Neurochem., 72, 2556 (1999)) and that a cathepsin B inhibitor inhibits nerve injury (see Eur. J. Neurosci., 10, 1723 (1998)).

In the brain ischemic model, it is known that the degradation of spectrin by calpain causes a damage and function disorder in the neurocyte (see Brain Res., 790, 1(1998)) and it is reported that an IL-1β receptor antagonist relieved the symptoms (see Brain Res. Bull., 29, 243 (1992)).

In myocardial ischemic model it is confirmed that cathepsin B activity increases in the lesion (see Biochem. Med. Metab. Biol., 45, 6 (1991)).

In the experiment utilizing ischemic liver injury model, it proved that necrosis and apoptosis of hepacyte were induced by means of protein-decomposing activity of calpain (see Gastroenterology, 116, 168 (1999)).

Besides, it is known that calpain causes cornea turbid in cataract by means of degradation of crystalline (see Biol. Chem., 268, 137 (1993)) and that in the lesion of contracted gut mucosa model it was confirmed that the activity of cathepsin B, H and L increased (see JPEN. J. Parenter. Enteral. Nutr., 19, 187 (1995)) and it is shown that cysteine protease is a cause of the diseases resulting from such protein degradation.

It has been revealed that cysteine protease is concerned with systemic disorders of organs and tissues by shock.

It is shown that IL-1β is concerned with septic shock and systemic inflammatory response syndrome (see Igakuno Ayumi, 169, 850 (1994)) and besides, it is reported that in endotoxin shock model induced by lipopolysaccharide, a calpain inhibitor prevented circulatory system disorder, disorders of liver and pancreas and acidosis by means of inhibitory effect of activation of nuclear factor κB (see Br. J. Pharmacol., 121, 695 (1997)).

Since it is reported that calpain is concerned with platelet coagulation process and a calpain inhibitor prevented the coagulation of platelets (see Am. J. Physiol., 259, C862 (1990)), it is conceivable that a cysteine protease inhibitor is useful for the disorder by blood coagulation. From the fact that calpain activity increased in the serum of the patients of purpura (thrombocytopenia) resulting from marrow transplantation, it is conceivable that calpain is concerned with the actual disease symptoms (see Bone Marrow Transplant., 24, 641 (1999)). Caspase-1 inhibitor inhibited the apoptosis of blood vessel endothelial cells, which is seen in the early phase of purpura (thrombocytopenia) and is thought to be important for the progression of the pathology afterwards (see Am. J. Hematol., 59, 279 (1998)), so it is expected that a cysteine protease inhibitor makes effect on purpura and hemolytic uremic syndrome.

The effect of cysteine protease and its inhibitor is being investigated in the field of cancer and metastasis of cancer.

Since the proliferations of pancreas cancer cells (see Cancer Res., 59, 4551 (1999)) and acute myeloid leukemia cells (see Clin. Lab. Haematol., 21, 173 (1999)) were inhibited by an inhibitor or receptor antagonist of caspase-1, it is expected that caspase-1 activity is essential for the process of proliferation of tumor cells, and that an inhibitor thereof is effective for these cancers. Cathepsin B activity increased in colon cancer metastasis model (see Clin. Exp. Metastasis, 16, 159 (1998)). Cathepsin K protein expression was recognized in human breast cancer cells and the relationship of cathepsin K and bone metastasis is shown (Cancer Res., 57, 5386 (1997)). Also, a calpain inhibitor inhibited migaration of the cells and it implied the possibility that calpain inhibition may inhibit metastasis of cancer (J. Biochem., 272, 32719 (1997)). From these, a cysteine protease inhibitor is presumed to show an inhibitory effect on the metastasis of various malignant tumors.

As to AIDS (see AIDS, 10, 1349 (1996)) and AIDS-related complex (ARC) (see Arch. Immunol. Ther. Exp. (Warsz), 41, 147 (1993)), it is shown that IL-1 is concerned with the progress of symptoms, so it is conceivable that cysteine protease inhibition leads to an effective therapy of AIDS and its complication.

Some parasites have cysteine protease activity in their body. Cysteine protease in the phagosome of malaria protozoan is an essential enzyme for supplying nutrition of the parasites. A result is given that the inhibitor of cysteine protease shows an inhibitory effect of the proliferation of the protozoan (see Blood, 87, 4448 (1996)). Thus, it is possible to apply the inhibitor of cysteine protease to malaria.

In Alzheimer-type dementia, it is said that adhesion of non-physiological protein called amyloid to brain is deeply involved with nervous function disorders. Cysteine protease has an activity of generating amyloid by decomposing its precursor protein. Clinically, it is shown that cathepsin B is an enzyme that possesses a processing activity of amyloid proteins in the brains of Alzheimer-type dementia patients (see Biochem. Biophys. Res. Commun., 177, 377 (1991)). Also, expressions of cathepsin B protein (see Virchows Arch. A. Pathol. Anat. Histpathol., 423, 185 (1993)), cathepsin S protein (see Am. J. Pathol., 146, 848 (1995)) and calpain protein (see Proc. Natl. Acad. Sci. USA, 90, 2628 (1993)) and increase of caspase-1 activity (see J. Neuropathol. Exp. Neurol., 58, 582 (1999)) were confirmed in the brain lesions. Besides, by the fact that calpain is concerned with the formation of paired helical filaments which accumulate in Alzheimer dementia patients and production of protein kinase C which stabilizes the protein by phosphorylation (see J. Neurochem., 66, 1539 (1996)) and by the knowledge that caspase is concerned with neurocyte death by β amyloid protein adhesion (see Exp. Cell Res., 234, 507 (1997)), it is implied that cysteine protease is concerned with the disease symptoms.

As to Huntington's chorea, cathepsin H activity increased in the patient's brain (see J. Neurol. Sci., 131, 65 (1995)), and the ratio of activated form of calpain increased (see J. Neurosci., 48, 181 (1997)). In Parkinson's diseases, the increase of expression of m-calpain was recognized in the mesencephalon of the patients (see Neuroscience, 73, 979 (1996)) and IL-1β protein was expressed in brain (see Neurosci. Let., 202, 17 (1995)). Therefore, it is speculated that cysteine protease is concerned with the genesis and progress of these diseases.

Besides, in the central nervous system, spectrin degradation by calpain is found in the process of injury on neurocyte observed in the traumatic brain injury model (see J. Neuropathol. Exp. Neurol., 58, 365 (1999)).

In spinal cord injured model it was recognized that in glia cells calpain messenger RNA increased and its activity increased in the lesion and the possibility was shown that calpain had much to do with the degeneration of myelin and actin after injury (see Brain Res., 816, 375 (1999)). And IL-1β was shown to be concerned with the genesis of multiple sclerosis (see Immunol. Today, 14, 260 (1993)). Therefore, it is conceivable that a cysteine protease inhibitor is promising as an agent for the treatment of these nerve-injuring diseases.

Normally, cathepsin S and cathepsin K do not exist in human arterial walls but it was confirmed that they expressed in arterial sclerosis lesion and they had an decomposing activity of alveolus elastica (see J. Clin. Invest., 102, 576 (1998)) and a calpain inhibitor and antisense of m-calpain inhibited the proliferation of human blood vessel smooth muscle cells and it is shown that m-calpain is concerned with the proliferation of smooth muscle (see Arteioscler. Thromb. Vssc. Biol., 18, 493 (1998)), so it is conceivable that a cysteine protease inhibitor is promising for the treatment of blood vessel lesion such as arteriosclerosis, restenosis after percutaneous transluminal coronary angioplasty (PTCA), etc.

It is reported that in liver, cathepsin B is activated in the process of injuring hepatocyte by bile acid (see J. Clin. Invest., 103, 137 (1999)) and so it is expected that a cysteine protease inhibitor is effective for cholestatic cirrhosis.

In lungs and respiratory system, it is shown that cathepsin S is an enzyme that plays a role in elastin degradation by alveolus macrophages (see J. Biol. Chem., 269, 11530 (1994)), so it is probable that cysteine protease is a cause of pulmonary emphysema. And it is also shown that lung injury (see J. Clin. Invest., 97, 963 (1996)), lung fibrosis (see Cytokine, 5, 57 (1993)) and bronchial asthma (see J. Immunol., 149, 3078 (1992)) are caused by production of IL-1β by caspase-1.

It is pointed out that cysteine protease is also concerned with diseases concerning bones and cartilages. Cathepsin K is specifically recognized in osteoclast and it has a decomposing activity against bone matrix (see J. Biol. Chem., 271, 12517 (1996)), so its inhibitor is expected to show an effect against osteoporosis, arthritis, rheumatoidarthritis, osteoarthritis, hypercalcemia and osteometastasis of cancer, where pathologic bone resorption is recognized. And since IL-1β is shown to be concerned with bone resorption and cartilage degradation, and a caspase-1 inhibitor and IL-1β receptor antagonist inhibit the bone resorption and symptoms of arthritis, a caspase-1 inhibitor and IL-1β receptor antagonist are expected to be effective for arthritis (see Cytokine, 8, 377 (1996)) and osteoporosis (J. Clin. Invest., 93, 1959 (1994)). And it is reported that IL-1β is also concerned with osteoarthritis (see Life Sci., 41, 1187 (1987)).

Cysteine protease is involved with production of various hormones. Since increase of messenger RNA of cathepsin S was recognized by stimuli of thytropin on thyroid epitheliocyte strains (see J. Biol. Chem., 267, 26038 (1992)), it is conceivable that a cysteine protease inhibitor is effective for hyperthyrodism.

Since quantity and activity of cathepsin B protein increased in the gingival sulcus liquid of periodontitis patients (see J. Clin. Periodontol., 25, 34 (1998)), it is pointed out that cysteine protease is concerned with periodontitis.

Therefore, it is expected that the compound that possesses the inhibitory activity of cysteine protease is useful as an agent for the prophylaxis and/or treatment of inflammatory diseases (periodontitis, arthritis, inflammatory bowel diseases, infectious diseases, pancreatitis, hepatitis, glomerulonephritis, endocarditis, myocarditis, etc.), diseases induced by apoptosis (graft versus host diseases, rejection of an organ transplantation, acquired immune deficiency syndrome (AIDS), AIDS-related complex (ARC), adult T cell leukemia, hairy cells leukemia, spondylopathy, disorders of respiratory apparatus, arthritis, HIV or HTLV-1 related diseases such as uveitis, virus-related diseases such as hepatitis C, cancer, collagenosis (systemic lupus erythematosus, rheumatoid arthritis, etc.), ulcerative colitis, Sjögren's syndrome, primary biliary cirrhosis, spontaneous thrombocytopenic purpura, autoimmune hemolytic anemia, myasthenia gravis, autoimmune diseases such as insulin dependent (type I) diabetes, diseases accompanying thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type A, B, C, F, etc.) or hepatitis medicamentosus and cirrhosis, dementia such as Alzheimer's diseases and Alzheimer's senile dementia, cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.), diseases induced by disorders of immune response (graft versus host diseases, rejection of an organ transplantation, allergic diseases (bronchial asthma, atopic dermatitis, allergic rhinitis, pollinosis, diseases induced by house dusts, irritable pneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), disease by degradation various proteins which compose the organism (myodystrophy, cataract, periodontitis, hepatocyte disease by bile acid such as cholestatic cirrhosis, etc.), decomposition of alveolus elastica such as pulmonary emphysema, ischemic diseases (brain ischemia, brain disorders (encephalopathy) by ischemic reperfusion, myocardial infarction, ischemic hepatopathy, etc.), shock (septic shock, systemic inflammatory response syndrome, endotoxin shock, acidosis, etc.), circulatory system disorders (arteriosclerosis, restenosis after percutaneous transluminal coronary angioplasty (PTCA), etc.)), blood coagulation disorders (thrombocytopenic purpura, hemolytic uremic syndrome, etc.), malignant tumor, acquired immune deficiency syndrome (AIDS) and AIDS-related complex (ARC), parasitic diseases such as malaria, nerve degenerative diseases (Alzheimer-type dementia, Huntington's chorea, Parkinson's diseases, multiple sclerosis, traumatic encephalopathy, traumatic spondylopathy, etc.), pulmopathy such as lung fibrosis, bone resorption diseases (osteoporosis, rheumatoid arthritis, arthritis, osteoarthritis, hypercalcemia, osteometastasis of cancer, etc.), endocrinesthenia such as hyperthyroidism.

On the other hand, what is the most important for inhibitors in inhibiting the activity of proteases is, the special reaction site which interacts with the amino acid residue that is the activity center of proteases. The surrounding structure of the reaction sites are represented by - - - P3P2P1-P1'P2'P3' - - - , centering peptide binding (P1-P1') of the reaction site, and at P1 site there exist amino acid residues fitting the substance specificity of proteases which the inhibitors aim. Some reaction sites against cysteine proteases are known, for Example, in the specification of WO99/54317, the followings are described; P1 position against calpain I, II (norvaline, phenylalanine, etc.), P1 position against calpain I (arginine, lysine, tyrosine, valine, etc.), P1 position against papain (homophenylalanine, arginine, etc.

P1 position against cathepsin B-homophenylalanine, phenylalanine, tyrosine, etc.), P1 position against cathepsin S (valine, norleucine, phenylalanine, etc.), P1 position against cathepsin L (homophenylalanine, lysine, etc.), P1 position against cathepsin K (arginine, homophenylalanine, leucine, etc.), P1 position against caspase (aspartic acid).

On the other hand, in the specification of WO 98/49190, it is disclosed that the compound of formula (A) or a pharmaceutically acceptable salt thereof has an inhibitory activity against cysteine proteases, (A)

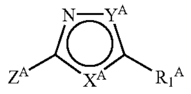

wherein $Z^A$ is a cysteine protease binding moiety;

$X^A$ and $Y^A$ are independently S, O or N, said N being optionally substituted with alkyl or alkenyl optionally substituted with 1–3 halogen atoms, or (C5–C6)aryl, arylalkyl or arylalkenyl optionally comprising 1–3 heteroatoms selected from N, O and S, and optionally substituted with halogen atom, cyano, nitro, haloalkyl, amino, aminoalkyl, dialkylamino, alkyl, alkenyl, alkynyl, alkoxy, haloalkoxy, carboxyl, carboalkoxy, arylcarboxamide, alkylthio or haloalkylthio;

$R_1^A$ is alkyl or alkenyl optionally substituted with 1–3 halo or hydroxy; alkylamino, dialkylamino, alkyldialkylamino; or cycloalkyl, alkylcycloalkyl, (C5–C12)aryl, (C5–C12)arylalkyl or (C5–C12)arylalkenyl optionally comprising 1–4 heteroatoms selected from N, O and S, and optionally substituted with halo, cyano, nitro, haloalkyl, amino, aminodialkyl, dialkylamino, alkyl, alkenyl, alkynyl, alkoxy, haloalkyl, carboxyl, carboalkoxy, alkylcarboxamide, (C5–C6)aryl, —O—(C5–C6)aryl, arylcarboxamide, alkylthio or haloalkylthio; and wherein at least one of Y or X is N.

DISCLOSURE OF THE INVENTION

The present inventors have energetically investigated to find out such compounds that have cysteine protease inhibitory activity and found that the oxadiazole derivative of formula (I) of the present invention accomplishes the purpose.

The oxadiazole derivative of formula (I) of the present invention is not known at all as a cysteine protease inhibitor at all.

The present invention relates to (1) an oxadiazole derivative of formula (I), (I)

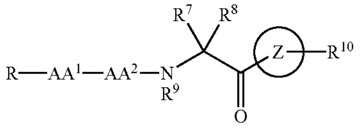

wherein R is (i) hydrogen, (ii) C1–8 alkyl, (iii) CycA, (iv) C1–8 alkyl substituted with a group selected from halogen atom, CycA, nitro, $CF_3$ and cyano, (v)

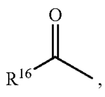

-continued (vi)

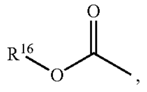

(vii)

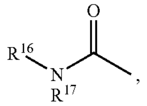

(viii)

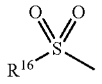

or (ix)

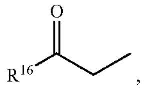

CycA is a C3–15 mono-, bi- or tri-cyclic carboring or a mono-, bi- or tri-cyclic 3–15 membered heteroring comprising 1–4 of nitrogen, 1–2 of oxygen and/or 1 of sulfur;

$R^{16}$ is (1) C1–8 alkyl, (2) C2–8 alkenyl, (3) C2–8 alkynyl, (4) CycA or (5) C1–8 alkyl, C2–8 alkenyl or C2–8 alkynyl substituted with a group selected from halogen atom, nitro, $CF_3$, cyano, CycA, $NR^{18}R^{19}$ and —NHC(O)-CycA;

$R^{17}$, $R^{18}$ and $R^{19}$ each independently represents hydrogen or C1–4 alkyl, $AA^1$ is (i) a single bond, or (ii)

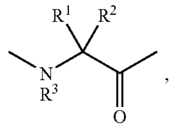

wherein $R^1$ and $R^2$ are the same or different to represent (i) hydrogen, (ii) C1–8 alkyl, (iii) CycA or (iv) C1–8 alkyl substituted with 1–5 of group selected from the following (1) to (8):

(1) $-NR^{21}R^{22}$, (2) $-OR^{23}$, (3) $-SR^{24}$, (4) $-COR^{25}$, (5) $-NR^{26}CONR^{21}R^{22}$, (6) guanidino, (7) CycA, (8) $-NR^{26}SO_2R^{21}$; or $R^1$ and $R^2$ are taken together to form C2–8 alkylene (wherein one carbon atom may be replaced by oxygen, sulfur or $-NR^{20}-$ and the alkylene may be substituted with $-NR^{21}R^{22}$ or $-OR^{23}$, $R^{20}$ is hydrogen, C1–4 alkyl, —COO—(C1–4 alkyl), phenyl or C1–4 alkyl substituted with phenyl, $R^{21}$, $R^{22}$, $R^{23}$, $R^{24}$ and $R^{26}$ are the same or different to represent hydrogen, C1–4 alkyl, phenyl or C1–4 alkyl substituted with phenyl, $R^{25}$ is C1–4 alkyl, phenyl, —$NR^{21}R^{22}$, wherein all symbols have the same meaning as above, —$OR^{23}$, wherein $R^{23}$ is the same meaning as above, or C1–4 alkyl substituted with phenyl, $R^3$ is hydrogen, C1–8 alkyl, phenyl or C1–8 alkyl substituted with phenyl or $R^3$ is taken together with R1 to form C2–6 alkylene, wherein one carbon atom may be replaced by oxygen, sulfur or —$NR^{20}$— and the alkylene may be substituted with —$NR^{21}R^{22}$ or —$OR^{23}$, or when $AA^1$ is (ii)

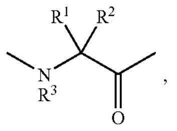

$AA^1$ and R may be taken together to form

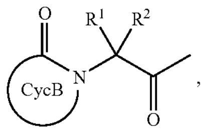

wherein

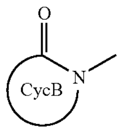

is a 5–12 membered mono- or bi-cyclic heteroring and the other symbols are the same meanings as above, $AA^2$ is (i) a single bond, (ii)

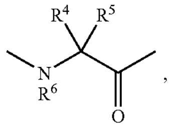

(iii)

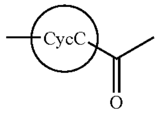

or (iv)

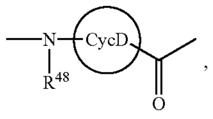

wherein $R^4$ and $R^5$ are the same or different to represent (1) hydrogen, (2) C1–8 alkyl, (3) CycA or (4) C1–8 alkyl substituted with 1–5 of group selected from the following (a) to (h):

(a) —$NR^{41}R^{42}$, (b) —$OR^{43}$, (c) —$SR^{44}$, (d) —$COR^{45}$, (e) —$NR^{46}CONR^{41}R^{42}$, (f) guanidino, (g) CycA, (h) —$NR^{46}SO_2R^{41}$; or $R^4$ and $R^5$ are taken together to form C2–8 alkylene, wherein one carbon atom may be replaced by oxygen, sulfur or —$NR^{40}$— and the alkylene may be substituted with —$NR^{41}R^{42}$ or —$OR^{43}$, $R^{40}$ is hydrogen, C1–4 alkyl, —COO—(C1–4 alkyl), phenyl or C1–4 alkyl substituted with phenyl, $R^{41}$, $R^{42}$, $R^{43}$, $R^{44}$ and $R^{46}$ are the same or different to represent hydrogen, C1–4 alkyl, phenyl or C1–4 alkyl substituted with phenyl, $R^{45}$ is C1–4 alkyl, phenyl, —$NR^{41}R^{42}$, wherein all symbols are the same meaning as above, —$OR^{43}$, wherein $R^{43}$ is the same meaning as above, or C1–4 alkyl substituted with phenyl, $R^6$ is hydrogen, C1–8 alkyl, phenyl or C1–8 alkyl substituted with phenyl or $R^6$ is taken together with $R^4$ to form C2–6 alkylene, wherein one carbon atom may be replaced by oxygen, sulfur or —$NR^{40}$— and the alkylene may be substituted with —$NR^{41}R^{42}$ or —$OR^{43}$, $R^{48}$ is hydrogen, C1–4 alkyl, phenyl or C1–4 alkyl substituted with phenyl or when $AA^1$ is a single bond, $R^{48}$ and R may be taken together to form C2–6 alkylene, wherein one carbon atom may be replaced by oxygen, sulfur or —$NR^{47}$, wherein $R^{47}$ is hydrogen or C1–4 alkyl, CycC is a 3–17 membered mono- or bi-cyclic heteroring, CycD is a C3–14 mono- or bi-cyclic carboring or a 3–14 membered mono- or bi-cyclic heteroring, or $AA^2$ and $AA^1$ are taken together to form, (i)

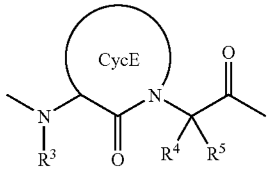

or (ii)

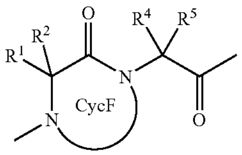

wherein CycE is a 4–18 membered mono- or bi-cyclic heteroring, CycF is a 5–8 membered monocyclic heteroring, and the other symbols have the same meanings as above, $R^7$ and $R^8$ are the same or different to represent (i) hydrogen, (ii) C1–8 alkyl, (iii) CycA or (iv) C1–8 alkyl substituted with 1–5 of group selected from the following (1) to (8);

(1) —$NR^{61}R^{62}$, (2) —$OR^{63}$, (3) —$SR^{64}$, (4) —$COR^{65}$, (5) —$NR^{66}CONR^{61}R^{62}$, (6) guanidino, (7) CycA, (8) —$NR^{66}SO_2R^{61}$, or $R^7$ and $R^8$ are taken together to form C2–8 alkylene, wherein one carbon atom may be replaced by oxygen, sulfur or —$NR^{60}$— and the alkylene may be substituted with —$NR^{61}R^{62}$ or —$OR^{63}$, $R^{60}$ is hydrogen, C1–4 alkyl, —COO—(C1–4 alkyl), phenyl or C1–4 alkyl substituted with phenyl, $R^{61}$, $R^{62}$, $R^{63}$, $R^{64}$ and $R^{66}$ are the same or different to represent hydrogen, C1–4 alkyl, phenyl or C1–4 alkyl substituted with phenyl, $R^{65}$ is C1–4 alkyl, phenyl, —$NR^{61}R^{62}$, wherein all symbols are the same meanings as above, —$OR^{63}$, wherein $R^{63}$ is the same meaning as above, or C1–4 alkyl substituted with phenyl, $R^9$ is hydrogen, C1–8 alkyl, phenyl or C1–8 alkyl substituted with phenyl or $R^9$ is taken together with $R^7$ to form C2–6 alkylene, wherein one carbon atom may be replaced by oxygen, sulfur or $—NR^{60}—$ and the alkylene may be substituted with $—NR^{61}R^{62}$ or $—OR^{63}$,

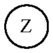 is 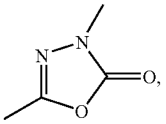 , 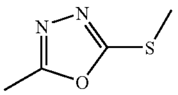 or 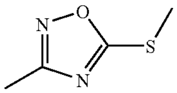 , $R^{10}$ is
(i) C1–8 alkyl,
(ii) C2–8 alkenyl,
(iii) CycA,
(iv) $—COR^{71}$ or
(v) C1–8 alkyl substituted with 1–3 of group selected from CycA, guanidino, $—COR^{71}—NR^{72}R^{73}$, $—OR^{74}$, cyano or $—P(O)(OR^{78})_2$, wherein $R^{71}$ is
(1) C1–4 alkyl,
(2) C1–4 alkoxy,
(3) CycA,
(4) —O-CycA,
(5) $—NR^{72}R^{73}$,
(6) C1–4 alkyl substituted with CycA,
(7) C1–4 alkoxy substituted with CycA, or
(8) hydroxy, $R^{72}$ and $R^{73}$ are the same or different to represent hydrogen, C1–8 alkyl, CycA or C1–8 alkyl substituted with CycA, $R^{74}$ is
(1) hydrogen,
(2) C1–8 alkyl,
(3) CycA,
(4) $—SiR^{75}R^{76}R^{77}$, wherein $R^{75}$, $R^{76}$ and $R^{77}$ are the same or different to represent C1–8 alkyl, phenyl or C1–8 alkyl substituted with phenyl, or
(5) C1–8 alkyl substituted with CycA, $R^{78}$ is C1–8 alkyl, phenyl, or C1–8 alkyl substituted with phenyl; and, CycA's included in R, $R^1$, $R^2$, $R^4$, $R^5$, $R^7$, $R^8$ and $R^{16}$ are the same or different, and CycA, CycB, CycC, CycD, CycE and CycF, independently, may be substituted with 1–5 of $R^{27}$:

$R^{27}$ is
(1) C1–8 alkyl,
(2) halogen atom,
(3) $—NR^{11}R^{12}$,
(4) $—OR^{13}$,
(5) a C5–10 mono-or bi-cyclic carboring,
(6) nitro,
(7) $CF_3$,
(8) cyano,
(9) a 5–10 membered mono- or bi-cyclic heteroring
(10) $—SR^{14}$,
(11) $—COR^{15}$,
(12) oxo,
(13) $—SO_2R^{15}$,
(14) $—OCF_3$ or
(15) C1–8 alkyl substituted with 1–5 of group selected from the following (a) to (m):

(a) halogen atom, (b) $—NR^{11}R^{12}$, (c) $—OR^{13}$, (d) a C5–10 mono- or bi-cyclic carboring, (e) nitro, (f) $CF_3$, (g) cyano, (h) a 5–10 membered mono- or bi-cyclic heteroring, (j) $—SR^{14}$, (k) $—COR^{15}$, (l) $—SO_2R^{15}$, (m) $—OCF_3$, wherein $R^{11}$ and $R^{12}$ are the same or different to represent hydrogen, C1–4 alkyl, —COO—(C1–4 alkyl), phenyl or C1–4 alkyl substituted with phenyl, $R^{13}$ and $R^{14}$ are the same or different to represent hydrogen, C1–4 alkyl, phenyl or C1–4 alkyl substituted with phenyl, $R^{15}$ is C1–4 alkyl, phenyl, $—NR^{11}R^{12}$, wherein all symbols have the same meanings as above, $—OR^{13}$, wherein $R^{13}$ is the same meaning as above, or C1–4 alkyl substituted with phenyl, or a non-toxic salt thereof, (2) a method for the preparation thereof and (3) a pharmaceutical agent comprising the oxadiazole derivative and non-toxic salt thereof as active ingredient.

DETAILED DESCRIPTION OF THE PRESENT INVENTION

In the compound of formula (I), in

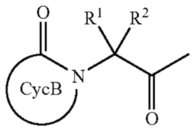 , which $AA^1$ and R together form,

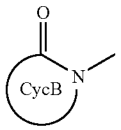

is a 5–12 membered heteroring containing 1–3 of nitrogen, 1 of oxygen, and/or 1 of sulfur (this heteroring may be substituted with 1–5 of $R^{27}$).

And to describe

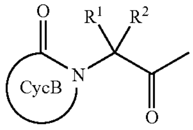

concretely, it is (i)

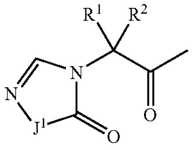 ,

-continued (ii)

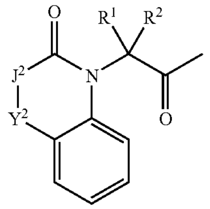

or (iii)

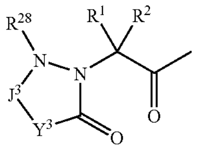

, wherein $J^1$ is oxygen, sulfur, —$NR^{29}$—, wherein $R^{29}$ is hydrogen, C1–4 alkyl, CycA or C1–4 alkyl substituted with CycA, C1–3 alkylene or C2–3 alkenylene, $J^2$ is a single bond or C1–2 alkylene, $Y^2$ is —N═CH—, —CH═N— or C1–2 alkylene, $J^3$ is carbonyl or C1–3 alkylene, $Y^3$ is C1–3 alkylene, oxygen or —$NR^{29}$—, wherein $R^{29}$ is the same meaning as above, $R^{28}$ is hydrogen, C1–4 alkyl, CycA or C1–4 alkyl substituted with CycA, or $R^{28}$ is taken together with $R^1$ to form C2–4 alkylene, and the other symbols have the same meaning as above and each ring may be substituted with 1–5 of $R^{27}$.

In the compound of formula (I), in (iii)

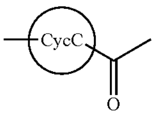

, which $AA^2$ represents, CycC is a 3–17 membered heteroring which contains 1–2 of nitrogen, 1 of oxygen and/or 1 of sulfur (this ring may be substituted with 1–5 of $R^{27}$).

And to describe

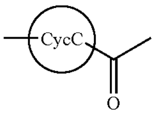

concretely, (iii-1)

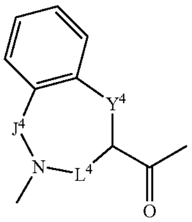

,

-continued (iii-2)

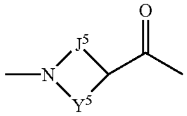

or (iii-3)

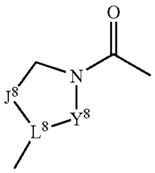

, wherein $J^4$, $Y^4$ and $L^4$ are the same or different to represent a single bond or C1–3 alkylene, wherein $J^4$, $Y^4$ and $L^4$ do not represent a single bond at the same time, $J^5$ is C1–6 alkylene, $Y^5$ is a single bond, C1–3 alkylene or —$NR^{67}$—, wherein $R^{67}$ is hydrogen, C1–4 alkyl, phenyl or C1–4 alkyl substituted with phenyl, $J^8$ is C1–5 alkylene, wherein one carbon atom may be replaced by oxygen, $Y^8$ is a single bond or C1–4 alkylene, $L^8$ is —N— or —CH—, and the other symbols have the same meaning as above and each ring may be substituted with 1–5 of $R^{27}$.

And in (iv)

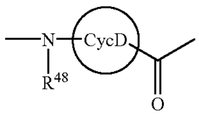

, which $AA^2$ represents, CycD is a C3–14 mono- or bi-cyclic carboring or 3–14 membered heteroring which contains 1–2 of nitrogen, 1 of oxygen and/or 1 of sulfur (this carboring and heteroring may be substituted with 1–5 of $R^{27}$).

And to describe

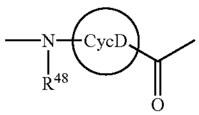

concretely, it is (iv-1)

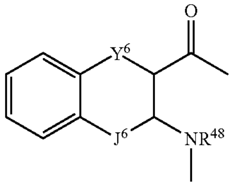

,

-continued (iv-2)

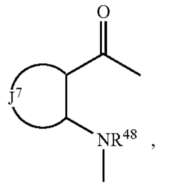
, (iv-3)

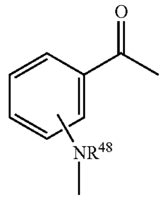

or (iv-4)

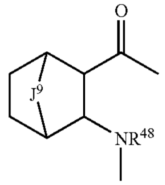
, wherein $J^6$ and $Y^6$ are the same or different to represent a single bond or C1–3 alkylene, wherein $J^6$ and $Y^6$ do not represent a single bond at the same time, $J^7$ is C1–6 alkylene, wherein one carbon atom may be replaced by oxygen, sulfur or —$NR^{67}$—, wherein $R^{67}$ has the same meaning as above, $J^9$ is C1–3 alkylene, oxygen, sulfur or —$NR^{67}$—, wherein $R^{67}$ is the same meaning as above, and the other symbols have the same meanings as above and each ring may be replaced by 1–5 of $R^{27}$.

In the compounds of the formula (I), in (i)

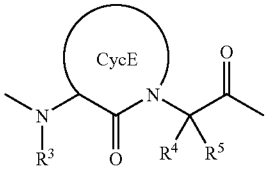
, which $AA^1$ and $AA^2$ together form,

CycE is a 4–18 membered heteroring which contains 1–2 of nitrogen, 1 of oxygen and/or 1 of —$S(O)_p$— (this heteroring may be substituted with 1–5 of $R^{27}$).

And to describe

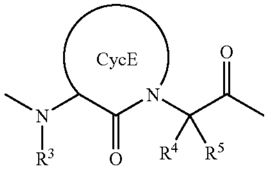

concretely, it is (i-1)

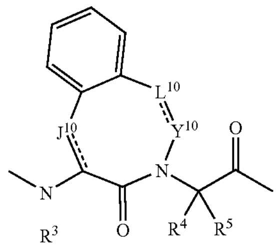

or (i-2)

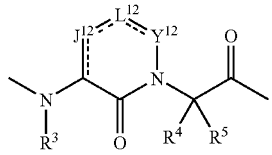
, wherein ----- is a single bond or a double-bond, $J^{10}$ and $Y^{10}$ are the same or different to represent a single bond or C1–3 alkylene, $L^{10}$ is a single bond, C1–3 alkylene, —$NR^{57}$—, wherein $R^{57}$ is hydrogen, C1–4 alkyl, phenyl or C1–4 alkyl substituted with phenyl, —N═, oxygen or —$S(O)_p$—, wherein p is 0 or an integer of 1 to 2, $J^{12}$ and $Y^{12}$ are the same or different to represent a single bond or C1–3 alkylene, $L^{12}$ is C1–3 alkylene, —$NR^{57}$—, wherein $R^{57}$ is the same meaning as above), —N═, ═N—, oxygen or —$S(O)_p$—, wherein p has the same meaning as above, and the other symbols have the same meanings as above and each ring may be substituted with 1–5 of $R^{27}$.

And in (ii)

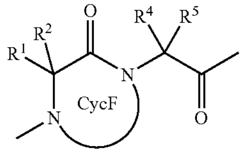
, which $AA^1$ and $AA^2$ together form,

CycF is a 5–8 membered heteroring containing 2 of nitrogen.

And to describe

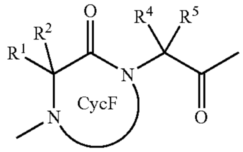

concretely, it is

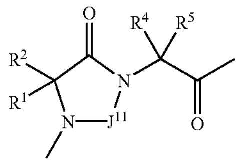

wherein $J^{11}$ is carbonyl or C2–4 alkylene and the other symbols have the same meaning as above and the ring therein may be substituted with 1–5 of $R^{27}$.

In the present specification, C1–4 alkyl is methyl, ethyl, propyl, butyl and isomers thereof.

In the present specification, C1–8 alkyl is methyl, ethyl, propyl, butyl, pentyl, hexyl, heptyl, octyl and isomers thereof.

In the present specification, C2–8 alkenyl is, ethyl, propyl, butyl, pentyl, hexyl, heptyl, octyl containing 1–3 of double bond and isomers thereof. For example, vinyl, propenyl, butenyl, hexenyl, hexadienyl, octadienyl, etc. are included.

In the present specification, C2–8 alkynyl is ethyl, propyl, butyl, pentyl, hexyl, heptyl, octyl containing 1–3 of triple bond and isomers thereof. For example, ethynyl, propynyl, butynyl, pentynyl, hexynyl, heptynyl, octynyl, etc. are included.

In the present specification, C1–4 alkyl substituted with phenyl is phenylmethyl, phenylethyl, phenylpropyl, phenylbutyl and isomers thereof.

In the present specification, C1–2 alkylene is, methylene, ethylene and isomers thereof.

In the present specification, C1–3 alkylene is, methylene, ethylene, trimethylene and isomers thereof.

In the present specification, C1–4 alkylene is methylene, ethylene, trimethylene, tetramethylene and isomers thereof.

In the present specification, C1–5 alkylene is methylene, ethylene, trimethylene, tetramethylene, pentamethylene and isomers thereof In the present specification, C1–6 alkylene is methylene, ethylene, trimethylene, tetramethylene, pentamethylene, hexamethylene and isomers thereof.

In the present specification, C2–4 alkylene is ethylene, trimethylene, tetramethylene and isomers thereof.

In the present specification, C2–6 alkylene is ethylene, trimethylene, tetramethylene, pentamethylene, hexamethylene and isomers thereof.

In the present specification, C2–8 alkylene is ethylene, trimethylene, tetramethylene, pentamethylene, hexamethylene, heptamethylene, octamethylene and isomers thereof.

In the present specification, C2–6 alkylene whose one carbon atom may be replaced by oxygen, sulfur, $—NR^{20}—$, $—NR^{40}—$ or $—NR^{60}—$ is ethylene, trimethylene, tetramethylene, pentamethylene, hexamethylene and isomers thereof, wherein one carbon atom thereof may be replaced by oxygen, sulfur, $—NR^{20}—$, $—NR^{40}—$, or $—NR^{60}—$, for example, such groups are $—CH_2—O—CH_2—$, $—CH_2—CH_2—O—CH_2—$, $—CH_2—CH_2—S—CH_2—$, $—CH_2—CH_2—NH—CH_2—$, $—CH_2—CH_2—O—CH_2—CH_2—$, $—CH_2—CH_2—S—CH_2—CH_2—$, $—CH_2—CH_2—NH—CH_2—CH_2—$, $—CH_2—CH_2—N(CH_3)—CH_2—CH_2—$, etc.

In the present specification, C2–8 alkylene whose one carbon atom may be replaced by oxygen, sulfur, $—NR^{20}—$, $—NR^{40}—$ or $—NR^{60}—$ is ethylene, trimethylene, tetramethylene, pentamethylene, hexamethylene, heptamethylene, octamethylene and isomers thereof, wherein one carbon atom may be replaced by oxygen, sulfur, $—NR^{20}—$, $—NR^{40}—$ or $—NR^{60}—$, for example, such groups are $—CH_2—O—CH_2—$, $—CH_2—CH_2—O—CH_2—$, $—CH_2—CH_2—S—CH_2—$, $—CH_2—CH_2—NH—CH_2—$, $—CH_2—CH_2—O—CH_2—CH_2—$, $—CH_2—CH_2—S—CH_2—CH_2—$, $—CH_2—CH_2—NH—CH_2—CH_2—$, $—CH_2—CH_2—N(CH_3)—CH_2—CH_2—$, etc.

In the present specification, C2–3 alkenylene means vinylene and allylene and isomers thereof.

In the present specification, halogen atom means chlorine, fluorine, bromine and iodine atom.

In the present specification, mono- or bi-cyclic C5–10 carboring is mono- or bi-cyclic C5–10 carboaryl or partially or completely saturated one thereof. For example, cyclopentane, cyclohexane, cycloheptane, cyclopentene, cyclohexene, cyclopentadiene, cyclohexadiene, benzene, pentalene, indene, naphthalene, azulene, perhydropentalene, perhydroindene, perhydronaphthalene, perhydroazulene, adamantyl ring, etc. are included.

In the present specification, mono-, bi- or tri-cyclic C3–15 carboring is mono-, bi- or tri-cyclic carboaryl or partially or completely saturated one thereof. For example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, perhydroindene, perhydronaphthalene, perhydroazulene, perhydrofluorene, perhydrophenanthrene, perhydroanthracene, perhydroacenaphthylene, perhydrobiphenylene, adamantyl ring etc. are included.

In the present specification, mono- or bi-cyclic 5–10 membered heteroring containing 1–4 of nitrogen, 1 of oxygen and/or sulfur is mono- or bi-cyclic 5–10 membered heteroaryl containing 1–4 of nitrogen, 1 of oxygen and/or sulfur or partially or completely saturated one thereof.

Above 5–10 membered mono- or bi-cyclic heteroaryl containing 1–4 of nitrogen, 1 of oxygen and/or 1 of sulfur is, for example, pyrrole, imidazole, triazole, tetrazole, pyrazole, pyridine, pyrazine, pyrimidine, pyridazine, azepine, diazepine, furan, pyrane, oxepine, thiophene, thiaine (thiopyrane), thiepine, oxazole, isooxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, etc.

Above partially or completely saturated mono- or bi-cyclic 5–10 membered heteroaryl containing 1–4 of nitrogen, 1 of oxygen and/or 1 of sulfur is, for example, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyrane, tetrahydropyrane, dihydrothiophene, tetrahydrothiophene, dihydrothiaine (dihydrothiopyrane), tetrahydrothiaine (tetrahydrothiopyrane), oxazoline (dihydrooxazole), oxazolidine (tetrahydroxazole), dihydroisoxazole, tetrahydroisoxazole, oxadiazoline (dihydroxadiazole), oxadiazolidine (tetrahydroxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, etc.

In the present specification, a 3–15 membered mono-, bi- or tri-cyclic heteroring containing 1–4 of nitrogen, 1–2 of oxygen and/or 1 of sulfur is 3–15 membered mono-, bi- or tri-cyclic heteroaryl containing 1–4 of nitrogen, 1–2 of oxygen and/or 1 of sulfur or partially or completely saturated one thereof.

Above 3–15 membered mono-, bi- or tri-cyclic heteroring containing 1–4 of nitrogen, 1–2 of oxygen and/or 1 of sulfur is, for example, pyrrole, imidazole, triazole, tetrazole, pyrazole, pyridine, pyrazine, pyrimidine, pyridazine, azepine, diazepine, furan, pyrane, oxepine, oxazepine, thiophene, thiaine (thiopyrane), thiepine, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzoxadiazole, benzothiazole, benzoimidazole, carbazole, acridine ring, etc.

Above partially or completely saturated mono-, bi- or tri-cyclic 3–15 membered heteroring containing 1–4 of nitrogen, 1–2 of oxygen and/or 1 of sulfur is, aziridine, oxirane, azetidine, oxetane, thiirane, thietane, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyrane, tetrahydropyrane, dihydrothiophene, tetrahydrothiophene, dihydrothiaine (dihydrothiopyrane), tetrahydrothiaine (tetrahydrothiopyrane), oxazoline (dihydroxazole), oxazolidine (tetrahydroxazole), dihydroisoxazole, tetrahydroisoxazole, oxadiazoline (dihydroxadiazole), oxadiazolidine (tetrahydroxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, benzoxazepine, benzoxadiazepine, benzothiazepine, benzothiadiazepine, benzazepine, benzodiazepine, indoloxazepine, indolotetrahydroxazepine, indoloxadiazepine, indolotetrahydroxadiazepine, indolothiazepine, indolotetrahydrothiazepine, indolothiadiazepine, indolotetrahydrothiadiazepine, indolazepine, indolotetrahydroazepine, indolodiazepine, indolotetrahydrodiazepine, benzofurazane, benzothiadiazole, benzotriazole, camphor, imidazothiazole, dihydrocarbazole, tetrahydrocarbazole, perhydrocarbazole, dihydroacridine, tetrahydroacridine, perhydroacridine, dioxolane, dioxane, dioxazine ring etc.

In the present specification, a 5–12 membered heteroring containing 1–3 of nitrogen, 1 of oxygen and/or 1 of sulfur atom, i.e.

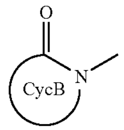

is, for example, a ring represented by

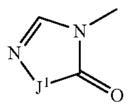
,
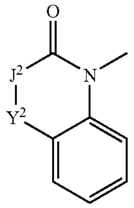
or
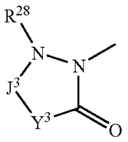
.

Specifically, 2-oxo-1,3,4-triazoline, 5-oxo-1,2,4-oxadiazoline, 5-oxo-1,2,4-thiadiazoline, 4-oxoimidazoline, 3,4-dihydro-4-oxopyrimidine, 3,4,5,6-tetrahydro-4-oxopyrimidine, 2-oxoindoline, 2-oxo-tetrahydroquinoline, 1,2-dihydro-2-oxoquinazoline, 1,2-dihydro-2-oxoquinoxaline, 3-oxopyrazolidine, perhydro-3-oxopyridazine, 2-oxo-1,3,4-oxadiazolidine, perhydro-2-oxo-1,3,4-oxadiazine, etc. are included.

In the specification, 3–17 membered heteroring containing 1–2 of nitrogen, 1 of oxygen and/or 1 of sulfur represented by CycC is, for example, a ring represented by

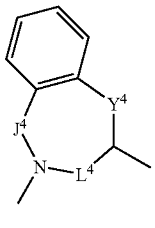
,
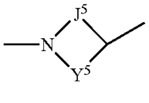
or
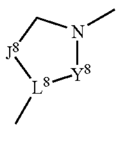
.

Specifically, pyrrolidine, imidazolidine, pyrazolidine, piperidine, piperazine, perhydropyrimidine, perhydropyridazine, thiazolidine, indoline, isoindoline, tetrahydroquinoline, tetrahydroisoquinoline, etc. are included.

In the specification, a C3–14 mono- or bi-cyclic carboring or 3–14 membered heteroring containing 1–2 of nitrogen, 1 of oxygen, and/or 1 of sulfur represented by CycD is, for example, a ring represented by

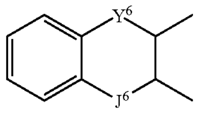, 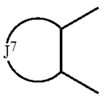, 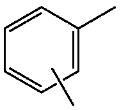, or

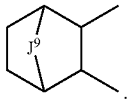.

Specifically, cyclopentane, cyclohexane, cycloheptane, benzene, indan, tetrahydronaphthalene, oxorane, oxane, thiorane, thian, pyrrolidine, piperidine, bicyclo[2.2.1]heptane, bicyclo[2.2.2]octane, 7-azabicyclo[2.2.1]heptane, 7-oxobicyclo[2.2.1]heptane, 7-thiabicyclo[2.2.1]heptane, etc. are included.

In the specification, 4–18 membered heteroring containing 1–2 of nitrogen, 1 of oxygen and/or 1 of —$S(O)_p$—, i.e. CycE is, for example, a ring represented by

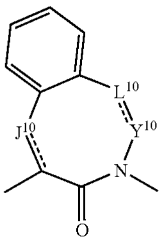 or 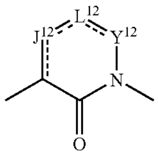.

Specifically, 2-oxopyrrolidine, 2-oxopiperidine, 2-oxoperhydroazepine, 2-oxopiperazine, 3-oxomorpholine, 1,1,-dioxo-3-isothiazolidine, 1,1-dioxo-3-isothiazine, 4-oxodiazepine, 2-oxoindoline, 2-oxo-tetrahydroquinoline, 1,1-dioxo-3-benzisothiazolidine, 1,1-dioxo-3-benzisothiazine, etc. are included.

In the present invention, 5–8 membered heteroring which contains 2 of nitrogen. i.e. CycF is, for example, a ring represented by

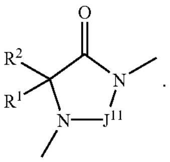.

Specifically, 2,4-dioxoimidazolidine, 2-oxopiperazine, 2-oxoperhydrodiazepine substituted by $R^1$ and $R^2$ are included.

In the present invention, as may be easily understood by those skilled in the art, the symbol:

indicates that the substituent attached thereto is in front of the sheet (β-position) unless specified,

indicates that the substituent attached thereto is behind the sheet (α-position) unless specified, and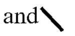

indicates that the substituent attached thereto is in β-position or α-position or a mixture thereof.

In the formula (I), all groups represented by R are preferable, but preferably, R is (i) hydrogen, (ii) C1–8 alkyl, (iii) CycA, (iv) C1–8 alkyl substituted with a group selected from CycA and nitro, (v)

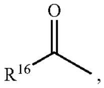, (vi)

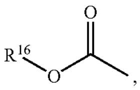, (vii)

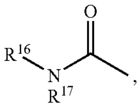, (viii)

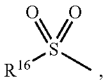, or (ix)

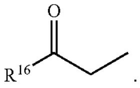.

more preferably, C1–8 alkyl or C1–8 alkyl substituted with CycA or nitro.

Any group represented by $R^{16}$ is preferable, but more preferably, $R^{16}$ is

[I] (1) C1–8 alkyl, (2) C2–8 alkenyl, (3) C2–8 alkynyl, (4) CycA, or (5) C1–8 alkyl substituted with a group selected from CycA or —NHC(O)-CycA, (6) C2–8 alkenyl substituted with CycA or (7) C2–8 alkynyl substituted with CycA, wherein CycA may be substituted with 1–5 of $R^{27a}$, and $R^{27a}$ is (1) C1–8 alkyl, (2) halogen, (3) —$NR^{11}R^{12}$, (4) —$OR^{13}$, (5) phenyl, (6) nitro, (7) $CF_3$, (8) cyano, (9) tetrazole,

(10) —$SR^{14}$,

(11) —$COR^{15}$,

(12) oxo or

(13) C1–8 alkyl substituted with 1–5 of group selected from the following (a) to (k):

(a) halogen, (b) —$NR^{11}R^{12}$, (c) —$OR^{13}$, (d) phenyl, (e) nitro, (f) $CF_3$, (g) cyano, (h) tetrazole, (j) —$SR^{14}$, (k) —$COR^{15}$, or

[II] (a) C1–8 alkyl, C2–8 alkenyl or C2–8 alkynyl substituted with a group selected from halogen, $CF_3$, nitro, cyano or $NR^{18}R^{19}$ or (b) (1) CycA containing 1–5 of substituent $R^{27}$ or (2) C1–8 alkyl, C2–8 alkenyl or C2–8 alkynyl substituted with CycA, which contains 1–5 of substituent $R^{27}$, wherein at least one of R27 described in (1) and (2) is selected from (i) a C5–10 mono- or bi-cyclic carboring, (ii) a 5–10 membered mono- or bi-cyclic heteroring, (iii) —$SO_2R^{15}$, (iv) —$OCF_3$ or (v) C1–8 alkyl substituted with 1–5 of the group selected from (a) halogen, (b) —$NR^{11}R^{12}$, (c) —$OR^{13}$, (d) a C5–10 mono-or bi-cyclic carboring, (e) nitro, (f) $CF_3$, (g) cyano, (h) a 5–10 membered mono- or bi-cyclic heteroring, (j) —$SR^{14}$, (k) —$COR^{15}$, (1) —$SO_2R^{15}$ and (m) —$OCF_3$ (at least one is a C5–10 mono-or bi-cyclic carboring, a 5–10 mono- or bi-cyclic heteroring, —$SO_2R^{15}$ or —$OCF_3$))

Particularly preferably,

[I] (1) C1–8 alkyl, (2) C2–8 alkenyl, (3) C2–8 alkynyl, (4) CycA or (5) C1–8 alkyl substituted with a group selected from CycA or —NHC(O)-CycA, (6) C2–8 alkenyl substituted with CycA or (7) C2–8 alkynyl substituted with CycA, wherein CycA is a mono- or bi-cyclic C5–10 carboaryl which may be substituted with 1–5 of $R^{27}$ or partially or completely saturated one thereof, or mono- or bi-cyclic 5–10 membered heteroaryl containing 1–2 of nitrogen, 1–2 of oxygen and/or 1 of sulfur atom, or partially or completely saturated one thereof or

[II] (a) C1–8 alkyl, C2–8 alkenyl or C2–8 alkynyl substituted with a group selected from halogen atom, $CF_3$, nitro, cyano and $NR^{18}R^{19}$, or (b) CycA containing 1–5 of substituent $R^{27}$ or (2) C1–8 alkyl, C2–8 alkenyl or C2–8 alkynyl substituted with CycA, which contains 1–5 of substituent $R^{27}$, wherein at least one of $R^{27}$ described in (1) and (2) is selected from (i) a C5–10 mono- or bi-cyclic carboring, (ii) a 5–10 membered mono- or bi-cyclic heteroring, (iii) —$SO_2R^{15}$, (iv) —$OCF_3$ or (v) C1–8 alkyl substituted with 1–5 of group selected from (a) halogen, (b) —$NR^{11}R^2$, (c) —$OR^{13}$, (d) a C5–10 mono- or bi-cyclic carboring, (e) nitro, (f) $CF_3$, (g) cyano, (h) a 5–10 membered mono- or bi-cyclic heteroring, (j) —$SR^{14}$, (k) —$COR^{15}$, (1) —$SO_2R^{15}$ and (m) $OCF_3$, wherein at least one group is selected from a C5–10 mono- or bi-cyclic carboring or a 5–10 membered mono- or bi-cyclic heteroring, —$SO_2R^{15}$ or $OCF_3$, above CycA is C5–10 mono- or bi-cyclic carboaryl or partially or completely saturated one, or 5–10 membered mono- or bi-cyclic heteroaryl containing 1–2 of nitrogen, 1–2 of oxygen and/or 1 of sulfur, or partially or completely saturated one thereof.

Particularly preferably, [I] (1) C1–4 alkyl, (2) C2–4 alkenyl, (3) C2–4 alkynyl, (4) CycA or (5) C1–4 alkyl, C2–4 alkenyl or C2–4 alkynyl substituted with CycA which is preferably cyclopentane, cyclohexane, benzene, naphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxazole, tetrahydroquinoline, tetrahydroquinazoline, tetrahydroquinoxaline, optionally substituted with 1–5 of $R^{27a}$ or

[II] (a) C1–8 alkyl, C2–8 alkenyl or C2–8 alkynyl substituted with a group selected from halogen, $CF_3$, nitro, cyano or $NR^{18}R^{19}$ or (b) (1) CycA which contains 1–5 of substituent $R^{27}$, or (2) C1–8 alkyl, C2–8 alkenyl or C2–8 alkynyl substituted with CycA which contains 1–5 of substituent $R^{27}$, wherein at least one of $R^{27}$ described in (1) and (2) is selected from (i) a C5–10 mono- or bi-cyclic carboring, (ii) a 5–10 membered mono- or bi-cyclic heteroring, (iii) —$SO_2R^{15}$, (iv) —$OCF_{13}$, or (v) C1–8 alkyl substituted with 1–5 of group selected from (a) halogen atom, (b) —$NR^{11}R^{12}$, (c) —$OR^{13}$, (d) a C5–1 mono- or bi-cyclic carboring, (e) nitro, (f) $CF_3$, (g) cyano, (h) a 5–10 membered mono- or bi-cyclic heteroring, (j) —$SR^{14}$, (k) —$COR^{15}$, (1) —$SO_2R^{15}$ or (m) —$OCF_3$, wherein at least one group is selected from a C5–10 mono- or bi-cyclic carboring, a 5–10 membered mono- or bi-cyclic heteroring, —$SO_2R^{15}$ or —$OCF_3$, and CycA is preferably cyclopentane, cyclohexane, benzene, naphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxadiazole, tetrahydroquinoline, tetrahydroquinazoline, or tetrahydroquinoxaline.

In the formula (I), $AA^1$ is preferably a single bond,

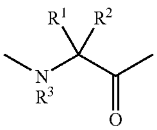

or

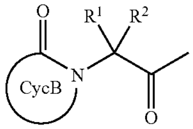

which is formed with R, but more preferably, $AA^1$ is a single bond or

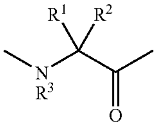

.

Any group represented by $R^1$ is preferable, but more preferably, $R^1$ is hydrogen, C1–8 alkyl, phenyl or C1–8 alkyl substituted with $NH_2$, C1–4 alkoxy, SH, $SCH_3$, phenyl, hydroxyphenyl, COOH, $CONH_2$, guanidino, imidazole or indole. Particularly preferably, $R^1$ is hydrogen, C1–8 alkyl, phenyl or C1–8 alkyl substituted with C1–4 alkoxy or phenyl. Then, any group represented by $R^2$ is preferable, but hydrogen is particularly preferable.

And C3–6 alkylene which $R^1$ and $R^2$ together form is also preferable.

Any group represented by $R^3$ is preferable, but more preferably $R^3$ is hydrogen or C1–4 alkyl.

And C2–4 alkylene which $R^3$ and $R^1$ together form is also preferable.

In the formula (I), $AA^2$ is all preferable, but more preferably, $AA^2$ is a single bond,

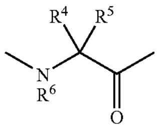, 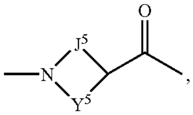, 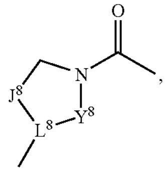,

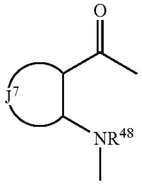, or 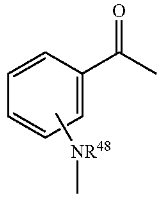.

Particularly preferably, $AA^2$ is a single bond,

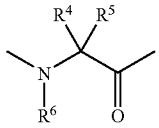, 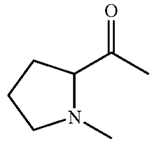, 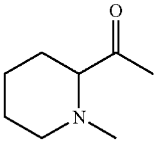,

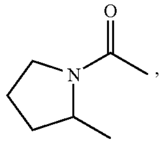, 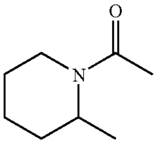, 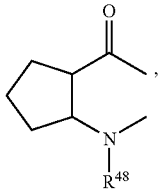,

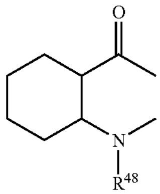, or 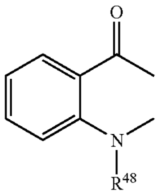.

Any group represented by $R^4$ is preferable, but more preferably, $R^4$ is hydrogen, C1–8 alkyl, phenyl or C1–8 alkyl substituted with $NH_2$, C1–4 alkoxy, SH, $SCH_3$, phenyl, hydroxyphenyl, COOH, $CONH_2$, guanidino, imidazole or indole. Particularly preferably, $R^4$ is hydrogen, C1–8 alkyl, phenyl or C1–8 alkyl substituted with C1–4 alkoxy or phenyl. Then, any group represented by $R^5$ is preferable, and hydrogen is particularly preferable.

And C3–6 alkylene which $R^4$ and $R^5$ together form is also preferable.

Any group represented by $R^6$ is preferable, but more preferably $R^6$ is hydrogen or C1–4 alkyl.

And C2–4 alkylene which $R^6$ and $R^4$ together form is also preferable.

$R^{48}$ is all preferable, but more preferably, $R^{48}$ is

[I] hydrogen, C1–4 alkyl, phenyl or C1–4 alkyl substituted with phenyl, or

[II] C2–6 alkylene, wherein one carbon atom may be replaced by oxygen, sulfur or $—NR^{47}—$, wherein $R^{47}$ is hydrogen or C1–4 alkyl to be formed together with $R^4$, when $AA^1$ is a single bond. Particularly preferably, $R^{48}$ is [I] hydrogen atom or C1–4 alkyl, or

[II] when $AA^1$ is a single bond, taken together with R to form tetramethylene, pentamethylene, $—CH_2—CH_2—O—CH_2—CH_2—$, $—CH_2—CH_2—NH—CH_2—CH_2—$ or $—CH_2—CH_2—N(CH_3)—CH_2—CH_2—$.

In the formula (I), all the groups which $AA^1$ and $AA^2$ together form are preferable, but preferably, it is (i)

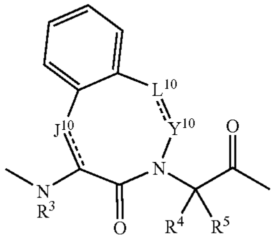, (ii)

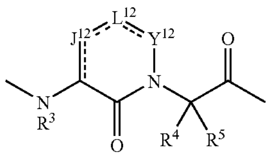, or (iii)

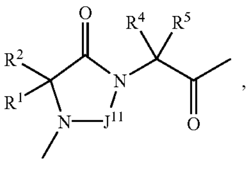, particularly preferably, it is

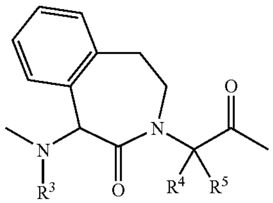,

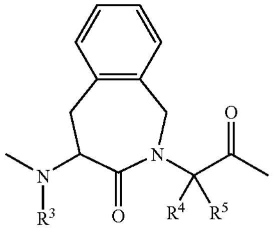,

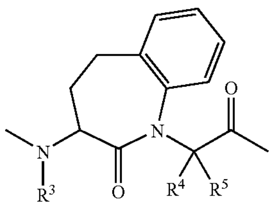,

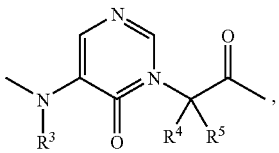,

-continued

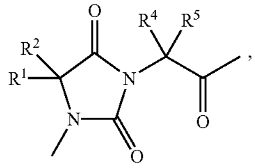

, or

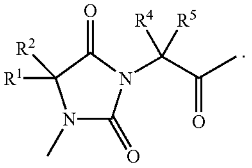

.

Any group represented by $R^7$ is preferable. More preferably, $R^7$ is hydrogen atom, C1–8 alkyl, phenyl, or C1–8 alkyl substituted with $NH_2$, C1–4 alkoxy, SH, $SCH_3$, phenyl, hydroxyphenyl, COOH, $CONH_2$, guanidino, imidazole or indole.

Particularly preferably, $R^7$ is hydrogen, C1–8 alkyl, phenyl, or C1–8 alkyl substituted with C1–4 alkoxy or phenyl. Then, any group represented by $R^8$ is preferable, but hydrogen is most preferable.

And C3–6 alkylene which $R^7$ and $R^8$ together form is also preferable.

Any group represented by $R^9$ is preferable, but more preferably $R^9$ is hydrogen or C1–4 alkyl.

And C2–4 alkylene which $R^9$ and $R^7$ together form is also preferable.

Any group represented by $R^{10}$ is preferable, but more preferably $R^{10}$ is C1–6 alkyl, CycA or C1–6 alkyl substituted with $COR^{71}$, $NR^{72}R^{73}$, hydroxy, $OR^{74}$ or CycA, more preferably C1–4 alkyl, or C1–4 alkyl substituted with phenyl, $NR^{72}R^{73}$ or C3–6 cycloalkyl.

In the present invention, preferable compounds are the compound of formula (Ia-1)

(Ia-1)

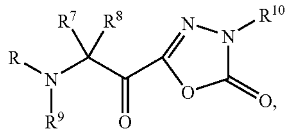

wherein all symbols have the same meanings as above, the compound of formula (Ib-1)

(Ib-1)

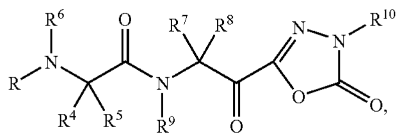

wherein all symbols have the same meanings as above, the compound of formula (Ic-1)

(Ic-1)

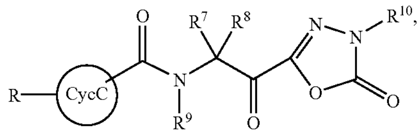

wherein all symbols have the same meanings as above), the compound of formula (Id-1)

(Id-1)

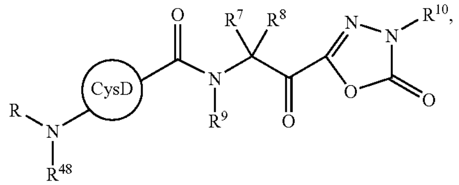

wherein all symbols have the same meanings as above), the compound of formula (Ie-1)

(Ie-1)

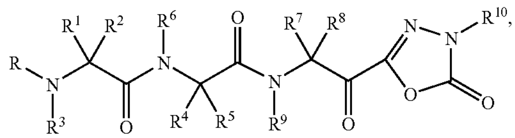

wherein all symbols have the same meanings as above), the compound of formula (If-1)

(If-1)

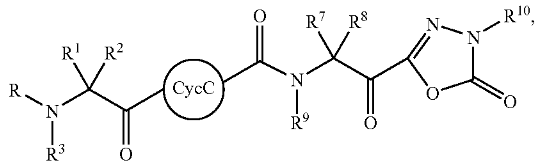

wherein all symbols have the same meanings as above, the compound of formula (Ig-1)

(Ig-1)

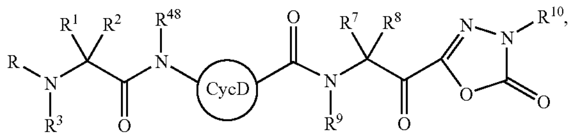

wherein all symbols have the same meanings as above, the compound of formula (Ih-1)

(Ih-1)

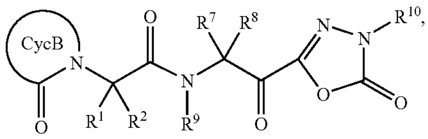

wherein all symbols have the same meanings as above, the compound of formula (Ii-1)

(Ii-1)

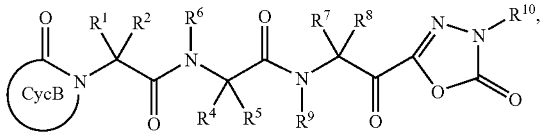

wherein all symbols have the same meanings as above, the compound of formula (Ij-1)

(Ij-1)

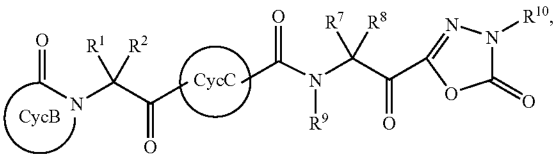

wherein all symbols have the same meanings as above, the compound of formula (Ik-1)

(Ik-1)

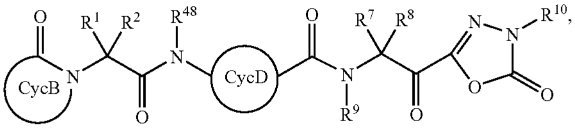

wherein all symbols have the same meanings as above, the compound of formula (Im-1)

(Im-1)

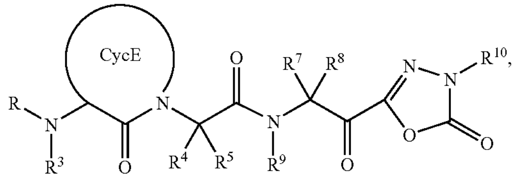

wherein all symbols have the same meanings as above, the compound of formula (In-1)

(In-1)

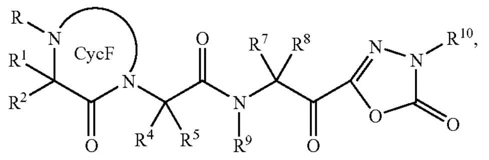

wherein all symbols have the same meanings as above, the compound of formula (Ia-2)

(Ia-2)

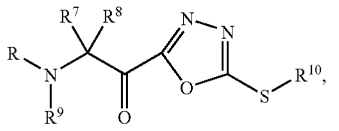

wherein all symbols have the same meanings as above, the compound of formula (Ib-2)

(Ib-2)

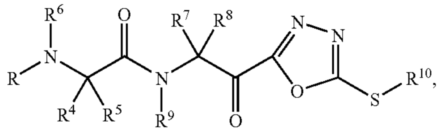

wherein all symbols have the same meanings as above, the compound of formula (Ic-2)

(Ic-2)

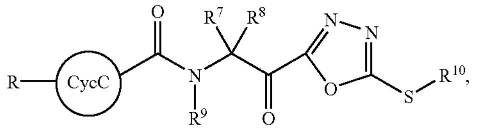

wherein all symbols have the same meanings as above, the compound of formula (Id-2)

(Id-2)

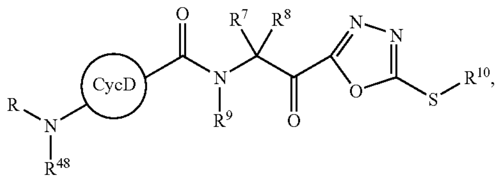

wherein all symbols have the same meanings as above, the compound of formula (Ie-2)

(Ie-2)

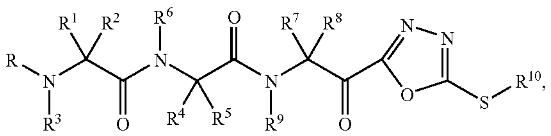

wherein all symbols have the same meanings as above, the compound of formula (If-2)

(If-2)

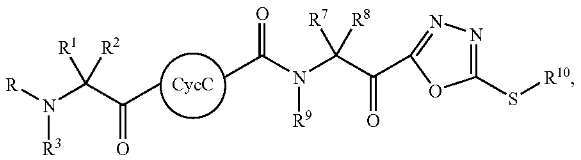

wherein all symbols have the same meanings as above, the compound of formula (Ig-2)

(Ig-2)

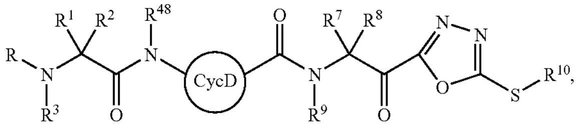

wherein all symbols have the same meanings as above, the compound of formula (Ih-2)

(Ih-2)

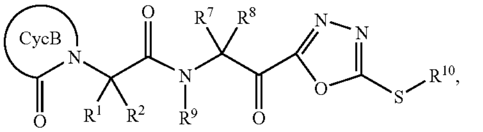

wherein all symbols have the same meanings as above, the compound of formula (Ii-2)

(Ii-2)

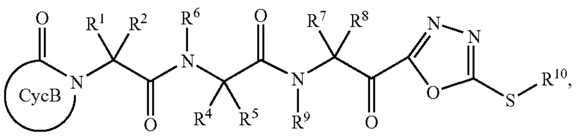

wherein all symbols have the same meanings as above, the compound of formula (Ij-2)

(Ij-2)

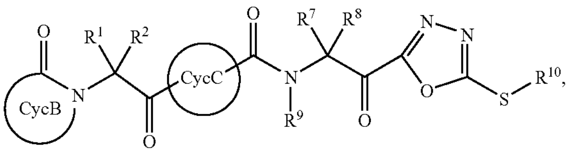

wherein all symbols have the same meanings as above, the compound of formula (Ik-2)

(Ik-2)

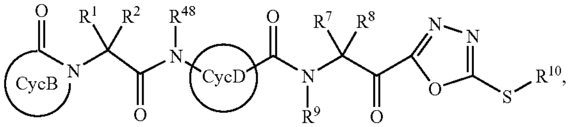

wherein all symbols have the same meanings as above, the compound of formula (Im-2)

(Im-2)

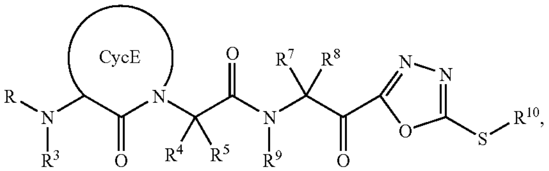

wherein all symbols have the same meanings as above, the compound of formula (In-2)

(In-2)

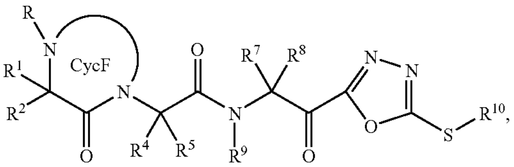

wherein all symbols have the same meanings as above, the compound of formula (Ia-3)

(Ia-3)

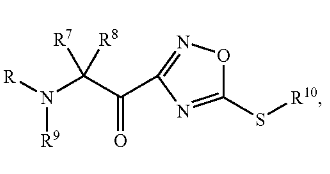

wherein all symbols have the same meanings as above, the compound of formula (Ib-3)

(Ib-3)

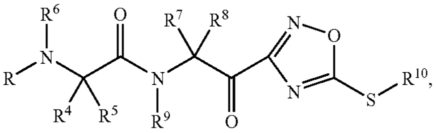

wherein all symbols have the same meanings as above, the compound of formula (Ic-3)

(Ic-3)

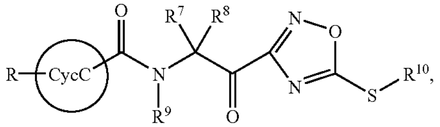

wherein all symbols have the same meanings as above, the compound of formula (Id-3)

(Id-3)

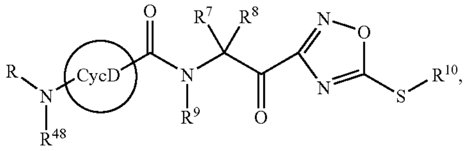

wherein all symbols have the same meanings as above, the compound of formula (Ie-3)

(Ie-3)

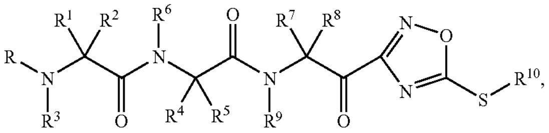

wherein all symbols have the same meanings as above, the compound of formula (If-3)

(If-3)

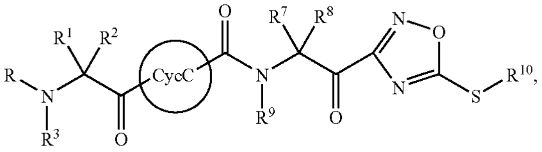

wherein all symbols have the same meanings as above, the compound of formula (Ig-3)

(Ig-3)

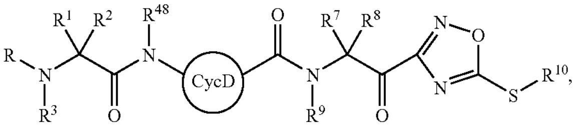

wherein all symbols have the same meanings as above, the compound of formula (Ih-3)

(Ih-3)

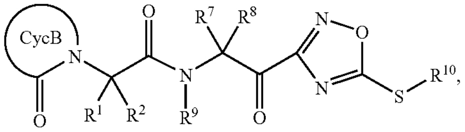

wherein all symbols have the same meanings as above, the compound of formula (Ii-3)

(Ii-3)

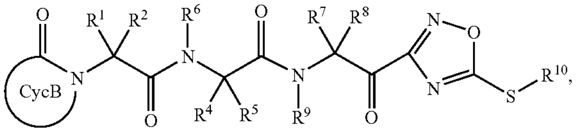

wherein all symbols have the same meanings as above, the compound of formula (Ij-3)

(Ij-3)

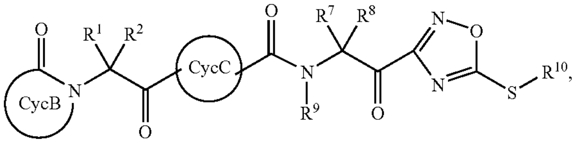

wherein all symbols have the same meanings as above, the compound of formula (Ik-3)

(Ik-3)

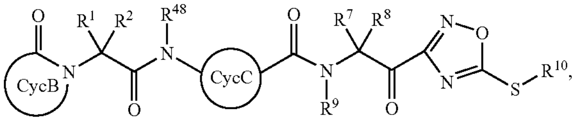

wherein all symbols have the same meanings as above, the compound of formula (Im-3)

(Im-3)

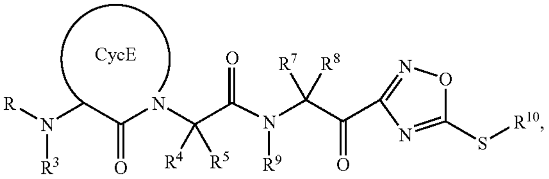

wherein all symbols have the same meanings as above, the compound of formula (In-3)

(In-3)

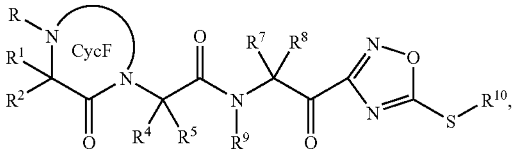

wherein all symbols have the same meanings as above, the non-toxic salt thereof.

Concretely, the compounds described in the following Examples and tables 1 to 36 are preferable.

In the tables below, the numbers in front of the group means the position of substituent, and Ph means phenyl.

TABLE 1

(I-1A)

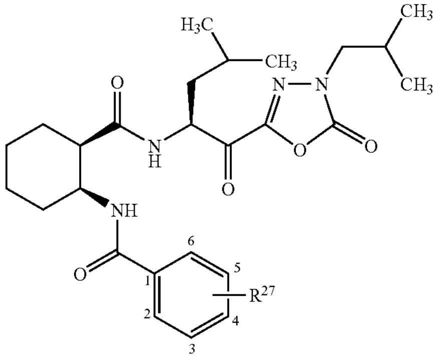

| No. | $R^{27}$ |
|---|---|
| 1 | 2-F |
| 2 | 3-F |
| 3 | 4-F |
| 4 | 2-CN |
| 5 | 3-CN |
| 6 | 4-CN |
| 7 | $3\text{-}NO_2$ |
| 8 | $4\text{-}NO_2$ |
| 9 | $3\text{-}CH_3$ |
| 10 | $4\text{-}CH_3$ |
| 11 | $2\text{-}CH_2\text{—}Cl$ |
| 12 | $4\text{-}CH_2\text{—}Cl$ |
| 13 | 4-Cl |
| 14 | $4\text{-}CF_3$ |
| 15 | $4\text{-}CH_2CH_3$ |
| 16 | $4\text{-}(CH_2)_3CH_3$ |
| 17 | $4\text{-}C(CH_3)_3$ |
| 18 | $4\text{-}N(CH_3)_2$ |
| 19 | $4\text{-}OCH_3$ |
| 20 | $4\text{-}OCH_2CH_3$ |
| 21 | 4-Ph |
| 22 | $2,3\text{-di-}CH_3$ |
| 23 | 3,5-di-F |
| 24 | 3,4-di-F |

TABLE 2

(I-2A)

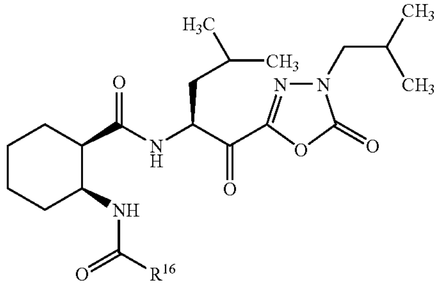

| No. | $R^{16}$ |
|---|---|
| 1 | 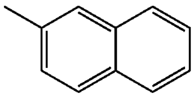 |
| 2 | 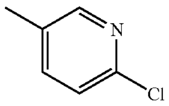 |
| 3 | 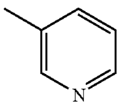 |
| 4 | 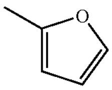 |
| 5 | 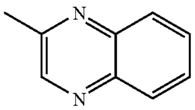 |
| 6 | 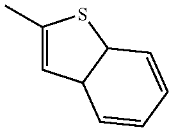 |
| 7 | 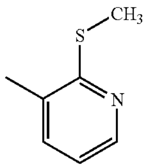 |
| 8 | 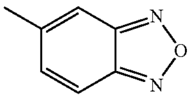 |
| 9 | 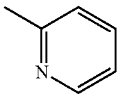 |
| 10 | 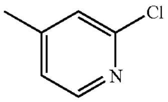 |

| | |
|---|---|
| 11 | 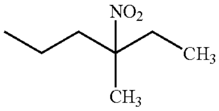 |
| 12 | 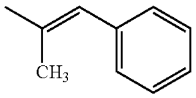 |
| 13 | 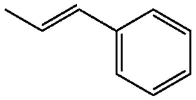 |
| 14 | 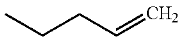 |
| 15 | 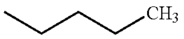 |
| 16 | 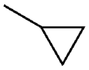 |
| 17 | 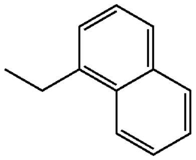 |
| 18 | 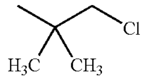 |
| 19 | 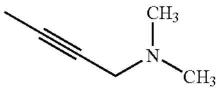 |
| 20 | 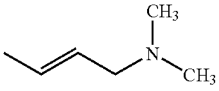 |
| 21 | 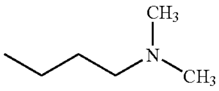 |
TABLE 3
(I-3A)
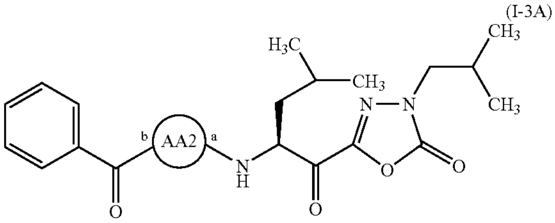
| No. | 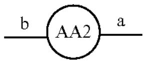 |
|---|---|
| 1 | 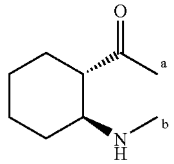 |
| 2 | 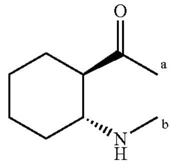 |
| 3 | 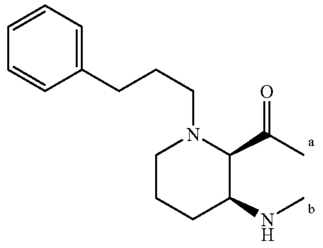 |
| 4 | 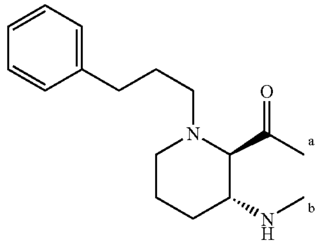 |
| 5 | 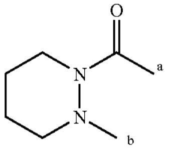 |
| 6 | 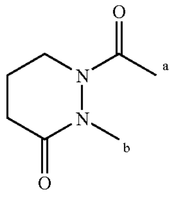 |

TABLE 3-continued
(I-3A)
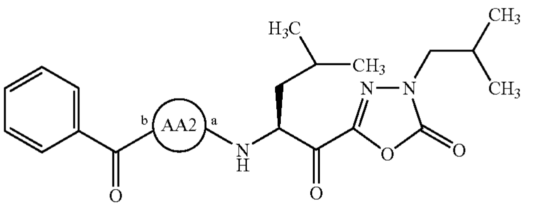
| No. | 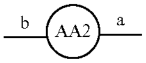 |
|---|---|
| 7 | 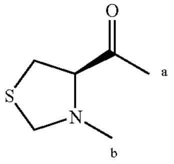 |
| 8 | 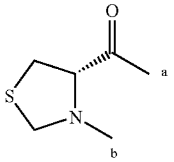 |
| 9 | 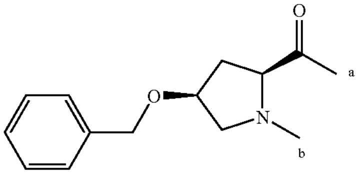 |
| 10 | 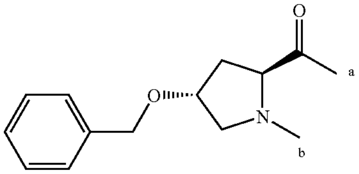 |
| 11 | 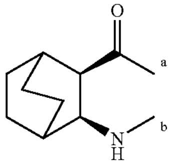 |
TABLE 3-continued
(I-3A)
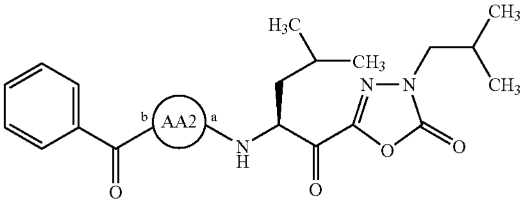
| No. | 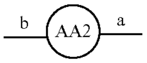 |
|---|---|
| 12 | 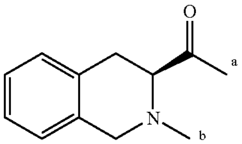 |
| 13 | 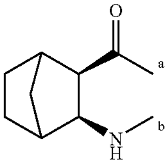 |
| 14 | 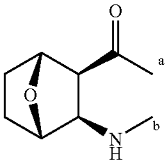 |
| 15 | 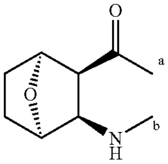 |
| 16 | 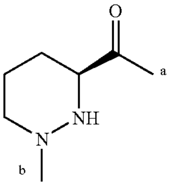 |
| 17 | 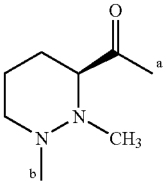 |

TABLE 4
(I-4A)
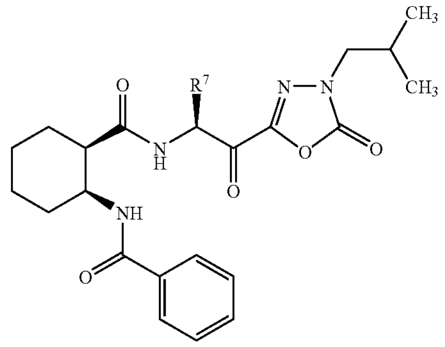
| No. | $R^7$ |
|---|---|
| 1 | 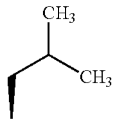 |
| 2 | 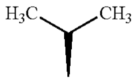 |
| 3 | 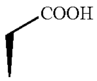 |
| 4 | 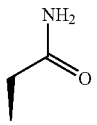 |
| 5 | 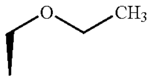 |
| 6 | 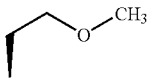 |
| 7 | 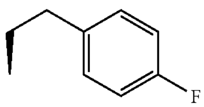 |
| 8 | 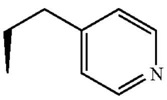 |
| 9 | 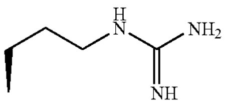 |
| 10 | 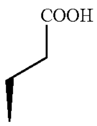 |
TABLE 4-continued
(I-4A)
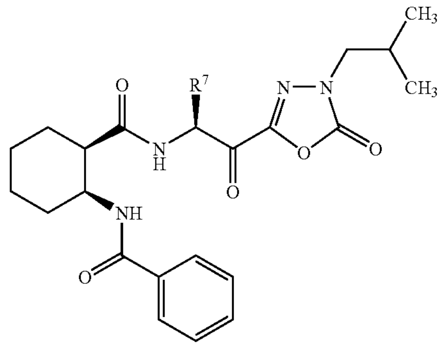
| No. | $R^7$ |
|---|---|
| 11 | 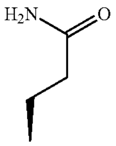 |
| 12 | 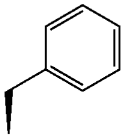 |
| 13 | 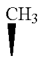 |
| 14 | 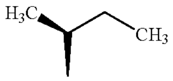 |
| 15 | 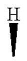 |
| 16 | 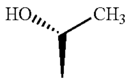 |
| 17 | 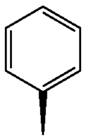 |
| 18 | 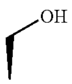 |
| 19 | 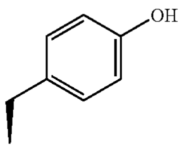 |

TABLE 4-continued
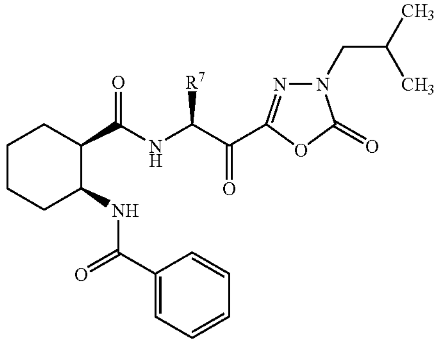
(I-4A)
| No. | $R^7$ |
|---|---|
| 20 | 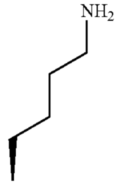 |
| 21 | 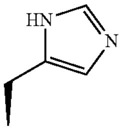 |
TABLE 5
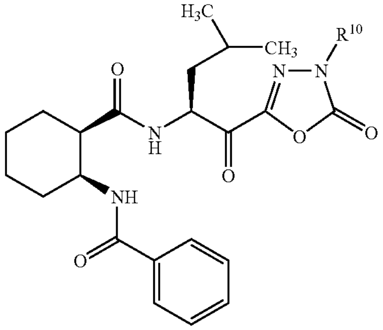
(I-5A)
| No. | $R^{10}$ |
|---|---|
| 1 | 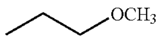 |
| 2 | 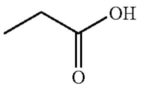 |
| 3 | 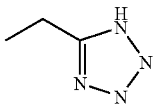 |
TABLE 5-continued
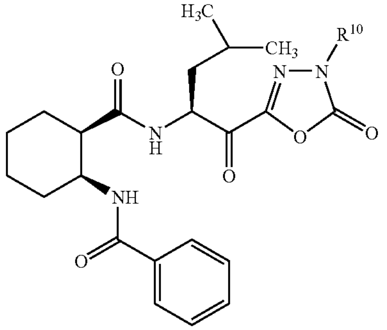
(I-5A)
| No. | $R^{10}$ |
|---|---|
| 4 | 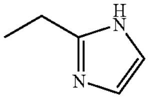 |
| 5 | 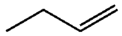 |
| 6 | 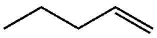 |
| 7 | 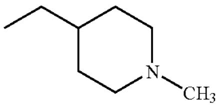 |
| 8 | 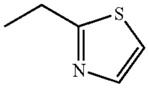 |
| 9 | 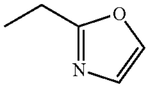 |
| 10 | 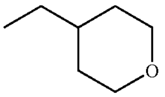 |
| 11 | 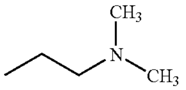 |
| 12 | 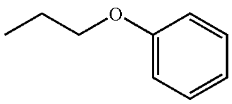 |
| 13 | 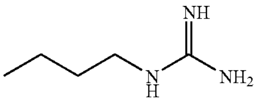 |
| 14 | 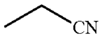 |
| 15 | 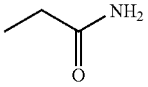 |

TABLE 5-continued
(I-5A)
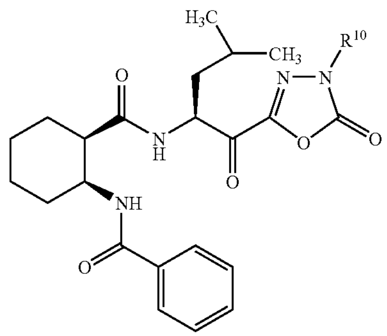
| No. | $R^{10}$ |
|---|---|
| 16 | 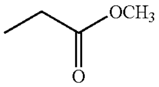 |
| 17 | 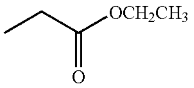 |
| 18 | 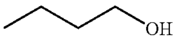 |
| 19 | 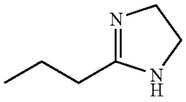 |
| 20 | 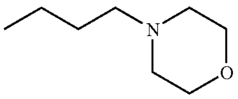 |
| 21 | 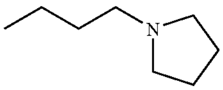 |
| 22 | 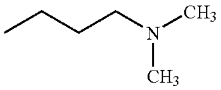 |
| 23 | 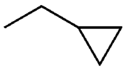 |
TABLE 6
(I-6A)
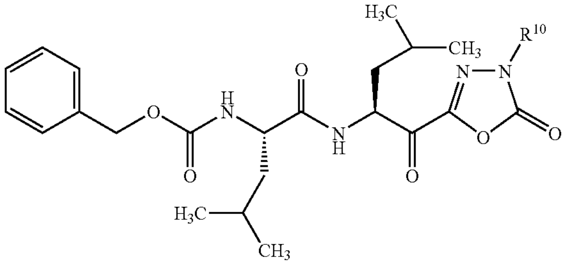
| No. | $R^{10}$ |
|---|---|
| 1 | 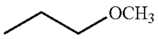 |
| 2 | 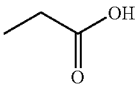 |
| 3 | 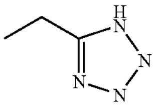 |
| 4 | 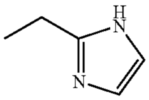 |
| 5 | 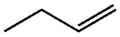 |
| 6 | 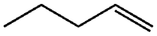 |
| 7 | 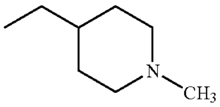 |
| 8 | 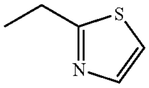 |
| 9 | 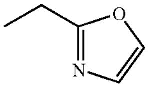 |
| 10 | 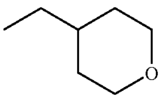 |
| 11 | 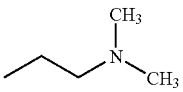 |
| 12 | 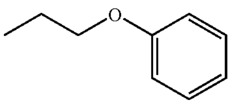 |

TABLE 6-continued
(I-6A)
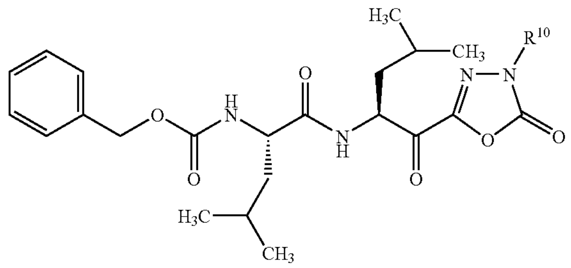
| No. | $R^{10}$ |
|---|---|
| 13 | 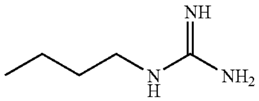 |
| 14 | 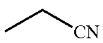 |
| 15 | 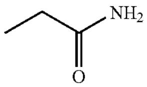 |
| 16 | 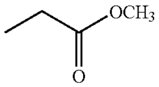 |
| 17 | 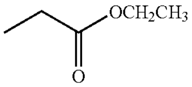 |
| 18 | 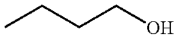 |
| 19 | 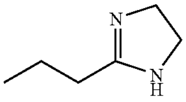 |
| 20 | 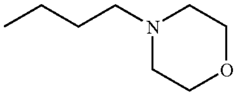 |
| 21 | 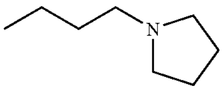 |
| 22 | 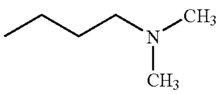 |
| 23 | 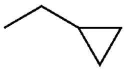 |
TABLE 7
(I-1B)
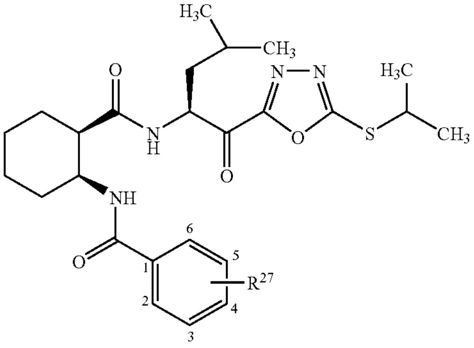
| No. | $R^{27}$ |
|---|---|
| 1 | 2-F |
| 2 | 3-F |
| 3 | 4-F |
| 4 | 2-CN |
| 5 | 3-CN |
| 6 | 4-CN |
| 7 | 3-$NO_2$ |
| 8 | 4-$NO_2$ |
| 9 | 3-$CH_3$ |
| 10 | 4-$CH_3$ |
| 11 | 2-$CH_2$—Cl |
| 12 | 4-$CH_2$—Cl |
| 13 | 4-Cl |
| 14 | 4-$CF_3$ |
| 15 | 4-$CH_2CH_3$ |
| 16 | 4-$(CH_2)_3CH_3$ |
| 17 | 4-$C(CH_3)_3$ |
| 18 | 4-$N(CH_3)_2$ |
| 19 | 4-$OCH_3$ |
| 20 | 4-$OCH_2CH_3$ |
| 21 | 4-Ph |
| 22 | 2,3-di-$CH_3$ |
| 23 | 3,5-di-F |
| 24 | 3,4-di-F |
TABLE 8
(I-2B)
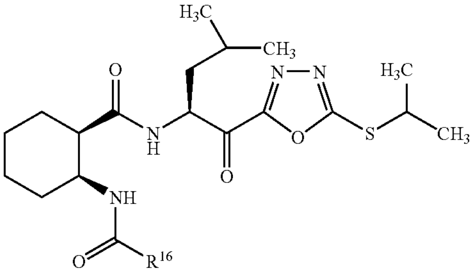
| No. | $R^{16}$ |
|---|---|
| 1 | 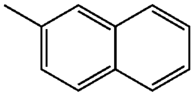 |
| 2 | 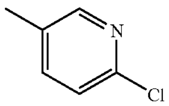 |

TABLE 8-continued
(I-2B)
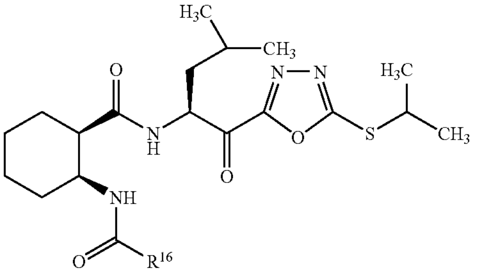
| No. | $R^{16}$ |
|---|---|
| 3 | 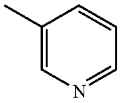 |
| 4 | 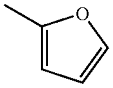 |
| 5 | 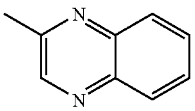 |
| 6 | 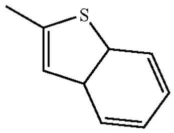 |
| 7 | 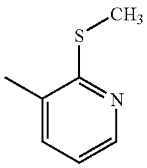 |
| 8 | 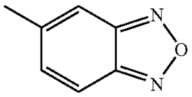 |
| 9 | 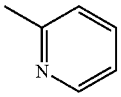 |
| 10 | 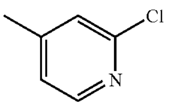 |
| 11 | 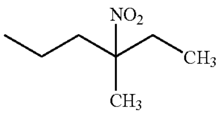 |
| 12 | 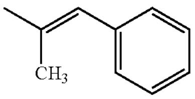 |
TABLE 8-continued
(I-2B)
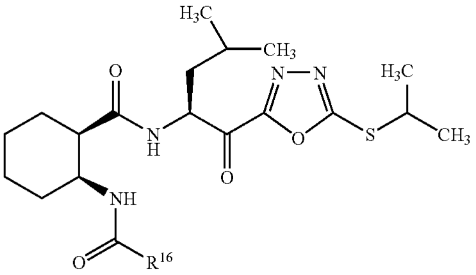
| No. | $R^{16}$ |
|---|---|
| 13 | 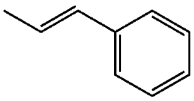 |
| 14 | 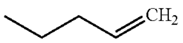 |
| 15 | 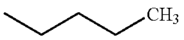 |
| 16 | 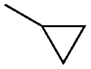 |
| 17 | 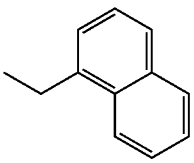 |
| 18 | 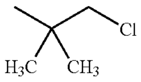 |
| 19 | 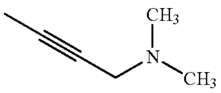 |
| 20 | 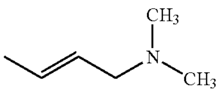 |
| 21 | 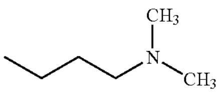 |

TABLE 9
(I-3B)
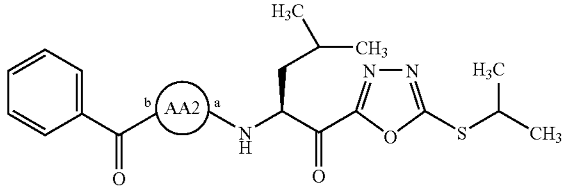
| No. | 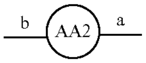 |
|---|---|
| 1 | 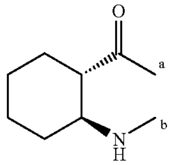 |
| 2 | 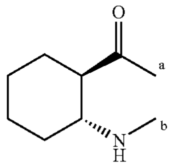 |
| 3 | 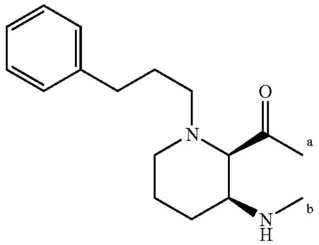 |
| 4 | 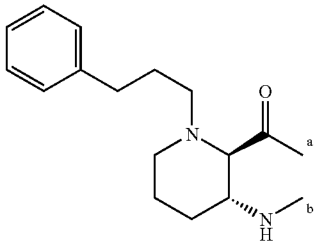 |
| 5 | 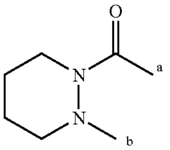 |
| 6 | 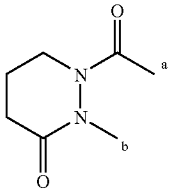 |
TABLE 9-continued
(I-3B)
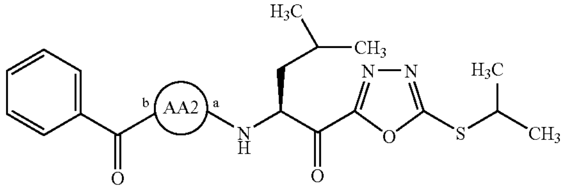
| No. | 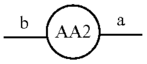 |
|---|---|
| 7 | 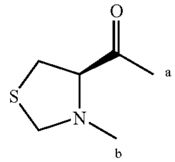 |
| 8 | 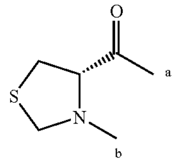 |
| 9 | 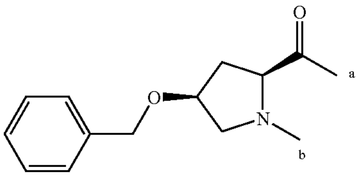 |
| 10 | 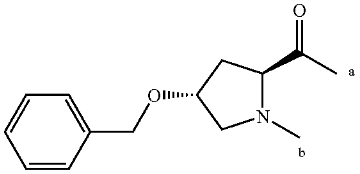 |
| 11 | 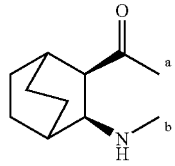 |
| 12 | 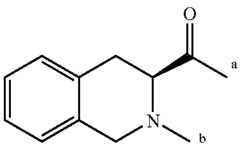 |
| 13 | 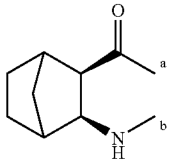 |

TABLE 9-continued
(I-3B)
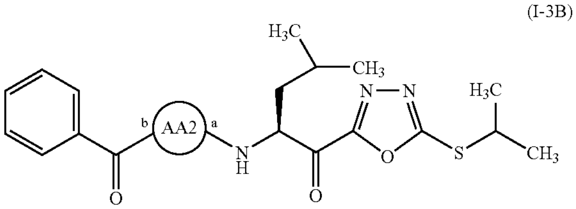
| No. | 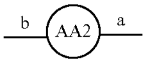 |
|---|---|
| 14 | 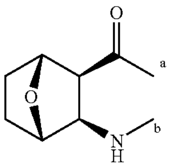 |
| 15 | 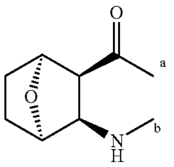 |
| 16 | 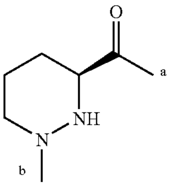 |
| 17 | 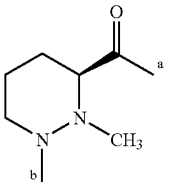 |
TABLE 10
(I-4B)
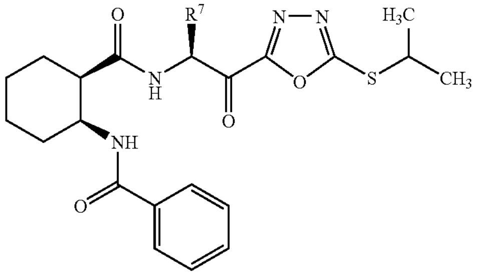
| No. | $R^7$ |
|---|---|
| 1 | 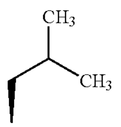 |
TABLE 10-continued
(I-4B)
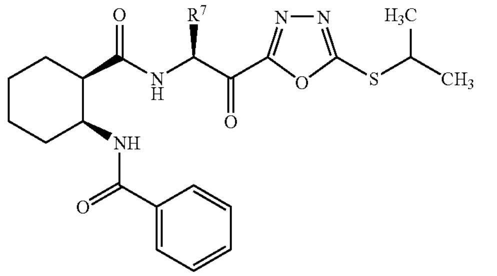
| No. | $R^7$ |
|---|---|
| 2 | 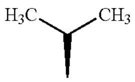 |
| 3 | 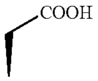 |
| 4 | 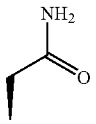 |
| 5 | 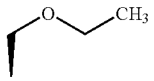 |
| 6 | 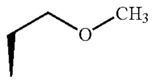 |
| 7 | 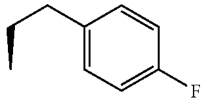 |
| 8 | 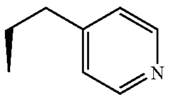 |
| 9 | 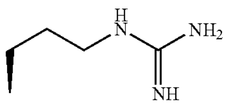 |
| 10 | 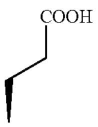 |
| 11 | 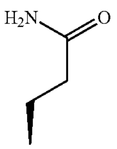 |

TABLE 10-continued
(I-4B)
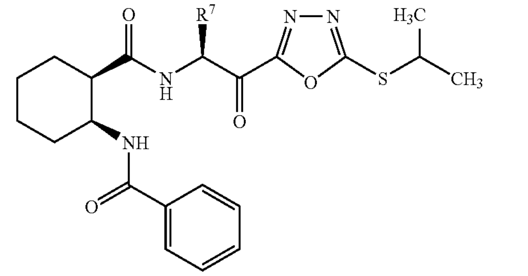
| No. | $R^7$ |
|---|---|
| 12 | 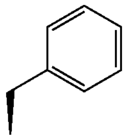 |
| 13 | 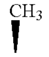 |
| 14 | 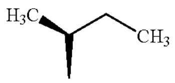 |
| 15 | 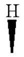 |
| 16 | 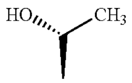 |
| 17 | 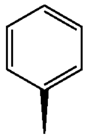 |
| 18 | 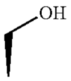 |
| 19 | 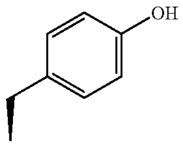 |
| 20 | 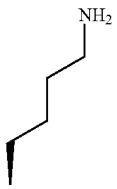 |
| 21 | 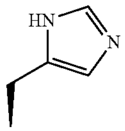 |
TABLE 11
(I-5B)
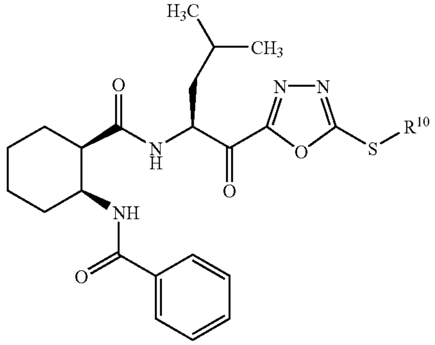
| No. | $R^{10}$ |
|---|---|
| 1 | 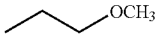 |
| 2 | 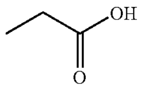 |
| 3 | 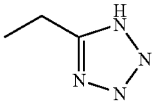 |
| 4 | 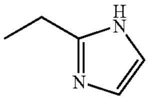 |
| 5 | 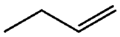 |
| 6 | 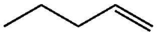 |
| 7 | 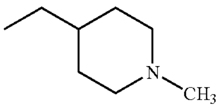 |
| 8 | 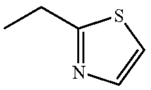 |
| 9 | 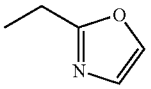 |
| 10 | 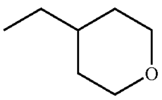 |
| 11 | 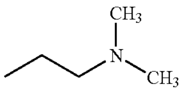 |
| 12 | 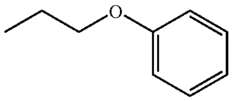 |

TABLE 11-continued
(I-5B)
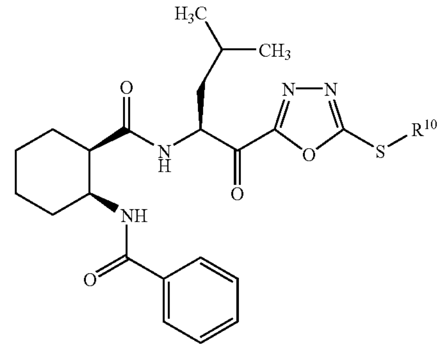
| No. | $R^{10}$ |
|---|---|
| 13 | 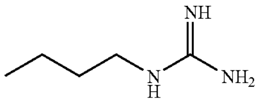 |
| 14 | 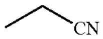 |
| 15 | 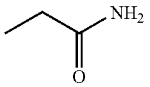 |
| 16 | 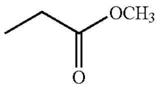 |
| 17 | 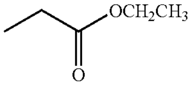 |
| 18 | 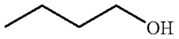 |
| 19 | 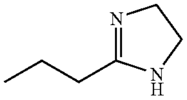 |
| 20 | 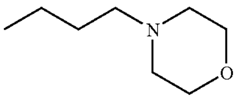 |
| 21 | 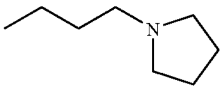 |
| 22 | 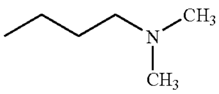 |
| 23 | 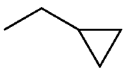 |
| 24 | 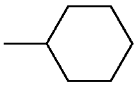 |
TABLE 11-continued
(I-5B)
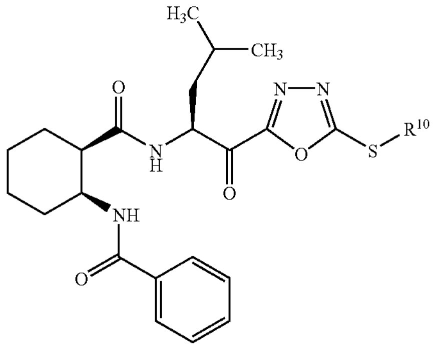
| No. | $R^{10}$ |
|---|---|
| 25 | 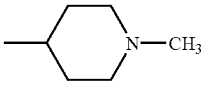 |
| 26 | 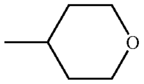 |
TABLE 12
(I-6B)
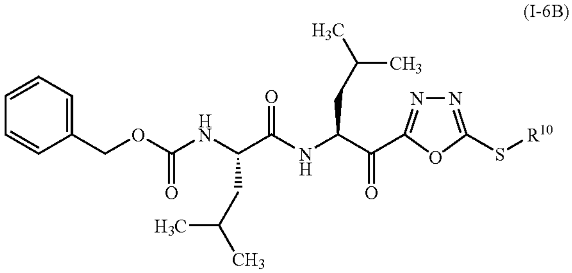
| No. | $R^{10}$ |
|---|---|
| 1 | 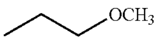 |
| 2 | 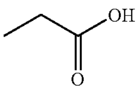 |
| 3 | 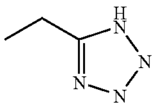 |
| 4 | 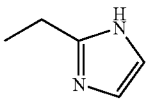 |
| 5 | 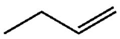 |
| 6 | 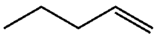 |

TABLE 12-continued
(I-6B)
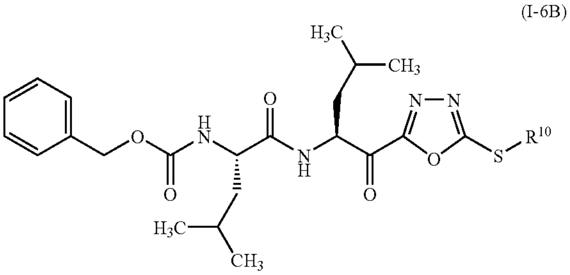
| No. | $R^{10}$ |
|---|---|
| 7 | 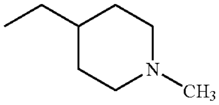 |
| 8 | 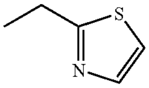 |
| 9 | 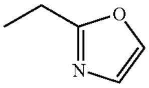 |
| 10 | 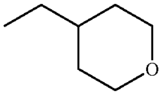 |
| 11 | 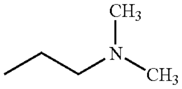 |
| 12 | 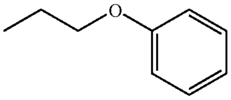 |
| 13 | 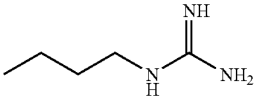 |
| 14 | 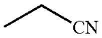 |
| 15 | 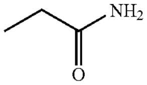 |
| 16 | 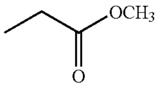 |
| 17 | 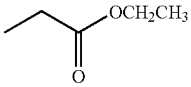 |
| 18 | 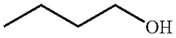 |
TABLE 12-continued
(I-6B)
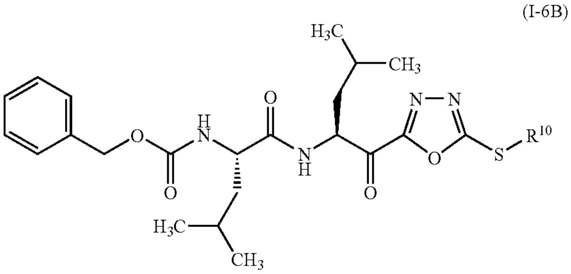
| No. | $R^{10}$ |
|---|---|
| 19 | 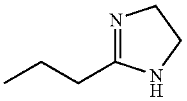 |
| 20 | 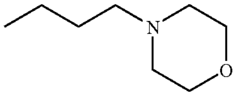 |
| 21 | 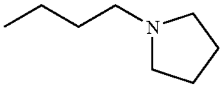 |
| 22 | 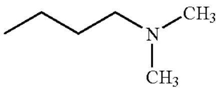 |
| 23 | 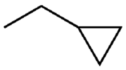 |
| 24 | 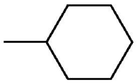 |
| 25 | 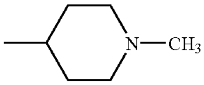 |
| 26 | 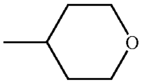 |
TABLE 13
(I-7A)
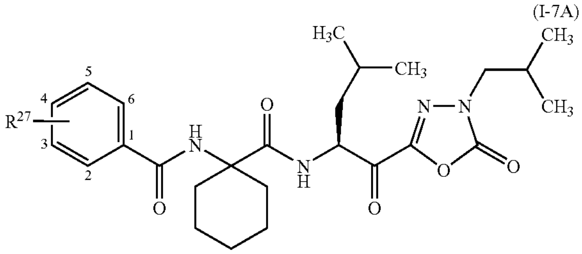
| No. | $R^{27}$ |
|---|---|
| 1 | 2-F |
| 2 | 3-F |

TABLE 13-continued
(I-7A)
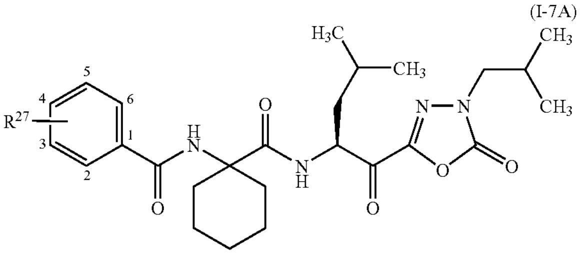
| No. | $R^{27}$ |
|---|---|
| 3 | 4-F |
| 4 | 2-CN |
| 5 | 3-CN |
| 6 | 4-CN |
| 7 | $3\text{-}NO_2$ |
| 8 | $4\text{-}NO_2$ |
| 9 | $3\text{-}CH_3$ |
| 10 | $4\text{-}CH_3$ |
| 11 | $2\text{-}CH_2\text{—}Cl$ |
| 12 | $4\text{-}CH_2\text{—}Cl$ |
| 13 | 4-Cl |
| 14 | $4\text{-}CF_3$ |
| 15 | $4\text{-}CH_2CH_3$ |
| 16 | $4\text{-}(CH_2)_3CH_3$ |
| 17 | $4\text{-}C(CH_3)_3$ |
| 18 | $4\text{-}N(CH_3)_2$ |
| 19 | $4\text{-}OCH_3$ |
| 20 | $4\text{-}OCH_2CH_3$ |
| 21 | 4-Ph |
| 22 | $2,3\text{-di-}CH_3$ |
| 23 | 3,5-di-F |
| 24 | 3,4-di-F |
TABLE 14
(I-8A)
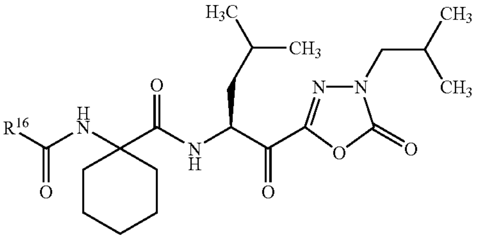
| No. | $R^{16}$ |
|---|---|
| 1 | 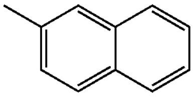 |
| 2 | 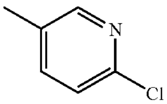 |
| 3 | 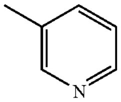 |
| 4 | 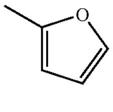 |
TABLE 14-continued
(I-8A)
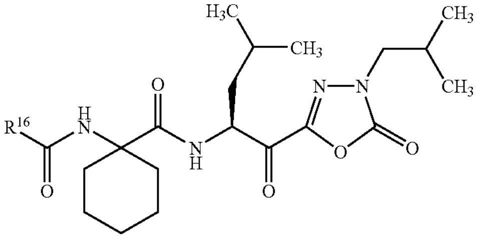
| No. | $R^{16}$ |
|---|---|
| 5 | 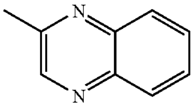 |
| 6 | 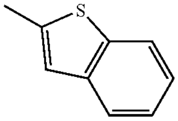 |
| 7 | 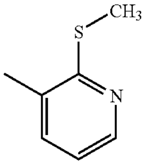 |
| 8 | 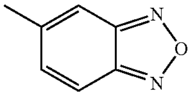 |
| 9 | 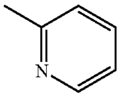 |
| 10 | 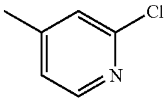 |
| 11 | 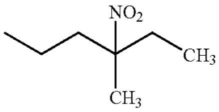 |
| 12 | 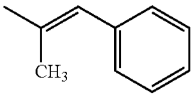 |
| 13 | 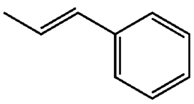 |
| 14 | 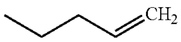 |
| 15 | 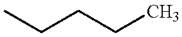 |

TABLE 14-continued
(I-8A)
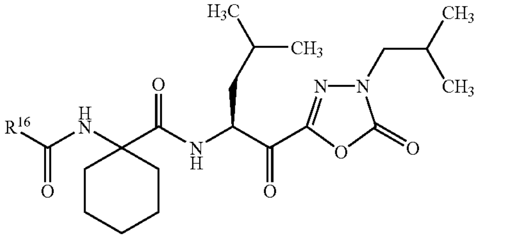
| No. | $R^{16}$ |
| --- | --- |
| 16 | 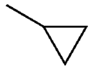 |
| 17 | 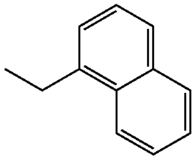 |
| 18 | 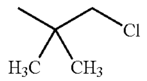 |
| 19 | 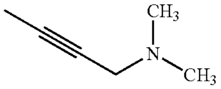 |
| 20 | 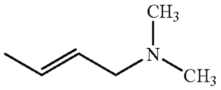 |
| 21 | 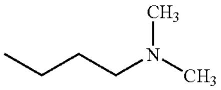 |
TABLE 15
(I-9A)
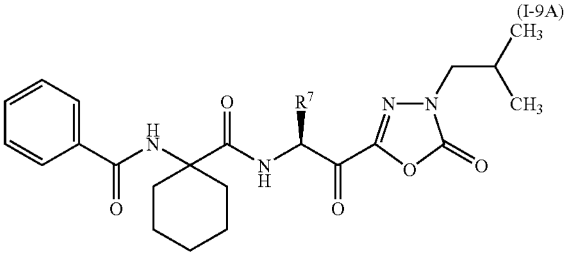
| No. | $R^7$ |
| --- | --- |
| 1 | 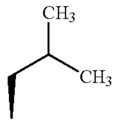 |
| 2 | 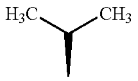 |
TABLE 15-continued
(I-9A)
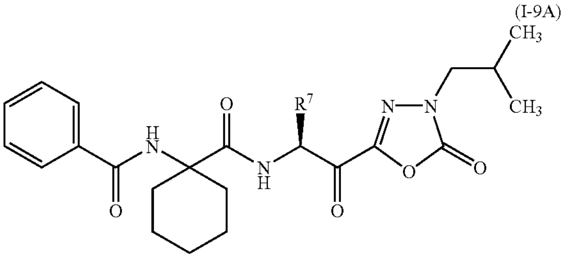
| No. | $R^7$ |
| --- | --- |
| 3 | 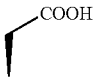 |
| 4 | 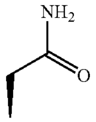 |
| 5 | 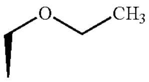 |
| 6 | 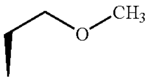 |
| 7 | 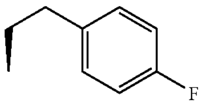 |
| 8 | 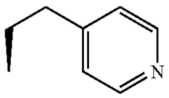 |
| 9 | 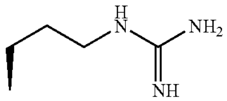 |
| 10 | 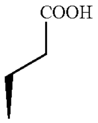 |
| 11 | 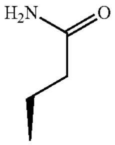 |
| 12 | 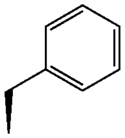 |

TABLE 15-continued
(I-9A)
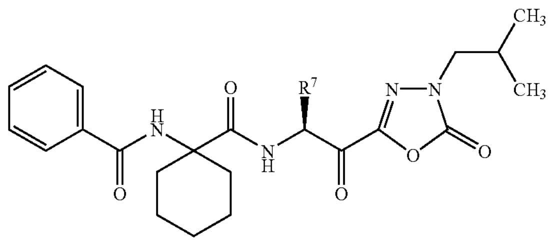
| No. | $R^7$ |
|---|---|
| 13 | 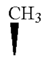 |
| 14 | 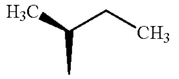 |
| 15 | 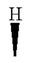 |
| 16 | 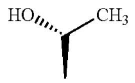 |
| 17 | 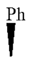 |
| 18 | 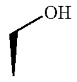 |
| 19 | 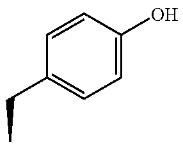 |
| 20 | 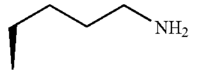 |
| 21 | 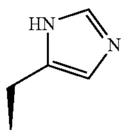 |
| 22 | 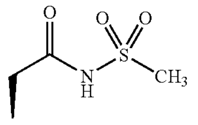 |
TABLE 16
(I-10A)
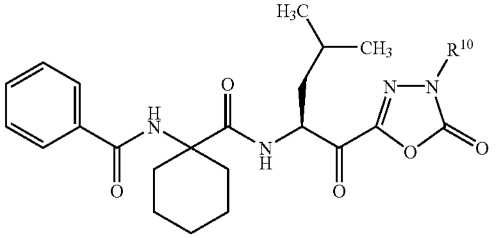
| No. | $R^{10}$ |
|---|---|
| 1 | 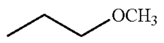 |
| 2 | 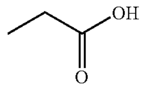 |
| 3 | 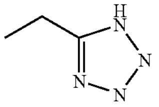 |
| 4 | 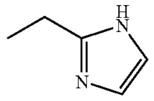 |
| 5 | 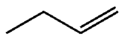 |
| 6 | 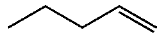 |
| 7 | 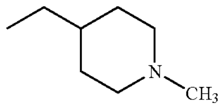 |
| 8 | 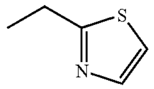 |
| 9 | 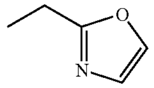 |
| 10 | 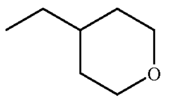 |
| 11 | 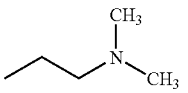 |
| 12 | 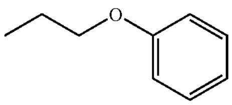 |
| 13 | 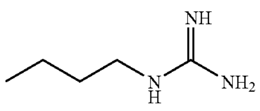 |

TABLE 16-continued
(I-10A)
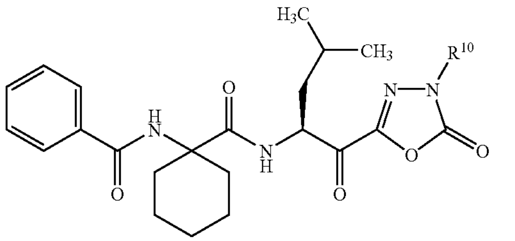
| No. | $R^{10}$ |
| --- | --- |
| 14 | 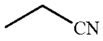 |
| 15 | 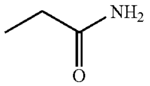 |
| 16 | 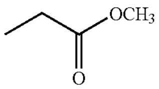 |
| 17 | 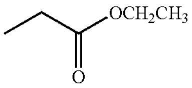 |
| 18 | 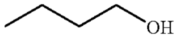 |
| 19 | 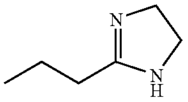 |
| 20 | 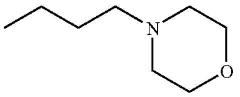 |
| 21 | 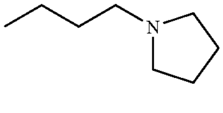 |
| 22 | 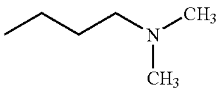 |
| 23 | 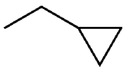 |
TABLE 17
(I-7B)
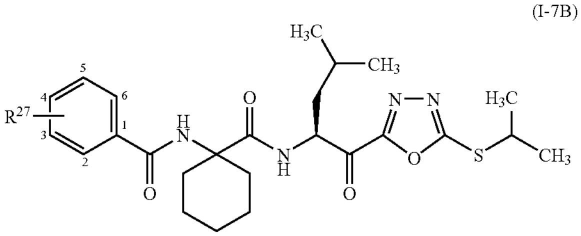
| No. | $R^{27}$ |
| --- | --- |
| 1 | 2-F |
| 2 | 3-F |
| 3 | 4-F |
| 4 | 2-CN |
| 5 | 3-CN |
| 6 | 4-CN |
| 7 | 3-$NO_2$ |
| 8 | 4-$NO_2$ |
| 9 | 3-$CH_3$ |
| 10 | 4-$CH_3$ |
| 11 | 2-$CH_2$—Cl |
| 12 | 4-$CH_2$—Cl |
| 13 | 4-Cl |
| 14 | 4-$CF_3$ |
| 15 | 4-$CH_2CH_3$ |
| 16 | 4-$(CH_2)_3CH_3$ |
| 17 | 4-$C(CH_3)_3$ |
| 18 | 4-$N(CH_3)_2$ |
| 19 | 4-$OCH_3$ |
| 20 | 4-$OCH_2CH_3$ |
| 21 | 4-Ph |
| 22 | 2,3-di-$CH_3$ |
| 23 | 3,5-di-F |
| 24 | 3,4-di-F |
TABLE 18
(I-8B)
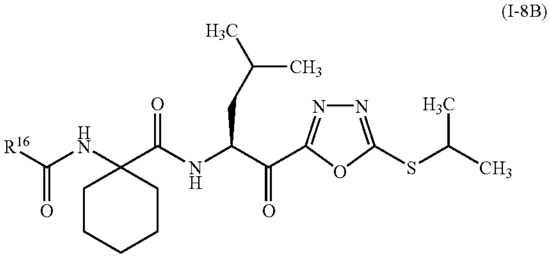
| No. | $R^{16}$ |
| --- | --- |
| 1 | 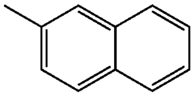 |
| 2 | 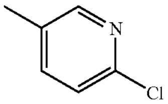 |
| 3 | 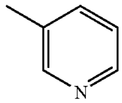 |
| 4 | 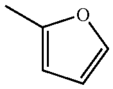 |
| 5 | 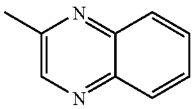 |
| 6 | 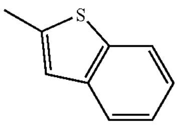 |

TABLE 18-continued
(I-8B)
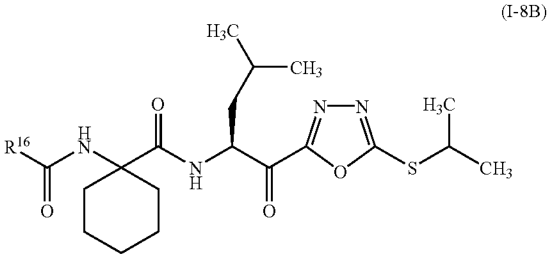
| No. | $R^{16}$ |
|---|---|
| 7 | 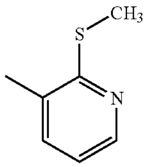 |
| 8 | 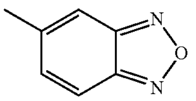 |
| 9 | 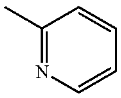 |
| 10 | 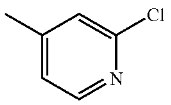 |
| 11 | 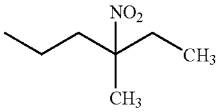 |
| 12 | 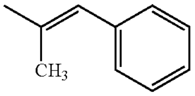 |
| 13 | 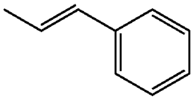 |
| 14 | 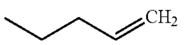 |
| 15 | 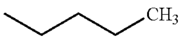 |
| 16 | 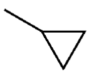 |
| 17 | 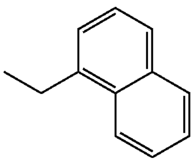 |
TABLE 18-continued
(I-8B)
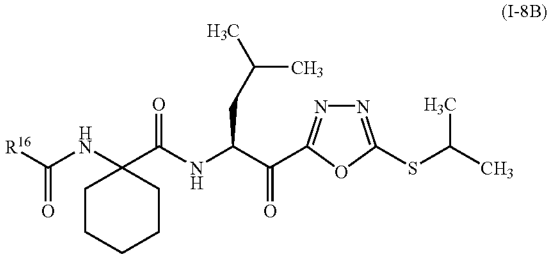
| No. | $R^{16}$ |
|---|---|
| 18 | 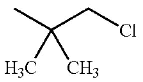 |
| 19 | 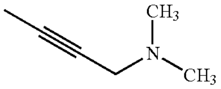 |
| 20 | 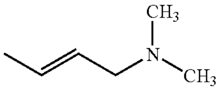 |
| 21 | 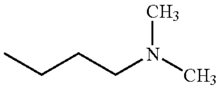 |
TABLE 19
(I-9B)
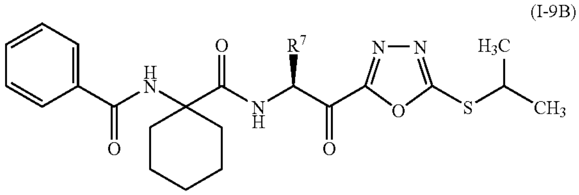
| No. | $R^7$ |
|---|---|
| 1 | 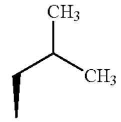 |
| 2 | 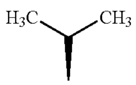 |
| 3 | 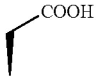 |
| 4 | 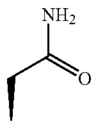 |
| 5 | 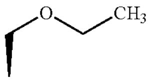 |

TABLE 19-continued
(I-9B)
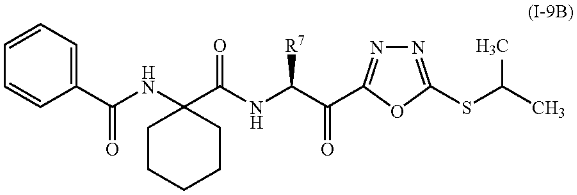
| No. | $R^7$ |
| --- | --- |
| 6 | 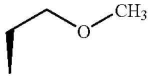 |
| 7 | 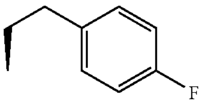 |
| 8 | 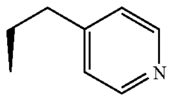 |
| 9 | 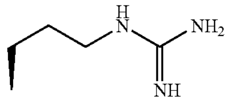 |
| 10 | 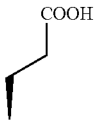 |
| 11 | 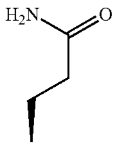 |
| 12 | 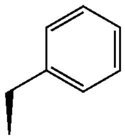 |
| 13 | 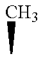 |
| 14 | 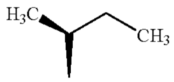 |
| 15 | 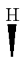 |
| 16 | 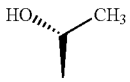 |
| 17 | 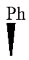 |
TABLE 19-continued
(I-9B)
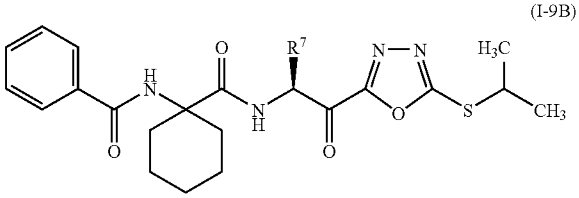
| No. | $R^7$ |
| --- | --- |
| 18 | 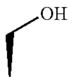 |
| 19 | 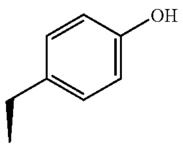 |
| 20 | 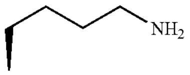 |
| 21 | 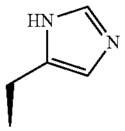 |
| 22 | 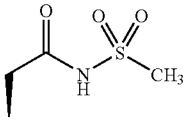 |
TABLE 20
(I-10B)
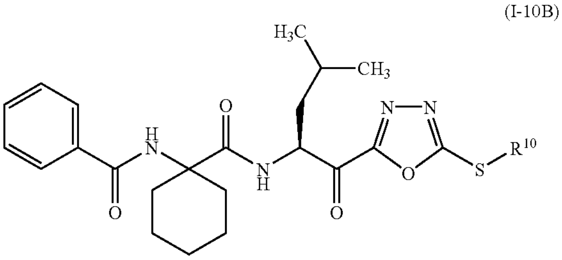
| No. | $R^{10}$ |
| --- | --- |
| 1 | 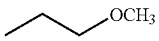 |
| 2 | 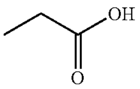 |
| 3 | 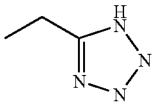 |

TABLE 20-continued
(I-10B)
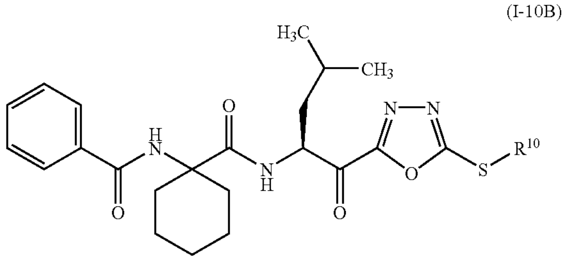
| No. | $R^{10}$ |
|---|---|
| 4 | 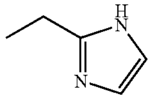 |
| 5 | 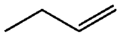 |
| 6 | 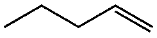 |
| 7 | 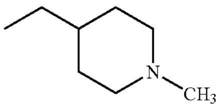 |
| 8 | 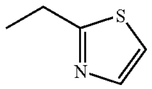 |
| 9 | 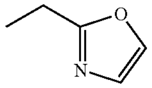 |
| 10 | 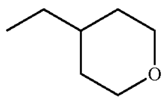 |
| 11 | 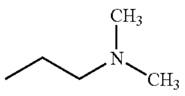 |
| 12 | 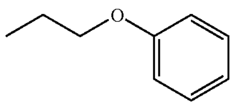 |
| 13 | 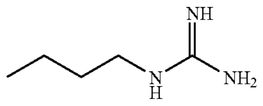 |
TABLE 20-continued
(I-10B)
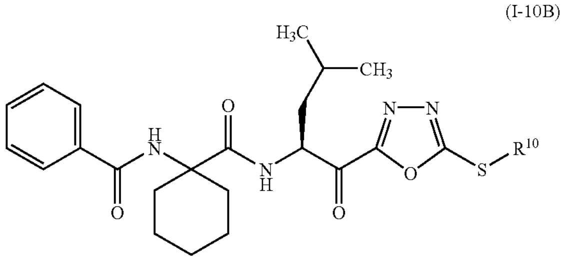
| No. | $R^{10}$ |
|---|---|
| 14 | 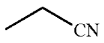 |
| 15 | 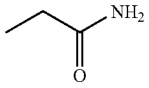 |
| 16 | 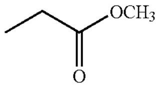 |
| 17 | 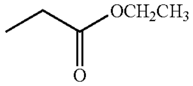 |
| 18 | 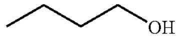 |
| 19 | 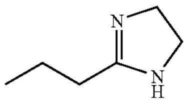 |
| 20 | 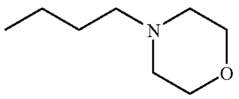 |
| 21 | 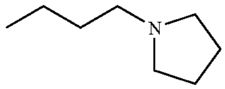 |
| 22 | 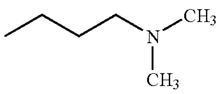 |
| 23 | 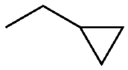 |
| 24 | 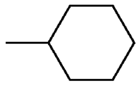 |
| 25 | 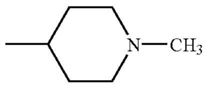 |
| 26 | 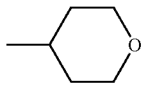 |

TABLE 21
(I-11A)
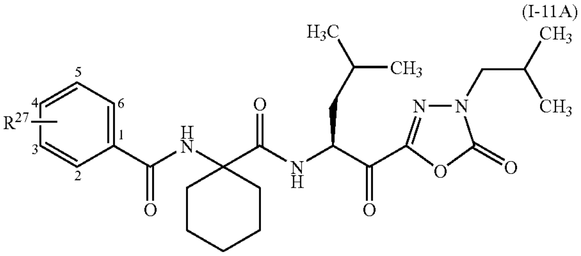
| No. | $R^{27}$ |
|---|---|
| 1 | $2\text{-}CH_2N(CH_3)_2$ |
| 2 | $3\text{-}CH_2N(CH_3)_2$ |
| 3 | $4\text{-}CH_2N(CH_3)_2$ |
| 4 | 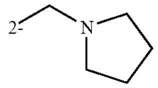 |
| 5 | 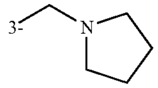 |
| 6 | 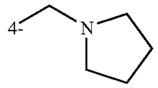 |
| 7 | 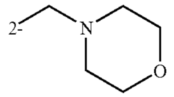 |
| 8 | 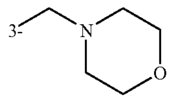 |
| 9 | 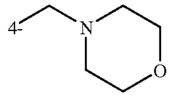 |
TABLE 22
(I-11B)
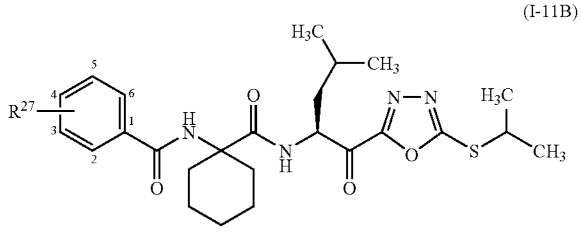
| No. | $R^{27}$ |
|---|---|
| 1 | $2\text{-}CH_2N(CH_3)_2$ |
| 2 | $3\text{-}CH_2N(CH_3)_2$ |
| 3 | $4\text{-}CH_2N(CH_3)_2$ |
| 4 | 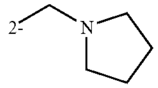 |
TABLE 22-continued
(I-11B)
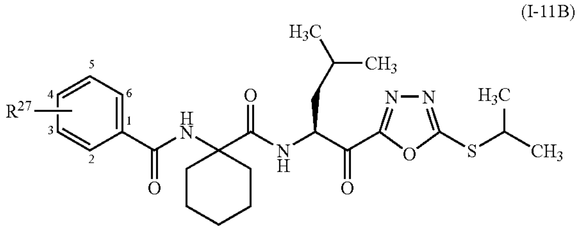
| No. | $R^{27}$ |
|---|---|
| 5 | 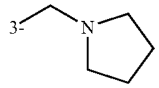 |
| 6 | 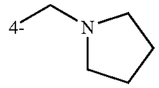 |
| 7 | 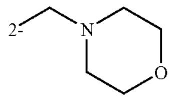 |
| 8 | 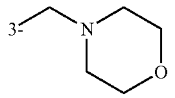 |
| 9 | 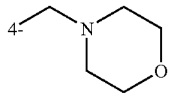 |
TABLE 23
(I-1C)
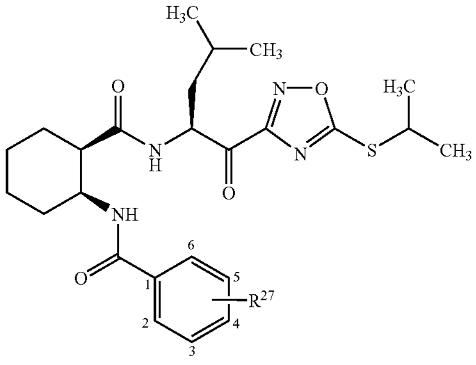
| No. | $R^{27}$ |
|---|---|
| 1 | 2-F |
| 2 | 3-F |
| 3 | 4-F |
| 4 | 2-CN |
| 5 | 3-CN |
| 6 | 4-CN |
| 7 | $3\text{-}NO_2$ |
| 8 | $4\text{-}NO_2$ |
| 9 | $3\text{-}CH_3$ |
| 10 | $4\text{-}CH_3$ |
| 11 | $2\text{-}CH_2\text{—}Cl$ |
| 12 | $4\text{-}CH_2\text{—}Cl$ |
| 13 | 4-Cl |

TABLE 23-continued
(I-1C)
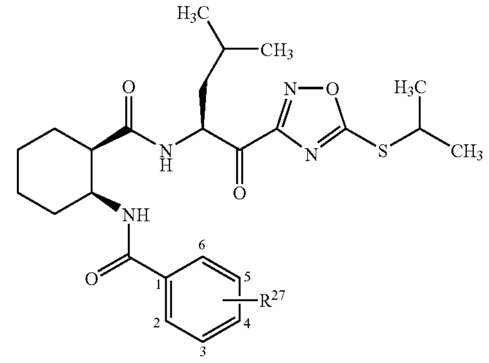
| No. | $R^{27}$ |
|---|---|
| 14 | 4-$CF_3$ |
| 15 | 4-$CH_2CH_3$ |
| 16 | 4-$(CH_2)_3CH_3$ |
| 17 | 4-$C(CH_3)_3$ |
| 18 | 4-$N(CH_3)_2$ |
| 19 | 4-$OCH_3$ |
| 20 | 4-$OCH_2CH_3$ |
| 21 | 4-Ph |
| 22 | 2,3-di-$CH_3$ |
| 23 | 3,5-di-F |
| 24 | 3,4-di-F |
TABLE 24
(I-2C)
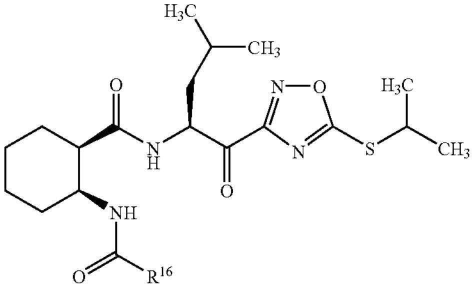
| No. | $R^{16}$ |
|---|---|
| 1 | 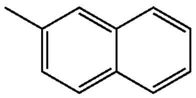 |
| 2 | 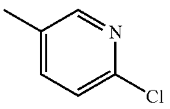 |
| 3 | 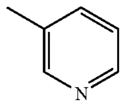 |
| 4 | 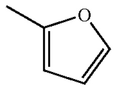 |
TABLE 24-continued
(I-2C)
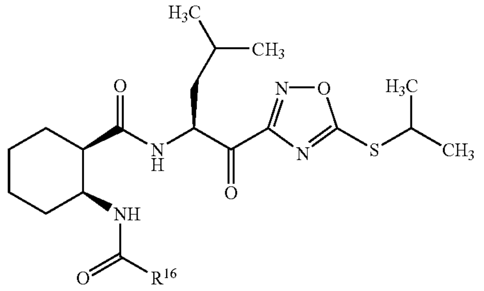
| No. | $R^{16}$ |
|---|---|
| 5 | 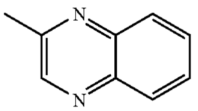 |
| 6 | 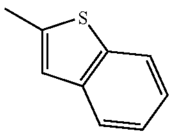 |
| 7 | 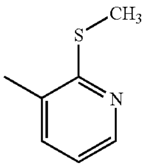 |
| 8 | 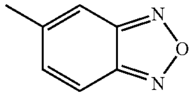 |
| 9 | 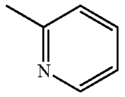 |
| 10 | 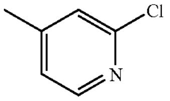 |
| 11 | 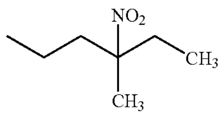 |
| 12 | 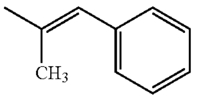 |
| 13 | 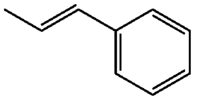 |
| 14 | 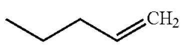 |
| 15 | 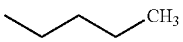 |

TABLE 24-continued
(I-2C)
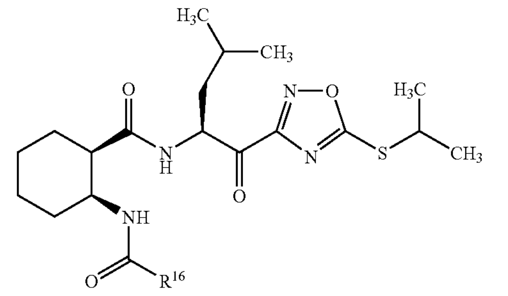
| No. | $R^{16}$ |
|---|---|
| 16 | 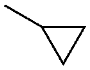 |
| 17 | 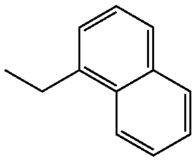 |
| 18 | 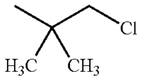 |
| 19 | 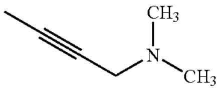 |
| 20 | 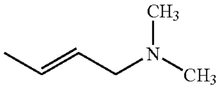 |
| 21 | 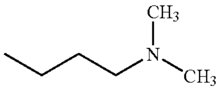 |
TABLE 25
(I-3C)
| No. | 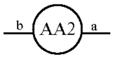 |
|---|---|
| 1 | 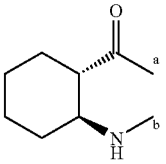 |
TABLE 25-continued
(I-3C)
| No. | 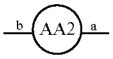 |
|---|---|
| 2 | 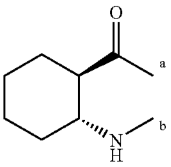 |
| 3 | 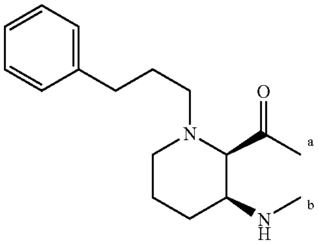 |
| 4 | 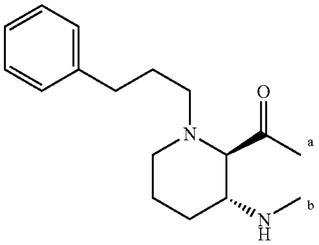 |
| 5 | 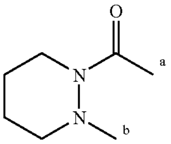 |
| 6 | 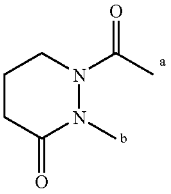 |
| 7 | 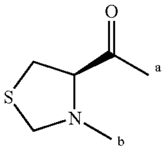 |
| 8 | 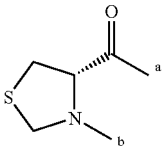 |

TABLE 25-continued
(I-3C)
| No. | 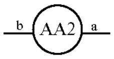 |
|---|---|
| 9 | 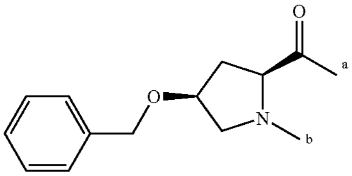 |
| 10 | 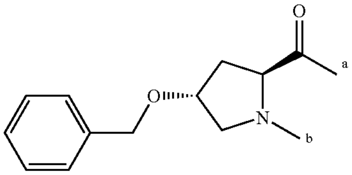 |
| 11 | 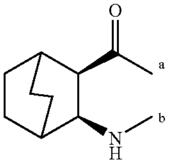 |
| 12 | 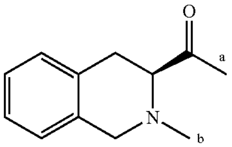 |
| 13 | 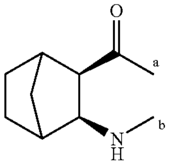 |
| 14 | 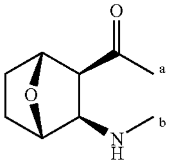 |
| 15 | 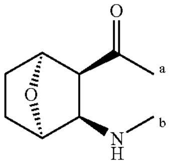 |
| 16 | 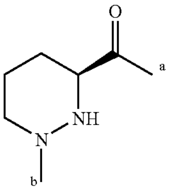 |
TABLE 25-continued
(I-3C)
| No. | 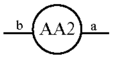 |
|---|---|
| 17 | 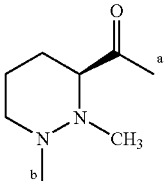 |
TABLE 26
(I-4C)
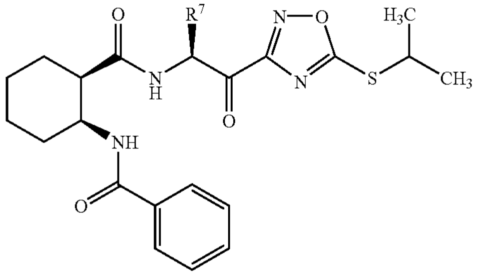
| No. | $R^7$ |
|---|---|
| 1 | 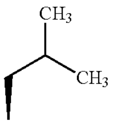 |
| 2 | 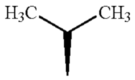 |
| 3 | 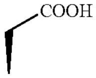 |
| 4 | 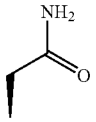 |
| 5 | 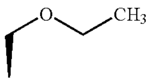 |
| 6 | 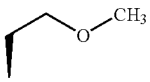 |
| 7 | 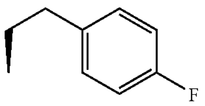 |

TABLE 26-continued
(I-4C)
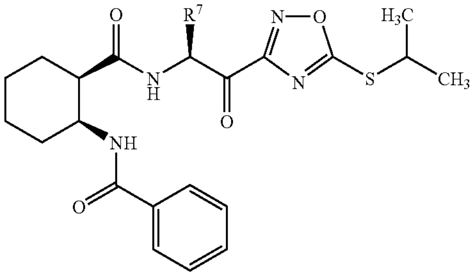
| No. | $R^7$ |
|---|---|
| 8 | 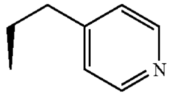 |
| 9 | 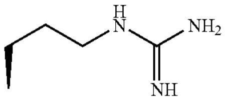 |
| 10 | 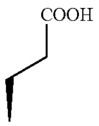 |
| 11 | 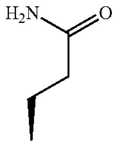 |
| 12 | 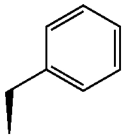 |
| 13 | 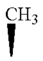 |
| 14 | 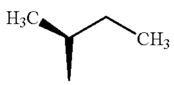 |
| 15 | 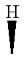 |
| 16 | 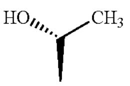 |
| 17 | 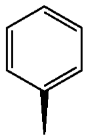 |
| 18 | 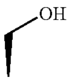 |
| 19 | 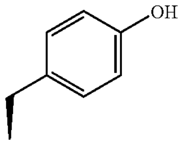 |
| 20 | 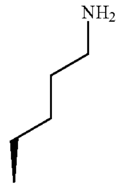 |
| 21 | 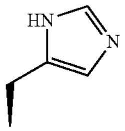 |
TABLE 26-continued
(I-4C)
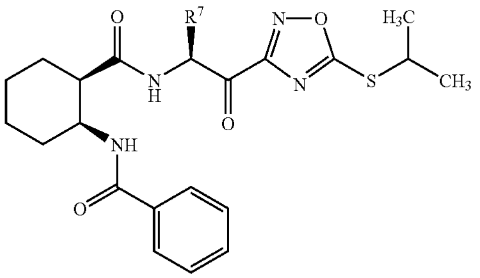
TABLE 27
(I-5C)
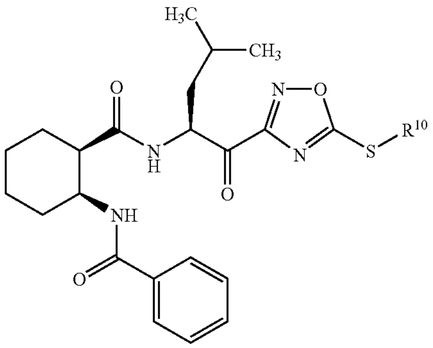
| No. | $R^{10}$ |
|---|---|
| 1 | 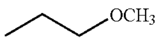 |
| 2 | 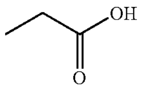 |

TABLE 27-continued
(I-5C)
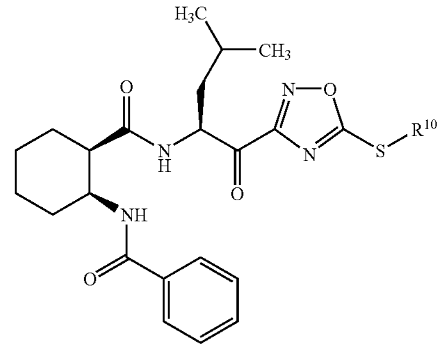
| No. | $R^{10}$ |
|---|---|
| 3 | 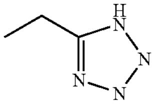 |
| 4 | 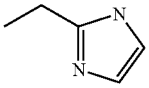 |
| 5 | 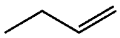 |
| 6 | 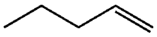 |
| 7 | 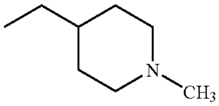 |
| 8 | 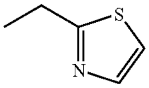 |
| 9 | 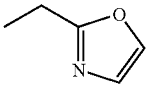 |
| 10 | 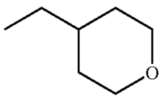 |
| 11 | 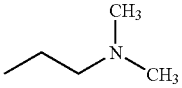 |
| 12 | 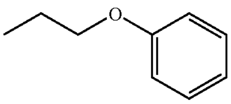 |
| 13 | 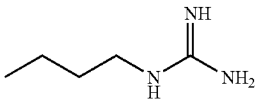 |
| 14 | 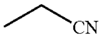 |
TABLE 27-continued
(I-5C)
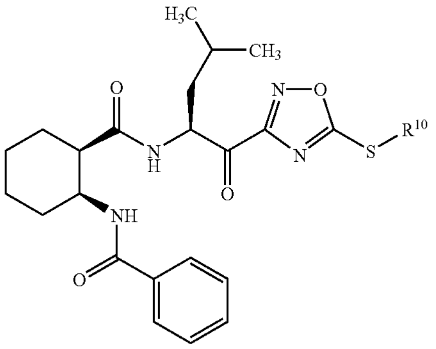
| No. | $R^{10}$ |
|---|---|
| 15 | 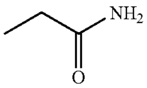 |
| 16 | 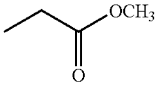 |
| 17 | 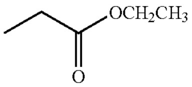 |
| 18 | 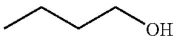 |
| 19 | 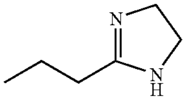 |
| 20 | 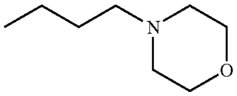 |
| 21 | 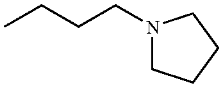 |
| 22 | 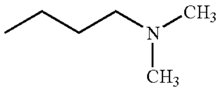 |
| 23 | 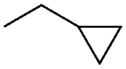 |
| 24 | 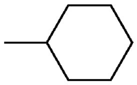 |
| 25 | 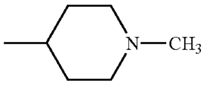 |

TABLE 27-continued
(I-5C)
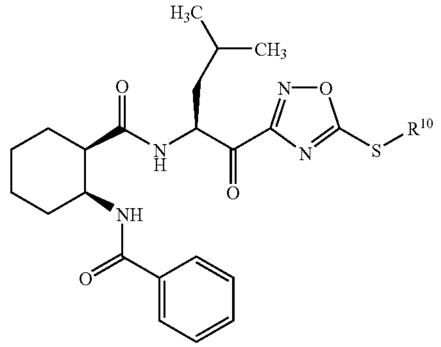
| No. | $R^{10}$ |
|---|---|
| 26 | 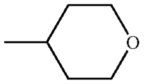 |
TABLE 28
(I-6C)
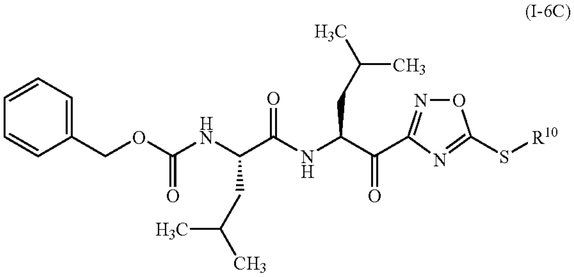
| No. | $R^{10}$ |
|---|---|
| 1 | 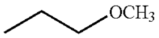 |
| 2 | 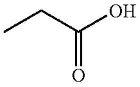 |
| 3 | 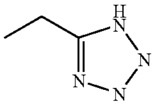 |
| 4 | 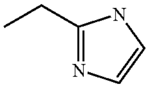 |
| 5 | 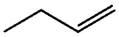 |
| 6 | 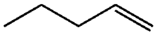 |
| 7 | 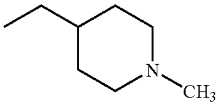 |
TABLE 28-continued
(I-6C)
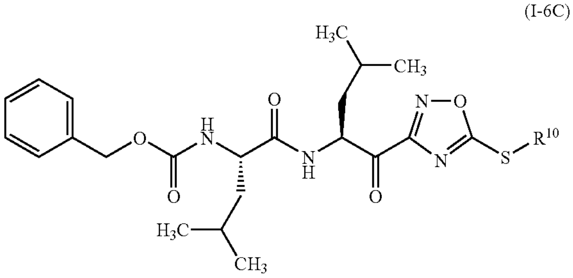
| No. | $R^{10}$ |
|---|---|
| 8 | 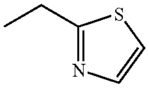 |
| 9 | 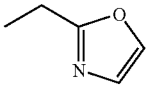 |
| 10 | 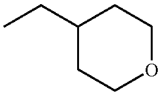 |
| 11 | 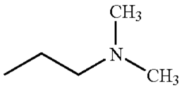 |
| 12 | 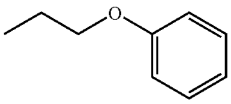 |
| 13 | 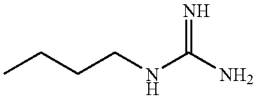 |
| 14 | 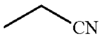 |
| 15 | 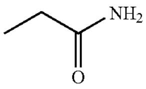 |
| 16 | 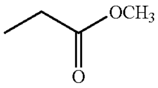 |
| 17 | 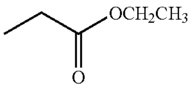 |
| 18 | 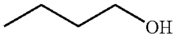 |
| 19 | 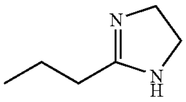 |

TABLE 28-continued
(I-6C)
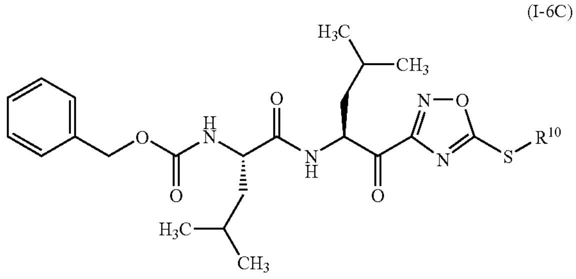
| No. | $R^{10}$ |
|---|---|
| 20 | 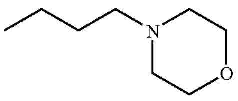 |
| 21 | 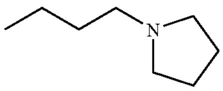 |
| 22 | 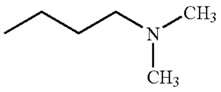 |
| 23 | 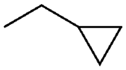 |
| 24 | 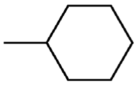 |
| 25 | 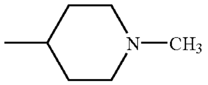 |
| 26 | 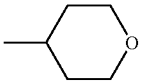 |
TABLE 29
(I-7C)
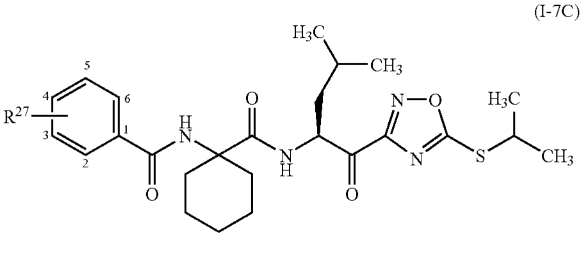
| No. | $R^{27}$ |
|---|---|
| 1 | 2-F |
| 2 | 3-F |
| 3 | 4-F |
| 4 | 2-CN |
| 5 | 3-CN |
| 6 | 4-CN |
| 7 | $3\text{-}NO_2$ |
| 8 | $4\text{-}NO_2$ |
| 9 | $3\text{-}CH_3$ |
TABLE 29-continued
(I-7C)
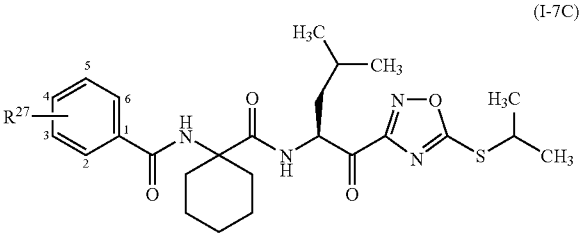
| No. | $R^{27}$ |
|---|---|
| 10 | $4\text{-}CH_3$ |
| 11 | $2\text{-}CH_2\text{—}Cl$ |
| 12 | $4\text{-}CH_2\text{—}Cl$ |
| 13 | 4-Cl |
| 14 | $4\text{-}CF_3$ |
| 15 | $4\text{-}CH_2CH_3$ |
| 16 | $4\text{-}(CH_2)_3CH_3$ |
| 17 | $4\text{-}C(CH_3)_3$ |
| 18 | $4\text{-}N(CH_3)_2$ |
| 19 | $4\text{-}OCH_3$ |
| 20 | $4\text{-}OCH_2CH_3$ |
| 21 | 4-Ph |
| 22 | $2,3\text{-di-}CH_3$ |
| 23 | 3,5-di-F |
| 24 | 3,4-di-F |
TABLE 30
(I-8C)
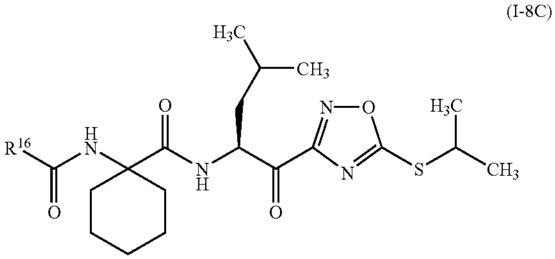
| No. | $R^{16}$ |
|---|---|
| 1 | 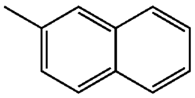 |
| 2 | 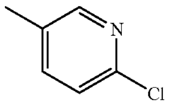 |
| 3 | 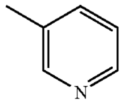 |
| 4 | 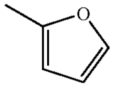 |
| 5 | 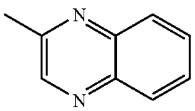 |

TABLE 30-continued
(I-8C)
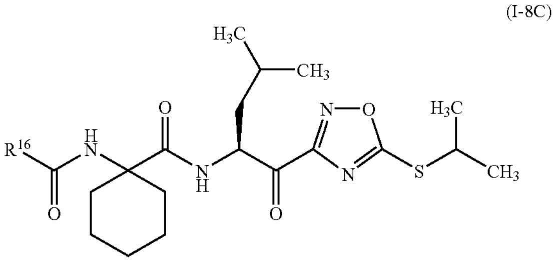
| No. | $R^{16}$ |
|---|---|
| 6 | 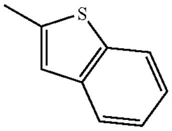 |
| 7 | 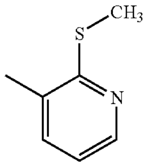 |
| 8 | 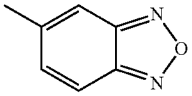 |
| 9 | 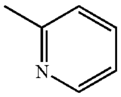 |
| 10 | 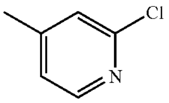 |
| 11 | 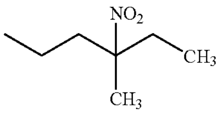 |
| 12 | 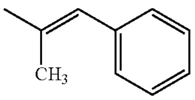 |
| 13 | 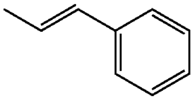 |
| 14 | 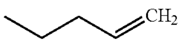 |
| 15 | 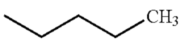 |
| 16 | 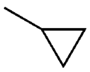 |
TABLE 30-continued
(I-8C)
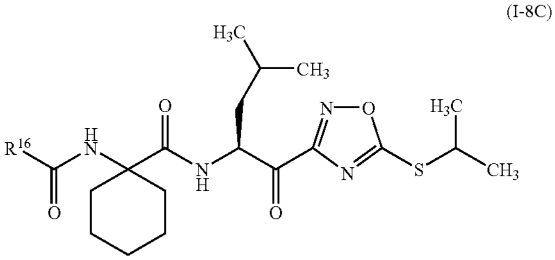
| No. | $R^{16}$ |
|---|---|
| 17 | 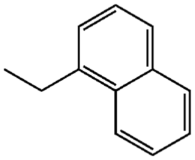 |
| 18 | 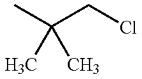 |
| 19 | 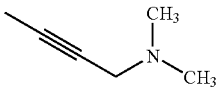 |
| 20 | 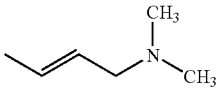 |
| 21 | 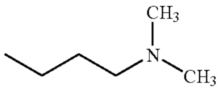 |
TABLE 31
(I-9C)
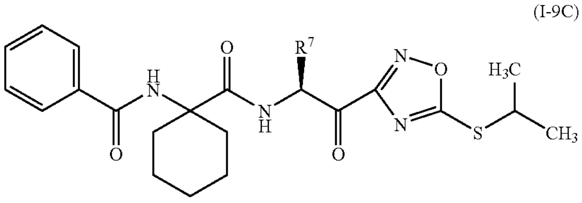
| No. | $R^7$ | No. | $R^7$ |
|---|---|---|---|
| 1 | 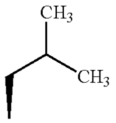 | 12 | 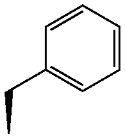 |
| 2 | 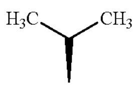 | 13 | 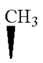 |
| 3 | 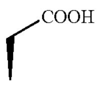 | 14 | 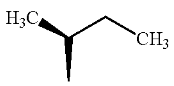 |

TABLE 31-continued
(I-9C)
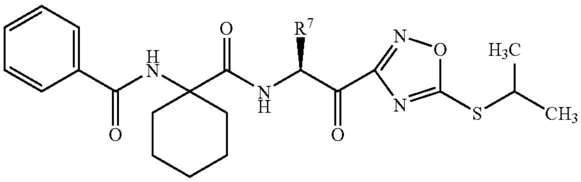
| No. | $R^7$ | No. | $R^7$ |
|---|---|---|---|
| 4 | 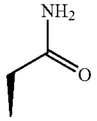 | 15 | 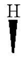 |
| 5 | 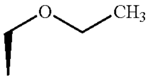 | 16 | 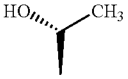 |
| 6 | 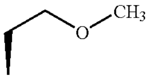 | 17 | 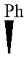 |
| 7 | 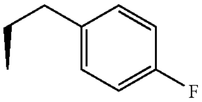 | 18 | 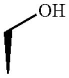 |
| 8 | 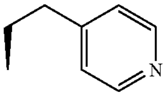 | 19 | 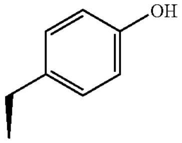 |
TABLE 31-continued
(I-9C)
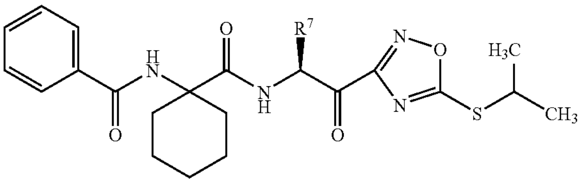
| No. | $R^7$ | No. | $R^7$ |
|---|---|---|---|
| 9 | 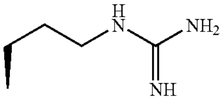 | 20 | 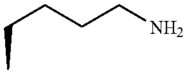 |
| 10 | 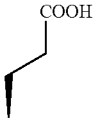 | 21 | 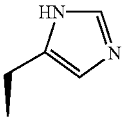 |
| 11 | 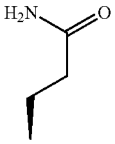 | 22 | 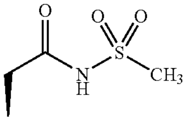 |
TABLE 32
(I-10C)
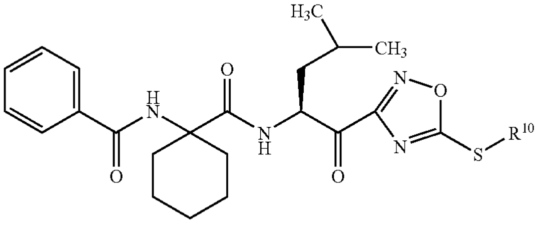
| No. | $R^{10}$ | No. | $R^{10}$ |
|---|---|---|---|
| 1 | 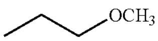 | 14 | 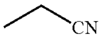 |
| 2 | 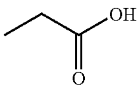 | 15 | 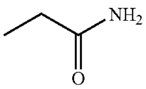 |

TABLE 32-continued
(I-10C)
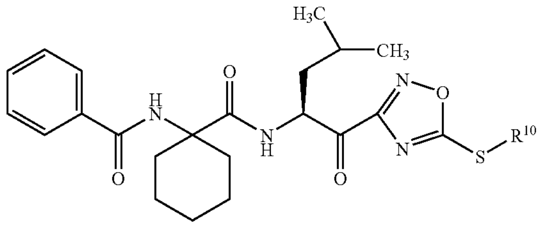
| No. | $R^{10}$ | No. | $R^{10}$ |
|---|---|---|---|
| 3 | 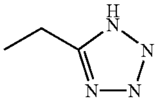 | 16 | 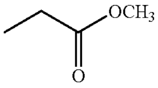 |
| 4 | 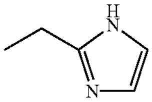 | 17 | 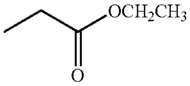 |
| 5 | 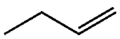 | 18 | 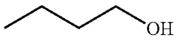 |
| 6 | 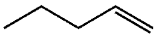 | 19 | 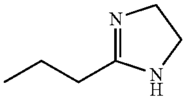 |
| 7 | 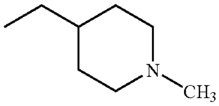 | 20 | 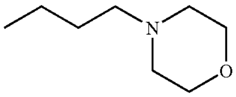 |
| 8 | 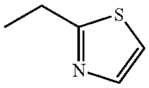 | 21 | 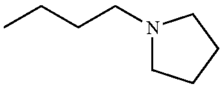 |
| 9 | 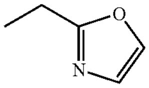 | 22 | 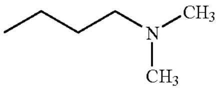 |
| 10 | 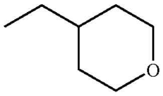 | 23 | 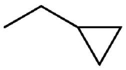 |
| 11 | 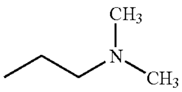 | 24 | 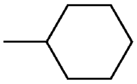 |
| 12 | 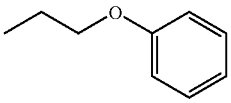 | 25 | 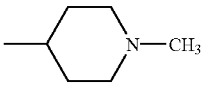 |
| 13 | 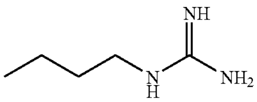 | 26 | 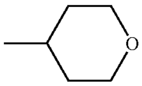 |

TABLE 33
(I-11C)
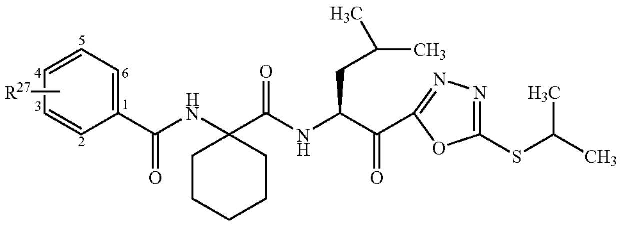
| No. | $R^{27}$ |
|---|---|
| 1 | 2-$CH_3N(CH_3)_2$ |
| 2 | 3-$CH_3N(CH_3)_2$ |
| 3 | 4-$CH_3N(CH_3)_2$ |
| 4 | 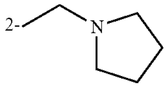 |
| 5 | 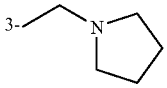 |
| 6 | 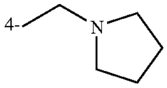 |
| 7 | 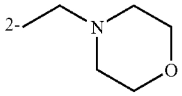 |
| 8 | 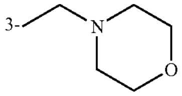 |
| 9 | 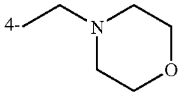 |

TABLE 34
(I-12A)
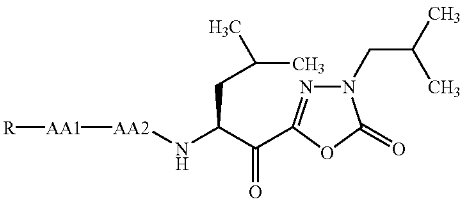
| No. | R—AA1—AA2 |
|---|---|
| 1 | 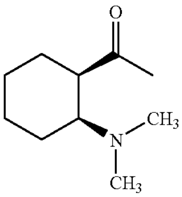 |
| 2 | 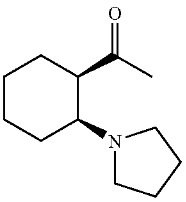 |
| 3 | 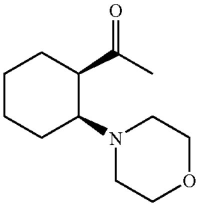 |
| 4 | 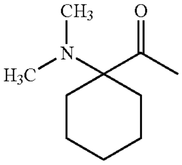 |
| 5 | 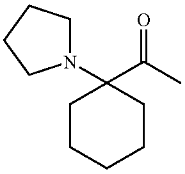 |
| 6 | 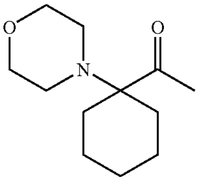 |
TABLE 35
(I-12B)
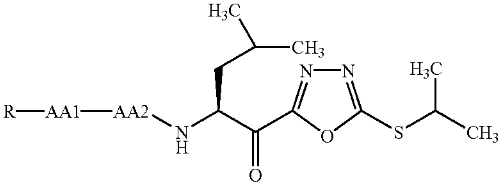
| No. | R—AA1—AA2 |
|---|---|
| 1 | 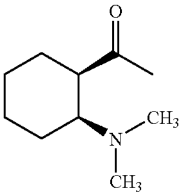 |
| 2 | 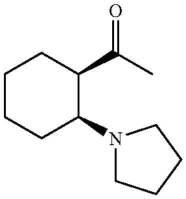 |
| 3 | 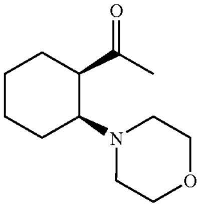 |
| 4 | 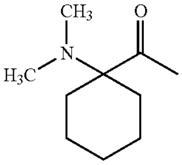 |
| 5 | 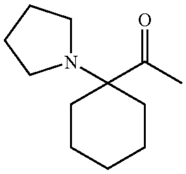 |
| 6 | 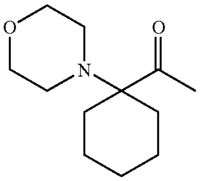 |

TABLE 36

(I-12C)

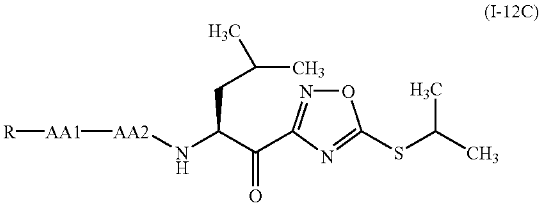

| No. | R—AA1—AA2 |
|---|---|
| 1 | 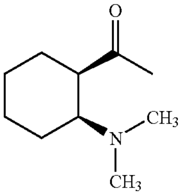 |
| 2 | 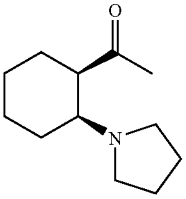 |
| 3 | 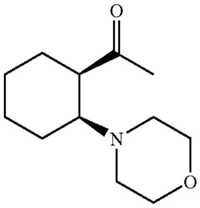 |
| 4 | 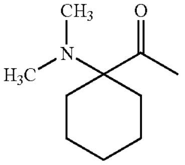 |
| 5 | 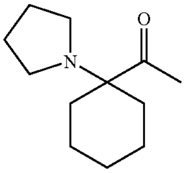 |
| 6 | 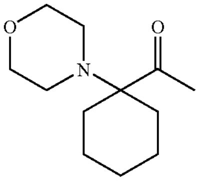 |

In the present invention, isomers are included unless specified. For example, alkyl, alkoxy, alkylthio, alkenyl, alkynyl and alkyene include straight and branched ones. Furthermore, the present invention includes isomers in double bond, ring, fused ring (E, Z, cis, trans), isomers by the presence of asymmetric carbon etc. (R, S, α, β, enantiomer, diastereomer), optical isomers having optical rotation (D, L, d, 1, +, −), polars by chromatography separation (more polar, less polar), equilibrium compound, a compound of arbitrary ratios of those and racemic mixture.

Salts

The compounds of formula (I) of the present invention may be converted into corresponding non-toxic salts by conventional methods. Non-toxic salts include alkali metal salts, alkaline earth metal salts, amine salts, acid-addition salts and corresponding quaternary ammonium salts if the compound of formula (I) contains residues of amino acid.

Non-toxic and water-soluble salts are preferable. Appropriate non-toxic salts include salts of alkali metals (potassium, sodium etc.), salts of alkaline-earth metals (calcium, magnesium, etc.), ammonium salts and salts of pharmaceutically-acceptable organic amines (tetramethyl ammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc.

Non-toxic, water-soluble acid-addition salts are preferable. Appropriate acid-addition salts are, inorganic salts such as hydrochloride, hydrobromide, sulfate, phosphate, nitrate, or organic salts such as acetate, trifluoroacetate, lactate, tartrate, oxalate, fumarate, malate, citrate, benzoate, methanesulfonate, ethanesulfonate, benzenesulfonate, toluenesulfonate, isethionate, glucuronate, gluconate.

The compounds of formula (I) of the present invention or a salt thereof may be converted into hydrate by a conventional method.

Process for the Preparation of the Compounds of the Present Invention (1) Among the compounds of formula (I), the compound wherein $AA^1$ and $AA^2$ represent a single bond at the same time and none of R, $R^7$, $R^8$ and $R^{10}$ contains carboxy, hydroxy, amino, thiol, or guanidino, and R does not represent hydrogen, i.e. the compound of formula (IA)

(IA)

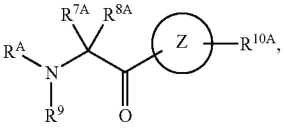

wherein $R^A$, $R^{7A}$, $R^{8A}$ and $R^{10A}$ have the same meanings as R, $R^7$, $R^8$ and $R^{10}$, with proviso that none of them contains carboxy, hydroxy, amino, thiol or guanidino and $R^A$ is not hydrogen and the other symbols have the same meanings as above, may be prepared by subjecting to oxidation reaction a compound of formula (IIA)

(IIA)

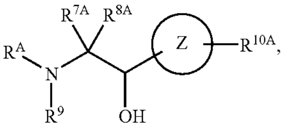

wherein all symbols have the same meaning as above.

This oxidation reaction is known, for example, (1) a method of Swern oxidation, (2) a method utilizing Dess-Martin reagent, and (3) a method utilizing TEMPO reagent, etc.

may be included.

To describe them concretely, (1) the method of Swern oxidation is carried out, for example, in an inert organic solvent (chloroform, methylene chloride, etc.) by subjecting to a reaction oxalyl chloride and dimethylsulfoxide at −78° C. and then subjecting to a reaction the obtained solution with an alcohol compound, and then subjecting to a reaction with a tertiary amine such as at a temperature of −78 to 20° C.

(2) the method utilizing Dess-Martin reagent is carried out, for example, in an inert organic solvent (chloroform, dichloromethane, etc.) in the presence of Dess-Martin reagent (1,1,1-triacetoxy-1,1-dihydro-1,2-benzoiodoxol-3-(1H)-one) at a temperature of 0~40° C.

(3) the method utilizing TEMPO reagent is carried out, for example, in an inert organic solvent (chloroform, methylene chloride, etc.), in the presence of TEMPO reagent (2,2,6,6-tetramethyl-1-piperidinyloxy, free radical) at a temperature of 20 to 60° C.

These reactions of (1), (2) and (3) are desirably carried out under the atmosphere of an inert gas (argon, nitrogen, etc.) under anhydrous conditions.

The present invention further includes other oxidation reactions which oxidize alcohol to ketone easily and selectively. For example, Jones oxidation, oxidation by pyridinium chlorochromate (PCC), sulfur trioxide-pyridine complex or ones described in "Comprehensive Organic Transformations", Richard C. Larock, VCH Publishers, Inc., (1989) 604–614, may be used.

(2) Among the compounds of formula (I), the compound wherein R is hydrogen and none of $R^7$, $R^8$, $R^{10}$ contains carboxy, hydroxy, amino, thiol, or guanidine group, i.e. the compound of formula (IE), (IE)

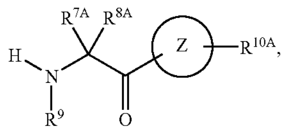

wherein all symbols have the same meaning as above, may be prepared by subjecting to a deprotection reaction of amino-protective group the compound among the compounds of formula (IA) prepared according to the above-described method, wherein $R^A$ is a protective group for amino group, i.e. the compound of formula (IA-2), (IA-2)

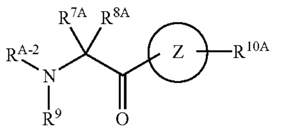

wherein $R^{A-2}$ is a protective group of amino group, and the other symbols have the same meanings as above.

As protective groups for amino group, for example, benzyloxycarbonyl, t-butoxycarbonyl, trifluoroacetyl, 9-fluorenylmethoxycarbonyl may be included, and other groups that can be easily and selectively eliminated may also be used instead. For example, the groups described in T. W. Greene, Protective Groups in Organic Synthesis, Wiley, New York, 1991 may be used.

Deprotection reaction for protective groups of amino group is known, for example, 1) deprotection reaction under alkaline conditions, 2) deprotection reaction under acidic conditions, 3) deprotection reaction by hydration, etc. may be included.

To explain these methods concretely, 1) deprotection reaction under alkaline conditions is carried out, for example, in an organic solvent (methanol, tetrahydrofuran, dioxane, dimethylformamide, etc.) using a hydroxide of alkali metals (sodium hydroxide, potassium hydroxide, lithium hydroxide, etc.), hydroxide of alkaline earth metals (barium hydroxide, calcium hydroxide, etc.), organic amine (triethylamine, N-methylmorpholine, diisopropylethylamine, piperidine, etc.) or a quaternary ammonium salt (tetrabutyl ammonium fluoride etc.) or a solution thereof or a mixture thereof at a temperature of 0 to 40° C.;

2) deprotection reaction under acidic conditions is carried out, for example, in an organic solvent (methylene chloride, chloroform, dioxane, ethyl acetate, anisole, etc.), using organic acid (acetic acid, trifluoroacetic acid, methanesulfonic acid, etc.) or inorganic acid (hydrochloric acid, sulfuric acid, etc.) or a mixture thereof (hydrobromic acid/acetic acid, etc.) at a temperature of 0 to 100° C.;

3) deprotection reaction by hydration is, for example, carried out in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitrites such as acetonitrile, amides such as dimethylformamide, water, ethyl acetate, acetic acid or a mixture of more than two from above, etc.) in the presence of a catalyst (palladium-carbon, palladium black, palladium hydroxide, platinum oxide, Raney nickel, etc.) under the atmosphere of hydrogen of normal or suppressed pressure, or in the presence of ammonium formate at a temperature of 0 to 200° C.

As easily understood by those skilled in the art, the compounds of the present invention may be easily prepared by selecting these reactions.

(3) Among the compounds of formula (I), the compound wherein $AA^1$ and $AA^2$ represent a single bond at the same time, and at least one of R, $R^7$, $R^8$ and $R^{10}$ contains carboxy, hydroxy, amino, thiol or guanidino, or R is hydrogen; i.e. the compound of formula (IB), (IB)

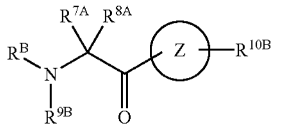

wherein $R^B$, $R^{7B}$, $R^{8B}$ and $R^{10B}$ have the same meanings as R, $R^7$, $R^8$ and $R^{10}$, but at least one of them contains carboxy, hydroxy, amino, thiol or guanidino or $R^B$ is hydrogen and the other symbols have the same meanings as above, may be prepared by subjecting to a deprotection reaction of a protective group of carboxy, hydroxy, amino, thiol or guanidino, the compound among the compounds of formula (IA) prepared according to the above-described method, wherein at least one of $R^{A}$, $R^{7A}$, $R^{8A}$ or $R^{10A}$ contains a protected form of carboxy, hydroxy, amino, thiol or guanidino, i.e. the compound of formula (IA-1), (IA-1)

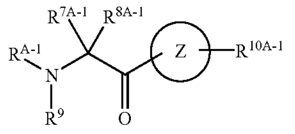

wherein $R^{A-1}$, $R^{7A-1}$, $R^{8A-1}$ and $R^{10A-1}$ have the same meanings as $R^{A}$, $R^{7A}$, $R^{8A}$ and $R^{10A}$ respectively, but at least one of $R^{A-1}$, $R^{7A-1}$, $R^{8A-1}$ and $R_{10A-1}$ contains a protected form of carboxy, hydroxy, amino, thiol or guanidino, or $R^{A-1}$ is a protective group of amino, and the other symbols have the same meanings as above, or the compound among the compound of formula (IE) prepared according to the above-described method, wherein at least one of $R^{7A}$, $R^{8A}$ and $R^{10A}$ contains a protected form of carboxy, hydroxy, amino, thiol or guanidino; i.e. the compound of formula (IE-1), (IE-1)

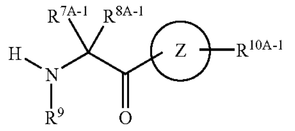

wherein all symbols have the same meanings as above.

Protective groups for carboxy include, for example, methyl, ethyl, t-butyl and benzyl.

Protective groups for hydroxy include, for example, methoxymethyl, 2-tetrahydropyranyl, t-butyldimethylsilyl, t-butyldiphenylsilyl, acetyl and benzyl.

Protective groups for amino include those shown above.

Protective groups for thiol include, for example, benzyl, methoxybenzyl, methoxymethyl, 2-tetrahydropyranyl, diphenylmethyl and acetyl.

Protective groups for guanidino include, for example, benzyloxycarbonyl, t-butoxycarbonyl and 9-fluorenylmethoxycarbonyl. As protective groups for carboxy, hydroxy, amino, thiol or guanidino group, other groups than above listed, if easily and selectively eliminated, may also be used instead. For example, the groups described in T. W. Greene, Protective Groups in Organic Synthesis, Wiley, New York, 1991 may be used.

Deprotection reactions of the protective groups for carboxy, hydroxy, amino, thiol or guanidino are well known, for example, 1) a deprotection reaction under alkaline conditions,
2) a deprotection reaction under acidic conditions,
3) a deprotection reaction by hydration,
4) a deprotection reaction of silyl-containing groups, etc. The methods of 1), 2) and 3) are carried out by the methods described above.
4) A deprotection reaction of silyl-containing group is carried out, for example, in a water-miscible organic solvent (tetrahydrofuran, acetonitrile, etc.) using tetrabutylammonium fluoride at a temperature of 0 to 40° C.

As easily understood by those skilled in the art, the target compounds of the present invention may be easily prepared by selecting these reactions.

(4) Among the compounds of formula (I), the compound wherein $AA^1$ and $AA^2$ do not represent a single bond at the same time, and R, $AA^1$, $AA^2$, $R^7$, $R^8$ and $R^{10}$ represent a group which do not contain carboxy, hydroxy, amino, thiol, guanidino; i.e. the compound of formula (IC), (IC)

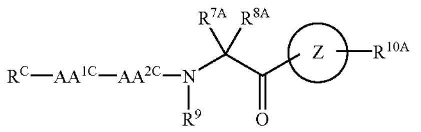

wherein $R^C$, $AA^{1C}$ and $AA^{2C}$ have the same meanings as R, $AA^1$ and $AA^2$, but none of them contains carboxy, hydroxy, amino, thiol, guanidino and $AA^{1C}$ and $AA^{2C}$ do not represent a single bond at the same time and $R^C$ does not represent a hydrogen atom. The other symbols have the same meanings as above, may be prepared according to the following [1] or [2].

[1] The compound of formula (IC) may be prepared by subjecting to an oxidation reaction the compound of formula (IIC), (IIC)

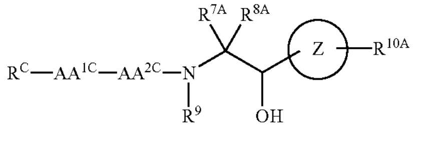

wherein all symbols have the same meanings as above.

Oxidation reaction is carried out according to the method above described.

[2] The compound of formula (IC) may be prepared by subjecting to amidation reaction the compound of formula (IE) and the compound of formula (X), $R^{C}$-$AA^{1C}$-$AA^{2C}$-OH (X)

wherein all symbols have the same meanings as above.

Amidation reaction is known, for example, 1) a method using acid halide,
2) a method using mixed anhydride,
3) a method using a condensing agent (EDC, DCC, etc.), etc.

To explain these methods concretely, 1) the method using acid halide is carried out, for example, by subjecting to a reaction carboxylic acid and acid-halogenating agent (oxalyl chloride, thionyl chloride, etc.) in an organic solvent (chloroform, methylene chloride, diethyl ether, tetrahydrofuran, etc.) or without a solvent, at a temperature between −20° C. and refluxing temperature, and then subjecting to a reaction thus obtained acid halide in the presence of tertiary amine (pyridine, triethylamine, dimethylaniline, dimethylaminopyridine, etc.) in an inert organic solvent (chloroform, methylene chloride, diethyl ether, tetrahydrofuran, etc.) at a temperature between 0 to 40° C.

And it may be carried out by subjecting to a reaction with acid halide in an organic solvent (dioxane, tetrahydrofuran, etc.) using an aqueous alkali solution (an aqueous solution of sodium bicarbonate or sodium hydroxide, etc.) at a temperature between 0 to 40° C.

2) The method using mixed anhydride is carried out, for example, by subjecting to a reaction in an organic solvent (chloroform, methylene chloride, diethyl ether, tetrahydrofuran, etc.) or without a solvent, in the presence of tertiary amine (pyridine, triethylamine, dimethylaniline, dimethylaminopyridine, etc.), carboxylic acid with acid halide (pivaloyl chloride, tosyl chloride, mesylchloride, etc.) or acid derivative (chloroethyl formate, chloroisobutyl formate, etc.) at a temperature between 0 to 40° C., and then subjecting to a reaction thus obtained mixed anhydride with amine in an organic solvent (chloroform, methylene chloride, diethyl ether, tetrahydrofuran, etc.) at a temperature between 0 to 40° C.

3) The method using a condensing agent is carried out, for example, in an organic solvent (chloroform, methylene chloride, dimethylformamide, diethyl ether, tetrahydrofuran, etc.) or without a solvent, in the presence or absence of a tertiary amine (pyridine, triethylamine, dimethylaniline, dimethylaminopyridine, etc.), using a condensing agent (1,3-dicychlorohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, etc.) in the presence or absence of 1-hydroxybenzotriazole (1-HOBt), by subjecting to a reaction carboxylic acid and amine at a temperature between 0 and 40° C.

The reactions 1), 2) and 3) are desirably carried out under atmosphere of inert gas (argon, nitrogen, etc.) and anhydrous conditions.

(5) Among the compounds of formula (I), the compound wherein $AA^1$ and $AA^2$ do not represent a single bond at the same time, and at least one of R, $AA^1$, $AA^2$, $R^7$, $R^8$, $R^{10}$ contains carboxy, hydroxy, amino, thiol, guanidino, i.e. the compound of formula (ID), (ID)

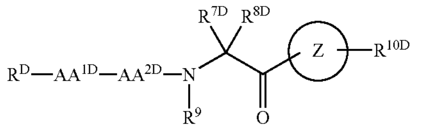

wherein $R^D$, $AA^{1D}$, $AA^{2D}$, $R^{7D}$, $R^{8D}$ and $R^{10D}$ have the same meaning as R, $AA^1$, $AA^2$, $R^1$, $R^8$ and $R^{10}$ respectively, with proviso that $AA^{1D}$ and $AA^{2D}$ do not represent a single bond at the same time, and at least one of $R^D$, $AA^{1D}$, $AA^{2D}$, $R^{7D}$, $R^{8D}$ or $R^{10D}$ represents a group which contains carboxy, hydroxy, amino, thiol, guanidino, or $R^D$ is hydrogen. And the other symbols have the same meanings as above.) may be prepared by subjecting to a deprotection reaction of protective groups of carboxy, hydroxy, amino, thiol, or guanidino the compound among the compounds of formula (IC), which was prepared by the previous method, wherein at least one of R, $AA^{1C}$, $AA^{2C}$, $R^{7A}$, $R^{8A}$ or $R^{10A}$ contains a protected form of carboxy, hydroxy, amino, thiol or guanidino, i.e. the compound of formula (IC-1), (IC-1)

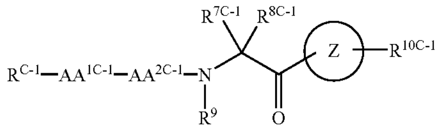

wherein $R^{C-1}$, $AA^{1C-1}$, $AA^{2C-1}$, $R^{7C-1}$, $R^{8C-1}$ and $R^{10C-1}$ have the same meanings as $R^C$, $AA^{1C}$, $AA^{2C}$, $R^{7A}$, $R^{8A}$ and $R^{10A}$, with proviso that $R^{C-1}$, $R^{1C-1}$, $AA^{2C-1}$, $R^{7C-1}$, $R^{8C-1}$ and $R^{10C-1}$ contains at least one protected carboxy, hydroxy, amino, thiol or guanidino, or $R^{C-1}$ is a protective group of amino. And the other symbols have the same meaning as above.

Deprotection reaction of carboxy, hydroxy, amino, thiol, guanidino is carried out as hereinbefore described.

And the compounds of formula (IIA) and (IIC) may be prepared according to the method by the following reaction scheme (1).

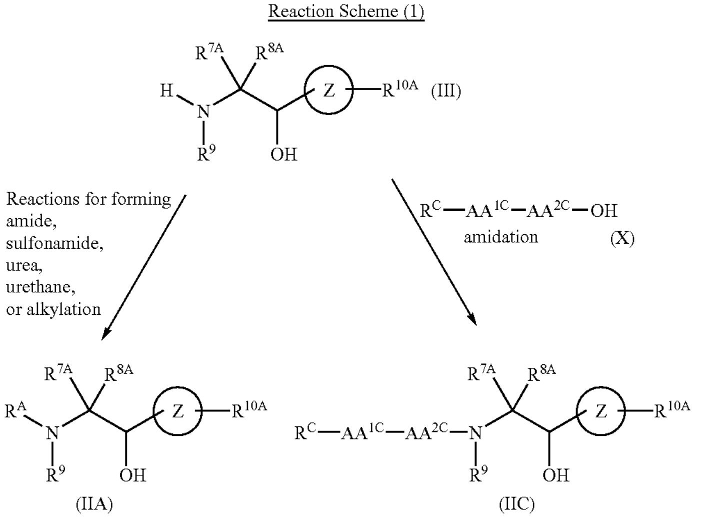
In the reaction scheme (1), all symbols have the same meanings as hereinbefore described.
The compound of formula (III) may be prepared according to the method by the following reaction scheme (2).
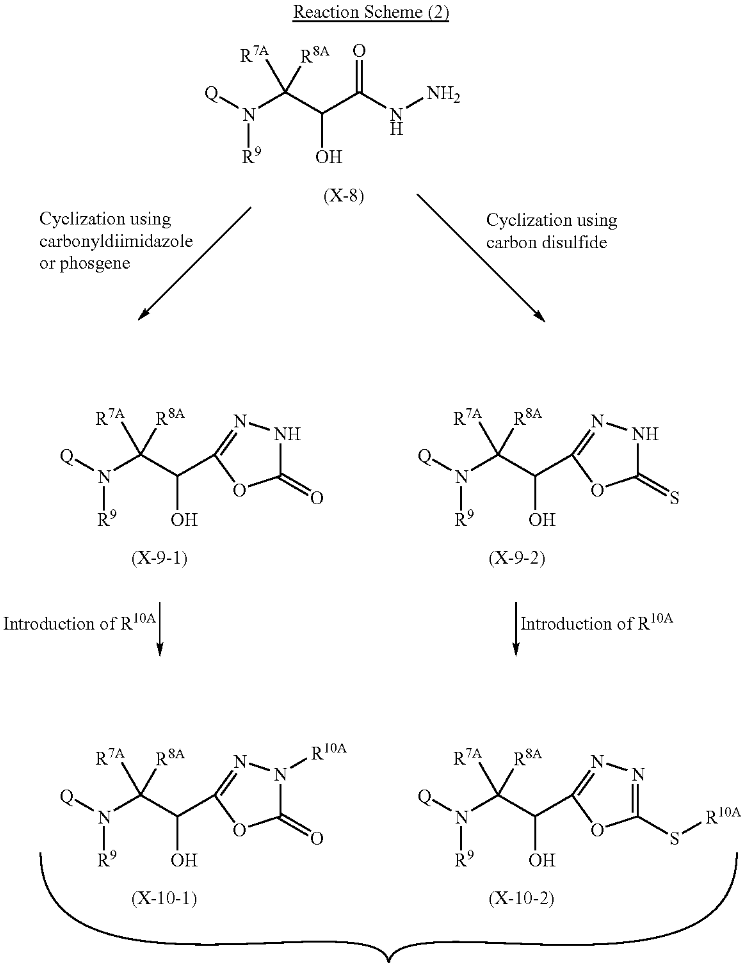

-continued

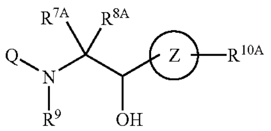

(X-10)

Q deprotection

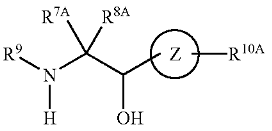

(III)

In the reaction scheme (2), Q is t-butoxycarbonyl or benzyloxycarbonyl. The other symbols have the same meanings as hereinbefore described.

The compound of formula (X-8) may be prepared according to the method by the following reaction scheme (3).

Reaction Scheme (3)

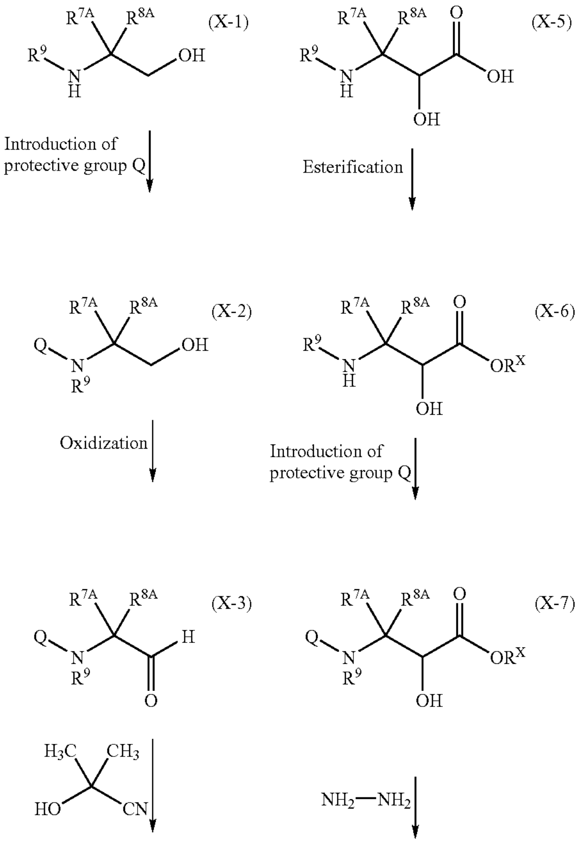

-continued

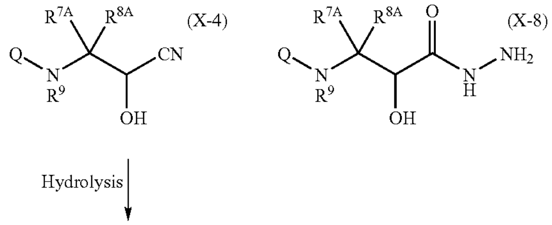

In the reaction scheme (3), $R^X$ is methyl, ethyl or t-butyl. The other symbols have the same meanings as above.

Among the compounds of formula (III), the compound wherein Z ring is

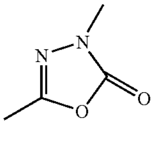

and $R^9$ is hydrogen atom, i.e. the compound of formula (III-1), (III-1)

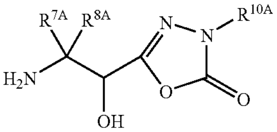

wherein all symbols have the same meanings as above, may be prepared by the method in the following reaction scheme (4).

Reaction Scheme (4)

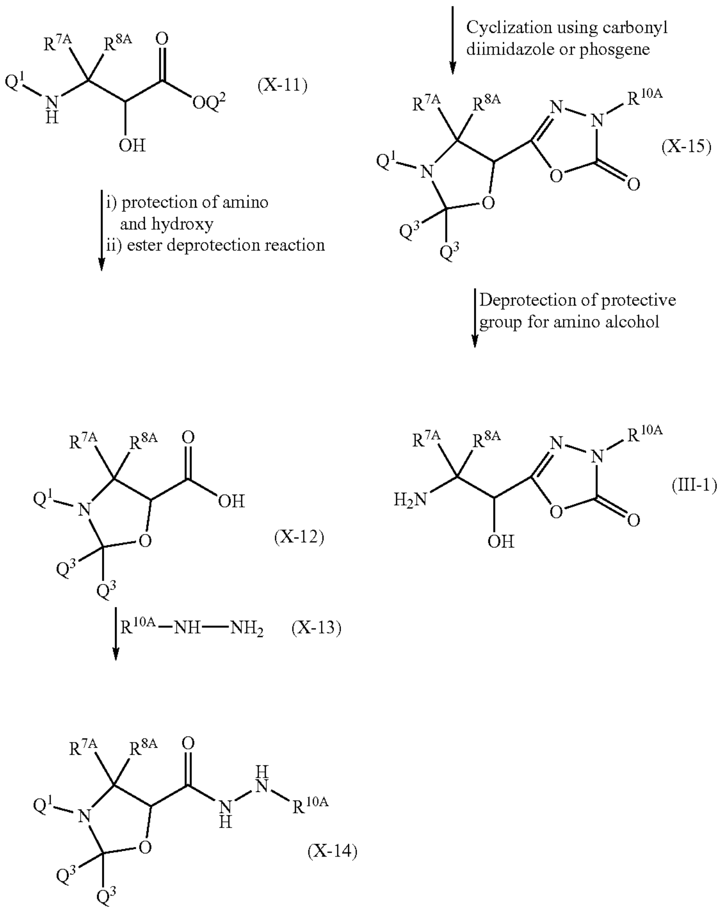

(X-11)

(X-15)

(X-12)

(III-1)

(X-13)

(X-14)

In the reaction scheme (4), $Q^1$ is t-butoxycarbonyl, $Q^2$ is methyl or ethyl, and

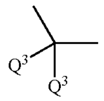

is a protective group for amino alcohol (for example, $Q^3$ is methyl or ethyl).

Among the compounds of formula (IIA) and (IIC), the compound wherein Z is

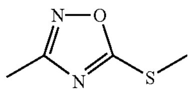

i.e. the compound of formula (IIA-1), (IIA-1)

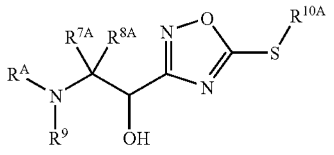

wherein all symbols have the same meanings as above, and the compound of formula (IIC-1), (IIC-1)

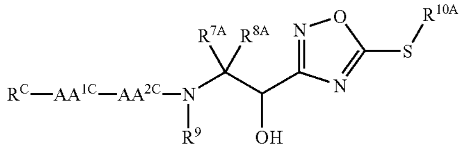

wherein all symbols have the same meanings as above, may be prepared by the methods described by the reaction schemes (5) and (6).
Reaction Scheme (5)
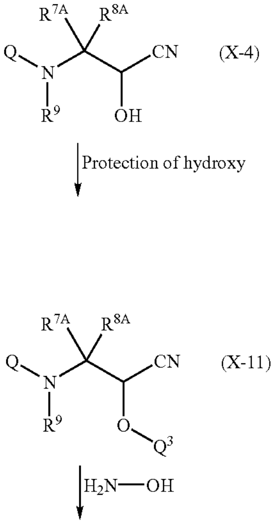
(X-4)
(X-11)
-continued
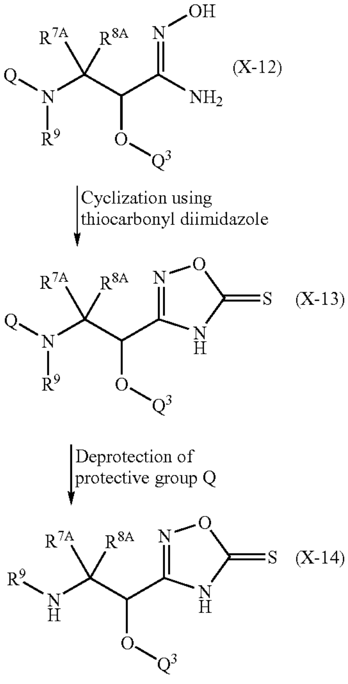
(X-12)
(X-13)
(X-14)
Reaction Scheme (6)
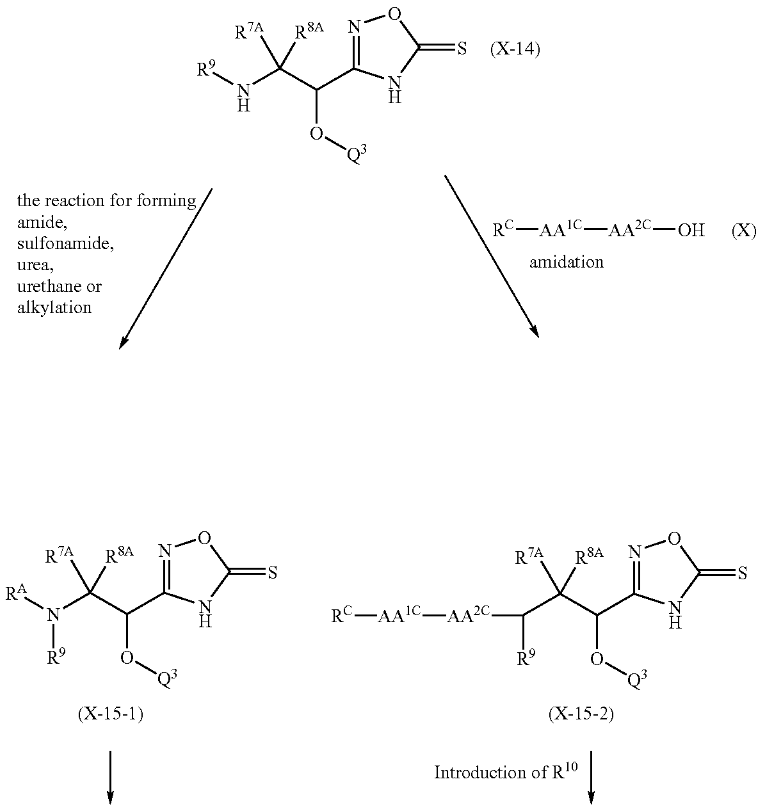
(X-14)
(X)
(X-15-1)
(X-15-2)

-continued

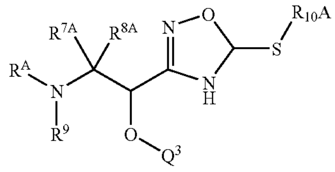

(X-16-1)

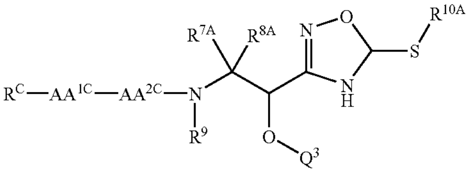

(X-16-1)

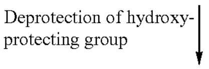

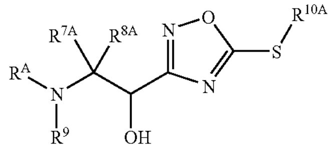

(IIA-1)

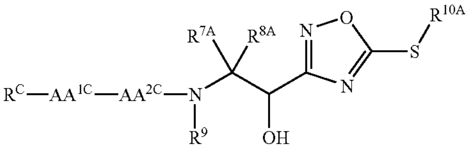

(IIC-1)

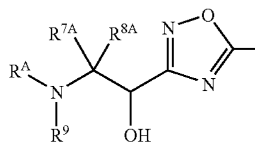

(IIA-1)

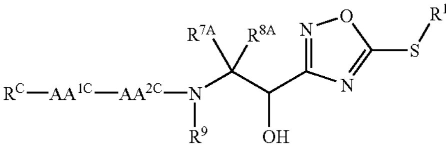

(IIC-1)

In the reaction schemes (5) and (6), $Q^3$ is a protective group for hydroxy (t-butyldimethylsilyl, trimethylsilyl, etc.) and the other symbols have the same meanings as above.

The starting materials, i.e. the compounds of formula (X), (X-1) and (X-4) are known per se or may be prepared by known methods.

All reactions in the reaction schemes may be carried out by conventional methods. Other starting materials and agents in the present invention are known per se or may be prepared by conventional methods.

In each reaction of the present specification, reaction products may be purified by conventional techniques. For example, purification may be carried out by distillation under atmospheric or reduced pressure, by high performance liquid chromatography, thin layer chromatography or column chromatography using silica gel or magnesium silicate, by washing or by recrystallization, etc. Purification may be carried out after each reaction, or after a series of reactions.

Pharmacological Activity of the Compounds of the Present Invention

It was confirmed by the following experiments that the compounds of the present invention of formula (I) have an inhibitory activity against cysteine protease.

(i) Measurement of Cathepsin K Inhibitory Activity

65 μL of Cathepsin K enzyme reaction buffer (50 mmol/L of 2-(N-morpholino)ethanesulfonate, 2 mmol/L of ethylenediamine tetraacetate (EDTA) and 4 mmol/L of dithiothreitol (DTT) were mixed to adjust to pH 5.5), 5 μL of cysteine protease inhibitor solution of several concentrations, 20 μL of synthesized substrate (t-butyloxycarbonyl-L-alanyl-glycyl-L-prolyl-L-arginine-4-methyl-chromanyl-7-amide) solution of several concentrations and 10 μL of cathepsin K enzyme solution were mixed and the increase of fluorescence intensity when reacted at 37° C. was measured (λex (excitation wavelength)=355 nm, λem (fluorescence wavelength)=460 nm). As to the substrate and the compound of the present invention, enzyme reactions were carried out in combination of several appropriate concentrations and Dixon plotting was prepared, to define the absolute value of X-coordinate of the intersection point of the graph as Ki value.

It was confirmed that the compound of the present invention of formula (I) had an inhibitory activity more than 50% at 10 μM. For example, the Ki values of inhibitory activity of the compounds of example 3 and example 7 (2) were, 1.3 nM and 14 nM respectively.

(ii) Measurement of Cathepsin B Inhibitory Activity

10 μL of Synthesized substrate (carbobenzoxy-L-arginyl-L-arginine-4-methyl-chromanyl-7-amide or carbobenzoxy-L-phenylalanyl-L-arginine-4-methyl-chromanyl-7-amide) solution of several concentrations, 10 μL of cysteine protease inhibitor solution of several concentrations, 70 μL of cathepsin B enzyme reaction buffer (mixture of 400 mmol/L in acetic acid, 4 mmol/L EDTA, 8 mmol/L DDT to adjust to pH 5.5) and 10 μL of cathepsin B enzyme solution were mixed and the increase of fluorescence intensity was measured (λex (excitation wavelength)=355 nm, λem (fluorescence wavelength)=460 nm) when reacted at 37° C.

It was confirmed that the compound of the present invention of formula (I) had an inhibitory activity more than 50% at 10 μM. For example, the inhibitory activity of the compound of example 3 (5) was 100% at 1 μM.

(iii) Measurement of Cathepsin S Inhibitory Activity

10 μL of synthesized substrate (carbobenzoxy-L-leucyl-L-leucyl-L-arguinine-4-methyl-chromanyl-7-amide) solution and 5 μL of cysteine protease inhibitor solution of several concentrations, 75 μL of cathepsin S enzyme reaction buffer (100 mmol/L of sodium phosphate, 2 mmol/L of EDTA, 2 mmol/L of DTT were mixed to adjust to pH 6.5) and 10 μL of cathepsin S enzyme solution were mixed and the increase of fluorescence intensity was measured (λex (excitation wavelength)=355 nm, λem (fluorescence wavelength)=460 nm) when reacted at 37° C.

It was confirmed that the compound of the present invention of formula (I) has an inhibitory effect more than 50% at 10 μM. For example, the inhibitory activity of the compound of example 3 (7) was 100% at 1 μM.

(iv) Measurement of Cathepsin L Inhibitory Activity

5 μL of Synthesized substrate (carbobenzoxy-L-phenylalanyl-L-arguine-4-methyl-chromanyl-7-amide or L-prolyl-L-phenylalanyl-L-arguinine-4-methyl-chromanyl-7-amide) solution and 5 μL of cysteine protease inhibitor solution of several concentrations, 80 μL of cathepsin L enzyme reaction buffer (400 mmol/L acetic acid, 4 mmol/L EDTA, 8 mmol/L DTT were mixed to adjust to pH 5.5) and 10 μL of cathepsin L enzyme solution were mixed and the increase of fluorescence intensity was measured (λex (excitation wavelength)=355 nm, λem (fluorescence wavelength)=460 nm) when reacted at 37° C.

It was confirmed that the compound of the present invention of formula (I) had an inhibitory activity of more than 50% at 10 μM. For example, the inhibitory activity of the compound of example 1(21) was 92% at 1 μM.

(v) Measurement of Calpain Inhibitory Activity

The activity was measured according to the method described in Calcium-depending protease, Seibutsukagaku-Jikkenhou (Biochemistry Experimental Method) Tanpakubunkaikouso (Protease) I, 57 (1993).

(vi) Measurement of Caspase-1 Inhibitory Activity

50 μL of caspase-1 enzyme reaction solution (20 mmol/L of 4-(2-hydroxyethyl)-1-piperazinethanesulfonate-sodium hydroxide buffer pH 7.4, 10 mmol/L of potassium chloride, 1.5 mmol/L of magnesium chloride, 0.1 mmol/L EDTA, 10% glycerol) and 50 μL of cysteine protease inhibitor solution of several concentrations, 50 μL of caspase-1 enzyme solution and 100 μL of synthesized substrate (acetyl-L-tyrosinyl-L-valinyl-L-alanyl-L-aspartic acid-4-methyl-chromanyl-7-amide) solution of several concentrations were reacted at 37° C. and the fluorescence intensity was measured (λex (excitation wavelength)=355 nm, λem (fluorescence wavelength)=460 nm).

(vii) Investigation in Bone Resorption Inhibitory Activity Using Mouse Calvaria Cultivation System Mouse neonatal calvaria was cultured in D-minimum essential medium containing cysteine protease inhibitor (mixture of Penicillin G potassium (final concentration 100 U/ml), streptomycin sulfate (final concentration 0.1 mg/ml), bovine serum albumin (final concentration 0.1%), glutamine (final concentration 0.3 mg/ml) in D-minimal essential medium) with incitant (parathyroid hormone (PTH) or arotinoid) at 37° C. and the calcium concentration in the culture medium was measured.

(viii) Bone Resorption Pit Formation Test Using Rabbit Osteoclast Cells

Osteoclast cells collected from rabbit bones were sowed over slices of bovine cortical bone, dentine or teeth of toothed whale and were cultured at 37° C. in α-minimal essential medium containing final concentration 5% of fetal bovine serum and various concentrations of cysteine protease inhibitor. The pits formed on the slices by the osteoclast cells were observed and at the same time type-I collagen C-terminal telopeptide (CTx) concentration in culture medium was measured.

(ix) Investigation of Immune Reaction Inhibitory Effect Using Antigen-sensitized Mouse Spleen Cells Spleen cells were collected from mice sensitized by ovalbumin (OVA) several times. Inhibitory effect of cysteine protease inhibitors against immune response induced by OVA stimulus was investigated, using cytokine concentration and immunoglobulin concentration in culture solution as indicators.

(x) Investigation in Inhibitory Effect Against Bone Resorption Using the Rat PTH Hypercalcemia Model The effect of cysteine protease inhibitor (compulsory oral administration, intraperitoneal administration) on bone resorption which was promoted by intravenous administration of parathyroid hormone (PTH) solution (30 μg/ml) was investigated in rats, using calcium concentration in blood as an indicator.

(xi) Studies on Bone Resorption Inhibitory Effect Using TPTx Rat PTHrP- Induced Hypercalcemia Model The effect of cysteine protease inhibitor (compulsory oral administration, intraperitoneal administration) on bone resorption, promoted by subcutaneous administration of parathyroid hormone related peptide (PTHrP) to a fasting rat (thyroparathyroidectomized; TPTx) was investigated, using calcium concentration in blood as an indicator.

Toxicity

The toxicity of the compounds of the present invention is very low and therefore it was confirmed that the compounds are safe for pharmaceutical use.

INDUSTRIAL APPLICABILITY

Application to Pharmaceuticals

The compound of formula (I) of the present invention has an inhibitory activity against cysteine proteases, and therefore it is useful as an agent for the prophylaxis and/or treatment of inflammatory diseases (periodontitis, arthritis, inflammatory bowel diseases, infectious diseases, pancreatitis, hepatitis, glomerulonephritis, endocarditis, myocarditis, etc.), diseases induced by apoptosis (graft versus host diseases, rejection of an organ transplantation, acquired immune deficiency syndrome (AIDS), AIDS-related complex (ARC), adult T cell leukemia, hairy cells leukemia, spondylopathy, disorders of respiratory apparatus, arthritis, HIV or HTLV-1 related diseases such as uveitis, virus-related diseases such as hepatitis C, cancer, collagenosis (systemic lupus erythematosus, rheumatoid arthritis, etc.), ulcerative colitis, Sjoegren's syndrome, primary biliary cirrhosis, spontaneous thrombocytopenic purpura, autoimmune hemolytic anemia, myasthenia gravis, autoimmune diseases such as insulin dependent (type I) diabetes, diseases accompanying thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type A, B, C, F, etc.) or hepatitis medicamentosa and cirrhosis, dementia such as Alzheimer's diseases and Alzheimer's senile dementia, cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.), diseases induced by disorders of immune response (graft versus host diseases, rejection of an organ transplantation, allergic diseases (bronchial asthma, atopic dermatitis, allergic rhinitis, pollinosis, diseases induced by house dusts, irritable pneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), desease by decomposing various proteins which compose the organism (myodystrophy, cataract, periodontitis, hepatocyte desease by bile acid such as cholestatic cirrhosis, etc.), decomposition of alveolus elastica such as pulmonary emphysema, ischemic diseases (brain ischemia, brain disorders by ischemic reperfusion, myocardial infarction, ischemic hepatopathy, etc.), shock (septic shock, systemic inflammation response syndrome, endotoxin shock, acidosis, etc.), circulatory system disorders (arteriosclerosis, restenosis after percutaneous transluminal coronary angioplasty (PTCA), etc.)), blood coagulation disorders (thrombocytopenic purpura, hemolytic uremic syndrome, etc.), malignant tumor, acquired immune deficiency syndrome (AIDS) and AIDS-related complex (ARC), parasitic diseases such as malaria, nerve degenerative diseases (Alzheimer-type dementia, Huntington's chorea, Parkinson's diseases, multiple sclerosis, traumatic encephalopathy, traumatic spondylopathy, etc.), pulmopathy such as fibroid lungs, bone resorption diseases (osteoporosis, rheumatoid arthritis, arthritis, osteoarthritis, hypercalcemia, osteometastasis of cancer etc.), endocrinesthenia such as hyperthyroidism.

For the purpose described above, the compounds of formula (I), of the present invention, non-toxic salts thereof, acid addition salts thereof or hydrates thereof may normally be administered systemically or locally, usually by oral or parenteral administration.

The doses to be administered are determined depending upon, for example, age, body weight, symptom, the desired therapeutic effect, the route of administration, and the duration of the treatment. In the human adult, the doses per person at a time are generally from 1 mg to 1000 mg, by oral administration, up to several times per day, and from 1 mg to 100 mg, by parenteral administration (preferably intravenous administration), up to several times per day, or continuous administration for from 1 to 24 hours per day from vein.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules.

Capsules include hard capsules and soft capsules.

In such solid compositions, one or more of the active compound(s) may be used as a dosage form, as is normal practice, to admix with excipient (e.g. lactose, mannitol, glucose, microcrystalline cellulose, starch), combining agents (hydroxypropyl cellulose polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or asparatic acid) and the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, one or more of the active compound(s) are dissolved, suspended or emulsified in diluent commonly used (e.g. purified water, ethanol or mixture thereof). Furthermore, such liquid compositions may also comprise wetting agents or suspending agents, emulsifying agents, sweetening agents, flavouring agents, perfuming agents, preserving agents buffer agent etc.

Injections for parenteral administration include solutions, suspensions, emulsions and solids which are dissolved or suspended to use at a time to use. One or more of the active compound(s) in injections are dissolved, suspended and emulsified in a solvent. The solvents are, for example, distilled water for injection, physiological salt solution, vegetable oil, propylene glycol, polyethylene glycol, alcohol such as ethanol or mixture thereof. Moreover the injections may also include stabilizing agents, agents to assist dissolution (e.g. glutamic acid, aspartic acid or POLYSORBATE80 (registered trade mark)), suspending agents, emulsifying agents, soothing agents, buffer agents, preserving agents, etc. They are sterilized in the last process or manufactured and prepared by sterile procedure. They may also be manufactured in the form of sterile solid compositions such as freeze-dried one and they may be sterilized or dissolved to use in sterile distilled water for injection or some other solvents immediately before use.

Other compositions for parenteral administration include liquids for external use, and ointment, endermic liniments, inhale, spray, suppositories for rectal administration and pessaries for vaginal administration which comprise one or more of the active compound(s) and are prescribed by methods known per se.

Spray compositions may comprise additional substances other than diluents: e.g. stabilizing agents (e.g. sodium sulfite hydride), isotonic buffers (e.g. sodium chloride, sodium citrate or citric acid). For preparation of such spray compositions, for example, the method described in the U.S. Pat. No. 2,868,691 or 3,095,355 may be used.

BEST MODE FOR CARRYING OUT THE INVENTION

The following Reference Examples and Examples illustrate the present invention, but do not limit the present invention.

The solvents in the parentheses show the eluting or developing solvents and the ratios of the solvents used are by volume in chromatographic separations or TLC.

The solvents in the parentheses in NMR show the solvents used in measurement. TBS represents t-butyldimethylsilyl.

REFERENCE EXAMPLE 1

(2S)-2-(N-t-butoxycarbonylamino)-4-methylpentanol

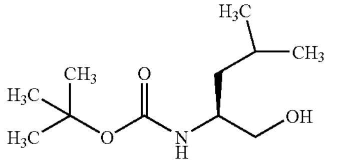

To a solution of (2S)-2-amino-4-methylpentanol((L)-leucinol) (20 g) in tetrahydrofuran (1000 ml) was added di-t-butyldicarbonate (43 ml) dropwise at 0° C. and the mixture was stirred for 1.5 hours at room temperature. The reaction mixture was concentrated to give the crude product having the following physical data of the title compound.

TLC: Rf 0.50 (chloroform:methanol=10:1);

NMR ($CDCl_3$): δ 4.58 (br, 1H), 3.81–3.45 (m, 3H), 1.80–1.60 and 1.37–1.25 (each m, totally 3H), 1.45 (s, 9H), 0.95–0.91 (m, 6H).

REFERENCE EXAMPLE 2

(2S)-2-(N-t-butoxycarbonylamino)-4-methylpentanal

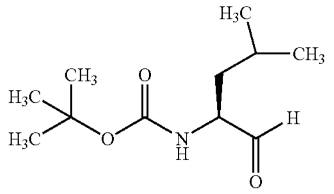

To a solution of the compound prepared in Reference Example 1 in dimethylsulfoxide (344 ml) were added triethylamine (72 ml) and sulfur trioxide-pyridine complex (82 g) in dimethylsulfoxide (280 ml) at room temperature and the mixture was stirred for 1 hour. The reaction mixture was poured into ice-water and was extracted with ethyl acetate. The organic layer was washed with 10% aqueous solution of citric acid, water and saturated aqueous solution of sodium chloride successively, dried over anhydrous sodium sulfate and was concentrated to give a crude product of the title compound having the following physical data.

TLC: Rf 0.45 (chloroform:methanol=10:1);

NMR ($CDCl_3$): δ 9.59 (s, 1H), 4.91 (br, 1H), 4.12 (br, 1H), 1.80–1.60 and 1.40–1.30 (each m, totally 3H), 1.46 (s, 9H), 1.00–0.87 (m, 6H).

REFERENCE EXAMPLE 3

(3S)-3-(N-t-butoxycarbonylamino)-2-hydroxy-5-methylhexanenitrile

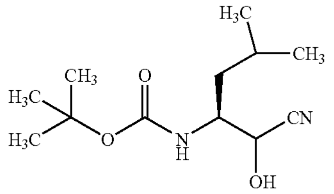

To a solution of the crude compound prepared in Reference Example 2 in methanol (180 ml) were added acetonecyanohydrine (19 ml) and potassium carbonate (4.7 g) at 0° C. and the mixture was stirred for 1 hour at room temperature. The reaction mixture was concentrated and the residue was extracted with ethyl acetate and water. The organic layer was washed with water and saturated aqueous solution of sodium chloride, dried over anhydrous sodium sulfate and was concentrated. The residue was purified by column chromatography on silica gel (n-hexane:ethyl acetate=3:1) to give the title compound (33.6 g) having the following physical data.

TLC: Rf 0.40 (n-hexane:ethyl acetate=3:1);

NMR ($CDCl_3$): δ 4.85–4.80 (m, 1H), 4.60–4.45 (m, 1H), 4.00–3.70 (m, 1H), 1.80–1.40 (m, 3H), 1.45 and 1.43 (each s, totally 9H), 1.00–0.90 (m, 6H).

REFERENCE EXAMPLE 4

(3S)-3-amino-2-hydroxy-5-methylhexanoic Acid Hydrochloride

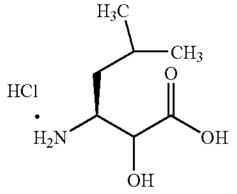

To the compound prepared in Reference Example 3 (33.6 g) was added conc. hydrochloric acid (300 ml) and the mixture was stirred for 5 hours at 80° C. The reaction mixture was concentrated to give a crude product of the title compound having the following physical data.

TLC: Rf 0.30 (chloroform:methanol:water=6:4:1).

REFERENCE EXAMPLE 5

(3S)-3-amino-2-hydroxy-5-methylhexanoic Acid Methyl Ester Hydrochloride

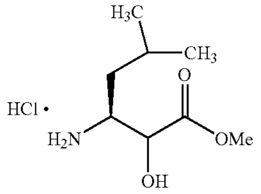

To methanol (1000 ml) was added thionyl chloride (92 ml) at −40° C. and the mixture was stirred for 10 minutes. To a solution of the compound prepared in Reference Example 4 in methanol (250 ml) was added the above prepared solution at −10° C. and the mixture was stirred for 4 hours at room temperature. The reaction mixture was concentrated to give a crude product of the title compound having the following physical data.

TLC: Rf 0.50 (chloroform:methanol:water=6:4:1).

REFERENCE EXAMPLE 6

(3S)-3-(N-t-butoxycarbonylamino)-2-hydroxy-5-methylhexanoic Acid Methyl Ester

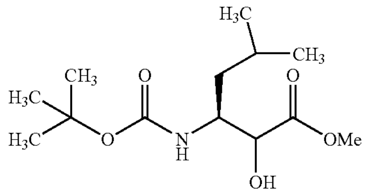

To a solution of the crude compound prepared in Reference Example 5 (32 g) in methylene chloride (300 ml) were added triethylamine (20 ml) and di-t-butyl carbonate (34 ml) at 0° C. and the mixture was stirred for 4 hours at room temperature. To the reaction mixture was added water and was extracted with ethyl acetate. The organic layer was washed with a 10% aqueous solution of citric acid, a saturated aqueous solution of sodium bicarbonate, water and saturated aqueous solution of sodium chloride successively, dried over anhydrous sodium sulfate and was concentrated. The residue was purified by column chromatography on silica gel (n-hexane:ethyl acetate=3:1) to give the title compound (28 g) having the following physical data.

TLC: Rf 0.40 and 0.35 (n-hexane:ethyl acetate=3:1);

NMR ($CD_3OD$): δ 4.10–4.09 (m, 1H), 4.04–3.95 and 3.93–3.85 (each m, totally 1H), 3.72 and 3.70 (each s, totally 3H), 1.70–1.08 (m, 3H), 1.43 and 1.40 (each s, totally 9H), 0.98–0.82 (m, 6H).

REFERENCE EXAMPLE 7

(3S)-3-(N-t-butoxycarbonylamino)-2-hydroxy-5-methylhexanoic Acid Hydrazide

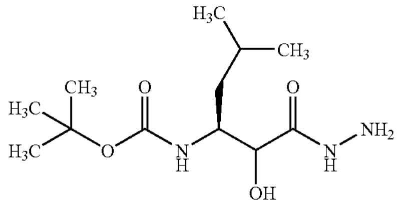

To hydrazine hydrate (99 ml) was added the compound prepared in Reference Example 6 (28 g) in methanol (110 ml) at 0° C. dropwise and the mixture was stirred for 1 hour at room temperature. To the reaction mixture was added water and was extracted with methylene chloride. The organic layer was washed with saturated aqueous solution of sodium chloride, dried over anhydrous sodium sulfate and was concentrated to give the title compound (21 g) having the following physical data.

TLC: Rf 0.40 (chloroform:methanol:water=9:1:0.1);

NMR ($CD_3OD$): δ 4.10 (d, J=3.6 Hz, 0.5H), 4.00–3.90 (m, 1.5H), 1.70–1.30 (m, 3H), 1.43 and 1.41 (each s, totally 9H), 0.95–0.88 (m, 6H).

REFERENCE EXAMPLE 8

(2S)-2-(N-t-butoxycarbonylamino)-4-methyl-1-(2-oxo-1,3,4-oxadiazolin-5-yl)pentanol

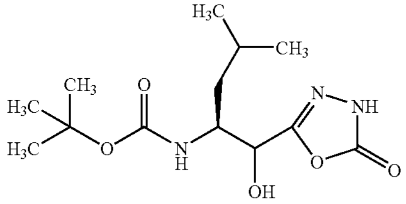

To a solution of the compound prepared in Reference Example 7 (20 g) and 1,1-carbonyldiimidazole (14 g) in tetrahydrofuran (400 ml) was added triethylamine (12 ml) at 0° C. and the mixture was stirred for 5 hours at room temperature. To the reaction mixture was added a 10% aqueous solution of citric acid and was extracted with ethyl acetate. The organic layer was washed with a saturated aqueous solution of sodium bicarbonate, water and saturated aqueous solution of sodium chloride successilvely, dried over anhydrous sodium sulfate and was concentrated. The residue was purified by column chromatography on silica gel (chloroform:methanol=20:1) to give the title compound (17 g) having the following physical data.

TLC: Rf 0.50 and 0.45 (chloroform:methanol=10:1);

NMR ($CDCl_3$): δ 4.87 and 4.80 (each brd, each J=9.3 Hz, totally 1H), 4.60–4.50 (m, 1H), 4.10–3.90 (m, 1H), 1.80–1.30 (m, 3H), 1.45 and 1.41 (each s, totally 9H), 1.00–0.80 (m, 6H).

REFERENCE EXAMPLE 9

(2S)-2-(N-t-butoxycarbonylamino)-4-methyl-1-[3-2-methylpropyl-2-oxo-1,3,4-oxadiazolin-5-yl]pentanol

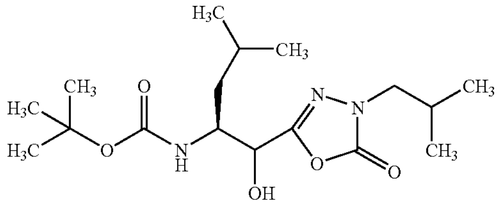

To a solution of the compound prepared in Reference Example 8 (4.5 g) in N,N-dimethylformamide (44 ml) was added potassium carbonate (4.1 g) and the mixture was stirred for 30 minutes at 0° C. To the reaction mixture was added isobutyl iodide (2.0 ml) and the mixture was stirred for 6 hours at 50° C. To the reaction mixture was added water and extracted with ethyl acetate. The organic layer was washed with water and saturated aqueous solution of sodium chloride successively, dried over anhydrous sodium sulfate and was concentrated. The residue was purified by column chromatography on silica gel (n-hexane:ethyl acetate=2:1) to give a crude product of the title compound (5.2 g) having the following physical data.

TLC: Rf 0.35 (n-hexane:ethyl acetate=3:1);

NMR ($CDCl_3$): δ 4.80–4.50 (m, 2H), 4.10–3.80 (m, 1H), 3.50–3.45 (m, 2H), 2.10–2.05 (m, 1H), 1.70–1.30 (m, 3H), 1.45 and 1.40 (s, 9H), 1.00–0.90 (m, 12H).

REFERENCE EXAMPLE 10

(2S)-2-amino-4-methyl-1-[3-(2-methylpropyl)-2-oxo-1,3,4-oxadiazolin-5-yl]pentanol Hydrochloride

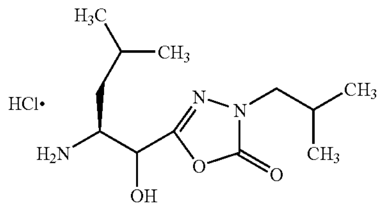

To a solution of the compound prepared in Reference Example 9 (1.01 g) in methanol (3 ml) was added 4N hydrochloric acid-ethyl acetate (11 ml) and the mixture was stirred for 30 minutes at room temperature. The reaction mixture was concentrated to give a crude product of the title compound having the following physical data.

TLC: Rf 0.46 (chloroform:methanol:water=6:4:1).

REFERENCE EXAMPLE 11

(2S)-N-[(2S)-1-hydroxy-4-methyl-1-(3-(2-methylpropyl)-2-oxo-1,3,4-oxadiazolin-5-yl)-2-pentyl]-2-benzyloxycarbonylamino-4-methylpentanamide

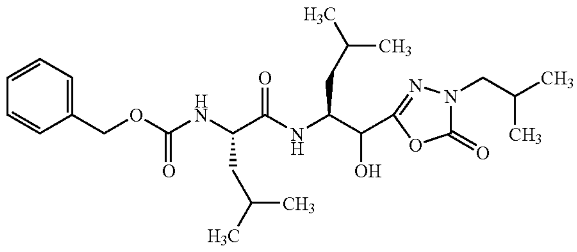

To a solution of N-benzyloxycarbonyl-(L)-leucine (901 mg), 1-hydroxybenzotriazole (581 mg) and 1-ethyl-3-(3-dimethylaminopropyl)carbodiimide hydrochloride (651 mg) in N,N-dimethylformamide (4 ml) was added a solution of the compound prepared in Reference Example 10 in N,N-dimethylformamide (2 ml) dropwise at 0° C. and thereto was added N-methyl morpholine (0.37 ml) at 0° C. and the mixture was stirred overnight at room temperature. To the reaction mixture was added water and was extracted with ethyl acetate. The organic layer was washed with a saturated aqueous solution of sodium bicarbonate, water and saturated aqueous solution of sodium chloride successively, dried over anhydrous sodium sulfate and was concentrated. The residue was purified by column chromatography on silica gel (n-hexane:ethyl acetate=2:1) to give the title compound (1.28 g) having the following physical data.

TLC: Rf 0.70 (n-hexane:ethyl acetate=1:1);

NMR ($CDCl_3$): δ 7.40–7.30 (m, 5H), 6.50–6.38 (m, 1H), 5.20–5.08 (m, 3H), 4.60–4.10 (m, 3H), 3.50–3.40 (m, 2H), 2.20–2.00 (m, 1H), 1.70–1.20 (m, 6H), 1.00–0.80 (m, 18H).

EXAMPLE 1

(2S)-N-[(2S)-2-(4-methyl-1-(3-(2-methylpropyl)-2-oxo-1,3,4-oxadiazolin-5-yl)-1-oxo-2-pentyl]-2-benzyloxycarbonylamino-4-methylpentanamide

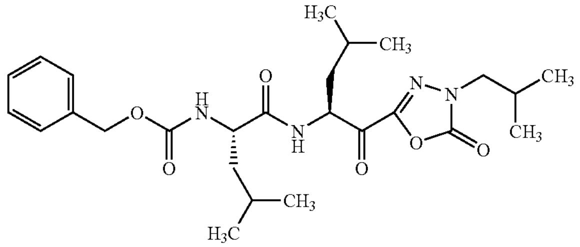

To a solution of the compound prepared in Reference Example 11 (1.23 g) in methylene chloride (17 ml) were added TEMPO reagent (2,2,6,6-tetramethyl-1-piperidinyloxy, free radical) (38 mg) and (diacetoxyiodo)benzene (1.57 g), and the mixture was stirred for 3.5 hours at room temperature. To the reaction mixture was added a saturated aqueous solution of sodium thiosulfate and was extracted with ethyl acetate. The organic layer was washed with water and saturated aqueous solution of sodium chloride successively, dried over anhydrous sodium sulfate and was concentrated. The residue was purified by column chromatography on silica gel (n-hexane:ethyl acetate=3:1) to give the compound of the present invention (1.12 g) having the following physical data.

TLC: Rf 0.50 (n-hexane:ethyl acetate=3:1);

NMR ($CDCl_3$): δ 7.40–7.30 (m, 5H), 6.51 (brd, J=7.5 Hz, 1H), 5.33 (ddd, J=9.9, 7.5, 4.2 Hz, 1H), 5.20–5.10 (m, 1H), 5.12 (s, 2H), 4.28–4.15 (m, 1H), 3.68 (dd, J=13.8, 6.9 Hz, 1H), 3.63 (dd, J=13.8, 6.9 Hz, 1H), 2.25–2.13 (m, 1H), 1.75–1.43 (m, 6H), 1.00–0.88 (m, 18H).

EXAMPLE 1 (1) TO EXAMPLE 1 (22)

By the same procedure as described in Reference Example 9→Reference Example 10→Reference Example 11→Example 1, using the compound prepared in Reference Example 8 or 2-(N-t-butoxycarbonylamino)-4-methyl-1-(2-oxo-(1,3,4-oxadiazolin)-5-yl)pentanol, and isobutyl bromide or a corresponding halogenated compound, the compounds of the present invention having the following data were obtained.

EXAMPLE 1 (1)

(2S)-N-[4-methyl-1-(3-methyl-2-oxo-1,3,4-oxadiazolin-5-yl)-1-oxo-2-pentyl]-2-benzyloxycarbonylamino-4-methylpentanamide

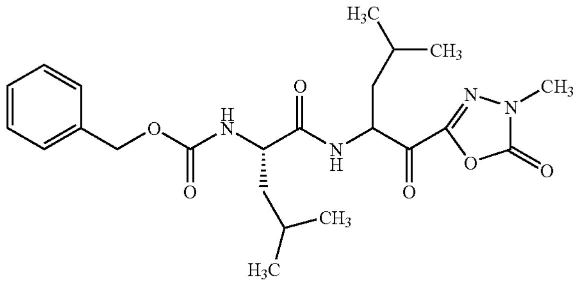

TLC: Rf 0.52 (n-hexane:ethyl acetate=1:1);

NMR ($CDCl_3$): δ 7.35 (s, 5H), 6.67 and 6.50 (each brd, J=6.6 Hz, totally 1H), 5.30 (m, 1H), 5.20–5.03 (m, 3H), 4.22 (m, 1H), 3.55 and 3.54 (each s, totally 3H), 1.84–1.40 (m, 6H), 1.05–0.84 (m, 12H).

EXAMPLE 1 (2)

(2S)-N-[4-methyl-1-(3-(2-methylpropyl)-2-oxo-1,3,4-oxadiazolin-5-yl)-1-oxo-2-pentyl]-2-benzyloxycarbonylamino-4-methylpentanamide

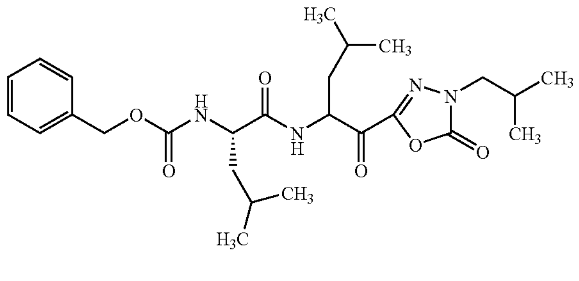

TLC: Rf 0.21 (n-hexane:ethyl acetate=4:1);

NMR ($CDCl_3$): δ 7.35 (s, 5H), 6.61 and 6.43 (each br, totally 1H), 5.33 (m, 1H), 5.15–4.95 (m, 3H), 4.21 (m, 1H), 3.68 (dd, J=14.1, 7.2 Hz, 1H), 3.63 (dd, J=14.1, 7.2 Hz, 1H), 2.18 (m, 1H), 1.78–1.42 (m, 6H), 1.04–0.84 (m, 18H).

EXAMPLE 1 (3)

(2S)-N-[(2S)-4-methyl-1-(3-methoxymethyl-2-oxo-1,3,4-oxadiazolin-5-yl)-1-oxo-2-pentyl]-2-benzyloxycarbonylamino-4-methylpentanamide

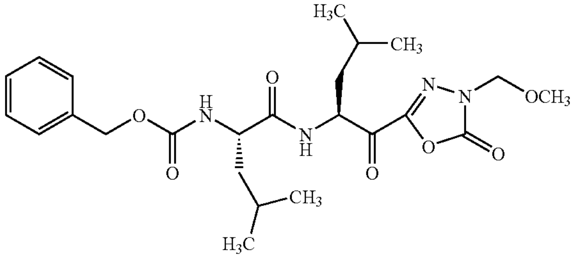

TLC: Rf 0.67 (n-hexane:ethyl acetate=1:1);

NMR ($CDCl_3$): δ 7.35 (s, 5H), 6.59 (brd, J=6.3 Hz, 1H), 5.30 (m, 1H), 5.20–5.09 (m, 5H), 4.21 (m, 1H), 3.48 (s, 3H), 1.80–1.40 (m, 6H), 1.02–0.88 (m, 12H).

EXAMPLE 1 (4)

(2S)-N-[(2S)-1-(3-butyl-2-oxo-1,3,4-oxadiazolin-5-yl)-4-methyl-1-oxo-2-pentyl]-2-benzyloxycarbonylamino-4-methylpentanamide

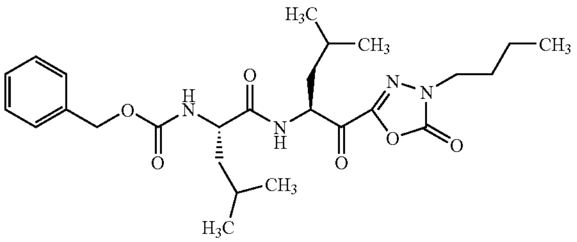

TLC: Rf 0.67 (n-hexane:ethyl acetate=1:1);

NMR ($CDCl_3$): δ 7.35 (s, 5H), 6.43 (brd, J=7.2 Hz, 1H), 5.33 (m, 1H), 5.18–5.05 (m, 3H), 4.20 (m, 1H), 3.84 (t, J=7.2 Hz, 2H), 1.83–1.31 (m, 10H), 1.02–0.88 (m, 15H).

EXAMPLE 1 (5)

(2S)-N-[(2S)-1-(3-benzyl-2-oxo-1,3,4-oxadiazolin-5-yl)-4-methyl-1-oxo-2-pentyl]-2-benzyloxycarbonylamino-4-methylpentanamide

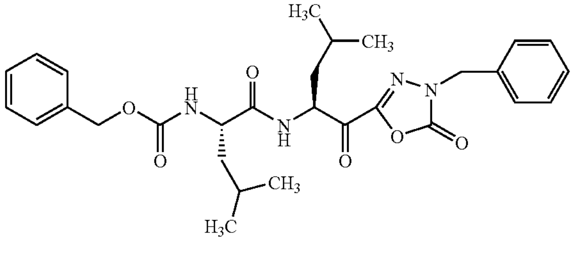

TLC: Rf 0.38 (n-hexane:ethyl acetate=1:1);

NMR ($CDCl_3$): δ 7.19 (m, 10H), 6.42 (brd, J=8.2 Hz, 1H), 5.30 (m, 1H), 5.18–5.05 (m, 3H), 5.03 (d, J=15.0 Hz, 1H), 4.97 (d, J=15.0 Hz, 1H), 4.19 (m, 1H), 1.80–1.40 (m, 6H), 1.00–0.88 (m, 12H).

EXAMPLE 1 (6)

(2S)-N-[(2S)-4-methyl-1-oxo-1-(3-propyl-2-oxo-1,3,4-oxadiazolin-5-yl)-2-pentyl]-2-benzyloxycarbonylamino-4-methylpentanamide

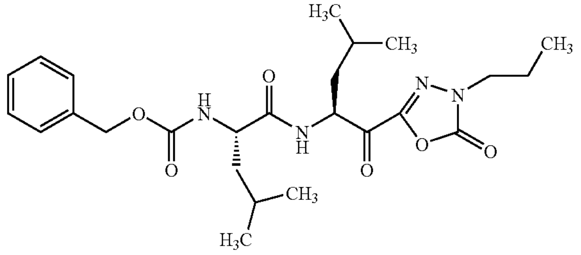

TLC: Rf 0.40 (n-hexane:ethyl acetate=2:1);

NMR ($CDCl_3$): δ 7.35 (s, 5H), 6.47 (brd, J=7.0 Hz, 1H), 5.34 (m, 1H), 5.16–5.00 (m, 3H), 4.20 (m, 1H), 3.81 (t, J=6.2 Hz, 2H), 1.83 (m, 2H), 1.80–1.40 (m, 6H), 1.00–0.88 (m, 15H)

EXAMPLE 1 (7)

(2S)-N-[(2S)-4-methyl-1-oxo-1-(3-pentyl-2-oxo-1,3,4-oxadiazolin-5-yl)-2-pentyl]-2-benzyloxycarbonylamino-4-methylpentanamide

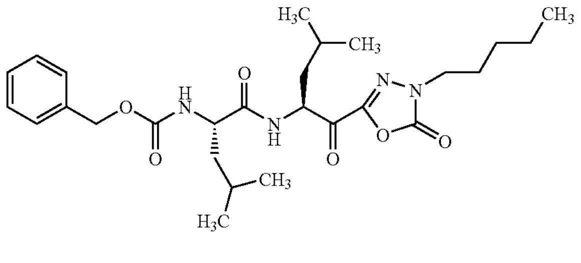

TLC: Rf 0.47 (n-hexane:ethyl acetate=2:1);

NMR ($CDCl_3$): δ 7.35 (s, 5H), 6.63 and 6.43 (each brd, J=8.0 Hz, totally 1H), 5.34 (m, 1H), 5.20–5.05 (m, 3H), 4.20 (m, 1H), 3.83 (m, 2H), 1.80 (quintet, J=4.2 Hz, 2H), 1.73–1.30 (m, 10H), 1.00–0.88 (m, 15H).

EXAMPLE 1 (8)

(2S)-N-[(2S)-4-methyl-1-(3-(1-methylethyl)-2-oxo-1,3,4-oxadiazolin-5-yl)-1-oxo-2-pentyl]-2-benzyloxycarbonylamino-4-methylpentanamide

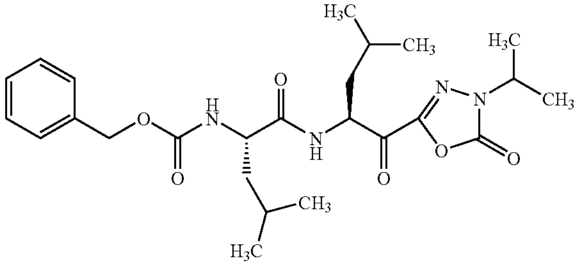

TLC: Rf 0.75 (n-hexane:ethyl acetate=1:1);

NMR ($CDCl_3$) δ 7.40–7.30 (m, 5H), 6.48 (d, J=6.6 Hz, 1H) 5.42–5.32 (m, 1H), 5.18–5.03 (m, 3H), 4.48–4.39 (m, 1H), 4.28–4.17 (m, 1H), 1.78–1.40 (m, 6H), 1.43 (d, J=6.6 Hz, 3H), 1.42 (d, J=6.6 Hz, 3H), 1.00–0.93 (m, 12H).

EXAMPLE 1 (9)

(2S)-N-[(2S)-1-(3-ethyl-2-oxo-1,3,4-oxadiazolin-5-yl)-4-methyl-1-oxo-2-pentyl]-2-benzyloxycarbonylamino-4-methylpentanamide

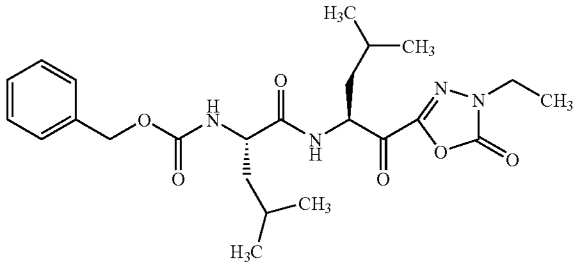

TLC: Rf 0.48 (n-hexane:ethyl acetate=2:1);

NMR ($CDCl_3$): δ 7.35 (m, 5H), 6.43 (m, 1H), 5.34 (m, 1H), 5.20–5.02 (m, 3H), 4.20 (m, 1H), 3.90 (q, J=7.2 Hz, 2H), 1.78–1.45 (m, 6H), 1.43 (t, J=7.2 Hz, 3H), 1.05–0.83 (m, 12H).

EXAMPLE 1 (10)

(2S)-N-[(2S)-1-(3-cyclohexylmethyl-2-oxo-1,3,4-oxadiazolin-5-yl)-4-methyl-1-oxo-2-pentyl]-2-benzyloxycarbonylamino-4-methylpentanamide

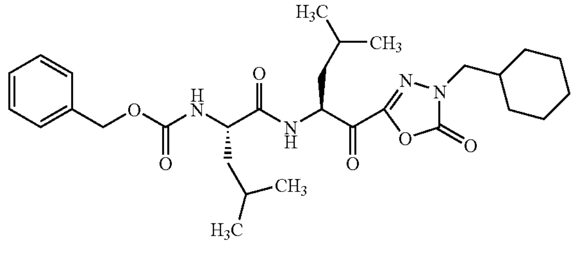

TLC: Rf 0.36 (n-hexane:ethyl acetate=3:1);

NMR ($CDCl_3$): δ 7.35 (s, 5H), 6.62 and 6.46 (each brd, J=8.2 Hz, totally 1H), 5.35 (m, 1H), 5.20–5.00 (m, 3H), 4.21 (m, 1H), 3.70 (dd, J=12.3, 7.2 Hz, 1H), 3.65 (dd, J=12.3, 7.2 Hz, 1H), 1.97–0.90 (m, 29H).

EXAMPLE 1 (11)

(2S)-N-[(2S)-1-(3-cyclohexyl-2-oxo-1,3,4-oxadiazolin-5-yl)-4-methyl-1-oxo-2-pentyl]-2-benzyloxycarbonylamino-4-methylpentanamide

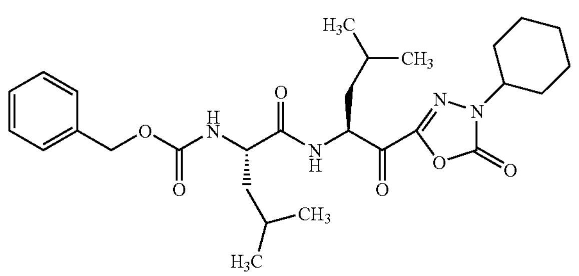

TLC: Rf 0.50 (n-hexane:ethyl acetate=3:1);

NMR ($CDCl_3$): δ 7.40–7.30 (m, 5H), 6.45 (brd, J=6.3 Hz, 1H), 5.40–5.30 (m, 1H), 5.18–5.07 (m, 3H), 4.27–4.15 (m, 1H), 4.04 (tt, J=11.7, 3.9 Hz, 1H), 2.00–1.83 (m, 4H), 1.80–1.20 (m, 12H), 1.00–0.90 (m, 12H).

EXAMPLE 1 (12)

(2S)-N-[(2S)-4-methyl-1-oxo-1-(3-(3-phenylpropyl)-2-oxo-1,3,4-oxadiazolin-5-yl)-2-pentyl]-2-benzyloxycarbonylamino-4-methylpentanamide

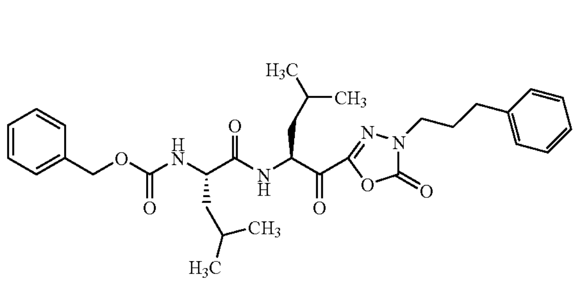

TLC: Rf 0.50 (n-hexane:ethyl acetate=3:1);

NMR ($CDCl_3$): δ 7.40–7.15 (m, 10H), 6.49 (brd, J=7.5 Hz, 1H), 5.38–5.28 (m, 1H), 5.18–5.02 (m, 3H), 4.27–4.13 (m, 1H), 3.86 (t, J=7.5 Hz, 2H), 2.71 (t, J=7.5 Hz, 2H), 2.15 (quintet, J=7.5 Hz, 2H), 1.75–1.45 (m, 6H), 1.00–0.92 (m, 12H).

EXAMPLE 1 (13)

(2S)-N-[4-methyl-1-oxo-1-(3-(2-trimethylsilylethoxymethyl)-2-oxo-1,3,4-oxadiazolin-5-yl)-2-pentyl]-2-benzyloxycarbonylamino-4-methylpentanamide

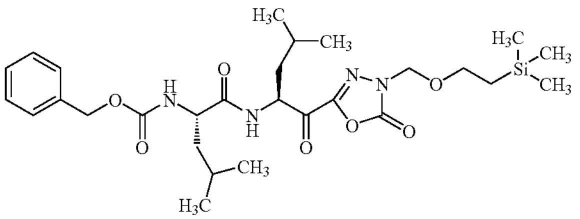

TLC: Rf 0.48 (n-hexane:ethyl acetate=7:3);

NMR ($CDCl_3$) δ 7.36 and 7.35 (each s, totally 5H), 6.67 and 6.53 (brd, J=7.8 Hz, totally 1H), 5.40–5.00 (m, 6H), 4.30–4.10 (m, 1H), 3.72 and 3.71 (each t, J=8.3 Hz, totally 2H), 1.80–1.40 (m, 6H), 1.10–0.80 (m, 14H), 0.02 (s, 9H).

EXAMPLE 1 (14)

(2S)-N-[(2S)-4-methyl-1-oxo-1 (3-phenethyl-2-oxo-1,3,4-oxadiazolin-5-yl)-2-pentyl]-2-benzyloxycarbonylamino-4-methylpentanamide

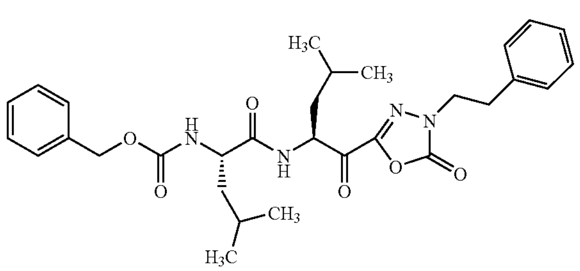

TLC: Rf 0.75 (n-hexane:ethyl acetate=1:1);

NMR ($CDCl_3$): δ 7.40–7.18 (m, 10H), 6.50 (brd, J=6.6 Hz, 1H), 5.29 (ddd, J=9.9, 6.6,4.5 Hz, 1H), 5.20–5.05 (m, 3H), 4.28–4.16 (m, 1H), 4.17–4.00 (m, 2H), 3.11 (t, J=7.5 Hz, 2H), 1.70–1.40 (m, 6H), 1.00–0.85 (m, 12H).

EXAMPLE 1 (15)

(2S)-N-[(2S)-4-methyl-1-oxo-1-(3-(thiophen-3-ylmethyl)-2-oxo-1,3,4-oxadiazolin-5-yl)-2-pentyl]-2-benzyloxycarbonylamino-4-methylpentanamide

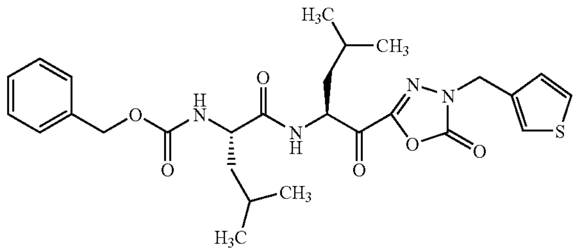

TLC: Rf 0.41 (n-hexane:ethyl acetate=2:1);

NMR ($CDCl_3$) δ 7.40–7.25 (m, 7H), 7.11 (d, J=4.8 Hz, 1H), 6.62 and 6.45 (each m, totally 1H), 5.30 (m, 1H), 5.20–4.80 (m, 5H), 4.20 (m, 1H), 1.78–1.40 (m, 6H), 1.03–0.84 (m, 12H).

EXAMPLE 1 (16)

(2S)-N-[(2S)-4-methyl-1-oxo-1-(3-(thiophen-2-ylmethyl)-2-oxo-1,3,4-oxadiazolin-5-yl)-2-pentyl]-2-benzyloxycarbonylamino-4-methylpentanamide

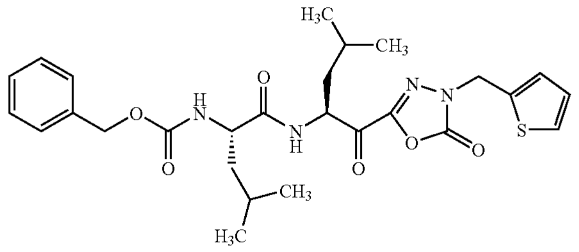

TLC: Rf 0.39 (n-hexane:ethyl acetate=2:1);

NMR ($CDCl_3$): δ 7.40–7.26 (m, 6H), 7.15 (d, J=3.3 Hz, 1H), 7.00 (dd, J=4.8, 3.3 Hz, 1H), 6.60 and 6.43 (each m, totally 1H), 5.30 (m, 1H), 5.23–4.95 (m, 5H), 4.20 (m, 1H), 1.80–1.40 (m, 6H), 1.03–0.83 (m, 12H).

EXAMPLE 1 (17)

(2S)-N-[(2S)-1-(3-cyclopropylmethyl-2-oxo-1,3,4-oxadiazolin-5-yl)-4-methyl-1-oxo-2-pentyl]-2-benzyloxycarbonylamino-4-methylpentanamide

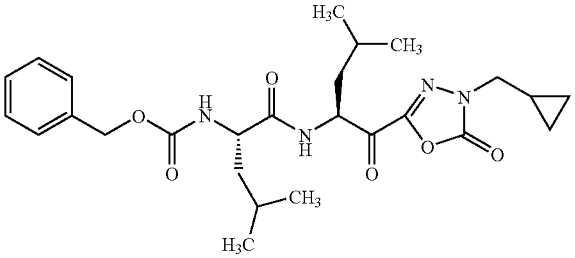

TLC: Rf 0.75 (n-hexane:ethyl acetate=1:1);

NMR ($CDCl_3$): δ 7.40–7.30 (m, 5H), 6.52 (brd, J=6.8 Hz, 1H), 5.41–5.30 (m, 1H), 5.10–5.02 (m, 3H), 4.30–4.12 (m, 1H), 3.76 (dd, J=14.6, 7.2 Hz, 1H), 3.63 (dd, J=14.6, 7.2 Hz, 1H), 1.80–1.42 (m, 6H), 1.36–1.18 (m, 1H), 1.03–0.82 (m, 12H), 0.70–0.60 (m, 2H), 0.48–0.38 (m, 2H).

EXAMPLE 1 (18)

(2S)-N-[(2S)-4-methyl-1-oxo-1-(3-(pyridin-2-ylmethyl)-2-oxo-1,3,4-oxadiazolin-5-yl)-2-pentyl]-2-benzyloxycarbonylamino-4-methylpentanamide

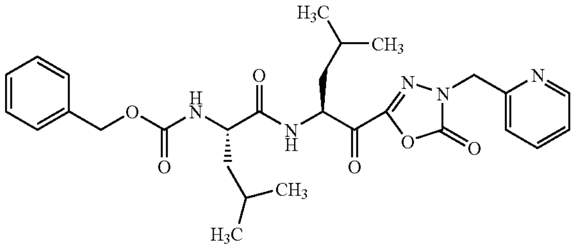

TLC: Rf 0.70 (n-hexane:ethyl acetate=1:2);

NMR ($CDCl_3$) δ 8.58 (d, J=7.6 Hz, 1H), 7.72 (dt, J=1.8, 7.6 Hz, 1H), 7.40–7.30 (m, 6H), 7.27 (t, J=7.6 Hz, 1H), 6.62 (brd, J=7.4 Hz, 1H), 5.30–5.20 (m, 2H), 5.18 (d, J=15.0 Hz, 1H), 5.10 (d, J=15.0 Hz, 1H), 5.11 (s, 2H), 4.30–4.10 (m, 1H), 1.90–1.40 (m, 6H), 0.98–0.82 (m, 12H).

EXAMPLE 1 (19)

(2S)-N-[(2S)-4-methyl-1-oxo-1-(3-(pyridin-3-ylmethyl)-2-oxo-1,3,4-oxadiazolin-5-yl)-2-pentyl]-2-benzyloxycarbonylamino-4-methylpentanamide

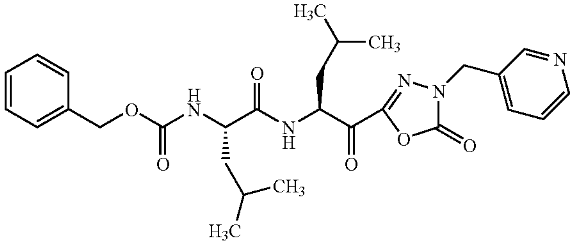

TLC: Rf 0.50 (n-hexane:ethyl acetate=1:2);

NMR ($CDCl_3$) δ 8.69 (d, J=1.8 Hz, 1H), 8.64 (dd, J=7.8, 1.8 Hz, 1H), 7.77 (dt, J=7.8, 1.8 Hz, 1H), 7.40–7.30 (m, 6H), 6.59 (brd, J=7.0 Hz, 1H), 5.30–5.10 (m, 2H), 5.11 (s, 2H), 5.03 (d, J=15.4 Hz, 1H), 4.95 (d, J=15.4 Hz, 1H), 4.30–4.10 (m, 1H), 1.90–1.40 (m, 6H), 1.00–0.80 (m, 12H).

EXAMPLE 1 (20)

(2S)-N-[(2S)-4-methyl-1-oxo-1-(3-(pyridin-4-ylmethyl)-2-oxo-1,3,4-oxadiazolin-5-yl)-2-pentyl]-2-benzyloxycarbonylamino-4-methylpentanamide

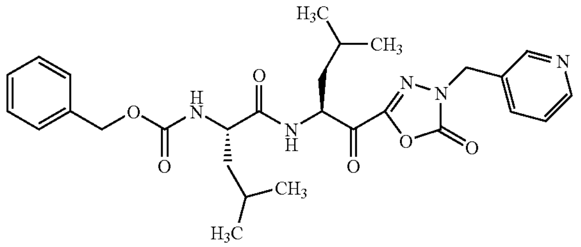

TLC: Rf 0.70 (n-hexane ethyl acetate=1:1);

NMR ($CDCl_3$): δ 8.66 (d, J=6.0 Hz, 2H), 7.40–7.30 (m, 5H), 7.30 (d, J=6.0 Hz, 2H), 6.58 (brd, J=6.3 Hz, 1H), 5.30–5.20 (m, 1H), 5.20–5.10 (m, 1H), 5.13 (s, 2H), 5.02 (d, J=15.6 Hz, 1H), 4.95 (d, J=15.6 Hz, 1H), 4.25–4.16 (m, 1H), 1.70–1.40 (m, 6H), 1.00–0.85 (m, 12H).

EXAMPLE 1 (21)

(2S)-N-[(2S)-1-(3-cyclobutylmethyl-2-oxo-1,3,4-oxadiazolin-5-yl)-4-methyl-1-oxo-2-pentyl]-2-benzyloxycarbonylamino-4-methylpentanamide

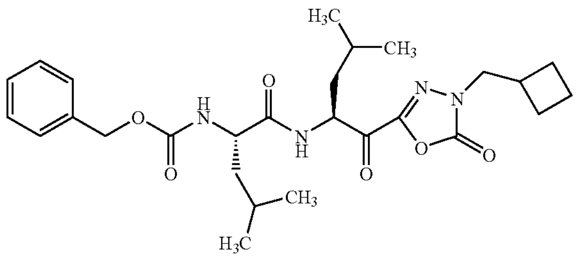

TLC: Rf 0.40 (n-hexane:ethyl acetate=3:1);

NMR ($CDCl_3$): δ 7.40–7.30 (m, 5H), 6.53 (brd, J=7.2 Hz, 1H), 5.38–5.29 (m, 1H), 5.20–5.10 (m, 1H), 5.12 (s, 2H), 4.28–4.17 (m, 1H), 3.87 (dd, J=14.1, 7.5 Hz, 1H), 3.84 (dd, J=14.1, 7.5 Hz, 1H), 2.85–2.70 (m, 1H), 2.20–2.00 and 2.00–1.75 (each m, totally 6H), 1.70–1.40 (m, 6H), 1.00–0.85 (m, 12H).

EXAMPLE 1 (22)

(2S)-N-[(2S)-1-(3-cyclopentylmethyl-2-oxo-1,3,4-oxadiazolin-5-yl)-4-methyl-1-oxo-2-pentyl]-2-benzyloxycarbonylamino-4-methylpentanamide

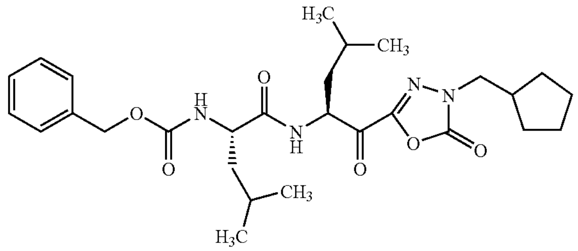

TLC: Rf 0.55 (n-hexane:ethyl acetate=2:1);

NMR ($CDCl_3$): δ 7.40–7.30 (m, 5H), 6.54 (brd, J=7.2 Hz, 1H), 5.34 (ddd, J=9.6, 7.2, 3.6 Hz, 1H), 5.20–5.05 (m, 1H), 5.11 (s, 2H), 4.30–4.15 (m, 1H), 3.79 (dd, J=13.8, 7.8 Hz, 1H), 3.73 (dd, J=13.8, 7.8 Hz, 1H), 2.43–2.30 (m, 1H), 1.85–1.25 (m, 14H), 1.00–0.82 (m, 12H).

EXAMPLE 2 TO EXAMPLE 2 (24)

By the same procedure as described in Reference Example 11→Example 1 using the compound prepared in Reference Example 10 or 2-amino-4-methyl-1-[3-(2-methyl)propyl-2-oxo-(1,3,4-oxadiazolin)-5-yl]pentanol hydrochloride and a compound which corresponds to N-benzyloxycarbonyl-(L)-leucine, the compounds having the following physical data were obtained.

EXAMPLE 2

N-[4-methyl-1-(3-(2-methylpropyl)-2-oxo-1,3,4-oxadiazolin-5-yl)-1-oxo-2-pentyl]cyclohexylcarboxamide

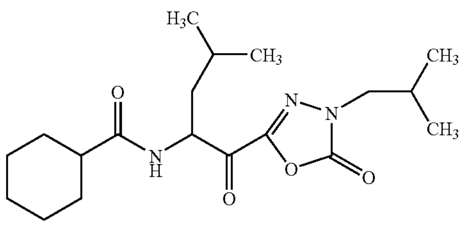

TLC: Rf 0.45 (n-hexane:ethyl acetate=3:1);

NMR ($CDCl_3$): δ 5.88 (d, J=7.8 Hz, 1H), 5.39 (m, 1H), 3.68 (dd, J=13.8, 6.9 Hz, 1H), 3.62 (dd, J=13.8, 6.9 Hz, 1H), 2.12–2.10 and 1.90–1.20 (each m, totally 15H), 1.00–0.96 (m, 12H).

EXAMPLE 2 (1)

N-[(2S)-4-methyl-1-(3-(2-methylpropyl)-2-oxo-1,3,4-oxadiazolin-5-yl)-1-oxo-2-pentyl]benzyloxycarboxamide

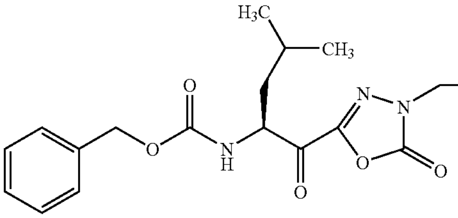

TLC: Rf 0.47 (n-hexane:ethyl acetate=4:1);

NMR ($CDCl_3$): δ 7.35 (s, 5H), 5.21 (m, 2H), 5.10 (s, 2H), 3.65 (m, 2H), 2.09 (m, 1H), 1.84–1.43 (m, 3H), 1.08–0.90 (m, 12H).

EXAMPLE 2 (2)

1-[(1S,2R)-2-benzoylaminocyclohexyl]-N-[4-methyl-1-(3-(2-methylpropyl)-2-oxo-1,3,4-oxadiazolin-5-yl)-1-oxo-2-pentyl]carboxamide

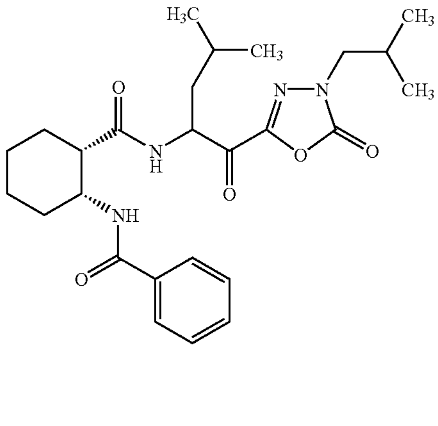

TLC: Rf 0.55 (n-hexane:ethyl acetate=1:1);

NMR ($CDCl_3$): δ 7.83–7.74 (m, 2H), 7.52–7.37 (m, 3H), 7.17–7.12 (m, 1H), 6.23 and 6.17 (each d, each J=7.0 and 7.6 Hz, totally 1H), 5.40–5.20 (m, 1H), 4.42–4.25 (m, 1H), 3.70–3.50 (m, 2H), 2.90–2.78 (m, 1H), 2.23–1.25 (m, 12H), 1.00–0.82 (m, 12H).

EXAMPLE 2 (3)

N-[4-methyl-1-(3-(2-methylpropyl)-2-oxo-1,3,4-oxadiazolin-5-yl)-1-oxo-2-pentyl]-4-benzyloxybenzamide

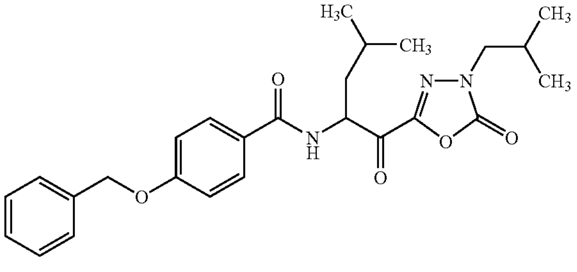

TLC: Rf 0.50 (n-hexane:ethyl acetate=3:1);

NMR ($CDCl_3$): δ 7.76 (d, J=8.7 Hz, 2H), 7.45–7.30 (m, 5H), 7.00 (d, J=8.7 Hz, 2H), 6.57 (d, J=8.1 Hz, 1H), 5.57 (ddd, J=9.3, 8.1, 3.9 Hz, 1H), 5.12 (s, 2H), 3.70 (dd, J=14.1, 7.2 Hz, 1H), 3.63 (dd, J=14.1, 7.2 Hz, 1H), 2.25–2.10 (m, 1H), 1.90–1.58 (m, 3H), 1.06–0.90 (m, 12H).

EXAMPLE 2 (4)

N-[4-methyl-1-(3-(2-methylpropyl)-2-oxo-1,3,4-oxadiazolin-5-yl)-1-oxo-2-pentyl]-3-benzyloxybenzamide

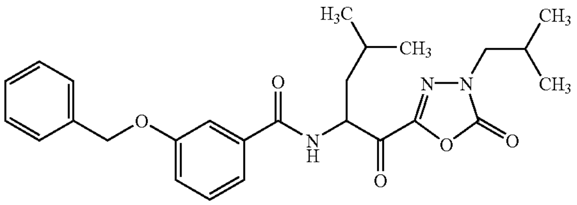

TLC: Rf 0.50 (n-hexane:ethyl acetate=3:1);

NMR ($CDCl_3$) δ 7.47–7.30 (m, 8H), 7.18–7.10 (m, 1H), 6.63 (d, J=7.8 Hz, 1H), 5.58 (ddd, J=9.9, 7.8, 3.9 Hz, 1H), 5.10 (s, 2H), 3.70 (dd, J=14.1, 7.2 Hz, 1H), 3.64 (dd, J=14.1, 7.2 Hz, 1H), 2.25–2.10 (m, 1H), 1.87–1.58 (m, 3H), 1.05 (d, J=6.0 and 6.6 Hz, 3H), 0.99 (d, J=6.0 and 6.6 Hz, 9H).

EXAMPLE 2 (5)

N-[4-methyl-1-(3-(2-methylpropyl)-2-oxo-1,3,4-oxadiazolin-5-yl)-1-oxo-2-pentyl]-2-benzyloxybenzamide

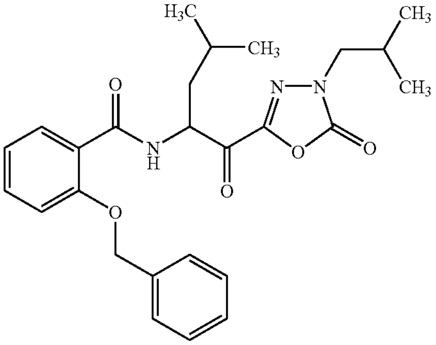

TLC: Rf 0.55 (n-hexane:ethyl acetate=3:1);

NMR ($CDCl_3$) δ 8.37 (d, J=6.3 Hz, 1H), 8.17 (dd, J=8.1, 1.8 Hz, 1H), 7.52 (dt, J=1.8, 8.1 Hz, 1H), 7.55–7.38 (m, 5H), 7.12–7.08 (m, 2H), 5.36 (dt, J=6.3, 3.9 Hz, 1H), 5.20 (d, J=10.2 Hz, 1H), 5.16 (d, J=10.2 Hz, 1H), 3.67 (dd, J=13.8, 7.2 Hz, 1H), 3.60 (dd, J=13.8, 7.2 Hz, 1H), 2.23–2.08 (m, 1H), 1.50–1.10 (m, 3H), 0.96 (d, J=6.6 Hz, 3H), 0.95 (d, J=6.6 Hz, 3H), 0.85 (d, J=6.3 Hz, 3H), 0.70 (d, J=6.3 Hz, 3H).

EXAMPLE 2 (6)

1-[(1R,2S)-2-benzoylaminocyclohexyl]-N-[4-methyl-1-(3-(2-methylpropyl)-2-oxo-1,3,4-oxadiazolin-5-yl)-1-oxo-2-pentyl]carboxamide

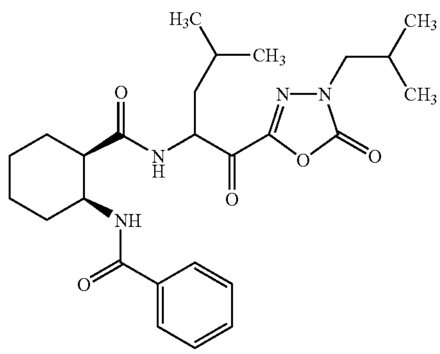

TLC: Rf 0.75 (n-hexane:ethyl acetate=7:3);

NMR ($CDCl_3$): δ 7.83–7.74 (m, 2H), 7.50–7.37 (m, 3H), 7.15–7.11 (m, 1H), 6.25 and 6.19 (each d, each J=7.8 Hz, totally 1H), 5.40–5.20 (m, 1H), 4.42–4.27 (m, 1H), 3.75–3.53 (m, 2H), 2.90–2.79 (m, 1H), 2.22–1.38 (m, 12H), 1.01–0.90 (m, 6H), 0.88 (d, J=5.8 Hz, 3H), 0.83 (d, J=6.2 Hz, 3H).

EXAMPLE 2 (7)

N-[4-methyl-1-(3-(2-methylpropyl)-2-oxo-1,3,4-oxadiazolin-5-yl)-1-oxo-2-pentyl]cinnamamide

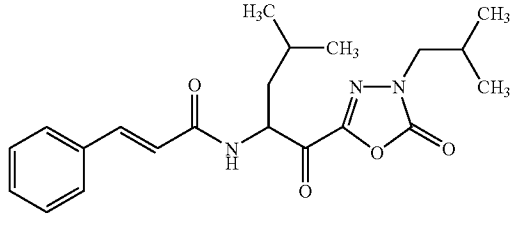

TLC: Rf 0.40 (n-hexane:ethyl acetate=3:1);

NMR ($CDCl_3$): δ 7.64 (d, J=15.6 Hz, 1H), 7.52–7.49 (m, 2H), 7.40–7.36 (m, 3H), 6.45 (d, J=15.6 Hz, 1H), 6.13 (d, J=8.1 Hz, 1H), 5.56 (ddd, J=9.9, 8.1, 4.2 Hz, 1H), 3.70 (dd, J=13.8, 7.2 Hz, 1H), 3.64 (dd, J=13.8, 7.2 Hz, 1H), 2.28–2.13 (m, 1H), 1.83–1.52 (m, 3H), 1.05 (d, J=6.0 Hz, 3H), 0.99 (d, J=6.9 Hz, 6H), 0.98 (d, J=6.3 Hz, 3H).

EXAMPLE 2 (8)

2-methylpropoxy-N-[4-methyl-1-(3-(2-methylpropyl)-2-oxo-1,3,4-oxadiazolin-5-yl)-1-oxo-2-pentyl]carboxamide

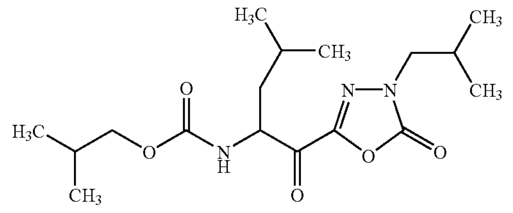

TLC: Rf 0.50 (n-hexane:ethyl acetate=3:1);

NMR ($CDCl_3$): δ 5.30–5.10 (m, 2H), 3.84 (d, J=6.6 Hz, 2H), 3.70 (dd, J=13.8, 7.0 Hz, 1H), 3.63 (dd, J=13.8, 7.0 Hz, 1H), 2.30–2.08 (m, 1H), 2.00–1.40 (m, 4H), 1.03–0.91 (m, 18H).

EXAMPLE 2 (9)

N-[4-methyl-1-(3-(2-methylpropyl)-2-oxo-1,3,4-oxadiazolin-5-yl)-1-oxo-2-pentyl]benzamide

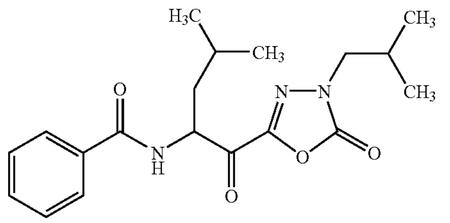

TLC: Rf 0.40 (n-hexane:ethyl acetate=3:1);

NMR ($CDCl_3$): δ 7.82–7.79 (m, 2H), 7.54 (tt, J=7.2, 1.8 Hz, 1H), 7.48–7.43 (m, 2H), 6.59 (d, J=7.8 Hz, 1H), 5.62 (ddd, J=9.9, 7.8, 4.2 Hz, 1H), 3.70 (dd, J=13.8, 7.2 Hz, 1H), 3.64 (dd, J=13.8, 7.2 Hz, 1H), 2.25–2.15 (m, 1H), 1.85–1.50 (m, 3H), 1.07 (d, J=6.0 Hz, 3H), 1.00 (d, J=6.0 Hz, 9H).

EXAMPLE 2 (10)

N-[4-methyl-1-(3-(2-methylpropyl)-2-oxo-1,3,4-oxadiazolin-5-yl)-1-oxo-2-pentyl]-3-cyclopentylpropionamide

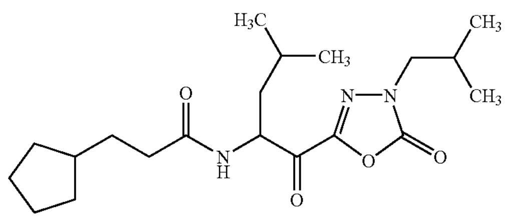

TLC: Rf 0.65 (n-hexane:ethyl acetate=7:3);

NMR ($CDCl_3$): δ 5.89 (d, J=8.0 Hz, 1H), 5.41 (ddd, J=10.0, 8.0, 4.0 Hz, 1H), 3.69 (dd, J=14.0, 7.0 Hz, 1H), 3.63 (dd, J=14.0, 7.0 Hz, 1H), 2.40–2.10 (m, 4H), 1.85–1.40 (m, 11H), 1.20–1.00 (m, 2H), 1.05–0.95 (m, 12H).

EXAMPLE 2 (11)

N-[4-methyl-1-(3-(2-methylpropyl)-2-oxo-1,3,4-oxadiazolin-5-yl)-1-oxo-2-pentyl]benzenesulfonamide

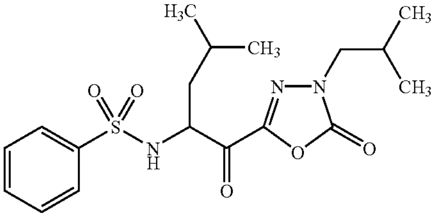

TLC: Rf 0.50 (n-hexane:ethyl acetate=7:3);

NMR ($CDCl_3$): δ 7.82–7.78 (m, 2H), 7.55 (tt, J=7.5, 1.8 Hz, 1H), 7.45 (t, J=7.5 Hz, 2H), 5.32 (d, J=10.2 Hz, 1H), 4.73 (ddd, J=10.2, 7.8, 6.6 Hz, 1H), 3.66 (dd, J=14.1, 7.2 Hz, 1H), 3.62 (dd, J=14.1, 7.2 Hz, 1H), 2.25–2.10 (m, 1H), 1.92–1.78 (m, 1H), 1.46–1.42 (m, 2H), 0.99 (d, J=6.6 Hz, 6H), 0.91 (d, J=6.6 Hz, 3H), 0.90 (d, J=6.6 Hz, 3H).

EXAMPLE 2 (12)

1-[(1R,2S)-2-benzoylaminocyclohexyl]-N-[(2S)-4-methyl-1-(3-(2-methylpropyl)-2-oxo-1,3,4-oxadiazolin-5-yl)-1-oxo-2-pentyl]carboxamide

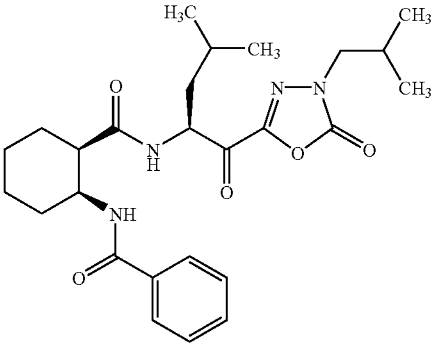

TLC: Rf 0.55 (n-hexane:ethyl acetate=1:1);

NMR ($CDCl_3$): δ 7.77 (dd, J=8.2, 1.6 Hz, 2H), 7.55–7.35 (m, 3H), 7.13 (d, J=8.4 Hz, 1H), 6.18 (d, J=8.2 Hz, 1H), 5.40–5.25 (m, 1H), 4.40–4.25 (m, 1H), 3.68 (dd, J=16.5, 7.0 Hz, 1H), 3.63 (dd, J=16.5, 7.0 Hz, 1H), 2.84 (q, J=4.9 Hz, 1H), 2.35–1.35 (m, 12H), 0.98 (d, J=6.6 Hz, 6H), 0.88 (d, J=5.8 Hz, 3H), 0.83 (d, J=6.2 Hz, 3H).

EXAMPLE 2 (13)

N-[4-methyl-1-(3-(2-methylpropyl)-2-oxo-1,3,4-oxadiazolin-5-yl)-1-oxo-2-pentyl]-2-benzoylaminobenzamide

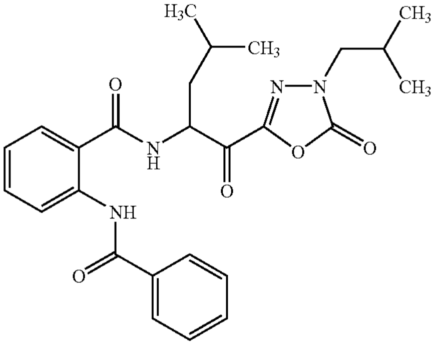

TLC: Rf 0.37 (n-hexane:ethyl acetate=7:3);

NMR ($CDCl_3$): δ 11.80 (s, 1H), 8.83 (d, J=8.4 Hz, 1H), 7.99 (dd, J=7.7, 1.9 Hz, 2H), 7.65–7.45 (m, 5H), 7.15 (t, J=7.7 Hz, 1H), 6.76 (d, J=7.6 Hz, 1H), 5.65–5.50 (m, 1H), 3.71 (dd, J=13.9, 7.1 Hz, 1H), 3.67 (dd, J=13.9, 7.4 Hz, 1H), 2.30–2.10 (m, 1H), 1.90–1.50 (m, 3H), 1.08 (d, J=5.8 Hz, 3H), 1.05–0.95 (m, 9H).

EXAMPLE 2 (14)

N-[4-methyl-1-(3-(2-methylpropyl)-2-oxo-1,3,4-oxadiazolin-5-yl)-1-oxo-2-pentyl]-1-[(2S)-N-benzoylpiperidin-2-yl]carboxamide

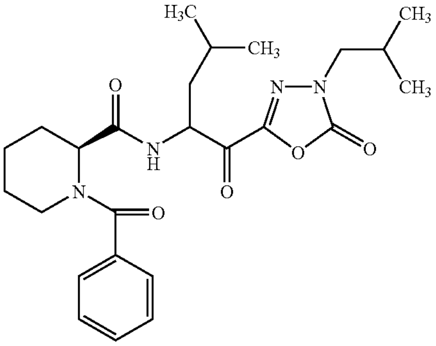

TLC: Rf 0.30 and 0.23 (n-hexane:ethyl acetate=7:3);

NMR ($CDCl_3$): δ 7.55–7.30 (m, 5H), 7.25–7.10 (m, 1H), 5.40–5.20 (m, 2H), 3.80–3.45 (m, 3H), 3.10–2.90 (m, 1H), 2.35–2.10 (m, 2H), 1.90–1.40 (m, 6H), 1.10–0.85 (m, 14H).

EXAMPLE 2 (15)

N-[4-methyl-2-(3-(2-methylpropyl)-2-oxo-1,3,4-oxadiazolin-5-yl)-2-oxo-2-pentyl]-1-[(2S)-N-phenethylpiperidin-2-yl]carboxamide

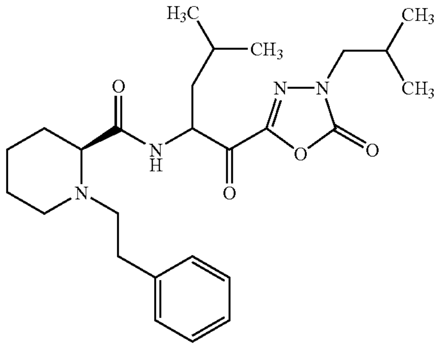

TLC: Rf 0.71 and 0.59 (n-hexane:ethyl acetate=3:2);

NMR ($CDCl_3$): δ 7.40–7.10 (m, 5H), 7.03 and 6.78 (each br, totally 1H), 5.30–5.10 (m, 1H), 3.66 (d, J=13.8 Hz, 1H), 3.62 and 3.61 (each d, J=13.8 Hz, totally 1H), 3.45–3.20 (m, 1H), 3.10–2.70 (m, 4H), 2.70–1.10 (m, 12H), 1.05–0.80 (m, 12H).

EXAMPLE 2 (16)

N-[4-methyl-1-(3-(2-methylpropyl)-2-oxo-1,3,4-oxadiazolin-5-yl)-1-oxo-2-pentyl)-1-[(2S)-N-benzylpiperidin-2-yl]carboxamide

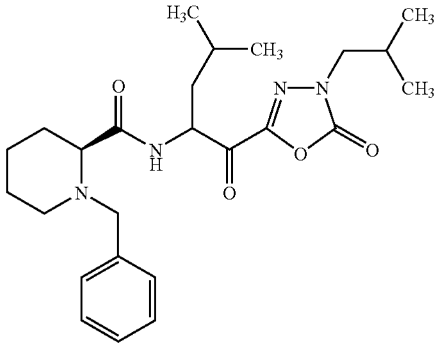

TLC: Rf 0.56 and 0.52 (n-hexane:ethyl acetate=2:1);

NMR ($CDCl_3$): δ 7.45–7.15 (m, 6H), 5.45–5.30 (m, 1H), 3.98 and 3.89 (each d, J=13.4 and 14.0 Hz, totally 1H), 3.75–3.55 (m, 2H), 3.29 and 3.17 (each d, J=14.0 and 13.4 Hz, totally 1H), 3.00–2.80 (m, 2H), 2.25–1.20 (m, 11H), 1.05–0.75 (m, 12H).

EXAMPLE 2 (17)

N-[(2S)-4-methyl-1-(3-(2-methylpropyl)-2-oxo-1,3,4-oxadiazolin-5-yl)-1-oxo-2-pentyl]-1-[(2S)-N-phenacylpiperidin-2-yl]carboxamide

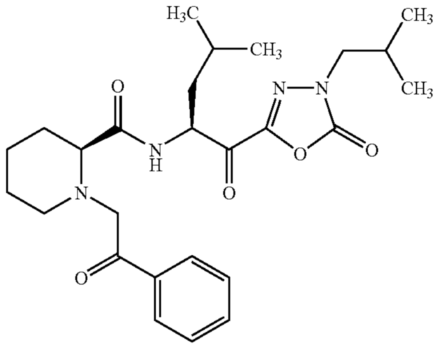

TLC: Rf 0.35 and 0.31 (n-hexane:ethyl acetate=2:1);

NMR ($CDCl_3$): δ 8.00–7.90 (m, 2H), 7.70–7.30 (m, 4H), 5.25–5.10 (m, 1H), 4.15 and 3.98 (each d, J=18.0 Hz, totally 1H), 3.90 (d, J=18.0 Hz, 1H), 3.75–3.50 (m, 2H), 3.20–3.00 (m, 2H), 2.25–1.20 (m, 1H), 1.05–0.70 (m, 12H).

EXAMPLE 2 (18)

N-[4-methyl-1-(3-(2-methylpropyl)-2-oxo-1,3,4-oxadiazolin-5-yl)-1-oxo-2-pentyl]-1-[(2S)-N-benzylcarbonylpiperidin-2-yl]carboxamide

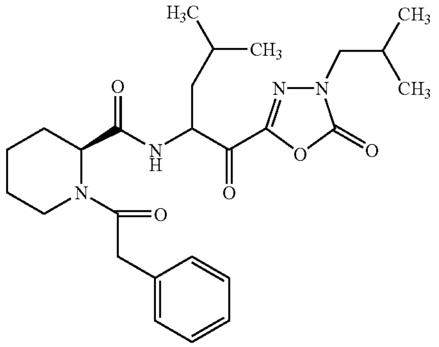

TLC: Rf 0.67 and 0.61 (n-hexane:ethyl acetate=1:1);

NMR ($CDCl_3$): δ 7.40–7.20 (m, 5H), 6.58 and 6.52 (each d, J=7.4 Hz, totally 1H), 5.35–5.05 (m, 2H), 3.95–3.75 (m, 3H), 3.67 (dd, J=14.0, 6.9 Hz, 1H), 3.61 (dd, J=14.0, 7.2 Hz, 1H), 3.15–2.90 (m, 1H), 2.30–2.00 (m, 2H), 2.00–1.10 (m, 8H), 1.05–0.80 (m, 12H).

EXAMPLE 2 (19)

N-[(2S)-4-methyl-1-(3-(2-methylpropyl)-2-oxo-1,3,4-oxadiazolin-5-yl)-1-oxo-2-pentyl]-1-[(3R)-N-benzoylpiperidin-3-yl]carboxamide

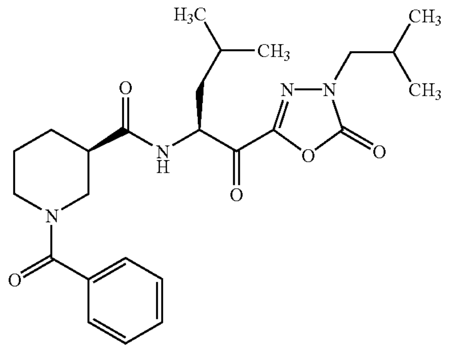

TLC: Rf 0.67 (chloroform:methanol=19:1);

NMR ($CDCl_3$): δ 7.50–7.30 (m, 5H), 6.97 (br, 1H), 5.34 (br, 1H), 4.30–4.10 (br, 1H), 3.68 (dd, J=14.0, 7.0 Hz, 1H), 3.63 (dd, J=14.0, 7.0 Hz, 1H), 3.65–3.45 (m, 2H), 3.29 (br, 1H), 2.54 (br, 1H), 2.30–1.30 (m, 8H), 0.99 (d, J=6.6 Hz, 12H).

EXAMPLE 2 (20)

N-[4-methyl-1-(3-(2-methylpropyl)-2-oxo-1,3,4-oxadiazolin-5-yl)-1-oxo-2-pentyl]-1-[(3R)-N-benzylpiperidin-3-yl]carboxamide

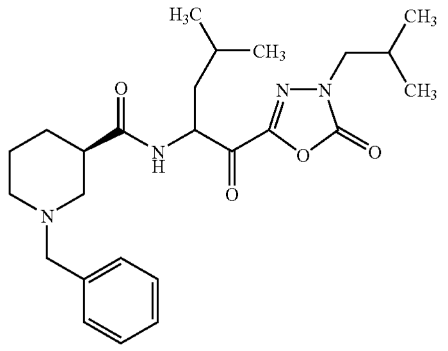

TLC: Rf 0.46 (chloroform:methanol=19:1);

NMR ($CDCl_3$): δ 8.84 and 8.68 (each br, totally 1H), 7.45–7.20 (m, 5H), 5.42–5.26 (m, 1H), 3.75–3.35 (m, 4H), 3.10–2.70 (m, 2H), 2.60–2.45 (m, 1H), 2.40–1.40 (m, 10H), 1.05–0.80 (m, 12H).

EXAMPLE 2 (21)

N-[(2S)-4-methyl-1-(3-(2-methylpropyl)-2-oxo-1,3,4-oxadiazolin-5-yl)-1-oxo-2-pentyl]-1-[(2S)-N-(3-phenylpropyl)piperidin-2-yl]carboxamide

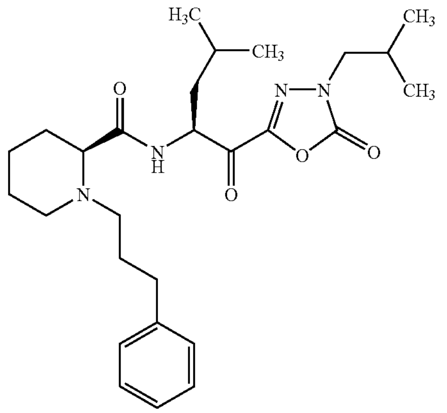

TLC: Rf 0.69 (chloroform:methanol=19:1);

NMR ($CDCl_3$): δ 7.40–7.10 (m, 6H), 5.45–5.30 (m, 1H), 3.68 (dd, J=13.8, 7.2 Hz, 1H), 3.64 (dd, J=13.8, 7.2 Hz, 1H), 3.20–3.05 (m, 1H), 2.85–2.50 (m, 4H), 2.30–1.20 (m, 14H), 1.05–0.90 (m, 12H).

EXAMPLE 2 (22)

N-[(2S)-4-methyl-1-(3-(2-methylpropyl)-2-oxo-1,3,4-oxadiazolin-5-yl)-1-oxo-2-pentyl]-1-[(2S)-N-phenethylpiperidin-2-yl]carboxamide

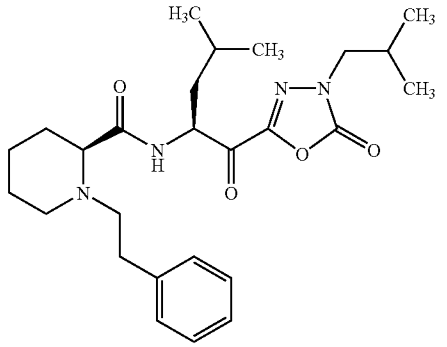

TLC: Rf 0.62 (chloroform:methanol=97:3);

NMR ($CDCl_3$): δ 7.30–7.10 (m, 5H), 6.74 (d, J=7.2 Hz, 1H), 5.25–5.10 (m, 1H), 3.66 (dd, J=13.9, 7.0 Hz, 1H), 3.61 (dd, J=13.9, 7.2 Hz, 1H), 3.40–3.25 (m, 1H), 3.05–2.70 (m, 4H), 2.45–1.10 (m, 12H), 1.05–0.85 (m, 12H).

EXAMPLE 2 (23)

N-[(2S)-4-methyl-1-(3-(2-methylpropyl)-2-oxo-1,3,4-oxadiazolin-5-yl)-1-oxo-2-pentyl]-1-[(2S)-N-(4-phenylbutyl)piperidin-2-yl]carboxamide

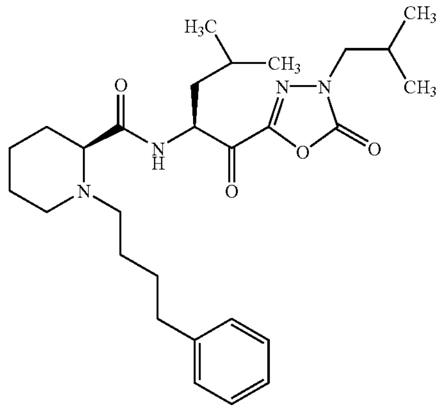

TLC: Rf 0.57 (chloroform:methanol=49:1);

NMR ($CDCl_3$): δ 7.35–7.10 (m, 6H), 5.40–5.25 (m, 1H), 3.67 (dd, J=13.9, 7.0 Hz, 1H), 3.63 (dd, J=13.9, 7.0 Hz, 1H), 3.15–3.00 (m, 1H), 2.80–2.40 (m, 4H), 2.30–1.20 (m, 16H), 1.05–0.85 (m, 12H).

EXAMPLE 2 (24)

N-[(2S)-4-methyl-1-(3-(2-methylpropyl)-2-oxo-1,3,4-oxadiazolin-5-yl)-1-oxo-2-pentyl]-1-(2-benzyloxy-cyclohexyl)carboxamide

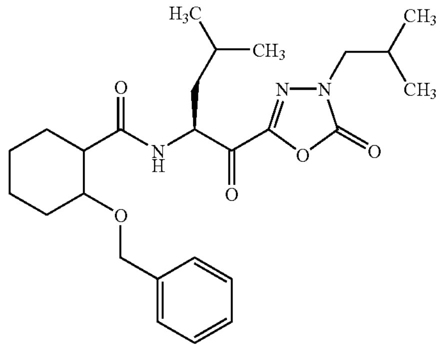

TLC: Rf 0.67 (n-hexane:ethyl acetate=3:2);

NMR ($CDCl_3$): δ 7.70–7.50 (m, 1H), 7.45–7.30 (m, 5H), 5.30–5.15 (m, 1H), 4.72 and 4.68 (each d, J=11.4 and 11.0 Hz, totally 1H), 4.55 and 4.46 (each d, J=11.0 and 11.4 Hz, totally 1H), 3.95–3.80 (m, 1H), 3.75–3.50 (m, 2H), 2.70–2.45 (m, 1H), 2.30–1.15 (m, 12H), 0.97, 0.88, 0.77 and 0.76 (each d, J=7.0, 6.2, 6.4 and 5.8 Hz, totally 12H).

REFERENCE EXAMPLE 12

(2S)-2-(N-t-butoxycarbonylamino)-4-methyl-1-(2-thioxo-1,3,4-oxadiazolin-5-yl)pentanol

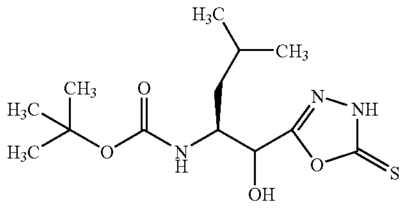

To an aqueous solution of the compound prepared in Reference Example 7 (3.0 g) in ethanol 95% aqueous solution (55 ml) were added potassium hydroxide (726 mg) and carbon disulfide (662 ml) and the mixture was stirred overnight at 90° C. The reaction solution was cooled down to room temperature and thereto was added cold 10% aqueous solution of citric acid and was extracted with ethyl acetate. The organic layer was washed with saturated aqueous solution of sodium chloride, dried over anhydrous sodium sulfate and was concentrated. The residue was purified by column chromatography on silica gel (ethyl acetate) and thereto was added 10% aqueous solution of citric acid, and was extracted with ethyl acetate and the organic layer was washed with saturated aqueous solution of sodium chloride, dried over anhydrous sodium sulfate and was concentrated to give the title compound (3.1 g) having the following physical data.

TLC: Rf 0.31 (n-hexane:ethyl acetate=1:1);

NMR ($CDCl_3$): δ 11.80 (br, 1H), 5.28 and 5.09 (each br, totally 1H), 5.00–4.40 (m, 2H), 4.20–3.90 (m, 1H), 2.00–1.20 (m, 3H), 1.47 and 1.43 (each s, totally 9H), 1.05–0.85 (m, 6H).

REFERENCE EXAMPLE 13

(2S)-2-(N-t-butoxycarbonylamino)-4-methyl-1-(5-(1-methylethylthio)-1,3,4-oxadiazol-2-yl)pentanol

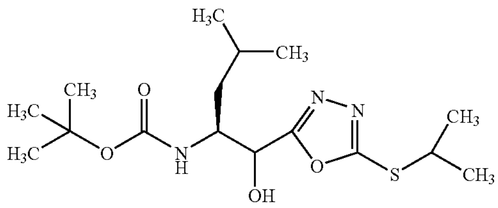

To a solution of the compound prepared in Reference Example 12 (634 mg) in N,N-dimethylformamide (4 ml) was added potassium carbonate (304 mg) at room temperature and the mixture was stirred for 3 hours. To the reaction mixture was added isopropyl bromide (207 ml) and the mixture was stirred for another 4 days. To the reaction mixture was added water and was extracted with ethyl acetate. The organic layer was washed with water and saturated aqueous solution of sodium chloride successively, dried over anhydrous sodium sulfate and was concentrated. The residue was purified by column chromatography on silica gel (n-hexane:ethyl acetate=4:1~1:1) to give the title compound (603 mg) having the following physical data.

TLC: Rf 0.59 (n-hexane:ethyl acetate=1:1);

NMR ($CDCl_3$): δ 4.95–4.75 (m, 2H), 4.61 (d, J=6.6 Hz, 0.5H), 4.20–3.80 (m, 2.5H), 1.80–1.20 (m, 3H), 1.49 (d, J=6.9 Hz, 3H), 1.48 (d, J=6.6 Hz, 3H), 1.45 and 1.38 (each s, totally 9H), 1.00–0.90 (m, 6H).

REFERENCE EXAMPLE 14

(2S)-2-amino-4-methyl-1-(5-(1-methylethylthio)-1,3,4-oxadiazol-2-yl)pentanol hydrochloride

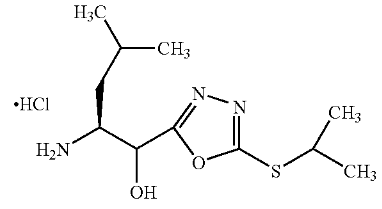

To a solution of the compound prepared in Reference Example 13 (291 mg) in ethyl acetate (3 ml) was added 4N hydrochloric acid-ethyl acetate (6 ml) at 0° C. and the mixture was stirred for 30 minutes. The reaction mixture was concentrated to give a crude product having the following physical data of the title compound.

TLC: Rf 0.33 (chloroform:methanol=9:1).

REFERENCE EXAMPLE 15

(2S)-N-[(2S)-4-methyl-1-(5-(1-methylethylthio)-1,3,4-oxadiazol-2-yl)-1-hydroxy-2-pentyl]-2-benzyloxycarbonylamino-4-methylpentanamide

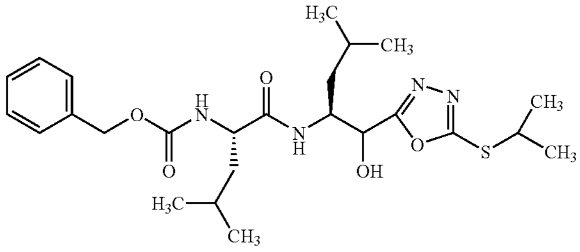

To a solution of the compound prepared in Reference Example 14 in N,N-dimethylformamide (2 ml) were added N-benzyloxycarbonyl-(L)-leucine (224 mg), 1-hydroxybenzotriazole (173 mg), 1-ethyl-3-(3-dimethylaminopropyl)carbodiimide hydrochloride (216 mg) and N-methyl morpholine(124 ml), and the mixture was stirred for 3.5 hours. Thereto was added N,N-dimethylpropanediamine and a cold 10% aqueous solution of citric acid, and was extracted with ethyl acetate. The organic layer was washed with a 10% aqueous solution of citric acid, a saturated aqueous solution of sodium bicarbonate, water and saturated aqueous solution of sodium chloride and dried over anhydrous sodium sulfate and was concentrated to give a crude product of the title compound (407 mg) having the following physical data.

TLC: Rf 0.51 (n-hexane:ethyl acetate=1:1);

NMR ($CDCl_3$): δ 7.40–7.25 (m, 5H), 6.85 and 6.66 (each d, J=9.2 and 8.0 Hz, totally 1H), 5.27 (d, J=7.4 Hz, 1H), 5.15–4.00 (m, 6H), 3.95–3.75 (m, 1H), 1.80–1.20 (m, 12H), 1.00–0.75 (m, 12H).

EXAMPLE 3

(2S)-N-[(2S)-4-methyl-1-(5-(1-methylethylthio)-1,3,4-oxadiazol-2-yl)-1-oxo-2-pentyl]-2-benzyloxycarbonylamino-4-methylpentanamide

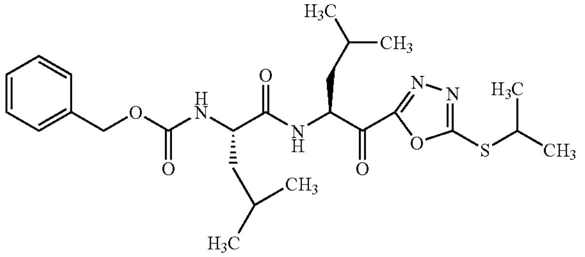

To a solution of the compound prepared in Reference Example 15 (390 mg) in methylene chloride (4 ml) was added (diacetoxyiodo)benzene (273 mg) and TEMPO reagent (2,2,6,6-tetramethyl-1-piperidinyloxy, free radical) (13 mg) at room temperature and the mixture was stirred overnight. To the reaction mixture was added a saturated aqueous solution of sodium bicarbonate and was extracted with chloroform. The organic layer was washed with saturated aqueous solution of sodium chloride, dried over anhydrous sodium sulfate and was concentrated. The residue was purified by column chromatography on silica gel to give the compound of the present invention (350 mg) having the following physical data.

TLC: Rf 0.56 (n-hexane:ethyl acetate=2:1);

NMR ($CDCl_3$): δ 7.35 (s, 5H), 6.63 (d, J=7.2 Hz, 1H), 5.50–5.35 (m, 1H), 5.20–5.05 (m, 3H), 4.30–4.10 (m, 1H), 4.04 (septet, J=6.6 Hz, 1H), 1.90–1.40 (m, 6H), 1.54 (d, J=6.6 Hz, 6H), 1.05–0.80 (m, 12H).

EXAMPLE 3 (1) TO EXAMPLE 3 (9)

By the same procedure as described in Reference Example 15→Example 3 using the compound prepared in Reference Example 14 or a corresponding amide derivative and N-benzyloxycarbonyl-(L)-leucine or a corresponding carboxylic acid derivative, the compounds of the present invention having the following physical data were obtained.

EXAMPLE 3 (1)

1-[(1R,2S)-2-benzoylaminocyclohexyl]-N-[(2S)-4-methyl-1-(5-(1-methylethylthio)-1,3,4-oxadiazol-2-yl) 1-oxo-2-pentyl]carboxamide

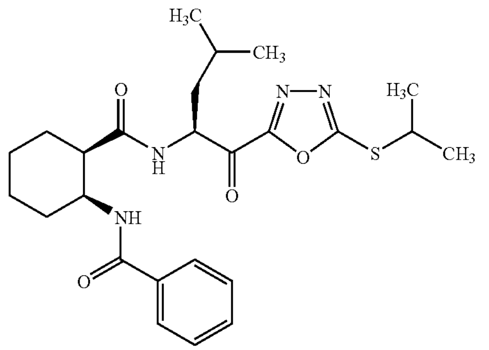

TLC: Rf 0.61 (n-hexane ethyl acetate=1:1);

NMR ($CDCl_3$): δ 7.77 (dd, J=7.9, 1.7 Hz, 2H), 7.55–7.35 (m, 3H), 7.20 (d, J=8.0 Hz, 1H), 6.29 (d, J=7.6 Hz, 1H), 5.50–5.35 (m, 1H), 4.40–4.25 (m, 1H), 4.04 (septet, J=6.8 Hz, 1H), 2.87 (q, J=5.0 Hz, 1H), 2.20–1.30 (m, 11H), 1.54 (d, J=6.8 Hz, 1H), 0.91 (d, J=6.2 Hz, 3H), 0.85 (d, J=6.2 Hz, 3H).

EXAMPLE 3 (2)

(2S)-N-[(2S)-4-methyl-1-(5-methylthio-1,3,4-oxadiazol-2-yl)-1-oxo-2-pentyl]-2-benzyloxycarbonylamino-4-methylpentanamide

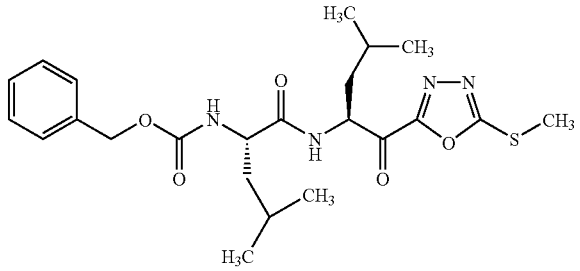

TLC: Rf 0.32 (hexane:ethyl acetate=2:1);

NMR ($CDCl_3$): δ 7.35 (s, 5H), 6.65 (d, J=8.4 Hz, 1H), 5.50–5.35 (m, 1H), 5.20–5.02 (m, 3H), 4.30–4.15 (m, 1H), 2.79 (s, 3H), 1.90–1.40 (m, 6H), 1.10–0.85 (m, 12H).

EXAMPLE 3 (3)

1-[(1R,2S)-2-benzoylaminocyclohexyl]-N-[(2S)-4-methyl-1-(5-methylthio-1,3,4-oxadiazol-2-yl)-1-oxo-2-pentyl]carboxamide

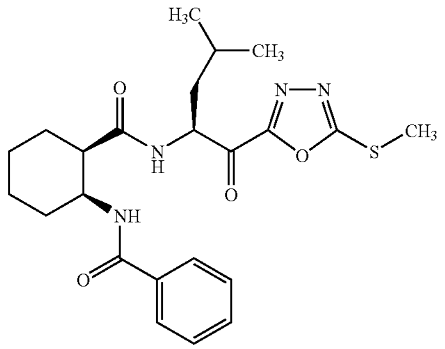

TLC: Rf 0.47 (n-hexane:ethyl acetate=1:1);

NMR ($CDCl_3$): δ 7.85–7.70 (m, 2H), 7.55–7.35 (m, 3H), 7.19 (d, J=8.4 Hz, 1H), 6.29 (d, J=7.6 Hz, 1H), 5.50–5.35 (m, 1H), 4.40–4.25 (m, 1H), 2.87 (q, J=5.0 Hz, 1H), 2.79 (s, 3H), 2.20–1.40 (m, 11H), 0.91 (d, J=6.2 Hz, 3H), 0.85 (d, J=6.2 Hz, 3H).

EXAMPLE 3 (4)

(2S)-N-[(2S)-1-(5-benzylthio-1,3,4-oxadiazol-2-yl)-4-methyl-1-oxo-2-pentyl]-2-benzyloxycarbonylamino-4-methylpentanamide

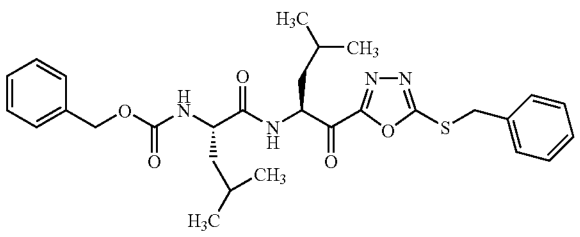

TLC: Rf 0.53 (hexane:ethyl acetate=2:1);

NMR ($CDCl_3$): δ 7.50–7.25 (m, 10H), 6.64 (d, J=7.4 Hz, 1H), 5.50–5.35 (m, 1H), 5.20–5.00 (m, 3H), 4.55 (s, 2H), 4.30–4.15 (m, 1H), 1.90–1.40 (m, 6H), 1.05–0.80 (m, 12H).

EXAMPLE 3 (5)

1-[(1R,2S)-2-benzoylaminocyclohexyl]-N-[(2S)-1-(5-benzylthio-1,3,4-oxadiazol-2-yl)-4-methyl-1-oxo-2-pentyl]carboxamide

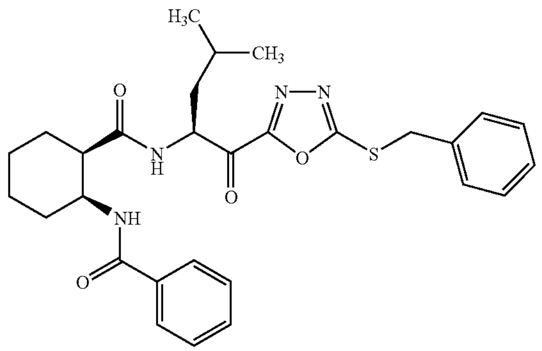

TLC: Rf 0.56 (n-hexane:ethyl acetate=1:1);

NMR ($CDCl_3$): δ 7.76 (dd, J=8.2, 1.8 Hz, 2H), 7.60–7.30 (m, 8H), 7.19 (d, J=8.0 Hz, 1H), 6.27 (d, J=7.6 Hz, 1H), 5.50–5.30 (m, 1H), 4.55 (s, 2H), 4.40–4.25 (m, 1H), 2.86 (q, J=5.0 Hz, 1H), 2.20–1.30 (m, 11H), 0.90 (d, J=6.2 Hz, 3H), 0.85 (d, J=6.2 Hz, 3H).

EXAMPLE 3 (6)

1-[(1R,2S)-2-benzoylaminocyclohexyl]-N-[(2S)-1-(5-methylthio-1,3,4-oxadiazol-2-yl)-1-oxo-2-hexyl] carboxamide

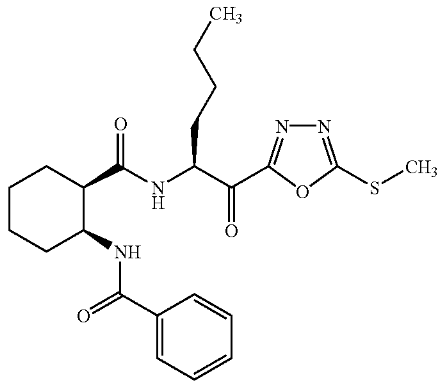

TLC: Rf 0.31 (n-hexane:ethyl acetate=1:1);

NMR ($CDCl_3$) δ 7.76 (d, J=6.9 Hz, 2H), 7.53–7.36 (m, 3H), 7.26 (brd, J=8.7 Hz, 1H), 6.39 (brd, J=8.4 Hz, 1H), 5.37 (ddd, J=8.4, 6.6, 4.8 Hz, 1H), 4.33 (m, 1H), 2.83 (m, 1H), 2.80 (s, 3H), 2.20–1.18 (m, 14H), 0.77 (t, J=6.9 Hz, 3H).

EXAMPLE 3 (7)

1-[(1R,2S)-2-benzoylaminocyclohexyl]-N-[(2S)-1-(5-methylthio-1,3,4-oxadiazol-2-yl)-1-oxo-4-phenyl-2-butyl]carboxamide

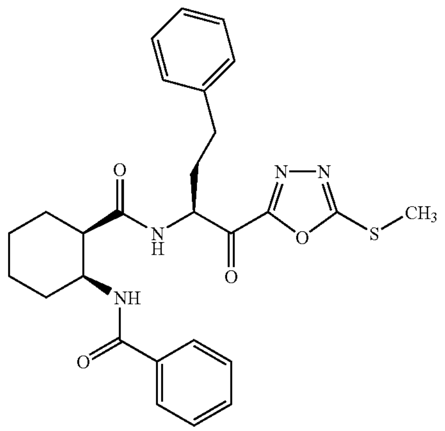

TLC: Rf 0.52 (n-hexane:ethyl acetate=2:3);

NMR ($CDCl_3$): δ 7.77 (dd, J=8.0, 1.5 Hz, 2H), 7.55–7.00 (m, 9H), 6.41 (d, J=7.2 Hz, 1H), 5.40 (brd, J=7.7, 4.4 Hz, 1H) 4.40–4.15 (m, 1H), 2.80–2.60 (m, 6H), 2.50–1.40 (m, 10H).

EXAMPLE 3 (8)

(2S)-N-[(2S)-1-(5-methylthio-1,3,4-oxadiazol-2-yl)-1-oxo-2-hexyl]-2-benzyloxycarbonylamino-4-methylpentanamide

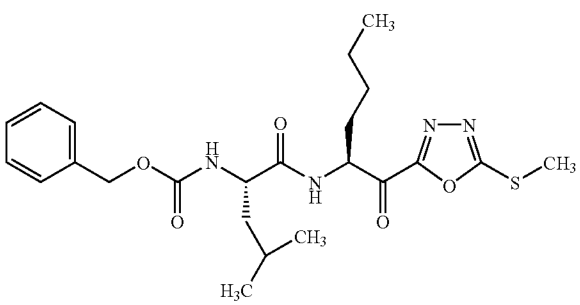

TLC: Rf 0.73 (n-hexane:ethyl acetate=1:1);

NMR ($CDCl_3$): δ 7.35 (s, 5H), 6.84 and 6.71 (each brd, J=6.6 Hz, totally 1H), 5.40 (m, 1H), 5.20–5.08 (m, 3H), 4.22 (m, 1H), 2.79 (s, 3H), 2.02 (m, 1H), 1.82–1.22 (m, 8H), 1.02–0.82 (m, 9H).

EXAMPLE 3 (9)

(2S)-N-[(2S)-1-(5-methylthio-1,3,4-oxadiazol-2-yl)-1-oxo-4-phenyl-2-butyl]-4-methyl-2-benzyloxycarbonylaminopentanamide

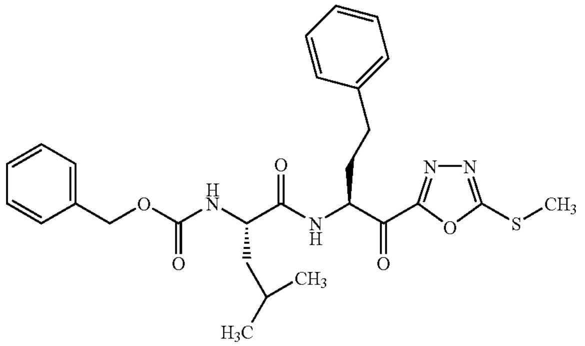

TLC: Rf 0.52 (n-hexane:ethyl acetate=1:1);

NMR ($CDCl_3$): δ 7.40–7.10 (m, 10H), 6.80 (brd, J=6.6 Hz, 1H), 5.42 (dt, J=7.8, 4.6 Hz, 1H), 5.20–5.00 (m, 3H), 4.30–4.10 (m, 1H), 2.78 (s, 3H), 2.71 (t, J=7.5 Hz, 2H), 2.55–2.00 (m, 2H), 1.80–1.30 (m, 3H), 1.00–0.80 (m, 6H).

EXAMPLE 4

1-[(1R,2S)-2-benzoylaminocyclohexyl]-N-[(2S)-1-(3-cyclopropylmethyl-2-oxo-1,3,4-oxadiazolin-5-yl)-4-methyl-1-oxo-2-pentyl]carboxamide

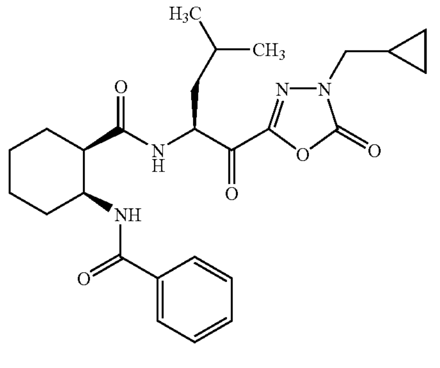

By the same procedure as described in Reference Example 11→Example 1 using (2S)-2-amino-4-methyl-1-[3-cyclopropylmethyl-2-oxo-(1,3,4-oxadiazolin)-5-yl]pentanol in place of the compound prepared in Reference Example 10 and (2S,1R)-2-(benzoylamino)cyclohexylcarboxylic acid in place of N-benzyloxycarbonyl-(L)-leucine, the compound of the present invention having the following physical data was obtained.

TLC: Rf 0.53 (n-hexane:ethyl acetate=1:1);

NMR ($CDCl_3$): δ 7.77 (dd, J=7.8, 1.6 Hz, 2H), 7.55–7.35 (m, 3H), 7.13 (d, J=8.0 Hz, 1H), 6.22 (d, J=7.8 Hz, 1H), 5.45–5.30 (m, 1H), 4.40–4.25 (m, 1H), 3.76 (dd, J=14.6, 7.1 Hz, 1H), 3.63 (dd, J=14.6, 7.3 Hz, 1H), 2.85 (q, J=5.1 Hz, 1H), 2.20–1.10 (m, 12H), 0.89 (d, J=5.8 Hz, 3H), 0.84 (d, J=6.2 Hz, 3H), 0.70–0.35 (m, 4H).

REFERENCE EXAMPLE 16

2-(N-t-butoxycarbonylamino)-4-methyl-1-[3-(2-trimethylsilylethoxymethyl)-2-oxo-1,3,4-oxadiazolin-5-yl]pentanol

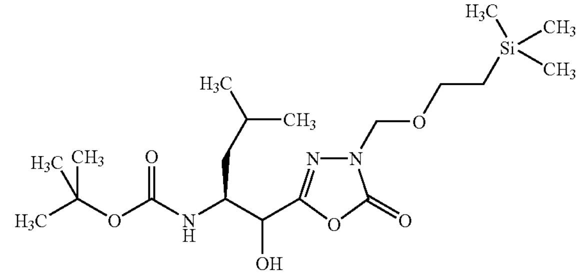

To a solution of the compound prepared in Reference Example 8 (6.02 g) in N,N-dimethylformamide (40 ml) was added potassium carbonate (3.04 g) at 0° C. and the mixture was stirred for 20 minutes. Thereto was added trimethylsilyl ethylchloromethyl ether (3.90 ml) and the mixture was stirred for 2 hours at room temperature. Thereto was added potassium carbonate (3.04 g) and trimethylsilyl ethylchloromethyl ether (3.90 ml), and the mixture was stirred for another 3 hours at room temperature. To the reaction mixture was added ice-water and was extracted with ethyl acetate. The organic layer was washed with water and saturated aqueous solution of sodium chloride successively, dried over anhydrous sulfate and was concentrated. The residue was purified by column chromatograohy on silica gel (chloroform:methanol=1:0 to 200:1) to give the title compound (2.94 g) having the following physical data.

TLC: Rf 0.74 (n-hexane:ethyl acetate=1:1);

NMR ($CDCl_3$): δ 5.15–5.00 (m, 2H), 4.80–4.50 (m, 3H), 4.20–3.80 (m, 1H), 3.67 (t, J=7.1 Hz, 2H), 1.80–1.20 (m, 3H), 1.46 and 1.42 (each s, totally 9H), 1.05–0.85 (m, 8H), 0.01 (s, 9H).

EXAMPLE 5 t-butoxy-N-[4-methyl-1-oxo-1-(3-(2-trimethylsilylethoxymethyl)-2-oxo-1,3,4-oxadiazolin-5-yl)-2-pentyl]carboxamide

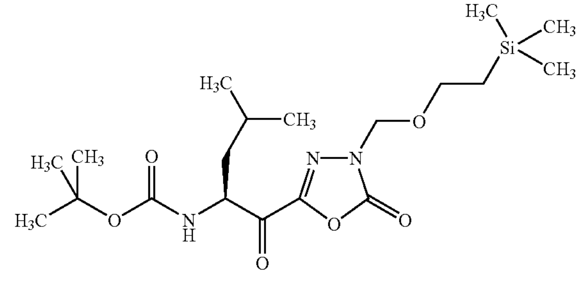

To a solution of oxalyl chloride (1.13 ml) in methylene chloride (26 ml) was added a solution of dimethylsulfoxide (1.84 ml) in methylene chloride (6 ml) over a period of 5 minutes at −70° C. and the mixture was stirred for 30 minutes. Thereto was added the compound prepared in Reference Example 16 (2.94 g) in methylene chloride (13 ml) over a period of 5 minutes and the mixture was stirred for 2 hours at −70° C. To the reaction mixture was added N-methyl morpholine (5.72 ml) and the mixture was allowed to warm to −20° C. To the reaction solution was added 10% aqueous solution of citric acid and was extracted with methylene chloride. The organic layer was washed with 10% aqueous solution of citric acid, water and saturated aqueous solution of sodium chloride successively, dried over anhydrous sodium sulfate and was concentrated. The residue was purified by column chromatography on silica gel (n-hexane:ethyl acetate=6:1) to give the compound of the present invention (1.17 g) having the following physical data.

TLC: Rf 0.57 (n-hexane:ethyl acetate=7:3);

NMR ($CDCl_3$): δ 5.23 (d, J=11.6 Hz, 1H), 5.18 (d, J=11.6 Hz, 1H), 5.15–4.90 (m, 2H), 3.75–3.65 (m, 2H), 1.90–1.40 (m, 3H), 1.43 (s, 9H), 1.02 (d, J=6.4 Hz, 3H), 1.02–0.90 (m, 2H), 0.97 (d, J=6.6 Hz, 3H), 0.02 (s, 9H).

EXAMPLE 6

(2S)-2-amino-4-methyl-1-[3-(2-trimethylsilylethoxymethyl)-2-oxo-1,3,4-oxadiazolin-5-yl]pentanone Hydrochloride

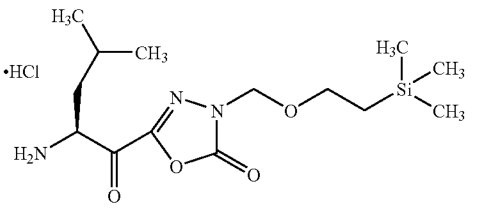

To a solution of the compound prepared in Example 5 (215 mg) in ethyl acetate (2 ml) was added 4N hydrochloric acid-ethyl acetate (4 ml) at 0° C. and the mixture was stirred for 1 hour. The reaction mixture was concentrated to give thr crude product of the compound of the present invention having the following physical data.

TLC: Rf 0.48 (chloroform:methanol=9:1).

EXAMPLE 7

1-[(1S,2R)-2-benzoylaminocyclohexyl]-N-[4-methyl-1-oxo-1-(3-(2-trimethylsilylethoxymethyl)-2-oxo-1,3,4-oxadiazolin-5-yl)-2-pentyl]carboxamide

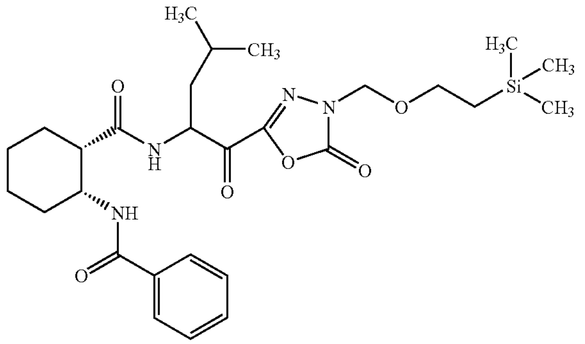

To a solution of the compound prepared in Example 6 in methylene chloride (2 ml) were added (+)-2-benzamidocyclohexanecarbonylchloride (which was prepared from (+)-2-benzamidocyclohexanecarboxylic acid ((2R,1S)-2-(benzoylamino)cyclohexanoic acid) (148 mg) and oxalyl chloride (61 μl)) and N-methyl morpholine (110 μl) and the mixture was stirred for 3 hours. To the reaction mixture was added N,N-dimethylpropandiamine and a cold 10% aqueous solution of citric acid and was extracted with ethytl acetate. The organic layer was washed with a 10% aqueous solution of citric acid, a saturated aqueous solution of sodium bicarbonate, water and saturated aqueous solution of sodium chloride successively, dried over anhydrous sodium sulfate and was concentrated. The residue was purified by column chromatography on silica gel (n-hexane:ethyl acetate=7:3) to give the compound of the present invention (120 mg) having the following physical data.

TLC: Rf 0.33 (n-hexane:ethyl acetate=7:3).

EXAMPLE 8

1-[(1S,2R)-2-benzoylaminocyclohexyl]-N-[1-(3-hydroxymethyl)-2-oxo-1,3,4-oxadiazolin-5-yl)-4-methyl-1-oxo-2-pentyl]carboxamide

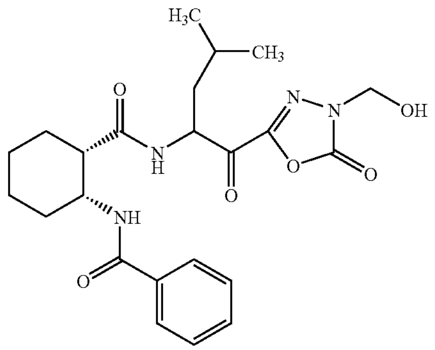

To a solution of the compound prepared in Example 7 (110 mg) in methylene chloride (4 ml) was added trifluoroacetic acid (2 ml) and the mixture was stirred for 2 hours at room temperature. The reaction mixture was concentrated and the residue was purified by column chromatography on silica gel (chloroform:methanol=100:1) to give the compound of the present invention (53 mg) having the following physical data.

TLC: Rf 0.46 (chloroform:methanol=9:1);

NMR ($CDCl_3$): δ 7.80–7.65 (m, 2H), 7.60–7.35 (m, 3H), 7.07 and 6.96 (each d, J=7.2 Hz, totally 1H), 6.55–6.30 (m, 1H), 5.31 and 5.25 (each d, J=11.4 Hz, totally 1H), 5.15 (d, J=11.4 Hz, 1H), 5.10–4.90 (m, 1H), 4.40–4.25 (m, 1H), 2.83 (q, J=4.9 Hz, 1H), 2.15–1.30 (m, 1H), 1.00–0.80 (m, 6H).

EXAMPLE 9 TO EXAMPLE 9 (5)

By the same procedure as described in Reference Example 11→Example 1 using an amine derivative corresponding to the compound prepared in Reference Example 10 and a carboxylic acid derivative corresponding to N-benzyloxycarbonyl-(L)-leucine, the compound of the present invention having the following physical data were obtained.

EXAMPLE 9

1-[(1S,2R)-2-benzoylaminocyclohexyl]-N-[(2S)-3-methyl-1-(3-methyl-2-oxo-1,3,4-oxadiazolin-5-yl)-1-oxo-2-butyl]carboxamide

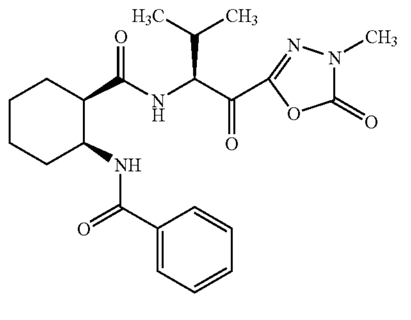

TLC: Rf 0.37 (chloroform:methanol=20:1);

NMR ($CDCl_3$): δ 7.77 (d, J=8.0 Hz, 2H), 7.51–7.39 (m, 3H), 7.17 (d, J=7.0 Hz, 1H), 6.23 (d, J=8.4 Hz, 1H), 5.24 (dd, J=8.4, 5.0 Hz, 1H), 4.36–4.30 (m, 1H), 3.55 (s, 3H), 2.84 (dt, J=5.0, 5.5 Hz, 1H), 2.27–2.18 (m, 1H), 2.10–2.03 and 1.95–1.80 (each m, totally 3H), 1.70–1.65 and 1.52–1.50 (each m, totally 5H), 0.95 (d, J=7.0 Hz, 3H), 0.83 (d, J=7.0 Hz, 3H).

EXAMPLE 9 (1)

1-[(1S,2R)-2-benzoylaminocyclohexyl]-N-[(2S)-1-(3-butyl-2-oxo-1,3,4-oxadiazolin-5-yl)-3-methyl-1-oxo-2-butyl]carboxamide

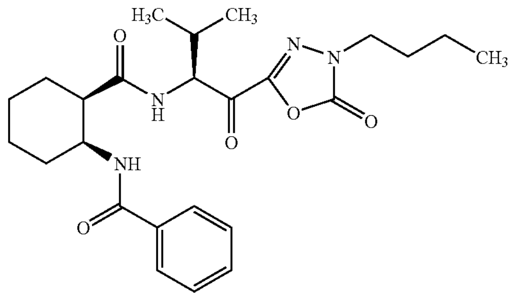

TLC: Rf 0.49 (chloroform:methanol=20:1);

NMR ($CDCl_3$): δ 7.76 (d, J=7.5 Hz, 2H), 7.51–7.39 (m, 3H), 7.19 (d, J=8.0 Hz, 1H), 6.24 (d, J=8.5 Hz, 1H), 5.27 (dd, J=8.5, 5.0 Hz, 1H), 4.38–4.31 (m, 1H), 3.84 (t, J=7.5 Hz, 2H), 2.84 (dt, J=6.0, 4.7 Hz, 1H), 2.28–2.18 (m, 1H), 2.10–2.04 and 1.95–1.66 (each m, totally 5H), 1.54–1.32 (m, 7H), 0.97 (t, J=7.5 Hz, 3H), 0.94 (d, J=7.0 Hz, 3H), 0.82 (d, J=7.0 Hz, 3H).

EXAMPLE 9 (2)

1-[(1S,2R)-2-benzoylaminocyclohexyl]-N-[(2S)-1-(3-(2-methylpropyl)-2-oxo-1,3,4-oxadiazolin-5-yl)-1-oxo-2-hexyl]carboxamide

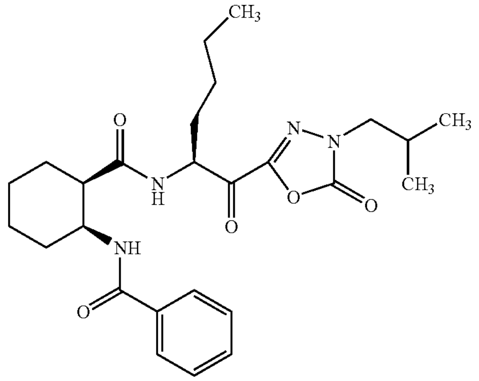

TLC: Rf 0.49 (n-hexane:ethyl acetate=1:1);

NMR ($CDCl_3$): δ 7.79 (m, 2H), 7.52–7.38 (m, 3H), 7.19 (brd, J=7.8 Hz, 1H), 6.28 (brd, J=7.5 Hz, 1H), 5.27 (m, 1H), 4.33 (m, 1H), 3.67 (dd, J=13.8, 7.2 Hz, 1H), 3.62 (dd, J=13.8, 7.2 Hz, 1H), 2.83 (m, 1H), 2.22–1.05 (m, 15H), 0.98 (m, 6H), 0.77 (m, 3H).

EXAMPLE 9 (3)

1-[(1S,2R)-2-benzoylaminocyclohexyl]-N-[(2S)-1-(3-(2-methylpropyl)-2-oxo-1,3,4-oxadiazolin-5-yl)-1-oxo-4-phenyl-2-butyl]carboxamide

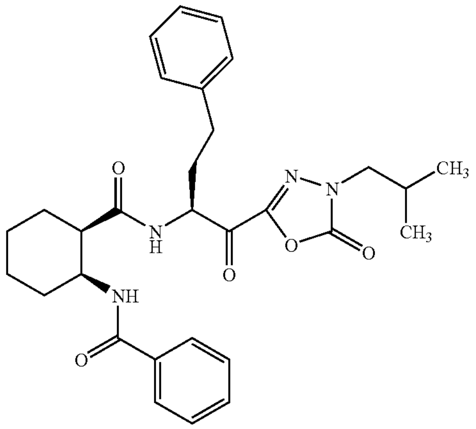

TLC: Rf 0.41 (n-hexane:ethyl acetate=1:1);

NMR ($CDCl_3$): δ 7.77 (dd, J=7.8, 1.6 Hz, 2H), 7.55–7.30 (m, 3H), 7.30–7.10 (m, 4H), 7.10–7.00 (m, 2H), 6.34 (d, J=7.4 Hz, 1H), 5.31 (dt, J=4.4, 8.0 Hz, 1H), 4.45–4.25 (m, 1H), 3.61 (d, J=7.2 Hz, 2H), 2.76 (q, J=4.9 Hz), 2.63 (t, J=7.3 Hz, 2H), 2.15–1.30 (m, 11H), 0.97 (d, J=7.0 Hz, 6H).

EXAMPLE 9 (4)

(2S)-N-[(2S)-1(3-(2-methylpropyl)-2-oxo-1,3,4-oxadiazolin-5-yl)-1-oxo-2-hexyl]-2-benzyloxycarbonylamino-4-methylpentanamide

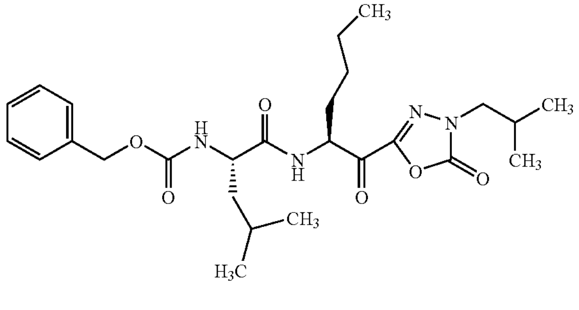

TLC: Rf 0.32 (n-hexane:ethyl acetate=3:1);

NMR ($CDCl_3$) δ 7.35 (s, 5H), 6.58 (brd, J=7.8 Hz, 1H), 5.30 (dt, J=4.8, 7.8 Hz, 1H), 5.13 (m, 3H), 4.22 (m, 1H), 3.68 (dd, J=13.8, 7.2 Hz, 1H), 3.63 (dd, J=13.8, 7.2 Hz, 1H), 2.19 (m, 1H), 2.00–1.23 (m, 9H), 1.00–0.85 (m, 15H).

EXAMPLE 9 (5)

(2S)-N-[(2S)-1-(3-(2-methylpropyl)-2-oxo-1,3,4-oxadiazolin-5-yl)-1-oxo-4-phenyl-2-butyl]-2-benzyloxycarbonylamino-4-methylpentanamide

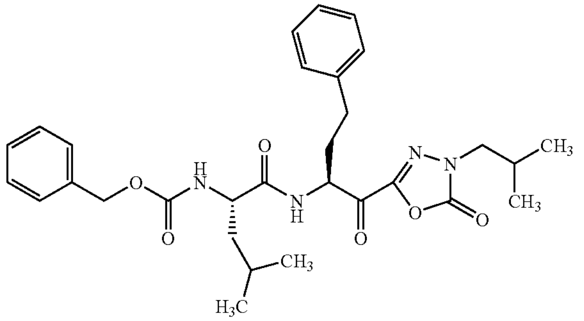

TLC: Rf 0.43 (n-hexane:ethyl acetate=2:1);

NMR ($CDCl_3$): δ 7.40–7.10 (m, 10H), 6.65 (d, J=5.8 Hz, 1H), 5.34 (dt, J=4.4, 8.0 Hz, 1H), 5.12 (s, 2H), 5.04 (d, J=7.4 Hz, 1H), 4.30–4.10 (m, 1H), 2.68 (t, J=7.3 Hz, 2H), 2.40–1.90 (m, 3H), 1.80–1.30 (m, 3H), 1.05–0.80 (m, 12H).

EXAMPLE 10 TO EXAMPLE 10 (104)

By the same procedure as described in Reference Example 11→Example 1 using the compound prepared in Reference Example 10 or a corresponding amine derivative and a corresponding carboxylic acid derivative in place of N-benzyloxycarbonyl-(L)-leucine, and optionally converting the product to hydrochloride by known methods, the compound of the present invention having the following physical data were obtained.

EXAMPLE 10

1-[(1R,2S)-2-(4-nitrobenzoylamino)cyclohexyl]-N-[4-methyl-1-(3-(2-methylpropyl)-2-oxo-1,3,4-oxadiazolin-5-yl)-1-oxo-2-pentyl]carboxamide

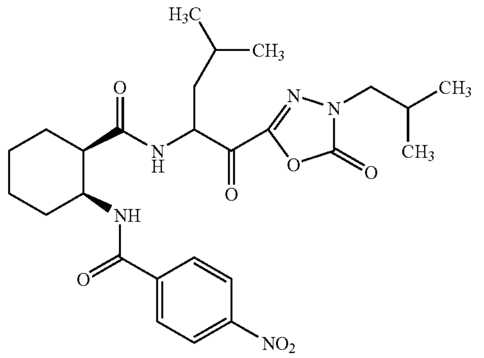

TLC: Rf 0.48 (n-hexane:ethyl acetate=1:1);

NMR ($CDCl_3$): δ 8.27 (d, J=9.0 Hz, 2H), 7.97 and 7.94 (each d, J=9.0 Hz, totally 2H), 7.60 and 7.46 (each d, J=7.5 Hz, totally 1H), 6.13 (brd, J=7.5 Hz, 1H), 5.41–5.26 (m, 1H), 4.30 (m, 1H), 3.66 (m, 2H), 2.83 (m, 1H), 2.30–1.40 (m, 12H), 1.10–0.90 (m, 12H).

EXAMPLE 10 (1)

1-[(1R,2S)-2-(4-methoxybenzoylamino)cyclohexyl]-N-[(2S)-4-methyl-1-(3-(2-methylpropyl)-2-oxo-1,3,4-oxadiazolin-5-yl)-1-oxo-2-pentyl]carboxamide

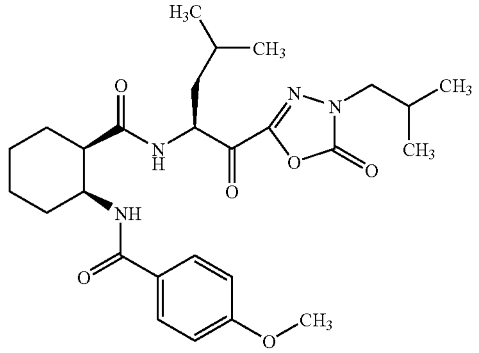

TLC: Rf 0.35 (n-hexane ethyl acetate=1:1);

NMR ($CDCl_3$): δ 7.73 (d, J=8.7 Hz, 2H), 7.01 (brd, J=7.8 Hz, 1H), 6.92 (d, J=8.7 Hz, 2H), 6.24 (brd, J=7.8 Hz, 1H), 5.33 (m, 1H), 4.33 (m, 1H), 3.85 (s, 3H), 3.68 and 3.61 (each dd, J=14.1, 7.2 Hz, each 1H), 2.81 (m, 1H), 2.23–1.40 (m, 12H), 0.98, 0.87 and 0.82 (each d, J=6.6 Hz, totally 12H).

EXAMPLE 10 (2)

1-[(1R,2S)-2-(naphthalen-2-ylcarbonylamino)cyclohexyl]-N-[(2S)-4-methyl-1-(3-(2-methylpropyl)-2-oxo-1,3,4-oxadiazolin-5-yl)-1-oxo-2-pentyl]carboxamide

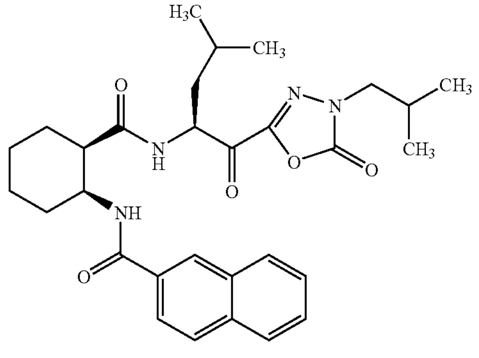

TLC: Rf 0.49 (n-hexane:ethyl acetate=1:1);

NMR ($CDCl_3$): δ 8.25 (s, 1H), 8.00–7.80 (m, 4H), 7.60–7.50 (m, 2H), 7.23 (m, 1H), 6.18 (brd, J=8.1 Hz, 1H), 5.38 (m, 1H), 4.40 (m, 1H), 3.67 and 3.61 (each dd, J=13.8, 7.2 Hz, each 1H), 2.90 (m, 1H), 2.22–1.40 (m, 12H), 0.97, 0.84 and 0.80 (each d, J=6.6 Hz, totally 12H).

EXAMPLE 10 (3)

1-[(1R,2S)-2-(quinoxalin-2-ylcarbonylamino)cyclohexyl]-N-[(2S)-4-methyl-1-oxo-1-(3-(2-methylpropyl)-2-oxo-1,3,4-oxadiazolin-5-yl)-2-pentyl]carboxamide

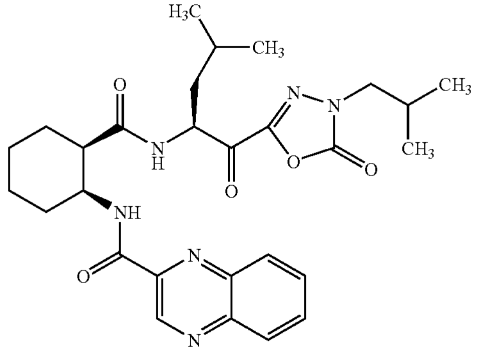

TLC: Rf 0.41 (n-hexane:ethyl acetate=1:1);

NMR ($CDCl_3$): δ 9.65 (s, 1H), 8.58 (brd, J=8.4 Hz, 1H), 8.23–8.10 (m, 2H), 7.90–7.80 (m, 2H), 6.20 (brd, J=8.1 Hz, 1H), 5.31 (m, 1H), 4.43 (m, 1H), 3.66 and 3.59 (each dd, J=14.1, 7.2 Hz, each 1H), 2.90 (m, 1H), 2.22–1.40 (m, 12H), 0.99, 0.76 and 0.68 (each d, J=6.3 Hz, totally 12H).

EXAMPLE 10 (4)

1-[(1R,2S)-2-(4-chlorobenzoylamino)cyclohexyl]-N-[4-methyl-1-oxo-1-(3-(2-methylpropyl)-2-oxo-1,3,4-oxadiazolin-5-yl)-2-pentyl]carboxamide

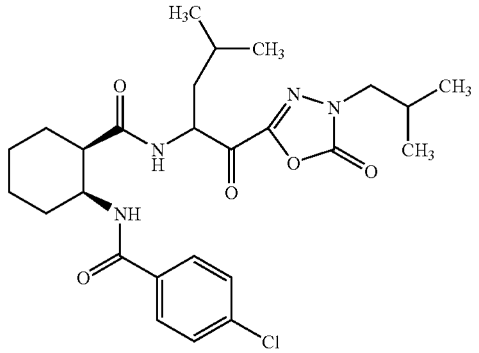

TLC: Rf 0.47 (n-hexane:ethyl acetate=1:1);

NMR ($CDCl_3$) δ 7.74 and 7.71 (each d, J=8.4 Hz, totally 2H), 7.40 (d, J=8.4 Hz, 2H), 7.23 and 7.18 (each brd, J=8.0 Hz, totally 1H), 6.20 and 6.18 (each brd, J=7.8 Hz, totally 1H), 5.40–5.23 (m, 1H), 4.30 (m, 1H), 3.65 (m, 2H), 2.82 (m, 1H), 2.23–1.40 (m, 12H), 1.05–0.84 (m, 12H).

EXAMPLE 10 (5)

1-[(1R,2S)-2-(benzo[b]thiophen-2-ylcarbonylamino) cyclohexyl]-N-[(2S)-4-methyl-1-oxo-1-(1-(2-methylpropyl)-2-oxo-1,3,4-oxadiazolin-5-yl)-2-pentyl] carboxamide

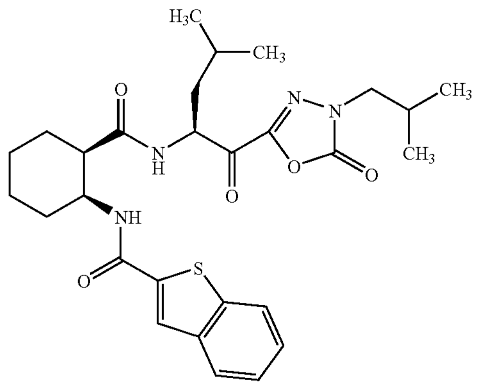

TLC: Rf 0.55 (n-hexane:ethyl acetate=1:1);

NMR ($CDCl_3$): δ 7.88–7.79 (m, 2H), 7.73 (s, 1H), 7.50–7.35 (m, 2H), 7.24 (m, 1H), 6.30 (brd, J=8.4 Hz, 1H), 5.38 (m, 1H), 4.40–4.30 (m, 1H), 3.68 and 3.61 (each dd, J=14.1, 7.2 Hz, each 1H), 2.88 (m, 1H), 2.22–1.40 (m, 12H), 0.99, 0.76 and 0.68 (each d, J=6.3 Hz, totally 12H).

EXAMPLE 10 (6)

1-[(1R,2S)-2-(4-fluorobenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

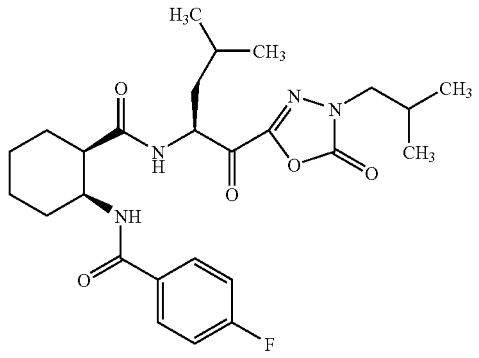

TLC: Rf 0.50 (n-hexane:ethyl acetate=1:1);

NMR ($CDCl_3$): δ 7.77 (dd, J=9.0, 5.4 Hz, 2H), 7.18 (brd, J=8.1 Hz, 1H), 7.10 (t, J=9.0 Hz, 2H), 6.19 (brd, J=7.8 Hz, 1H), 5.30 (m, 1H), 4.30 (m, 1H), 3.68 and 3.62 (each dd, J=13.87.2 Hz, each 1H), 2.82 (m, 1H), 2.25–1.40 (m, 12H), 0.98, 0.87 and 0.84 (each d, J=6.0 Hz, totally 12H).

EXAMPLE 10 (7)

1-[(1R,2S)-2-(4-t-butylbenzoylamino)cyclohexyl]-N-[(2S)-4-methyl-1-oxo-1-(1-(2-methylpropyl)-2-oxo-1,3,4-oxadiazolin-5-yl)-2-pentyl]carboxamide

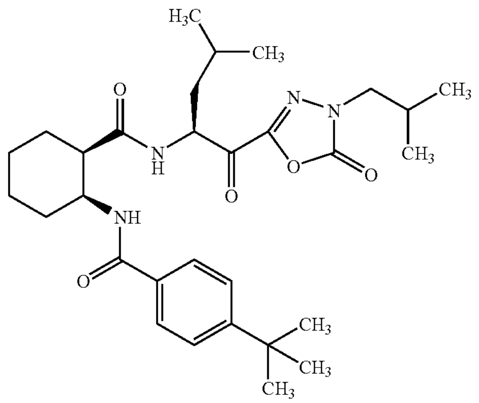

TLC: Rf 0.54 (n-hexane:ethyl acetate=1:1);

NMR ($CDCl_3$): δ 7.68 (d, J=8.7 Hz, 2H), 7.42 (d, J=8.7 Hz, 2H), 7.05 (brd, J=8.4 Hz, 1H), 6.21 (brd, J=7.5 Hz, 1H), 5.33 (m, 1H), 4.31 (m, 1H), 3.67 and 3.60 (each dd, J=13.8, 7.2 Hz, each 1H), 2.83 (m, 1H), 2.23–1.40 (m, 12H), 1.32 (s, 9H), 0.97, 0.86 and 0.81 (each d, J=6.0 Hz, totally 12H).

EXAMPLE 10 (8)

1-[(1R,2S)-2-(pyridin-2-ylcarbonylamino)cyclohexyl]-N-[4-methyl-1-oxo-1-(3-(2-methylpropyl)-2-oxo-1,3,4-oxadiazolin-5-yl)-2-pentyl]carboxamide

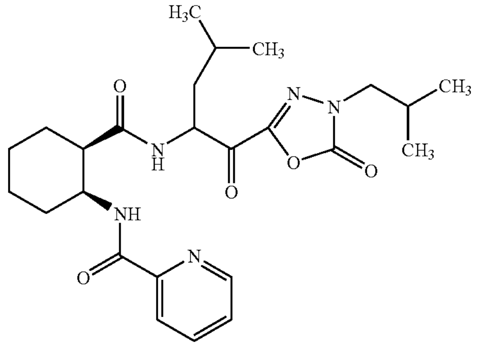

TLC: Rf 0.34 (n-hexane:ethyl acetate=1:1);

NMR ($CDCl_3$): δ 8.70–8.50 (m, 2H), 8.16 (m, 1H), 7.82 (m, 1H) 7.43 (m, 1H), 6.63 and 6.33 (each brd, J=7.5 Hz, totally 1H), 5.29 (m, 1H), 4.45 (m, 1H), 3.62 (m, 2H), 2.80 (m, 1H), 2.23–1.40 (m, 12H), 1.05–0.90 (m, 9H), 0.92 and 0.78 (each d, J=6.3 Hz, totally 3H).

EXAMPLE 10 (9)

1-[(1R,2S)-2-(naphthalen-1-ylmethylcarbonylamino)cyclohexyl]-N-[(2S)-4-methyl-1-oxo-1-(3-(2-methylpropyl)-2-oxo-1,3,4-oxadiazolin-5-yl)-2-pentyl]carboxamide

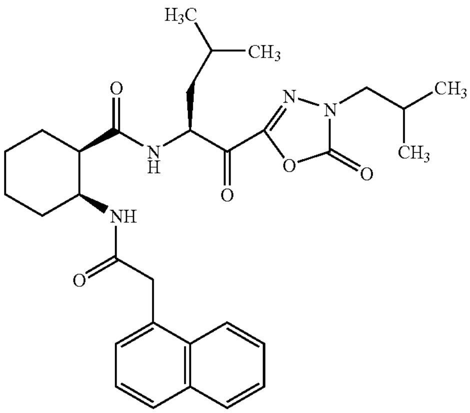

TLC: Rf 0.39 (n-hexane:ethyl acetate=1:1);

NMR ($CDCl_3$): δ 8.00–7.80 (m, 3H), 7.58–7.35 (m, 4H), 6.25 (brd, J=8.1 Hz, 1H), 6.10 (brd, J=7.2 Hz, 1H), 5.15 (m, 1H), 4.18 (m, 1H), 4.03 and 3.92 (each d, J=15.9 Hz, each 1H), 3.70 and 3.63 (each dd, J=13.8, 7.2 Hz, each 1H), 2.50 (m, 1H), 2.20 (m, 1H), 1.80–0.90 (m, 23H).

EXAMPLE 10 (10)

1-[(1R,2S)-2-(2-fluorobenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

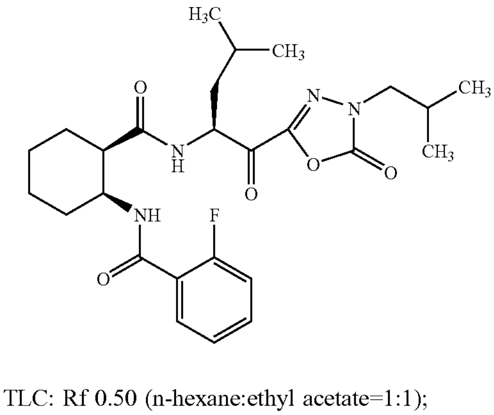

TLC: Rf 0.50 (n-hexane:ethyl acetate=1:1);

NMR ($CDCl_3$): δ 8.04 (dt, J=1.8, 7.8 Hz, 1H), 7.52–7.40 (m, 2H), 7.25 (brd, J=7.8 Hz, 1H), 7.11 (dd, J=11.7, 7.8 Hz, 1H), 6.24 (brd, J=7.5 Hz, 1H), 5.32 (m, 1H), 4.43 (m, 1H), 3.67 and 3.60 (each dd, J=13.5, 6.9 Hz, each 1H), 2.83 (m, 1H), 2.24–1.40 (m, 12H), 0.97, 0.90 and 0.84 (each d, J=6.6 Hz, totally 12H).

EXAMPLE 10 (11)

1-[(1R,2S)-2-(4-phenylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

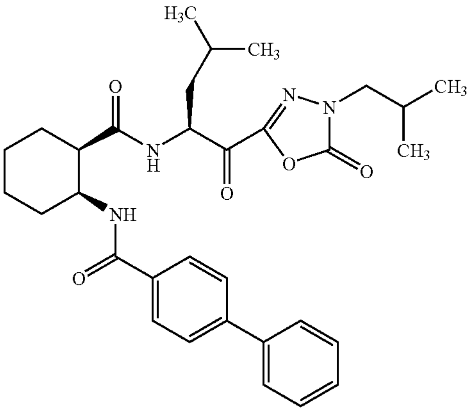

TLC: Rf 0.50 (n-hexane:ethyl acetate=1:1);

NMR ($CDCl_3$): δ 7.84 (d, J=8.7 Hz, 2H), 7.70–7.55 (m, 4H), 7.50–7.30 (m, 3H), 7.18 (brd, J=7.8 Hz, 1H), 6.18 (brd, J=7.5 Hz, 1H), 5.38 (m, 1H), 4.38 (m, 1H), 3.68 and 3.61 (each dd, J=13.5, 6.9 Hz, each 1H), 2.83 (m, 1H), 2.24–1.42 (m, 12H), 0.98, 0.86 and 0.84 (each d, J=6.3 Hz, totally 12H).

EXAMPLE 10 (12)

1-[(1R,2S)-2-(2-chloropyridin-5-ylcarbonylamino)cyclohexyl]-N-[(2S)-4-methyl-1-oxo-1-(3-(2-methylpropyl)-2-oxo-1,3,4-oxadiazolin-5-yl)-2-pentyl]carboxamide

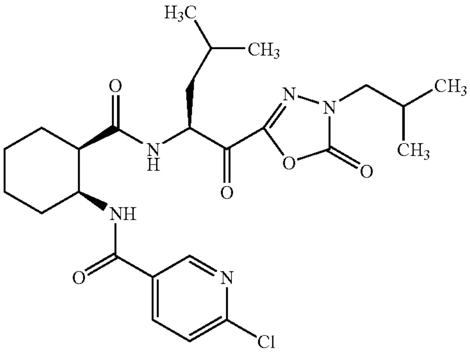

TLC: Rf 0.45 (n-hexane:ethyl acetate=1:1);

NMR ($CDCl_3$): δ 8.78 (d, J=2.7 Hz, 1H), 8.04 (dd, J=8.4, 2.7 Hz, 1H), 7.55 (brd, J=8.1 Hz, 1H), 7.40 (d, J=8.4 Hz, 1H), 6.10 (brd, J=7.5 Hz, 1H), 5.38 (m, 1H), 4.28 (m, 1H), 3.70 and 3.64 (each dd, J=13.5, 6.9 Hz, each 1H), 2.82 (m, 1H), 2.20 (m, 1H), 2.10–1.40 (m, 11H), 1.00, 0.93 and 0.90 (each d, J=6.3 Hz, totally 12H).

EXAMPLE 10 (13)

1-[(1R,2S)-2-(2-methylthiopyridin-3-ylcarbonylamino)cyclohexyl]-N-[(2S)-4-methyl-1-oxo-1-(3-(2-methylpropyl)-2-oxo-1,3,4-oxadiazolin-5-yl)-2-pentyl]carboxamide

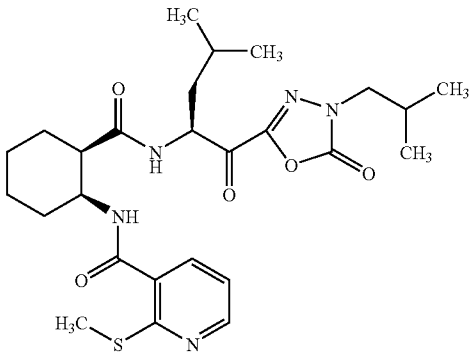

TLC: Rf 0.40 (n-hexane:ethyl acetate=1:1);

NMR ($CDCl_3$): δ 8.50 (dd, J=7.2, 1.5 Hz, 1H), 7.74 (dd, J=7.5, 1.5 Hz, 1H), 7.14 (brd, J=8.1 Hz, 1H), 7.03 (dd, J=7.5, 7.2 Hz, 1H), 6.17 (brd, J=7.5 Hz, 1H), 5.30 (m, 1H), 4.39 (m, 1H), 3.67 and 3.60 (each dd, J=13.8, 7.2 Hz, each 1H), 2.82 (m, 1H), 2.56 (s, 3H), 2.23–1.40 (m, 12H), 1.13, 0.97, 0.90, and 0.88 (each d, J=6.3 Hz, each 3H).

EXAMPLE 10 (14)

1-[(1R,2S)-2-(4-cyanobenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

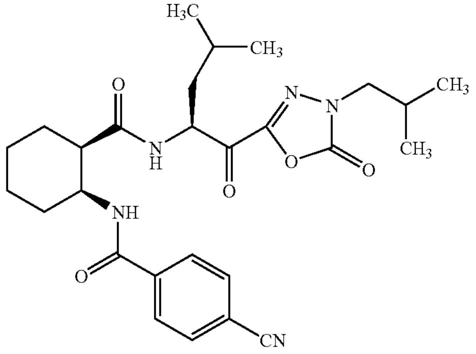

TLC: Rf 0.48 (n-hexane ethyl acetate=1:1);

NMR ($CDCl_3$): δ 7.87 (d, J=8.6 Hz, 2H), 7.73 (d, J=8.6 Hz, 2H), 7.53 (brd, J=8.0 Hz, 1H), 6.12 (brd, J=7.5 Hz, 1H), 5.38 (m, 1H), 4.30 (m, 1H), 3.71 and 3.62 (each dd, J=14.0, 7.4 Hz, each 1H), 2.82 (m, 1H), 2.30–1.40 (m, 12H), 1.04–0.88 (m, 12H).

EXAMPLE 10 (15)

1-[(1R,2S)-2-(4-dimethylaminobenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

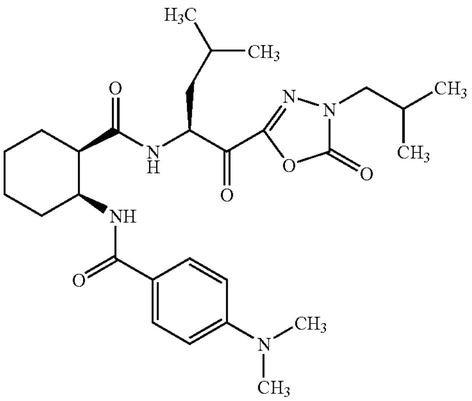

TLC: Rf 0.57 (chloroform methanol=9:1);

NMR ($CDCl_3$): δ 7.65 (d, J=9.0 Hz, 2H), 6.81 (brd, J=7.8 Hz, 1H), 6.66 (d, J=9.0 Hz, 2H), 6.32 (brd, J=7.2 Hz, 1H), 5.30 (m, 1H), 4.38 (m, 1H), 3.67 and 3.60 (each dd, J=13.8, 7.2 Hz, each 1H), 3.02 (s, 6H), 2.82 (m, 1H), 2.23–2.00 (m, 2H), 1.88 (m, 2H), 1.80–1.40 (m, 8H), 0.98 (d, J=6.9 Hz, 6H), 0.86 and 0.82 (each d, J=5.7 Hz, each 3H).

EXAMPLE 10 (16)

[(2S)-N-phenethylpyrrolidin-2-yl]-N-[(2S)-4-methyl-1-oxo-1-(3-(2-methylpropyl)-2-oxo-1,3,4-oxadiazolin-5-yl)-2-pentyl]carboxamide

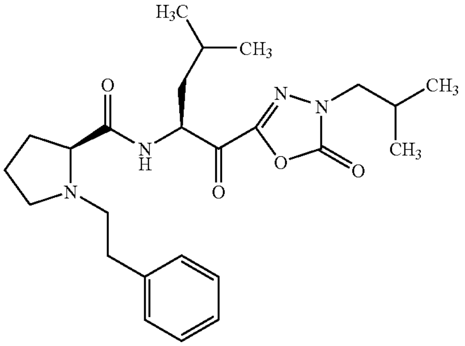

TLC: Rf 0.52 (HPTLC, chloroform:methanol=100:1);

NMR ($CDCl_3$): δ 7.48 and 7.38 (each brd, J=8.4 Hz, totally 1H), 7.35–7.17 (m, 5H), 5.23–5.12 (m, 1H), 3.66 and 3.60 (each dd, J=13.8, 7.2 Hz, each 1H), 3.43–3.32 (m, 1H), 3.15–2.99 (m, 1H), 2.93–2.65 (m, 4H), 2.45–2.31 (m, 1H), 2.30–2.10 (m, 2H), 1.90–1.62 (m, 4H), 1.62–1.10 (m, 2H), 1.05–0.90 (m, 12H).

EXAMPLE 10 (17)

[(2S)-N-(3-phenylpropyl)pyrrolidin-2-yl]-N-[1-oxo-1-(3-(2-methylpropyl)-2-oxo-1,3,4-oxadiazolin-5-yl)-2-pentyl]carboxamide

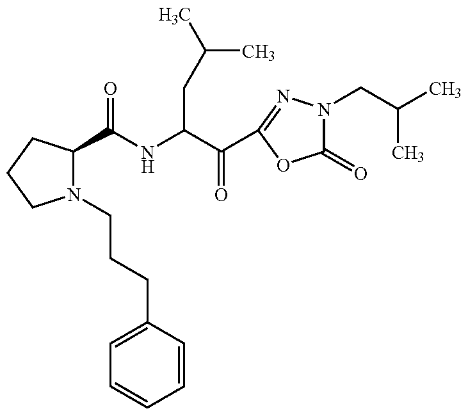

TLC: Rf 0.48 and 0.40 (HPTLC, chloroform:methanol=100:1);

NMR ($CDCl_3$): δ 7.93 and 7.82 (each brd, J=9.3 Hz, totally 1H), 7.32–7.12 (m, 5H), 5.42–5.25 (m, 1H), 3.72–3.53 (m, 2H), 3.25–3.19 (m, 1H), 3.08–3.04 (m, 1H), 2.82–2.42 (m, 4H), 2.40–2.13 (m, 1H), 2.13–2.08 (m, 2H), 1.90–1.42 (m, 8H), 1.05–0.83 (m, 12H).

EXAMPLE 10 (18)

[(2R)-N-phenethylpyrrolidin-2-yl]-N-[(2S)-4-methyl-1-oxo-1-(3-(2-methylpropyl)-2-oxo-1,3,4-oxadiazolin-5-yl)-2-pentyl]carboxamide

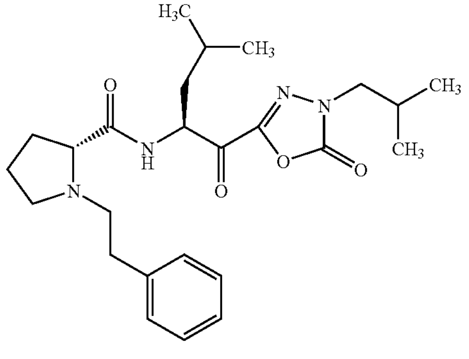

TLC: Rf 0.56 (HPTLC, chloroform:methanol=100:1);

NMR ($CDCl_3$): δ 7.53 and 7.37 (each brd, J=7.8 Hz, totally 1H), 7.27–7.15 (m, 5H), 5.23–5.13 (m, 1H), 3.66 and 3.60 (each dd, J=13.8, 7.2 Hz, each 1H), 3.43–3.32 (m, 1H), 3.15–2.99 (m, 1H), 2.95–2.65 (m, 4H), 2.50–2.32 (m, 1H), 2.30–2.10 (m, 2H), 1.90–1.73 (m, 4H), 1.60–1.10 (m, 2H), 1.05–0.90 (m, 12H).

EXAMPLE 10 (19)

1-[(1R,2S)-2-(4-dimethylaminomethylbenzoylamino)cyclohexyl]-N-[4-methyl-1-oxo-1-(3-(2-methylpropyl)-2-oxo-1,3,4-oxadiazolin-5-yl)-2-pentyl]carboxamide

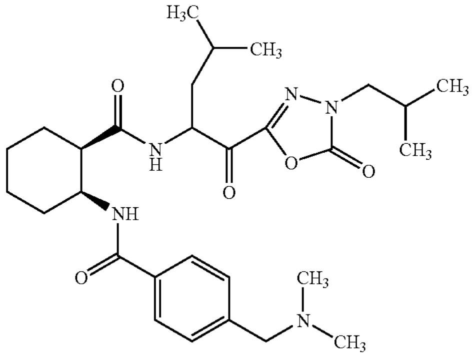

TLC: Rf 0.49 and 0.40 (chloroform:methanol=9:1);

NMR ($CDCl_3$): δ 7.76 and 7.72 (each d, J=8.0 Hz, totally 2H), 7.37 and 7.36 (each d, J=8.0 Hz, totally 2H), 7.20–7.05 (m, 1H), 6.34 and 6.26 (each d, J=7.0 and 7.6 Hz, totally 1H), 5.40–5.20 (m, 1H), 4.45–4.25 (m, 1H), 3.75–3.50 (m, 2H), 3.46 (s, 2H), 2.90–2.80 (m, 1H), 2.24 (s, 6H), 2.20–1.35 (m, 12H), 1.05–0.80 (m, 12H).

EXAMPLE 10 (20)

piperidino-N-[(2S)-4-methyl-1-oxo-1-(3-(2-methylpropyl)-2-oxo-1,3,4-oxadiazolin-5-yl)-2-pentyl]carboxamide

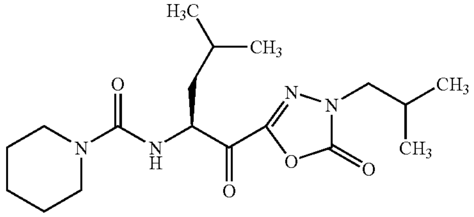

TLC: Rf 0.50 (n-hexane:ethyl acetate=1:1);

NMR ($CDCl_3$): δ 5.23 (ddd, J=9.6, 7.8 and 4.2 Hz, 1H), 4.82 (d, J=7.8 Hz, 1H), 3.68 and 3.61 (each dd, J=13.8 and 7.2 Hz, each 1H), 3.43–3.26 (m, 4H), 2.27–2.08 (m, 1H), 1.88–1.38 (m, 9H), 1.03–0.95 (m, 12H).

EXAMPLE 10 (21)

[(2R)-2-phenylaminocarbonylpiperidino]-N-[(2S)-4-methyl-1-oxo-1-(3-(2-methylpropyl)-2-oxo-1,3,4-oxadiazolin-5-yl)-2-pentyl]carboxamide

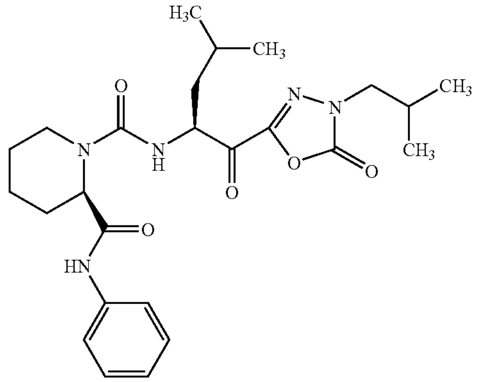

TLC: Rf 0.56 (n-hexane:ethyl acetate=1:1);

NMR ($CDCl_3$): δ 8.05 (brs, 1H), 7.54 (d, J=7.2 Hz, 2H), 7.32 (t, J=7.2 Hz, 2H), 7.09 (t, J=7.2 Hz, 1H), 5.25 (ddd, J=9.9, 7.2 and 3.9 Hz, 1H), 5.07–4.96 (m, 2H), 3.74–3.54 (m, 3H), 3.15 (td, J=12.6 and 2.4 Hz, 1H), 2.45–2.32 (m, 1H), 2.26–2.09 (m, 1H), 1.90–1.42 (m, 8H), 1.10–0.92 (m, 12H).

EXAMPLE 10 (22)

1-[(1R,2S)-2-benzoylaminocyclopentyl]-N-[(2S)-4-methyl-1-oxo-1-(3-(2-methylpropyl)-2-oxo-1,3,4-oxadiazolin-5-yl)-2-pentyl]carboxamide

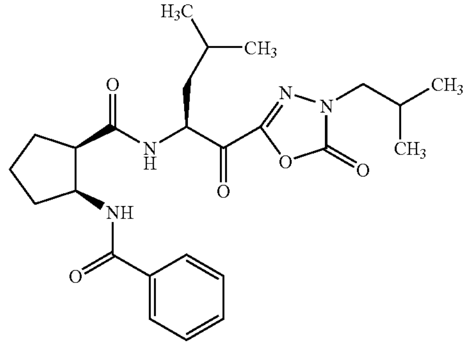

TLC: Rf 0.28 (n-hexane:ethyl acetate=1:1);

NMR ($CDCl_3$): δ 7.81–7.74 (m, 2H), 7.53–7.38 (m, 3H), 6.89 (brd, J=7.8 Hz, 1H), 6.13 (d, J=7.5 Hz, 1H), 5.33–5.21 (m, 1H), 4.71–4.58 (m, 1H), 3.67 (dd, J=13.5, 7.2 Hz, 1H), 3.61 (dd, J=13.5, 7.2 Hz, 1H), 3.05 (q, J=7.5 Hz, 1H), 2.24–1.30 (m, 10H), 0.98 (d, J=6.9 Hz, 6H), 0.70 and 0.69 (each d, J=6.0 Hz, totally 6H).

EXAMPLE 10 (23)

1-[(1R,2S)-2-(4-dimethylaminomethyl-2-fluorobenzoylamino)cyclohexyl]-N-[4-methyl-1-oxo-1-(3-(2-methylpropyl)-2-oxo-1,3,4-oxadiazolin-5-yl)-2-pentyl]carboxamide

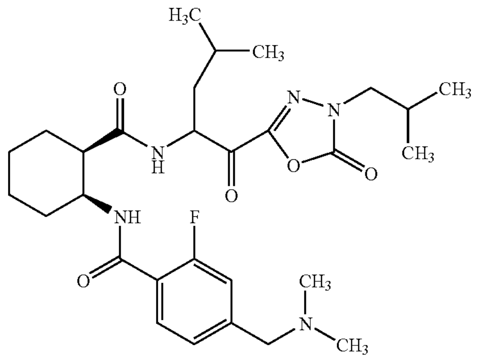

TLC: Rf 0.73 and 0.55 (chloroform:methanol=9:1);

NMR ($CDCl_3$): δ 8.01–7.90 (m, 1H), 7.45–7.32 (m, 1H), 7.20–7.08 (m, 2H), 6.42 and 6.24 (each brd, J=6.3 Hz, totally 1H), 5.38–5.25 (m, 1H), 4.51–4.40 (m, 1H), 3.70–3.50 (m, 2H), 3.46 (s, 2H), 2.84–2.70 (m, 1H), 2.25 (s, 6H), 2.20–1.40 (m, 12H), 1.02–0.80 (m, 12H).

EXAMPLE 10 (24)

1-[(1R,2S)-2-(3-dimethylaminomethylbenzoylamino)cyclohexyl]-N-[4-methyl-1-oxo-1-(3-(2-methylpropyl)-2-oxo-1,3,4-oxadiazolin-5-yl)-2-pentyl] carboxamide

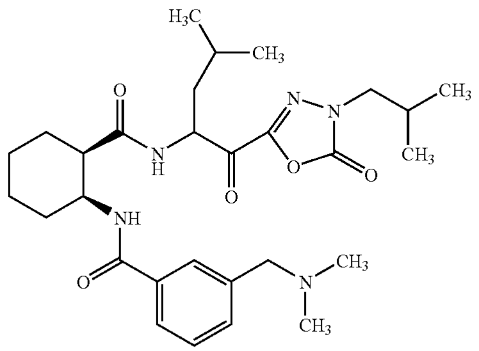

TLC: Rf 0.48 and 0.46 (chloroform:methanol=9:1);

NMR ($CDCl_3$): δ 7.75–7.60 (m, 2H), 7.50–7.30 (m, 2H), 7.10 (d, J=8.0 Hz, 1H), 6.29 and 6.24 (each d, J=8.2 Hz, totally 1H), 5.40–5.20 (m, 1H), 4.45–4.25 (m, 1H), 3.67 and 3.66 (each dd, J=14.0, 7.1 Hz, totally 1H), 3.63 and 3.60 (each dd, J=14.0, 7.1 Hz, totally 1H), 3.47 (s, 2H), 2.90–2.80 (m, 1H), 2.25 and 2.24 (each s, totally 6H), 2.20–1.35 (m, 12H), 1.05–0.80 (m, 12H).

EXAMPLE 10 (25)

1-[(1S,2R)-2-benzoylaminocyclopentyl]-N-[(2S)-4-methyl-1-oxo-1-(3-(2-methylpropyl)-2-oxo-1,3,4-oxadiazolin-5-yl)-2-pentyl]carboxamide

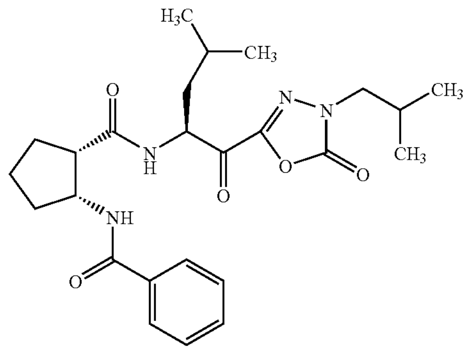

TLC: Rf 0.33 (n-hexane:ethyl acetate=1:1);

NMR ($CDCl_3$): δ 7.83–7.75 (m, 2H), 7.52–7.37 (m, 3H), 6.91 (brd, J=8.1 Hz, 1H), 6.23 (brd, J=5.7 Hz, 1H), 5.22–5.12 (m, 1H), 4.68–4.54 (m, 1H), 3.65 (dd, J=14.1, 7.2 Hz, 1H), 3.56 (dd, J=14.1, 7.2 Hz, 1H), 3.13–3.03 (m, 1H), 2.22–1.30 (m, 10H), 0.97 and 0.96 (each d, J=6.6 Hz, totally 6H), 0.94 and 0.91 (each d, J=6.6 Hz, totally 6H).

EXAMPLE 10 (26)

1-[(1R, 2S)-2-(2-dimethylaminomethylbenzoylamino)cyclohexyl]-N-[4-methyl-1-oxo-1-(3-(2-methylpropyl)-2-oxo-1,3,4-oxadiazolin-5-yl)-2-pentyl]carboxamide

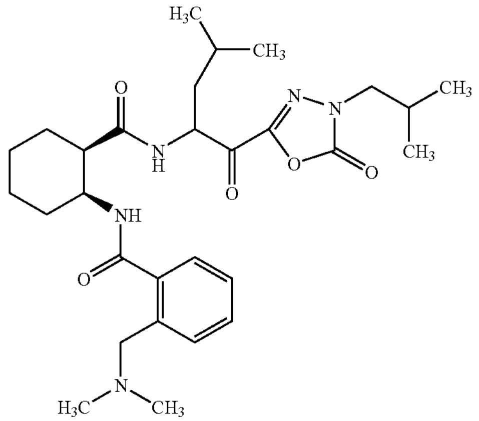

TLC: Rf 0.41 and 0.37 (chloroform:methanol=9:1);

NMR ($CDCl_3$): δ 10.65–10.45 (m, 1H), 8.05–7.90 (m, 1H), 7.45–7.30 (m, 2H), 7.25–7.10 (m, 1H), 7.01 and 6.36 (each d, J=7.0 and 7.4 Hz, totally 1H), 5.25–5.10 (m, 1H), 4.51 and 4.34 (each br, totally 1H), 3.80–3.30 (m, 4H), 3.10–2.90 (m, 1H), 2.23 and 2.20 (each s, totally 6H), 2.20–1.20 (m, 12H), 1.05–0.75 (m, 12H).

EXAMPLE 10 (27)

1-[(1R,2S)-2-(4-methylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

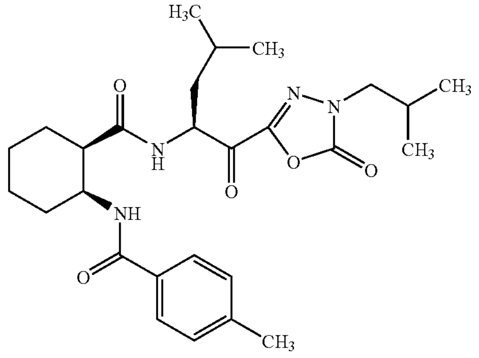

TLC: Rf 0.43 (n-hexane:ethyl acetate=1:1);

NMR ($CDCl_3$): δ 7.68 (d, J=8.4 Hz, 2H), 7.21 (d, J=8.4 Hz, 2H), 7.04 (brd, J=8.1 Hz, 1H), 6.16 (brd, J=7.2 Hz, 1H), 5.40–5.30 (m, 1H), 4.40–4.30 (m, 1H), 3.68 and 3.61 (each dd, J=13.8, 6.9 Hz, each 1H), 2.88–2.79 (m, 1H), 2.39 (s, 3H), 2.25–1.40 (m, 12H), 0.98, 0.87 and 0.82 (each d, J=6.3 Hz, totally 12H).

EXAMPLE 10 (28)

1-[(1R,2S)-2-(3-methylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

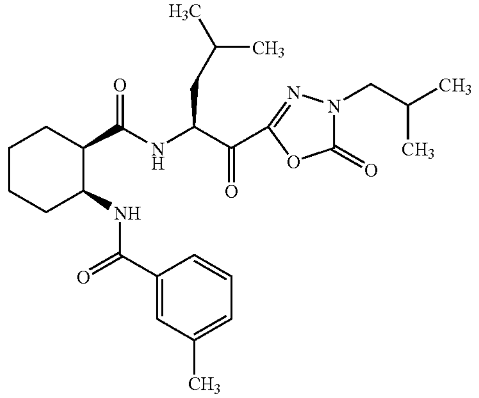

TLC: Rf 0.42 (n-hexane:ethyl acetate=1:1);

NMR ($CDCl_3$): δ 7.59 (s, 1H), 7.55 (t, J=6.0 Hz, 1H), 7.30 (d, J=6.0 Hz, 2H), 7.05 (brd, J=8.1 Hz, 1H), 6.14 (brd, J=7.5 Hz, 1H), 5.40–5.30 (m, 1H), 4.40–4.30 (m, 1H), 3.68 and 3.61 (each dd, J=13.8, 6.9 Hz, each 1H), 2.88–2.80 (m, 1H), 2.40 (s, 3H), 2.24–1.40 (m, 12H), 0.98, 0.87 and 0.82 (each d, J=6.3 Hz, totally 12H).

EXAMPLE 10 (29)

1-[(1R,2S)-2-(2-methylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

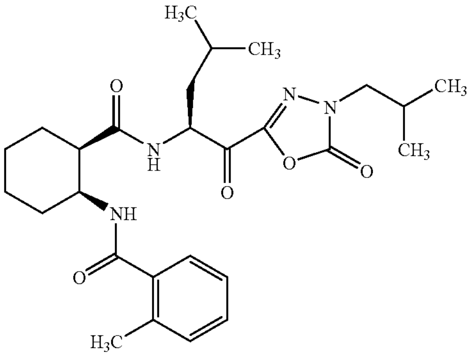

TLC: Rf 0.44 (n-hexane:ethyl acetate=1:1);

NMR ($CDCl_3$): δ 7.38–7.16 (m, 4H), 6.66 (brd, J=8.7 Hz, 1H), 6.13 (brd, J=8.1 Hz, 1H), 5.40–5.30 (m, 1H), 4.40–4.30 (m, 1H), 3.68 and 3.61 (each dd, J=13.8, 6.9 Hz, each 1H), 2.90–2.82 (m, 1H), 2.43 (s, 3H), 2.30–1.40 (m, 12H), 1.04–0.90 (m, 12H).

EXAMPLE 10 (30)

1-[(1R,2S)-2-(3-chlorobenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

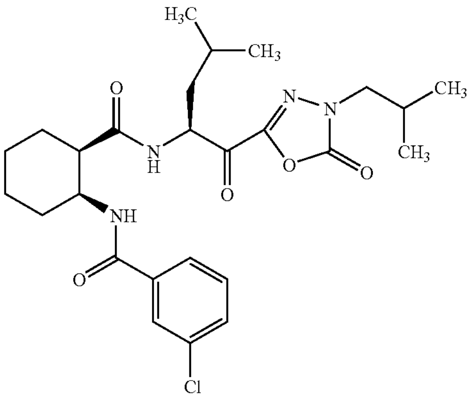

TLC: Rf 0.53 (n-hexane:ethyl acetate=1:1);

NMR ($CDCl_3$): δ 7.76 (t, J=1.8 Hz, 1H), 7.62 (d, J=7.5 Hz, 1H), 7.47 (dt, J=7.5, 1.8 Hz, 1H), 7.36 (t, J=7.5 Hz, 1H), 7.20 (brd, J=8.1 Hz, 1H), 6.10 (brd, J=8.1 Hz, 1H), 5.42–5.30 (m, 1H), 4.38–4.25 (m, 1H), 3.69 and 3.62 (each dd, J=14.1, 7.2 Hz, each 1H), 2.88–2.80 (m, 1H), 2.30–1.40 (m, 12H), 0.99, 0.89 and 0.86 (each d, J=6.0 Hz, totally 12H).

EXAMPLE 10 (31)

1-[(1R,2S)-2-(2-chlorobenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

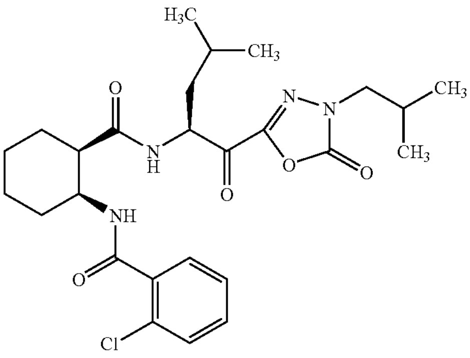

TLC: Rf 0.41 (n-hexane:ethyl acetate=1:1);

NMR ($CDCl_3$): δ 7.60 (dd, J=6.9, 2.4 Hz, 1H), 7.42–7.25 (m, 3H), 6.99 (brd, J=8.4 Hz, 1H), 6.14 (brd, J=7.8 Hz, 1H), 5.38–5.25 (m, 1H), 4.43–4.35 (m, 1H), 3.68 and 3.61 (each dd, J=13.8, 7.2 Hz, each 1H), 2.88–2.78 (m, 1H), 2.23–1.41 (m, 12H), 1.05–0.88 (m, 12H).

EXAMPLE 10 (32)

1-[(1R,2S)-2-(3-fluorobenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

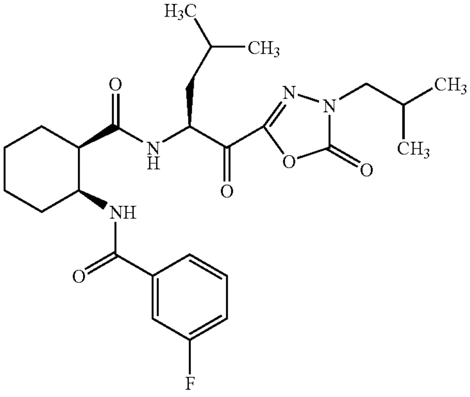

TLC: Rf 0.49 (n-hexane:ethyl acetate=1:1);

NMR ($CDCl_3$): δ 7.50 (m, 2H), 7.40 (m, 1H), 7.30–7.15 (m, 2H), 6.10 (brd, J=8.4 Hz, 1H), 5.42–5.31 (m, 1H), 4.38–4.26 (m, 1H), 3.68 and 3.61 (each dd, J=13.8, 7.2 Hz, each 1H), 2.85–2.80 (m, 1H), 2.30–1.40 (m, 12H), 0.98, 0.88, and 0.86 (each d, J=6.6 Hz, totally 12H).

EXAMPLE 10 (33)

1-[(1R,2S)-2-(2-methoxybenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

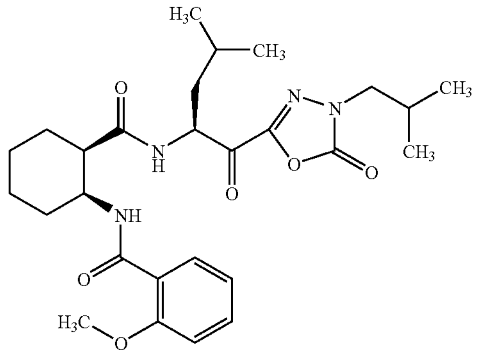

TLC: Rf 0.36 (n-hexane:ethyl acetate=1:1);

NMR ($CDCl_3$): δ 8.55 (brd, J=8.1 Hz, 1H), 8.18 (dd, J=7.8, 1.8 Hz, 1H), 7.46 (dt, J=1.8, 7.8 Hz, 1H), 7.08 (t, J=7.8 Hz, 1H), 6.97 (d, J=7.8 Hz, 1H), 6.58 (brd, J=7.8 Hz, 1H), 5.30–5.20 (m, 1H), 4.65–4.50 (m, 1H), 3.99 (s, 3H), 3.68 and 3.61 (each dd, J=13.8, 7.8 Hz, each 1H), 2.80–2.70 (m, 1H), 2.25–1.38 (m, 12H), 0.96, 0.78, and 0.74 (each d, J=6.3 Hz, totally 12H).

EXAMPLE 10 (34)

1-[(1R,2S)-2-(3-methoxybenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide

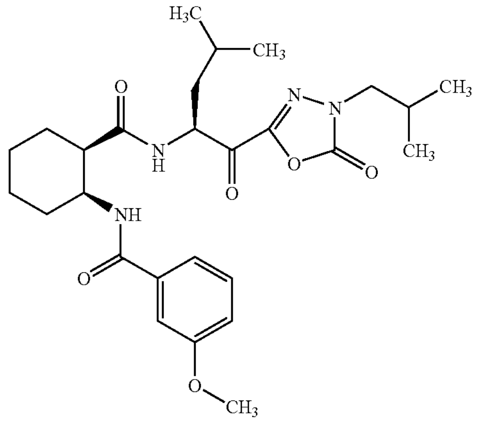

TLC: Rf 0.37 (n-hexane:ethyl acetate=1:1);

NMR ($CDCl_3$): δ 7.40–7.30 (m, 3H), 7.11 (brd, J=7.8 Hz, 1H), 7.02 (m, 1H), 6.14 (brd, J=7.8 Hz, 1H), 5.40–5.30 (m, 1H), 4.40–4.30 (m, 1H), 3.85 (s, 3H), 3.68 and 3.61 (each dd, J=13.8, 7.8 Hz, each 1H), 2.88–2.80 (m, 1H), 2.30–1.40 (m, 12H), 0.98, 0.90, and 0.88 (each d, J=6.3 Hz, totally 12H).

EXAMPLE 10 (35)

1-[(1R,2R)-2-benzoylaminocyclopentyl]-N-[(2S)-4-methyl-1-oxo-1-(3-(2-methylpropyl)-2-oxo-1,3,4-oxadiazolin-5-yl)-2-pentyl]carboxamide

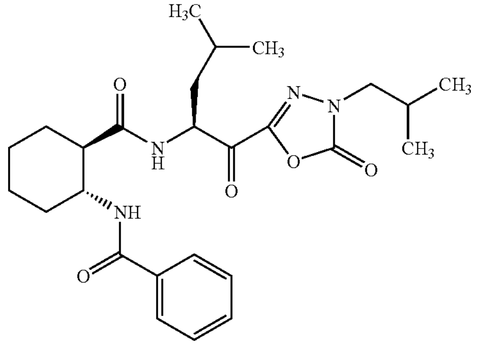

TLC: Rf 0.34 (n-hexane:ethyl acetate=1:1);

NMR ($CDCl_3$): δ 8.57 (brd, J=6.0 Hz, 1H), 7.82–7.73 (m, 2H), 7.58–7.42 (m, 3H), 6.27 (brd, J=6.0 Hz, 1H), 5.30–5.20 (m, 1H), 4.45–4.35 (m, 1H), 3.67 (dd, J=13.8, 7.2 Hz, 1H), 3.60 (dd, J=13.8, 7.2 Hz, 1H), 2.94–2.79 (m, 1H), 2.27–1.50 (m, 10H), 1.08–0.91 (m, 12H).

EXAMPLE 10 (36)

1-[(1S,2S)-2-benzoylaminocyclopentyl]-N-[(2S)-4-methyl-1-oxo-1-(3-(2-methylpropyl)-2-oxo-1,3,4-oxadiazolin-5-yl)-2-pentyl]carboxamide

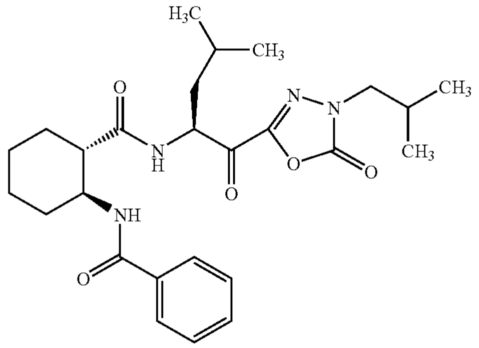

TLC: Rf 0.28 (n-hexane:ethyl acetate=1:1);

NMR ($CDCl_3$): δ 8.84 (brd, J=6.0 Hz, 1H), 7.77 (d, J=7.2 Hz, 2H), 7.58–7.42 (m, 3H), 6.26 (brd, J=5.7 Hz, 1H), 5.29–5.20 (m, 1H), 4.52–4.43 (m, 1H), 3.67 (dd, J=13.8, 7.2 Hz, 1H), 3.61 (dd, J=13.8, 7.2 Hz, 1H), 2.93–2.84 (m, 1H), 2.29–1.48 (m, 10H), 1.02 and 1.00 (each d, J=6.6 Hz, totally 6H), 0.98 (d, J=6.6 Hz, 6H).

EXAMPLE 10 (37)

1-[(1R,2S)-2-(4-dimethylaminomethyl-3-fluorobenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide Hydrochloride

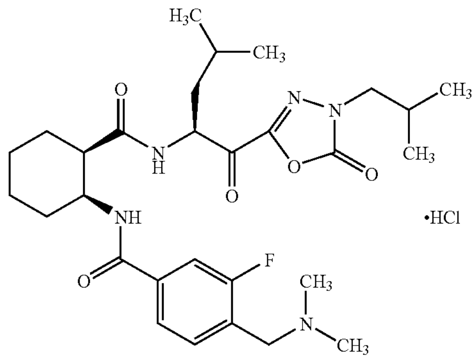

TLC: Rf 0.32 (chloroform:methanol=9:1);

NMR (DMSO-$d_6$): δ 8.47 and 8.37 (each brd, J=6.9 Hz, totally 1H), 8.03 and 7.88 (each brd, J=7.8 Hz, totally 1H), 7.80–7.58 (m, 3H), 4.90 (m, 1H), 4.42–4.25 (m, 3H), 3.56 and 3.51 (each dd, J=12.3, 6.9 Hz, each 1H), 2.74 (brs, 7H), 2.10–1.82 (m, 3H), 1.70–1.20 (m, 9H), 0.88, 0.74 and 0.69 (each d, J=6.0 Hz, totally 12H).

EXAMPLE 10 (38)

1-[(1R,2S)-2-(4-pyrrolidinomethylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide Hydrochloride

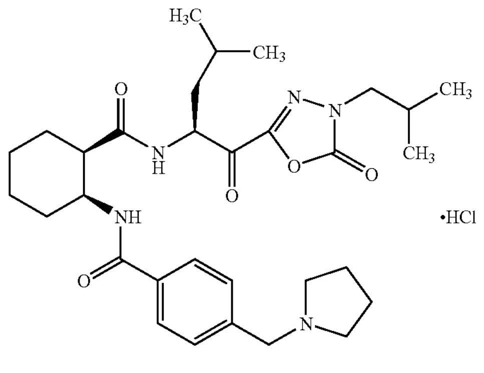

TLC: Rf 0.39 and 0.34 (chloroform:methanol=9:1);

NMR (DMSO-$d_6$): δ 8.48 and 8.38 (each d, J=6.6 Hz, totally 1H), 7.87–7.71 (m, 3H), 7.67–7.62 (m, 2H), 4.95–4.80 (m, 1H), 4.38 and 4.37 (each s, totally 2H), 4.30–4.14 (m, 1H), 3.61–3.45 (m, 2H), 3.32 (m, 2H), 3.03 (m, 2H), 2.78–2.74 (m, 1H), 2.02–1.87 (m, 7H), 1.69–1.23 (m, 9H), 0.89 (d, J=6.6 Hz, 3H), 0.88 (d, J=6.6 Hz, 3H), 0.84, 0.83, 0.74, and 0.69 (each d, J=6.0 Hz, totally 6H).

EXAMPLE 10 (39)

1-[(1R,2S)-2-(4-morpholinomethylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide Hydrochloride

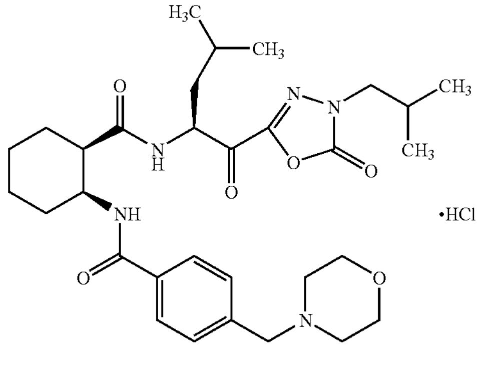

TLC: Rf 0.36 (n-hexane:ethyl acetate=1:3);

NMR (DMSO-$d_6$): δ 8.38 (d, J=6.9 Hz, 1H), 7.87–7.81 (m, 3H), 7.67 (d, J=8.1 Hz, 2H), 4.93–4.86 (m, 1H), 4.38 (br-s, 2H), 4.27 (m, 1H), 3.95–3.90 (m, 2H), 3.81–3.74 (m, 2H), 3.61–3.48 (m, 2H), 3.25–3.01 (m, 4H), 2.78–2.71 (m, 1H), 2.07–1.86 (m, 2H), 1.66–1.23 (m, 10H), 0.89 (d, J=6.9 Hz, 3H), 0.88 (d, J=6.9 Hz, 3H), 0.75 (d, J=6.0 Hz, 3H), 0.70 (d, J=6.0 Hz, 3H).

EXAMPLE 10 (40)

(4-dimethylaminomethyl)-N-[4-methyl-1-oxo-1-(3-(2-methylpropyl)-2-oxo-(1,3,4-oxadiazolin)-5-yl)pentyl]benzamide

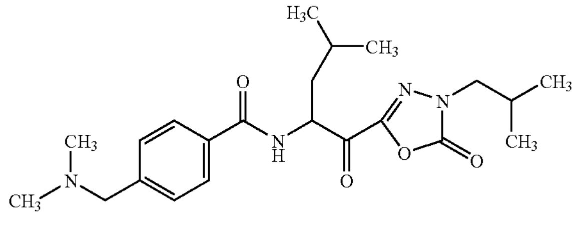

TLC: Rf 0.46 (chloroform:methanol=9:1);

NMR ($CDCl_3$): δ 7.76 (d, J=8.3 Hz, 2H), 7.40 (d, J=8.3 Hz, 2H), 6.58 (d, J=8.1 Hz, 1H), 5.65–5.55 (m, 1H), 3.70 (dd, J=12.5, 7.4 Hz, 1H), 3.65 (dd, J=12.5, 7.5 Hz, 1H), 3.48 (s, 2H), 2.25 (s, 6H), 2.25–2.10 (m, 1H), 1.85–1.55 (m, 3H), 1.06 (d, J=6.0 Hz, 3H), 1.00 (d, J=6.0 Hz, 9H).

EXAMPLE 10 (41)

(3-dimethylaminomethyl)-N-[4-methyl-1-oxo-1-(3-(2-methylpropyl)-2-oxo-(1,3,4-oxadiazolin)-5-yl)pentyl]benzamide

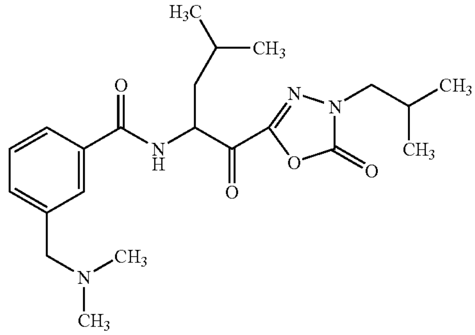

TLC: Rf 0.40 (chloroform:methanol=9:1);

NMR ($CDCl_3$): δ 7.75 (s, 1H), 7.72 (d, J=7.5 Hz, 1H), 7.48 (d, J=7.5 Hz, 1H), 7.41 (t, J=7.5 Hz, 1H), 6.71 (d, J=8.1 Hz, 1H), 5.65–5.55 (m, 1H), 3.70 (dd, J=13.7, 7.1 Hz, 1H), 3.65 (dd, J=13.7, 7.2 Hz), 3.48 (s, 2H), 2.26 (s, 6H), 2.25–2.10 (m, 1H), 1.90–1.60 (m, 3H), 1.06 (d, J=6.3 Hz, 3H), 1.00 (d, J=6.3 Hz, 3H), 0.99 (d, J=6.9 Hz, 6H).

EXAMPLE 10 (42)

1-[(1R,2S)-2-(2-dimethylaminomethyl-4-fluorobenzoylamino)cyclohexyl]-N-[4-methyl-1-oxo-1-(3-(2-methylpropyl)-2-oxo-1,3,4-oxadiazolin-5-yl)-2-pentyl]carboxamide

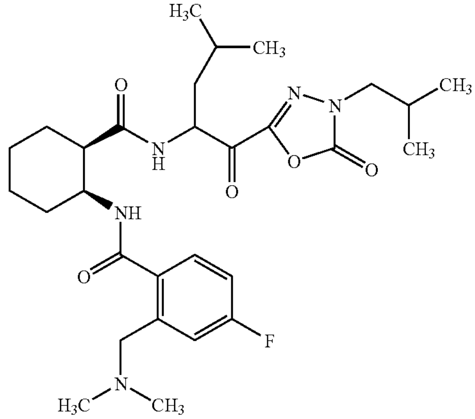

TLC: Rf 0.53 and 0.42 (chloroform:methanol=9:1);

NMR ($CDCl_3$): δ 10.51 and 10.45 (each brd, J=7.2 Hz, totally 1H), 8.02 and 7.99 (each t, J=5.4 Hz, totally 1H), 7.13–7.05 (m, 1H), 6.92–6.80 (m, 1H), 6.83 and 6.24 (each brd, J=6.9 Hz, totally 1H), 5.26–5.10 (m, 1H), 4.48 and 4.32 (each m, totally 1H), 3.80–3.30 (m, 4H), 3.10 and 2.90 (each m, totally 1H), 2.50–1.21 (m, 18H), 1.10–0.70 (m, 12H).

EXAMPLE 10 (43)

(2-dimethylaminomethyl)-N-[4-methyl-1-oxo-1-(3-(2-methylpropyl)-2-oxo-(1,3,4-oxadiazolin)-5-yl)pentyl]benzamide

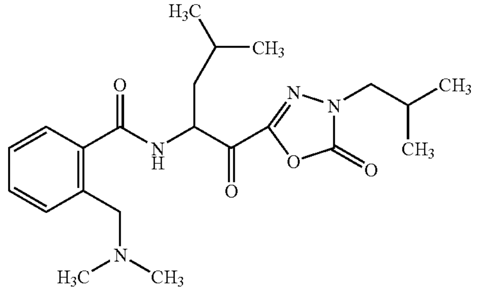

TLC: Rf 0.65 (chloroform methanol=9:1);

NMR ($CDCl_3$): δ 11.39 (d, J=5.1 Hz, 1H), 7.95–7.90 (m, 1H), 7.45–7.30 (m, 1H), 7.25–7.15 (m, 1H), 5.50–5.40 (m, 1H), 4.04 (d, J=12.2 Hz, 1H), 3.69 (dd, J=14.0, 7.0 Hz, 1H), 3.65 (dd, J=14.0, 7.0 Hz, 1H), 3.22 (d, J=12.2 Hz, 1H), 2.30 (s, 6H), 2.20 (septet, J=7.0 Hz, 1H), 1.85–1.50 (m, 3H), 1.10–0.90 (m, 12H).

EXAMPLE 10 (44)

2-phenyl-N-[4-methyl-1-oxo-1-(3-(2-methylpropyl)-2-oxo-(1,3,4-oxadiazolin)-5-yl)pentyl]benzamide

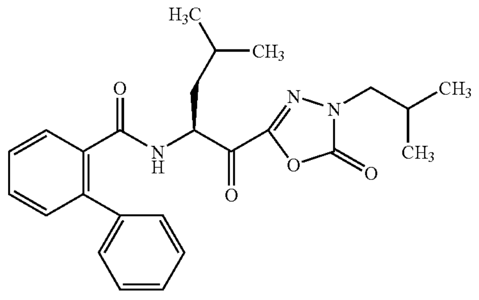

TLC: Rf 0.52 (n-hexane:ethyl acetate=2:1);

NMR ($CDCl_3$): δ 7.75–7.70 (m, 1H), 7.55–7.30 (m, 8H), 5.69 (d, J=7.5 Hz, 1H), 5.26 (ddd, J=9.8, 7.5, 4.1 Hz, 1H), 3.65 (dd, J=13.7, 7.0 Hz, 1H), 3.62 (dd, J=13.7, 7.0 Hz, 1H), 2.16 (septet, J=7.0 Hz, 1H), 1.45–1.05 (m, 3H), 0.98 (d, J=7.0 Hz, 6H), 0.85 (d, J=6.3 Hz, 3H), 0.79 (d, J=6.3 Hz, 3H).

EXAMPLE 10 (45)

1-[1-benzoylaminocyclohexyl]-N-[(2S)-4-methyl-1-oxo-1-(3-(2-methylpropyl)-2-oxo-1,3,4-oxadiazolin-5-yl)-2-pentyl]carboxamide

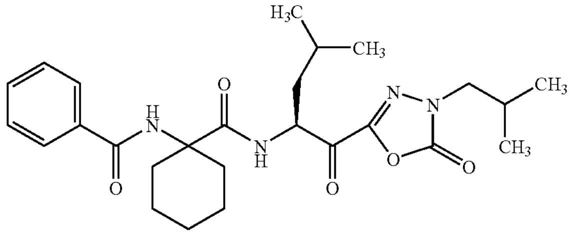

TLC: Rf 0.68 (n-hexane:ethyl acetate=1:1);

NMR ($CDCl_3$): δ 7.89 (d, J=6.6 Hz, 1H), 7.77 (d, J=6.9 Hz, 2H), 7.56 (t, J=6.9 Hz, 1H), 7.47 (t, J=6.9 Hz, 2H), 6.09 (brs, 1H), 5.38–5.23 (m, 1H), 3.64 and 3.58 (each dd, J=6.9 Hz, each 1H), 2.40–1.21 (m, 14H), 1.10–0.90 (m, 12H).

EXAMPLE 10 (46)

1-[(1R,2S)-2-(3-morpholinomethylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide Hydrochloride

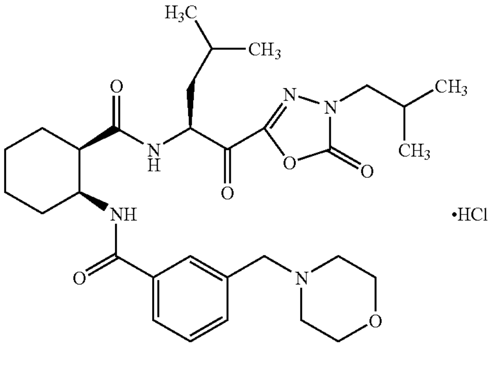

TLC: Rf 0.49 and 0.38 (chloroform:methanol=19:1);

NMR (DMSO-$d_6$): δ 8.47 and 8.37 (each d, J=6.0 Hz, totally 1H), 8.04 and 7.96 (each s, totally 1H), 7.83–7.65 (m, 3H), 7.52 (t-like, J=7.5 Hz, 1H), 4.94–4.84 (m, 1H), 4.37 (br-s, 2H), 4.31 (m, 1H), 3.94–3.90 (m, 2H), 3.80–3.72 (m, 2H), 3.61–3.48 (m, 2H), 3.38–3.04 (m, 4H), 2.73–2.71 (m, 1H), 2.06–1.90 (m, 3H), 1.71–1.23 (m, 9H), 0.90 (d, J=6.6 Hz, 6H), 0.84, 0.82, 0.75, and 0.69 (each d, J=6.0 Hz, totally 6H).

EXAMPLE 10 (47)

1-[(1R,2S)-2-(3-pyrrolidinomethylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide Hydrochloride

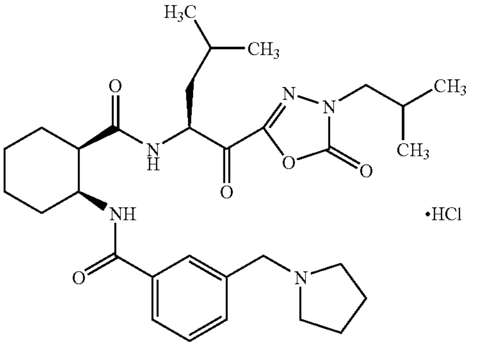

TLC: Rf 0.47 (chloroform:methanol=9:1);

NMR (DMSO-$d_6$): δ 8.37 (d, J=6.6 Hz, 1H), 8.00 (s, 1H), 7.79 (d, J=7.5 Hz, 2H), 7.73 (d, J=7.5 Hz, 1H), 7.51 (t-like, J=7.5 Hz, 1H), 4.95–4.86 (m, 1H), 4.39 and 4.37 (each s, totally 2H), 4.29 (m, 1H), 3.61–3.47 (m, 2H), 3.41–3.22 (m, 2H), 3.05 (m, 2H), 2.74–2.72 (m, 1H), 2.01–1.84 (m, 7H), 1.68–1.23 (m, 9H), 0.89 (d, J=6.6 Hz, 6H), 0.74 (d, J=6.0 Hz, 3H), 0.68 (d, J=6.0 Hz, 3H).

EXAMPLE 10 (48)

1-[(1R,2S)-2-(2-morpholinomethylbenzoylamino)cyclohexyl]-N-[4-methyl-1-oxo-1-(3-(2-methylpropyl)-2-oxo-1,3,4-oxadiazolin-5-yl)-2-butyl]carboxamide Hydrochloride

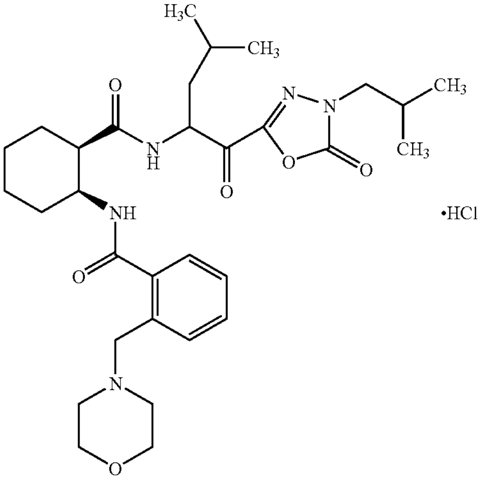

TLC: Rf 0.46 and 0.43 (chloroform:methanol=19:1);

NMR ($DMSO-d_6$): δ 8.55–8.30 (m, 2H), 7.76–7.69 (m, 1H), 7.59–7.49 (m, 3H), 4.92–4.85 (m, 1H), 4.50–4.27 (m, 3H), 3.91–3.88 (m, 2H), 3.80–3.67 (m, 2H), 3.63–3.48 (m, 2H), 3.32–3.00 (m, 4H), 2.80–2.69 (m, 1H), 2.18–1.80 (m, 4H), 1.74–1.23 (m, 8H), 0.90 and 0.89 (each d, J=6.6 Hz, totally 6H), 0.81 and 0.77 (each d, J=6.3 Hz, totally 6H).

EXAMPLE 10 (49)

1-[(1R,2S)-2-(4-dimethylaminomethylbenzoylamino)cyclohexyl]-N-[4-methyl-1-oxo-1-(3-cyclopropylmethyl-2-oxo-1,3,4-oxadiazolin-5-yl)-2-pentyl]carboxamide

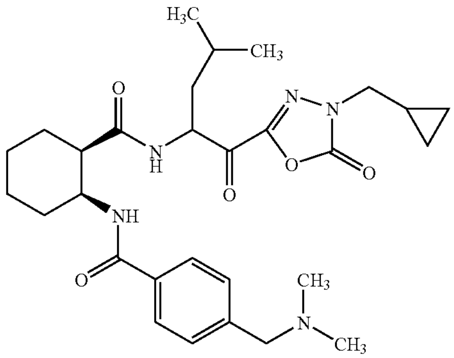

Free Compound

TLC: Rf 0.43 and 0.36 (chloroform:methanol=9:1);

NMR ($CDCl_3$): δ 7.76 and 7.72 (each d, J=8.4 Hz, totally 2H), 7.37 and 7.36 (each d, J=8.4 Hz, totally 2H), 7.13 and 7.10 (each d, J=7.4 Hz, totally 1H), 6.40–6.20 (m, 1H), 5.40–5.20 (m, 1H), 4.34 (br, 1H), 3.76 and 3.75 (each dd, J=14.3, 7.4 and 14.5, 7.1 Hz, totally 1H)3.63 and 3.60 (each dd, J=14.3, 7.4 and 14.5, 7.6 Hz, totally 1H), 3.46 and 3.45 (each s, totally 2H), 2.86 (br, 1H), 2.24 and 2.23 (each s, totally 6H), 2.20–1.35 (m, 11H), 1.35–1.10 (m, 1H), 1.00, 0.94, 0.89 and 0.83 (each d, J=6.2, 6.2, 5.8 and 5.8 Hz, totally 6H), 0.70–0.30 (m, 4H)

Hydrochloride

TLC: Rf 0.43 and 0.36 (chloroform:methanol=9:1);

NMR ($CDCl_3$): δ 7.85 and 7.81 (each d, J=8.6 Hz, totally 2H), 7.73 and 7.65 (each d, J=8.6 Hz, totally 2H), 7.47 and 7.16 (each d, J=8.0 Hz, totally 1H), 7.09 and 6.34 (each d, J=7.2 Hz, totally 1H), 5.45–5.20 (m, 1H), 4.45–4.10 (m, 3H), 3.78 and 3.76 (each dd, J=14.4, 7.1 and 14.3, 6.9 Hz, totally 1H), 3.64 and 3.61 (each dd, J=14.4, 7.7 and 14.3, 7.3 Hz, totally 1H), 3.05–2.60 (m, 7H), 2.20–1.35 (m, 11H), 1.35–1.10 (m, 1H), 1.05–0.80 (m, 6H), 0.70–0.30 (m, 4H).

EXAMPLE 10 (50)

1-[(1R,2S)-2-(4-fluorobenzoylamino)cyclohexyl]-N-[(2S)-4-methyl-1-oxo-1-(3-cyclopropylmethyl-2-oxo-1,3,4-oxadiazolin-5-yl)-2-pentyl]carboxamide

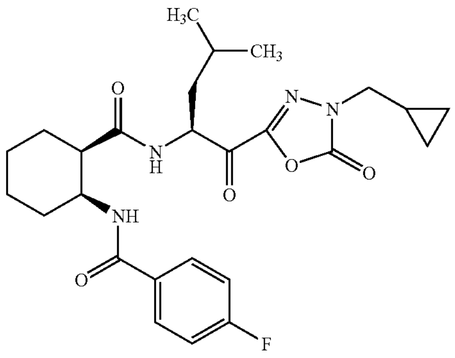

TLC: Rf 0.41 (n-hexane:ethyl acetate=1:1);

NMR ($CDCl_3$): δ 7.78 (dd, J=8.8, 5.4 Hz, 2H), 7.18 (d, J=8.6 Hz, 1H), 7.10 (t, J=8.8 Hz, 2H), 6.15 (d, J=8.0 Hz, 1H), 5.45–5.30 (m, 1H), 4.40–4.20 (m, 1H), 3.77 (dd, J=14.5, 7.2 Hz, 1H), 3.64 (dd, J=14.5, 7.6 Hz, 1H), 2.83 (q, J=5.1 Hz, 1H), 2.20–1.35 (m, 11H), 1.35–1.10 (m, 1H), 0.91 (d, J=6.2 Hz, 3H), 0.86 (d, J=6.2 Hz, 3H), 0.70–0.35 (m, 4H).

EXAMPLE 10 (51)

1-[(1R,2S)-2-(4-chlorobenzoylamino)cyclohexyl]-N-[(2S)-4-methyl-1-oxo-1-(3-cyclopropylmethyl-2-oxo-1,3,4-oxadiazolin-5-yl)-2-pentyl]carboxamide

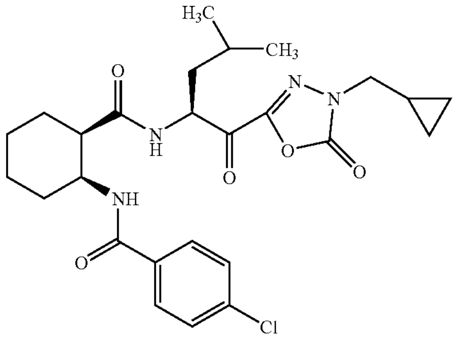

TLC: Rf 0.46 (n-hexane:ethyl acetate=1:1);

NMR ($CDCl_3$): δ 7.72 (d, J=8.6 Hz, 2H), 7.40 (d, J=8.6 Hz, 2H), 7.23 (d, J=8.0 Hz, 1H), 6.14 (d, J=8.0 Hz, 1H), 5.45–5.30 (m, 1H), 4.40–4.20 (m, 1H), 3.77 (dd, J=14.4, 7.0 Hz, 1H), 3.64 (dd, J=14.4, 7.7 Hz, 1H), 2.83 (q, J=5.1 Hz, 1H), 2.20–1.35 (m, 11H), 1.35–1.10 (m, 1H), 0.91 (d, J=5.8 Hz, 3H), 0.87 (d, J=5.8 Hz, 3H), 0.70–0.35 (m, 4H).

EXAMPLE 10 (52)

1-[(1R,2S)-2-(4-methoxybenzoylamino)cyclohexyl]-N-[(2S)-4-methyl-1-oxo-1-(3-cyclopropylmethyl-2-oxo-1,3,4-oxadiazolin-5-yl)-2-pentyl]carboxamide

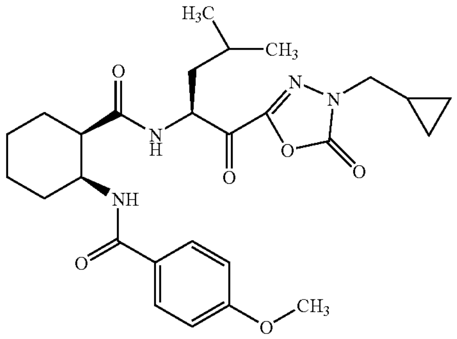

TLC: Rf 0.27 (n-hexane:ethyl acetate=1:1);

NMR ($CDCl_3$): δ 7.73 (d, J=9.0 Hz, 2H), 7.01 (d, J=8.2 Hz, 1H), 6.92 (d, J=9.0 Hz, 2H), 6.22 (d, J=7.6 Hz, 1H), 5.45–5.25 (m, 1H), 4.40–4.25 (m, 1H), 3.85 (s, 3H), 3.76 (dd, J=14.5, 7.1 Hz, 1H), 3.63 (dd, J=14.5, 7.5 Hz, 1H), 2.83 (q, J=5.1 Hz, 1H), 2.20–1.35 (m, 11H), 1.35–1.10 (m, 1H), 0.89 (d, J=5.8 Hz, 3H), 0.84 (d, J=6.0 Hz, 3H), 0.70–0.35 (m, 4H).

EXAMPLE 10 (53)

1-[(1R,2S)-2-(4-cyanobenzoylamino)cyclohexyl]-N-[(2S)-4-methyl-1-oxo-1-(3-cyclopropylmethyl-2-oxo-1,3,4-oxadiazolin-5-yl)-2-pentyl]carboxamide

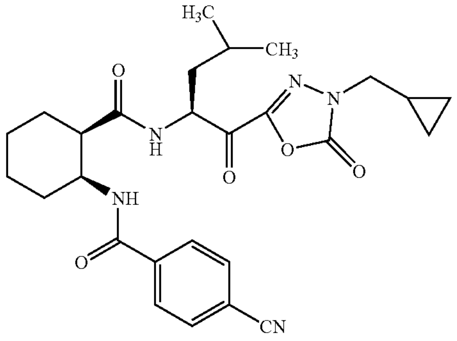

TLC: Rf 0.37 (n-hexane:ethyl acetate=1:1);

NMR ($CDCl_3$): δ 7.88 (d, J=8.4 Hz, 2H), 7.73 (d, J=8.4 Hz, 2H), 7.53 (d, J=8.4 Hz, 1H), 6.14 (d, J=8.0 Hz, 1H), 5.45–5.30 (m, 1H), 4.40–4.20 (m, 1H), 3.78 (dd, J=14.5, 7.1 Hz, 1H), 3.65 (dd, J=14.5, 7.6 Hz, 1H), 2.83 (q, J=5.1 Hz, 1H), 2.20–1.35 (m, 11H), 1.35–1.10 (m, 1H), 0.93 (d, J=6.2 Hz, 3H), 0.89 (d, J=6.2 Hz, 3H), 0.70–0.35 (m, 4H).

EXAMPLE 10 (54)

1-[(1R,2S)-2-(N-benzoyl-N-methylamino)cyclohexyl]-N-[(2S)-4-methyl-1-oxo-1-(3-cyclopropylmethyl-2-oxo-1,3,4-oxadiazolin-5-yl)-2-pentyl]carboxamide

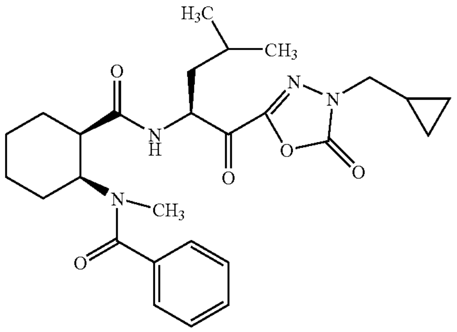

TLC: Rf 0.45 (n-hexane:ethyl acetate=1:1);

NMR ($CDCl_3$): δ 7.50–7.20 (m, 5H), 6.51–6.13 (br, 1H), 5.35-5.22 (m, 1H), 4.67–4.20 (br, 1H), 3.76 and 3.61 (each dd, J=14.7 and 7.2 Hz, each 1H), 3.33–3.02 (br, 1H), 2.88 (s, 3H), 2.62–2.35 (m, 1H), 2.04–1.07 (m, 11H), 1.07–0.79 (m, 6H), 0.70–0.56 and 0.50–0.32 (each m, each 2H).

EXAMPLE 10 (55)

1-[(1R,2S)-2-(N-(4-dimethylaminobenzoylamino) cyclohexyl]-N-[(2S)-4-methyl-1-oxo-1-(3-cyclopropylmethyl-2-oxo-1,3,4-oxadiazolin-5-yl)-2-pentyl] carboxamide

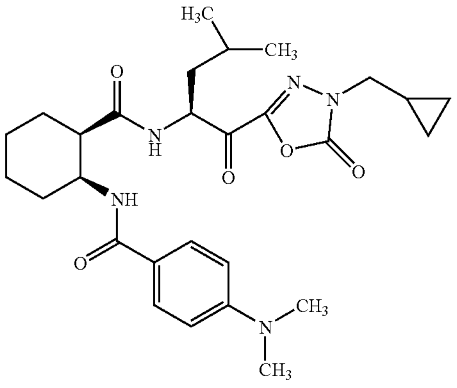

Free Compound

TLC: Rf 0.26 (n-hexane:ethyl acetate=1:1);

NMR ($CDCl_3$): δ 7.66 (d, J=9.0 Hz, 2H), 6.82 (d, J=8.0 Hz, 1H), 6.66 (d, J=9.0 Hz, 2H), 6.33 (d, J=7.6 Hz, 1H), 5.40–5.25 (m, 1H), 4.45–4.30 (m, 1H), 3.75 (dd, J=14.4, 7.3 Hz, 1H), 3.62 (dd, J=14.4, 7.4 Hz, 1H), 3.02 (s, 6H), 2.82 (q, J=5.0 Hz, 1H), 2.15–1.35 (m, 11H), 1.30–1.10 (m, 1H), 0.88 (d, J=5.8 Hz, 3H), 0.83 (d, J=6.4 Hz, 3H), 0.70–0.35 (m, 4H).

Hydrochloride

TLC: Rf 0.26 (n-hexane:ethyl acetate=1:1);

NMR ($CDCl_3$): δ 7.87 (d, J=8.4 Hz, 2H), 7.58 (d, J=8.4 Hz, 2H), 7.42 (d, J=7.8 Hz, 1H), 6.25 (d, J=7.6 Hz, 1H), 5.45–5.20 (m, 1H), 4.40–4.20 (m, 1H), 3.75 (dd, J=14.4, 7.2 Hz, 1H), 3.64 (dd, J=14.4, 7.7 Hz, 1H), 3.15 (s, 6H), 2.83 (q, J=4.8 Hz, 1H), 2.15–1.35 (m, 11H), 1.35–1.10 (m, 1H), 0.93 (d, J=6.2 Hz, 3H), 0.90 (d, J=6.2 Hz, 3H), 0.70–0.35 (m, 4H).

EXAMPLE 10 (56)

1-[(1R,2S)-2-(2-fluorobenzoylamino)cyclohexyl]-N-[(2S)-1-oxo-1-(3-cyclopropylmethyl-2-oxo-1,3,4-oxadiazolin-5-yl)-2-hexyl]carboxamide

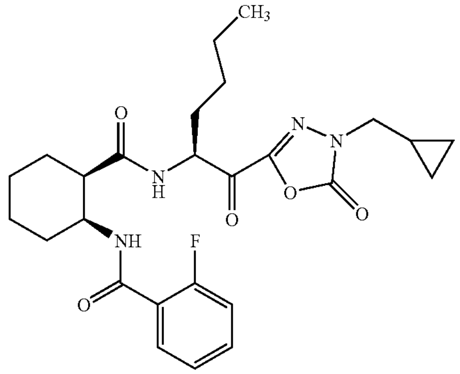

TLC: Rf 0.31 (n-hexane:ethyl acetate=3:2);

NMR ($CDCl_3$): δ 8.05 (dt, J=2.2, 7.9 Hz, 1H), 7.60–7.40 (m, 2H), 7.25 (dt, J=1.1, 7.5 Hz, 1H), 7.11 (ddd, J=12.0, 8.2, 1.1 Hz, 1H), 6.36 (d, J=7.6 Hz, 1H), 5.30 (dt, J=4.2, 7.6 Hz, 1H), 4.55–4.35 (m, 1H), 3.73 (dd, J=14.5, 7.2 Hz, 1H), 3.64 (dd, J=14.5, 7.6 Hz, 1H), 2.83 (q, J=5.0 Hz, 1H), 2.20–1.05 (m, 15H), 0.85–0.70 (m, 3H), 0.70–0.35 (m, 4H).

EXAMPLE 10 (57)

1-[(1R,2S)-2-(4-dimethylaminobenzoylamino)cyclohexyl]-N-[(2S)-1-oxo-1-(3-cyclopropylmethyl-2-oxo-1,3,4-oxadiazolin-5-yl)-2-hexyl]carboxamide

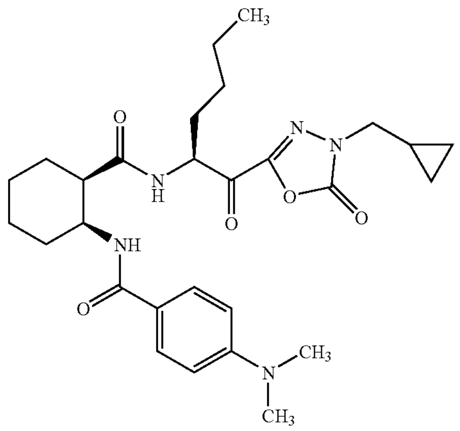

Free Compound

TLC: Rf 0.22 (n-hexane:ethyl acetate=1:1);

NMR ($CDCl_3$): δ 7.67 (d, J=9.0 Hz, 2H), 6.88 (d, J=8.2 Hz, 1H), 6.67 (d, J=9.0 Hz, 2H), 6.44 (d, J=7.2 Hz, 1H), 5.24 (ddd, J=8.4, 7.2 and 4.8 Hz, 1H), 4.45–4.30 (m, 1H), 3.74 (dd, J=14.2, 7.2 Hz, 1H), 3.65 (dd, J=14.2, 7.2 Hz, 1H), 3.01 (s, 6H), 2.82 (q, J=5.0 Hz, 1H), 2.15–1.15 (m, 15H), 0.85–0.70 (m, 3H), 0.70–0.35 (m, 4H).

Hydrochloride

TLC: Rf 0.22 (n-hexane:ethyl acetate=1:1);

NMR ($CDCl_3$): δ 7.88 (d, J=8.4 Hz, 2H), 7.60 (d, J=8.4 Hz, 2H), 7.46 (d, J=8.2 Hz, 1H), 6.40 (d, J=8.0 Hz, 1H), 5.28 (dt, J=4.7, 8.0 Hz, 1H), 4.40–4.20 (m, 1H), 3.75 (dd, J=14.9, 7.4 Hz, 1H), 3.67 (dd, J=14.9, 7.8 Hz, 1H), 3.16 (s, 6H), 2.84 (q, J=5.1 Hz, 1H), 2.15–1.15 (m, 15H), 0.90–0.70 (m, 3H), 0.70–0.35 (m, 4H).

EXAMPLE 10 (58)

1-[(1R,2S)-2-(4-dimethylaminomethylbenzoylamino)cyclohexyl]-N-[1-oxo-1-(3-cyclopropylmethyl-2-oxo-1,3,4-oxadiazolin-5-yl)-2-hexyl]carboxamide

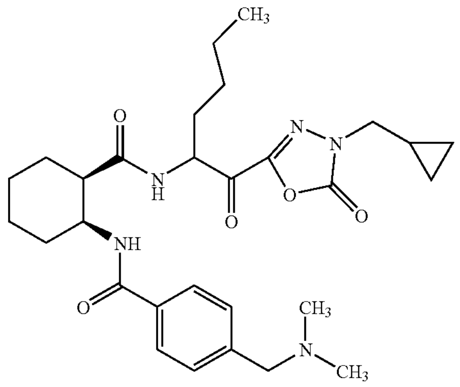

Free Compound

TLC: Rf 0.47 and 0.38 (chloroform:methanol=9:1);

NMR ($CDCl_3$): δ 7.76 and 7.73 (each d, J=8.0 and 8.2 Hz, totally 2H), 7.37 and 7.36 (each d, J=8.0 and 8.2 Hz, totally 2H), 7.17 (d, J=8.0 Hz, 1H), 6.45–6.30 (m, 1H), 5.35–5.15 (m, 1H), 4.45–4.25 (m, 1H), 3.75 and 3.73 (each dd, J=14.4, 7.1 Hz, totally 1H), 3.66 and 3.63 (each dd, J=14.4, 7.4 Hz, totally 1H), 3.46 (s, 2H), 2.90–2.80 (m, 1H), 2.24 (s, 6H), 2.20–1.10 (m, 15H), 0.90–0.70 (m, 3H), 0.70–0.35 (m, 4H).

Hydrochloride

TLC: Rf 0.47 and 0.38 (chloroform:methanol=9:1);

NMR ($CDCl_3$): δ 7.87 and 7.83 (each d, J=8.4 and 8.6 Hz, totally 2H), 7.72 and 7.66 (each d, J=8.4 and 8.6 Hz, totally 2H), 7.51 and 7.22 (each d, J=8.0 Hz, totally 1H), 6.91 and 6.39 (each d, J=6.6 and 7.8 Hz, totally 1H), 5.40–5.10 (m, 1H), 4.40–4.10 (m, 3H), 3.85–3.55 (m, 2H), 3.00–2.60 (m, 7H), 2.30–1.10 (m, 15H), 0.95–0.70 (m, 3H), 0.70–0.35 (m, 4H).

EXAMPLE 10 (59)

1-[(1R,2S)-2-(4-pyrrolidinomethylbenzoylamino)cyclohexyl]-N-[(2S)-4-methyl-1-oxo-1-(3-cyclopropylmethyl-2-oxo-1,3,4-oxadiazolin-5-yl)-2-pentyl]carboxamide Hydrochloride

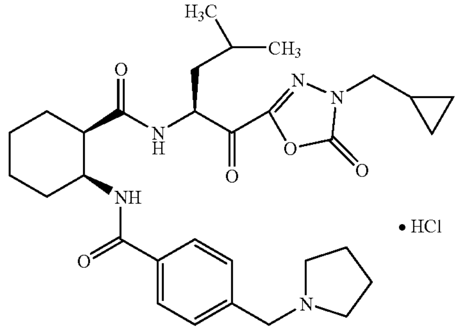

TLC: Rf 0.30 and 0.35 (chloroform:methanol=9:1);

NMR (DMSO-$d_6$) δ 8.50 and 8.39 (each d, J=6.3 Hz, totally 1H), 7.88–7.62 (m, 5H), 4.94–4.81 (m, 1H), 4.38 and 4.37 (each s, totally 2H), 4.32–4.12 (m, 1H), 3.70–3.50 (m, 2H), 3.38–3.25 (m, 2H), 3.08–2.96 (m, 2H), 2.80–2.72 (m, 1H), 2.00–1.88 (m, 7H), 1.68–1.22 (m, 8H), 1.17–1.06 (m, 1H), 0.86, 0.84, 0.75, and 0.71 (each d, J=6.3 Hz, totally 6H), 0.53–0.49 (m, 2H), 0.36–0.33 (m, 2H).

EXAMPLE 10 (60)

1-[(1R,2S)-2-(4-morpholinomethylbenzoylamino)cyclohexyl]-N-[(2S)-4-methyl-1-oxo-1-(3-cyclopropylmethyl-2-oxo-1,3,4-oxadiazolin-5-yl)-2-pentyl]carboxamide Hydrochloride

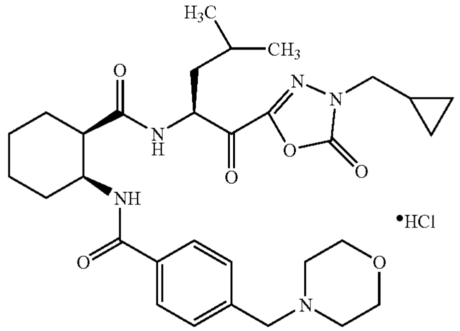

TLC: Rf 0.53 (chloroform:methanol=9:1);

NMR (DMSO-$d_6$): δ 8.40 (d, J=6.9 Hz, 1H), 7.87–7.81 (m, 3H), 7.66 (d, J=7.8 Hz, 2H), 4.93–4.86 (m, 1H), 4.37 (m, 2H), 4.27 (m, 1H), 3.95–3.90 (m, 2H), 3.81–3.73 (m, 2H), 3.67–3.54 (m, 2H), 3.41–3.05 (m, 4H), 2.79–2.72 (m, 1H), 2.06–1.87 (m, 1H), 1.56–1.23 (m, 10H), 1.17–1.06 (m, 1H), 0.76 (d, J=6.3 Hz, 3H), 0.72 (d, J=6.3 Hz, 3H), 0.52–0.50 (m, 2H), 0.36–0.33 (m, 2H).

EXAMPLE 10 (61)

1-[(1R,2S)-2-(2-dimethylaminomethyl-4-fluorobenzoylamino)cyclohexyl]-N-[4-methyl-1-oxo-1-(3-cyclopropylmethyl-2-oxo-1,3,4-oxadiazolin-5-yl)-2-pentyl]carboxamide

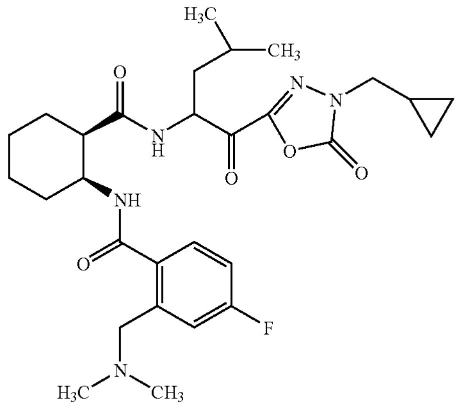

TLC: Rf 0.53 and 0.44 (chloroform:methanol=9:1);

NMR ($CDCl_3$): δ 10.50 and 10.44 (each brd, J=7.2 Hz, totally 1H), 8.03 and 7.99 (each t, J=5.4 Hz, totally 1H), 7.10–7.03 (m, 1H), 6.93–6.88 (m, 1H), 6.85 and 6.23 (each brd, J=7.5 Hz, totally 1H), 5.30–5.10 (m, 1H), 4.50 and 4.31 (each m, totally 1H), 3.80–3.30 (m, 4H), 3.05 and 2.92 (each m, totally 1H), 2.24 and 2.21 (each s, totally 6H), 2.30–1.10 (m, 12H), 0.99 and 0.78 (each m, totally 6H), 0.63 and 0.43 (each m, each 2H).

EXAMPLE 10 (62)

1-[(1R,2S)-2-(3-pyrrolidinomethylbenzoylamino) cyclohexyl]-N-[(2S)-4-methyl-1-oxo-1-(3-cyclopropylmethyl-2-oxo-1,3,4-oxadiazolin-5-yl)-2-pentyl] carboxamide Hydrochloride

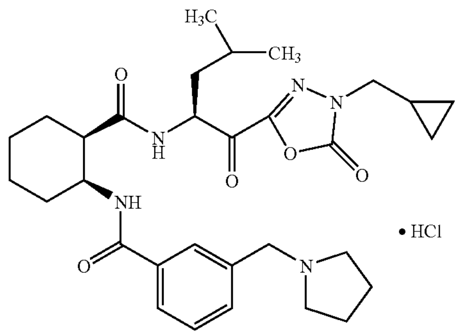

TLC: Rf0.35 (chloroform methanol=9:1);

NMR (DMSO-$d_6$) δ 8.49 and 8.38 (each d, J=6.6 Hz, totally 1H), 8.01 and 7.93 (each s, totally 1H), 7.80 (d, J=7.5 Hz, 2H), 7.74 (d, J=7.8 Hz, 1H), 7.51 (t-like, J=7.5 Hz, 1H), 4.93–4.87 (m, 1H), 4.39 and 4.37 (each s, totally 2H), 4.38 (m, 1H), 3.87–3.53 (m, 2H), 3.38–3.32 (m, 2H), 3.05 (m, 2H), 2.75–2.72 (m, 1H), 2.01–1.87 (m, 7H), 1.58–1.24 (m, 8H), 1.17–1.05 (m, 1H), 0.86, 0.84, 0.76, and 0.70 (each d, J=6.0 Hz, totally 6H), 0.54–0.48 (m, 2H), 0.36–0.33 (m, 2H).

EXAMPLE 10 (63)

1-[(1R,2S)-2-(4-dimethylaminomethyl-2-fluorobenzoylamino)cyclohexyl]-N-[4-methyl-1-oxo-1-(3-cyclopropylmethyl-2-oxo-1,3,4-oxadiazolin-5-yl)-2-pentyl]carboxamide

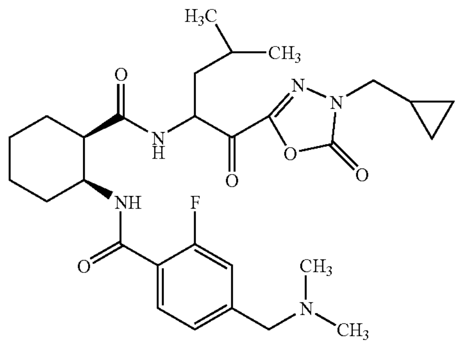

TLC: Rf 0.57 and 0.50 (chloroform:methanol=9:1);

NMR ($CDCl_3$): δ 8.02–7.92 (m, 1H), 7.48–7.35 (m, 1H), 7.21–7.05 (m, 2H), 6.39 and 6.22 (each brd, J=6.9 Hz, totally 1H), 5.42–5.25 (m, 1H), 4.52–4.38 (m, 1H), 3.80–3.54 (m, 1H), 3.43 (m, 2H), 2.82–2.75 (m, 1H), 2.24 (s, 6H), 2.15–1.40 (m, 11H), 1.30–1.15 (m, 1H), 0.99, 0.96, 0.87, and 0.80 (each d, J=6.3 Hz, totally 6H), 0.70 and 0.42 (each m, each 2H).

EXAMPLE 10 (64)

1-[(1R,2S)-2-(4-dimethylaminobenzoylamino)cyclohexyl]-N-[4-methyl-1-oxo-1-(3-cyclopropylmethyl-2-oxo-1,3,4-oxadiazolin-5-yl)-2-pentyl]carboxamide

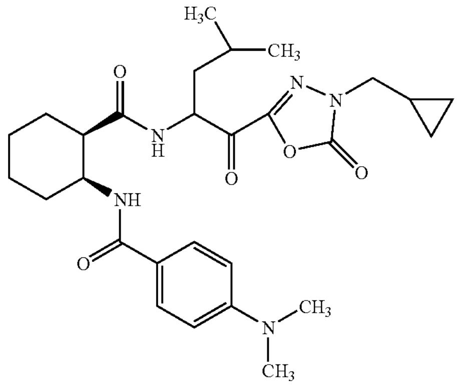

TLC: Rf 0.38 (toluene:ethyl acetate=1:1);

NMR ($CDCl_3$): δ 7.72 and 7.66 (each d, J=8.7 Hz, totally 2H), 6.87 and 6.81 (each d, J=8.4 Hz, totally 1H), 6.66 and 6.65 (each d, J=8.7 Hz, totally 2H), 6.33–6.29 (m, 1H), 5.35–5.20 (m, 1H), 4.38–4.33 (m, 1H), 3.79–3.70 (m, 1H), 3.65–3.55 (m, 1H), 3.01 (m, 6H), 2.88–2.80 (m, 1H), 2.15–1.45 (m, 11H), 1.29–1.16 (m, 1H), 0.99–0.82 (m, 6H), 0.64–0.61 (m, 2H), 0.42 (m, 2H).

EXAMPLE 10 (65)

1-[(1R,2S)-2-(3-dimethylaminomethylbenzoylamino) cyclohexyl]-N-[4-methyl-1-oxo-1-(3-cyclopropylmethyl-2-oxo-1,3,4-oxadiazolin-5-yl)-2-pentyl]carboxamide

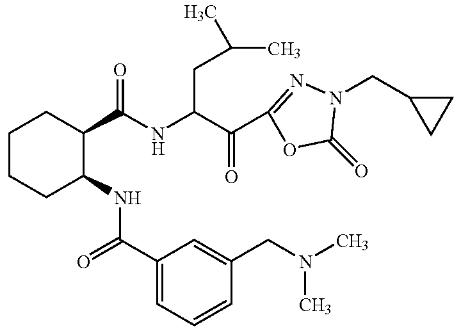

TLC: Rf 0.48 and 0.46 (chloroform:methanol=9:1);

NMR ($CDCl_3$): δ 7.75–7.60 (m, 2H), 7.50–7.30 (m, 2H), 7.09 (d, J=8.4 Hz, 1H), 6.31 and 6.26 (each d, J=7.8 and 8.0 Hz, totally 1H), 5.40–5.20 (m, 1H), 4.45–4.25 (m, 1H), 3.76 and 3.75 (each dd, J=14.5, 7.2 Hz, totally 1H), 3.63 and 3.61 (each dd, J=14.5, 7.4 Hz, totally 1H), 3.47 (s, 2H), 2.90–2.80 (m, 1H), 2.25 and 2.24 (each s, totally 6H), 2.20–1.35 (m, 11H), 1.35–1.10 (m, 1H), 1.00, 0.94, 0.88 and 0.83 (each d, J=6.2 Hz, totally 6H), 0.70–0.35 (m, 4H).

EXAMPLE 10 (66)

1-[(1R,2S)-2-(2-dimethylaminomethylbenzoylamino)cyclohexyl]-N-[4-methyl-1-oxo-1-(3-cyclopropylmethyl-2-oxo-1,3,4-oxadiazolin-5-yl)-2-pentyl]carboxamide

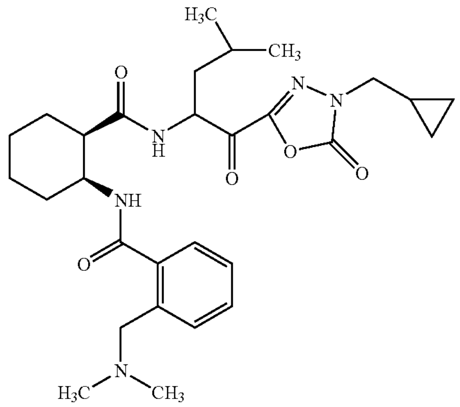

TLC: Rf 0.42 and 0.36 (chloroform:methanol=9:1);

NMR ($CDCl_3$): δ 10.65–10.45 (m, 1H), 8.05–7.90 (m, 1H), 7.45–7.30 (m, 2H), 7.25–7.10 (m, 1H), 7.00 and 6.34 (each d, J=7.0 and 7.2 Hz, totally 1H), 5.30–5.10 (m, 1H), 4.52 and 4.34 (each br, totally 1H), 3.80–3.30 (m, 4H), 3.10–2.85 (m, 1H), 2.23 and 2.21 (each s, totally 6H), 2.20–1.35 (m, 11H), 1.30–1.10 (m, 1H), 0.96, 0.95, 0.71 and 0.68 (each d, J=6.2, 6.2, 6.0 and 6.0 Hz, totally 6H), 0.65–0.35 (m, 4H).

EXAMPLE 10 (67)

(2S)-N-[2-oxo-2-(3-cyclopropylmethyl-2-oxo-1,3,4-oxadiazolin-5-yl)ethyl]-2-benzyloxycarbonylamino-4-methylpentanamide

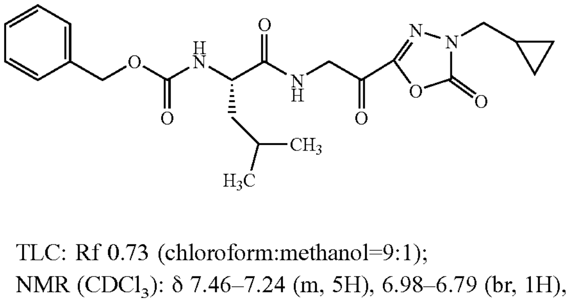

TLC: Rf 0.73 (chloroform:methanol=9:1);

NMR ($CDCl_3$): δ 7.46–7.24 (m, 5H), 6.98–6.79 (br, 1H), 5.34–5.18 (m, 1H), 5.12 (s, 2H), 4.60 (brs, 2H), 4.37–4.22 (m, 1H), 3.69 (d, J=7.5 Hz, 2H), 2.00–1.46 (m, 3H), 1.32–1.18 (m, 1H), 1.10–0.90 (m, 6H), 0.70–0.57 and 0.47–0.38 (each m, totally 4H).

EXAMPLE 10 (68)

(2S)-N-[(2S)-4-methoxy-1-oxo-1-(3-cyclopropylmethyl-2-oxo-1,3,4-oxadiazolin-5-yl)-2-butyl]-2-benzyloxycarbonylamino-4-methylpentanamide

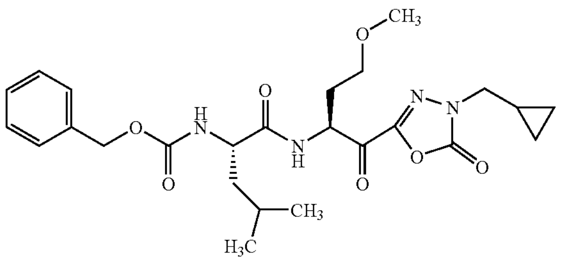

TLC: Rf 0.43 (n-hexane:ethyl acetate=1:1);

NMR ($CDCl_3$): δ 7.40–7.25 (m, 5H), 7.13 (d, J=6.0 Hz, 1H), 5.28 (q, J=6.0 Hz, 1H), 5.20–5.05 (m, 3H), 4.30–4.15 (m, 1H), 3.71 (dd, J=14.2, 7.5 Hz, 1H), 3.67 (dd, J=14.2, 7.5 Hz, 1H), 3.50–3.30 (m, 2H), 3.19 (s, 3H), 2.25–2.10 (m, 2H), 1.80–1.40 (m, 3H), 1.30–1.15 (m, 1H), 0.95 (d, J=6.3 Hz, 6H), 0.65–0.60 (m, 2H), 0.45–0.40 (m, 2H).

EXAMPLE 10 (69)

1-[(1R,2S)-2-benzoylaminocyclohexyl]-N-[(2S)-4-methoxy-1-oxo-1-(3-cyclopropylmethyl-2-oxo-1,3,4-oxadiazolin-5-yl)-2-butyl]carboxamide

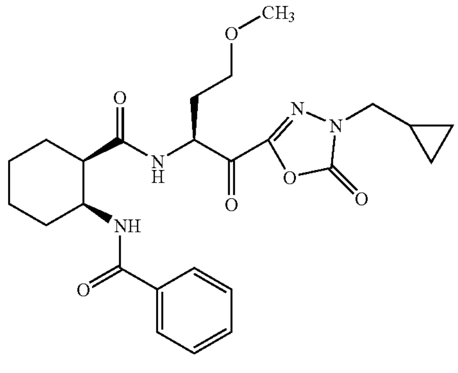

TLC: Rf 0.42 (n-hexane:ethyl acetate=1:2);

NMR ($CDCl_3$) δ 7.80–7.75 (m, 2H), 7.50–7.35 (m, 4H), 7.10 (d, J=6.0 Hz, 1H), 5.28 (q, J=6.0 Hz, 1H), 4.40–4.30 (m, 1H), 3.70 (dd, J=14.5, 7.2 Hz, 1H), 3.66 (dd, J=14.5, 7.2 Hz, 1H), 3.40 (t, J=6.0 Hz, 2H), 3.21 (s, 3H), 2.81 (q, J=4.8 Hz, 1H), 2.17 (q, J=6.0 Hz, 2H), 2.05–1.45 (m, 8H), 1.30–1.15 (m, 1H), 0.65–0.60 (m, 2H), 0.45–0.40 (m, 2H).

EXAMPLE 10 (70)

1-[(1R,2S)-2-(3-morpholinomethylbenzoylamino)cyclohexyl]-N-[(2S)-4-methyl-1-oxo-1-(3-cyclopropylmethyl-2-oxo-1,3,4-oxadiazolin-5-yl)-2-pentyl]carboxamide Hydrochloride

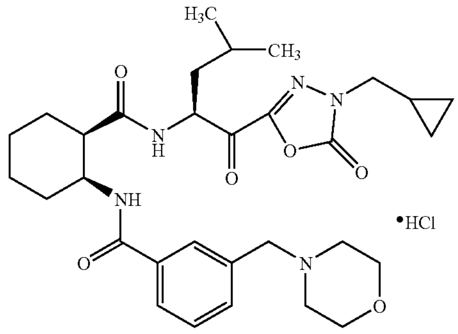

TLC: Rf 0.49 (chloroform:methanol=19:1);

NMR ($DMSO-d_6$) δ 8.48 and 8.38 (each d, J=6.6 Hz, totally 1H), 8.03 and 7.96 (each s, totally 1H), 7.81 (d, J=6.3 Hz, 2H), 7.72 (d, J=7.5 Hz, 1H), 7.53 (t-like, J=7.5 Hz, 1H), 4.92–4.86 (m, 1H), 4.39 (br-s, 2H), 4.30 (m, 1H), 3.95–3.91 (m, 2H), 3.78–3.69 (m, 2H), 3.67–3.53 (m, 2H), 3.41–3.08 (m, 4H), 2.74–2.72 (m, 1H), 2.02–1.90 (m, 2H), 1.79–1.21 (m, 9H), 1.18–1.04 (m, 1H), 0.86, 0.84, 0.76, and 0.71 (each d, J=6.0 Hz, totally 6H), 0.54–0.48 (m, 2H), 0.35–0.33 (m, 2H).

EXAMPLE 10 (71)

1-[(1R,2S)-2-(2-morpholinomethylbenzoylamino)cyclohexyl]-N-[(2S)-4-methyl-1-oxo-1-(3-cyclopropylmethyl-2-oxo-1,3,4-oxadiazolin-5-yl)-2-pentyl]carboxamide Hydrochloride

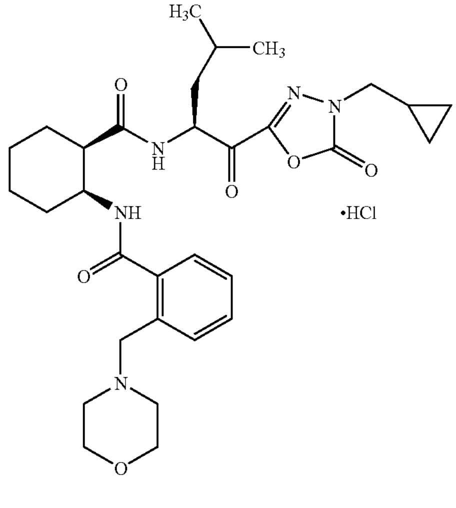

TLC: Rf 0.56 (chloroform:methanol=19:1);

NMR ($DMSO-d_6$): δ 8.56–8.21 (m, 2H), 7.75–7.70 (m, 1H), 7.59–7.53 (m, 3H), 4.92–4.85 (m, 1H), 4.50–4.33 (m, 3H), 3.91–3.88 (m, 2H), 3.79–3.55 (m, 4H), 3.38–3.08 (m, 4H), 2.80–2.71 (m, 1H), 1.98–1.77 (m, 2H), 1.67–1.22 (m, 9H), 1.18–1.06 (m, 1H), 0.89, 0.83, and 0.79 (each d, J=6.0 Hz, totally 6H), 0.56–0.49 (m, 2H), 0.37–0.34 (m, 2H).

EXAMPLE 10 (72)

(2S)-N-[(2S)-1-oxo-1-(3-cyclopropylmethyl-2-oxo-1,3,4-oxadiazolin-5-yl)-2-hexyl]-2-benzyloxycarbonylamino-4-methylpentanamide

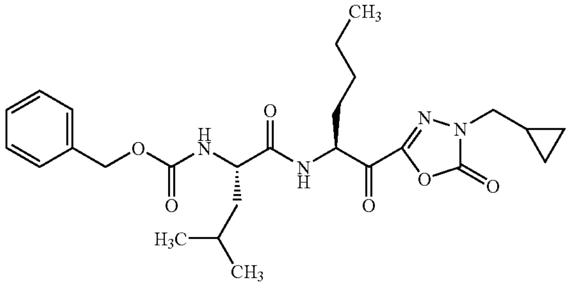

TLC: Rf 0.44 (n-hexane:ethyl acetate=2:1);

NMR ($CDCl_3$): δ 7.34 (s, 5H), 6.58 (brd, J=7.4 Hz, 1H), 5.29 (m, 1H), 5.11 (m, 3H), 4.22 (m, 1H), 3.74 and 3.64 (each dd, J=14.8, 7.4 Hz, each 1H), 2.03–1.80 (m, 1H), 1.80–1.10 (m, 9H), 1.02–0.80 (m, 9H), 0.60 and 0.43 (each m, each 2H).

EXAMPLE 10 (73)

1-[(1R,2S)-2-benzoylaminocyclohexyl]-N-[(2S)-1-oxo-1-(3-cyclopropylmethyl-2-oxo-1,3,4-oxadiazolin-5-yl)-2-hexyl]carboxamide

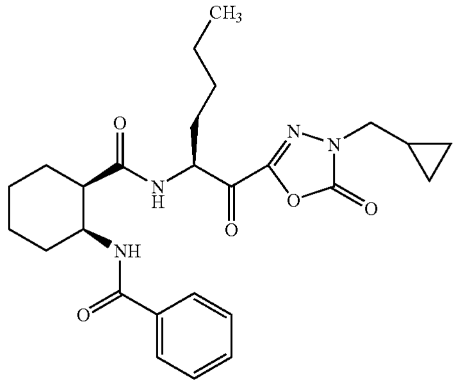

TLC: Rf 0.65 (chloroform:methanol=9:1);

NMR ($CDCl_3$): δ 7.80 (m, 2H), 7.58–7.31 (m, 3H), 7.20 (brd, J=8.2 Hz, 1H), 6.27 (brd, J=7.6 Hz, 1H), 5.29 (ddd, J=8.4, 7.6, 4.4 Hz, 1H), 4.38 (m, 1H), 3.75 and 3.64 (each dd, J=14.4, 7.4 Hz, each 1H), 2.83 (q, J=5.2 Hz, 1H), 2.23–1.13 (m, 15H), 0.83 (m, 3H), 0.63 and 0.82 (each m, each 2H).

EXAMPLE 10 (74)

1-[(1R,2S)-2-benzoylaminocyclohexyl]-N-[(2S)-4-methyl-1-oxo-1-(3-cyclohexyl-2-oxo-1,3,4-oxadiazolin-5-yl)-2-pentyl]carboxamide

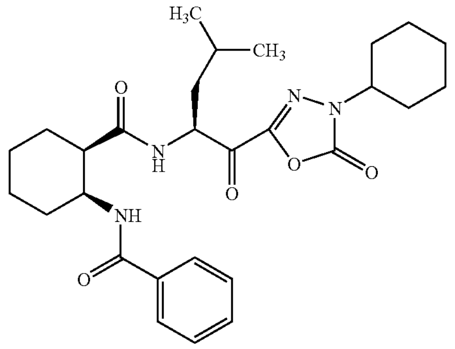

TLC: Rf 0.31 (n-hexane:ethyl acetate=1:1);

NMR ($CDCl_3$): δ 7.83–7.74 (m, 2H), 7.53–7.37 (m, 3H), 7.14 (d, J=8.1 Hz, 1H), 6.17 (d, J=7.8 Hz, 1H), 5.42–5.24 (m, 1H), 4.40–4.28 (m, 1H), 4.03 (tt, J=11.4, 3.9 Hz, 1H), 2.88–2.80 (m, 1H), 2.17–1.12 (m, 21H), 0.90 and 0.83 (each d, J=6.3 Hz, totally 6H).

EXAMPLE 10 (75)

(2S)-N-[(2S)-4-methyl-1-oxo-1-(3-ethoxymethyl-2-oxo-1,3,4-oxadiazolin-5-yl)-2-pentyl]-2-benzyloxycarbonylamino-4-methylpentanamide

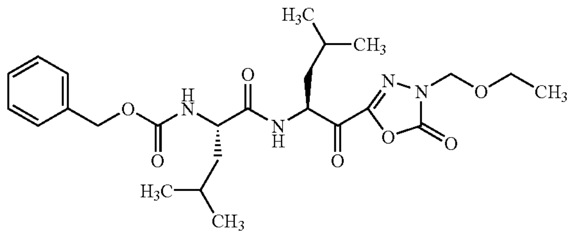

TLC: Rf 0.37 (n-hexane:ethyl acetate=2:1);

NMR ($CDCl_3$): δ 7.35 (s, 5H), 6.50 (d, J=7.0 Hz, 1H), 5.40–5.25 (m, 1H), 5.21 (s, 2H), 5.15–5.05 (m, 1H), 5.12 (s, 2H), 4.30–4.10 (m, 1H), 3.69 (q, J=7.0 Hz, 2H), 1.80–1.40 (m, 6H), 1.24 (t, J=7.0 Hz, 3H), 1.10–0.80 (m, 12H).

EXAMPLE 10 (76)

1-[(1R,2S)-2-benzoylaminocyclohexyl]-N-[(2S)-4-methyl-1-oxo-1-(3-ethoxymethyl-2-oxo-1,3,4-oxadiazolin-5-yl)-2-pentyl]carboxamide

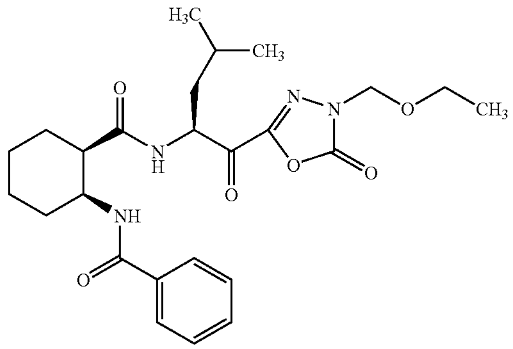

TLC: Rf 0.40 (n-hexane:ethyl acetate=1:1);

NMR ($CDCl_3$): δ 7.76 (dd, J=8.6, 2.0 Hz, 2H), 7.60–7.35 (m, 3H), 7.11 (d, J=8.0 Hz, 1H), 6.19 (d, J=7.2 Hz, 1H), 5.40–5.25 (m, 1H), 5.20 (s, 2H), 4.45–4.25 (m, 1H), 3.69 (q, J=7.0 Hz, 2H), 2.85 (q, J=5.0 Hz, 1H), 2.20–1.30 (m, 11H), 1.24 (t, J=7.0 Hz, 3H), 0.88 (d, J=6.0 Hz, 3H), 0.84 (d, J=6.0 Hz, 3H).

EXAMPLE 10 (77)

(2S)-N-[(2S)-4-methyl-1-oxo-1-(3-(2-methoxyethyl)-2-oxo-1,3,4-oxadiazolin-5-yl)-2-pentyl]-2-benzyloxycarbonylamino-4-methylpentanamide

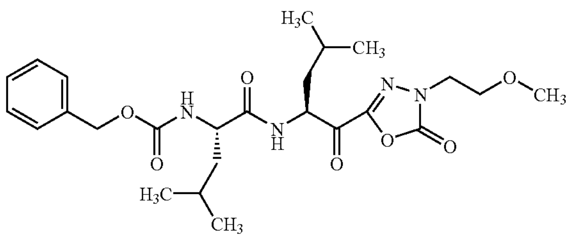

TLC: Rf 0.45 (n-hexane:ethyl acetate=1:1);

NMR ($CDCl_3$): δ 7.35 (s, 5H), 6.50 (d, J=7.4 Hz, 1H), 5.40–5.25 (m, 1H), 5.20–5.05 (m, 3H), 4.30–4.10 (m, 1H), 4.04 (dt, J=14.3, 5.5 Hz, 1H), 4.00 (dt, J=14.3, 5.1 Hz, 1H), 3.72 (t, J=5.3 Hz, 2H), 3.36 (s, 3H), 1.80–1.40 (m, 6H), 1.05–0.80 (m, 12H).

EXAMPLE 10 (78)

1-[(1R,2S)-2-benzoylaminocyclohexyl]-N-[(2S)-4-methyl-1-oxo-1-(3-methoxyethyl-2-oxo-1,3,4-oxadiazolin-5-yl)-2-pentyl]carboxamide

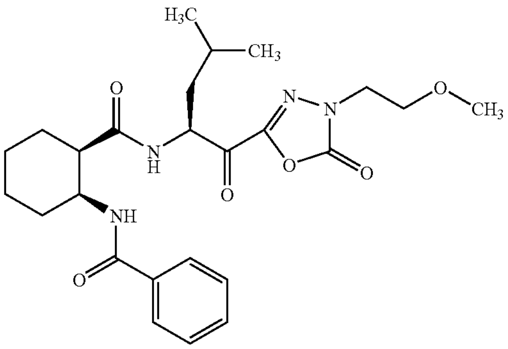

TLC: Rf 0.16 (n-hexane:ethyl acetate=1:1);

NMR ($CDCl_3$): δ 7.77 (dd, J=7.9, 1.6 Hz, 2H), 7.55–7.35 (m, 3H), 7.14 (d, J=8.4 Hz, 1H), 6.19 (d, J=7.8 Hz, 1H), 5.40–5.25 (m, 1H), 4.40–4.25 (m, 1H), 4.04 (dt, J=14.5, 5.6 Hz, 1H), 3.99 (dt, J=14.5, 5.0 Hz, 1H), 3.72 (t, J=5.3 Hz, 2H), 3.36 (s, 3H), 2.84 (q, J=5.2 Hz, 1H), 2.20–1.35 (m, 11H), 0.88 (d, J=6.0 Hz, 3H), 0.83 (d, J=6.2 Hz, 3H).

EXAMPLE 10 (79)

1-[(1R,2S)-2-benzoylaminocyclohexyl]-N-[(2S)-4-methyl-1-oxo-1-(3-butyl-2-oxo-1,3,4-oxadiazolin-5-yl)-2-pentyl]carboxamide

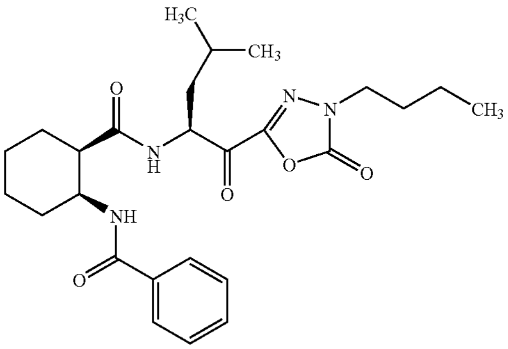

TLC: Rf0.45 (n-hexane:ethyl acetate=1:1);

NMR ($CDCl_3$): δ 7.77 (dd, J=7.9, 1.6 Hz, 2H), 7.55–7.35 (m, 3H), 7.13 (d, J=8.0 Hz, 1H), 6.19 (d, J=8.2 Hz, 1H), 5.40–5.25 (m, 1H), 4.40–4.25 (m, 1H), 3.84 (t, J=7.0 Hz, 2H), 2.84 (q, J=5.0 Hz, 1H), 2.20–1.20 (m, 15H), 0.97 (t, J=7.3 Hz, 3H), 0.89 (d, J=6.0 Hz, 3H), 0.83 (d, J=6.0 Hz, 3H).

EXAMPLE 10 (80)

1-[(1R,2S)-2-(4-fluorobenzoylamino)cyclohexyl]-N-[(2S)-1-oxo-1-(3-cyclopropylmethyl-2-oxo-1,3,4-oxadiazolin-5-yl)-2-hexyl]carboxamide

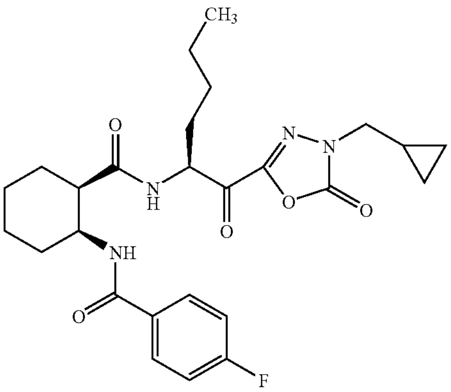

TLC: Rf 0.36 (n-hexane:ethyl acetate=3:2);

NMR ($CDCl_3$): δ 7.79 (dd, J=8.7, 5.4 Hz, 2H), 7.35–7.20 (m, 1H), 7.10 (t, J=8.7 Hz, 2H), 6.27 (d, J=7.6 Hz, 1H), 5.30 (dt, J=4.2, 7.6 Hz, 1H), 4.40–4.20 (m, 1H), 3.75 (dd, J=14.6, 7.2 Hz, 1H), 3.67 (dd, J=14.6, 7.6 Hz, 1H), 2.83 (q, J=5.0 Hz, 1H), 2.20–1.10 (m, 15H), 0.90–0.70 (m, 3H), 0.70–0.35 (m, 4H).

EXAMPLE 10 (81)

1-[(1R,2S)-2-benzoylaminocyclohexyl]-N-[(2S)-4-methyl1-oxo-1-(3-bis(methoxycarbonyl)methyl-2-oxo-1,3,4-oxadiazolin-5-yl)-2-pentyl]carboxamide

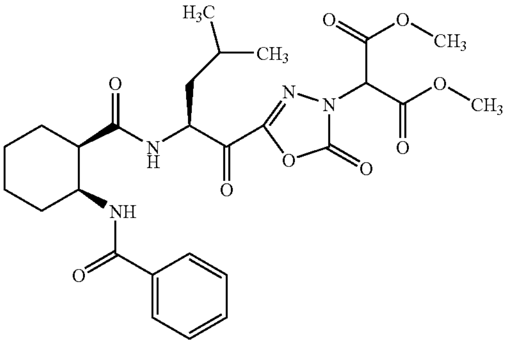

TLC: Rf 0.58 (ethyl acetate);

NMR ($CDCl_3$): δ 7.80–7.73 (m, 2H), 7.53–7.37 (m, 3H), 7.14 (brd, J=7.8 Hz, 1H), 6.18 (d, J=7.2 Hz, 1H), 5.52 (s, 1H), 5.34–5.24 (m, 1H), 4.42–4.29 (m, 1H), 3.89 and 3.88 (each s, totally 6H), 2.89–2.80 (m, 1H), 2.15–1.40 (m, 11H), 0.86 and 0.84 (each d, J=6.0 Hz, totally 6H).

EXAMPLE 10 (82)

(2S)-N-[(2S)-4-methyl-1-oxo-1-(3-bis(methoxycarbonyl)methyl-2-oxo-1,3,4-oxadiazolin-5-yl)-2-pentyl]-2-benzyloxycarbonylamino-4-methylpentanamide

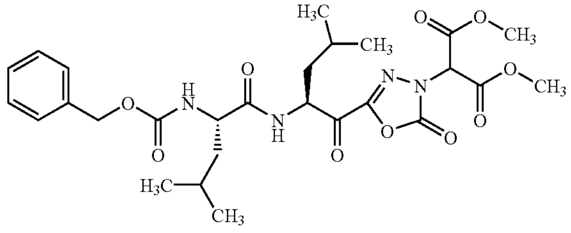

TLC: Rf 0.54 (n-hexane:ethyl acetate=1:2);

NMR ($CDCl_3$): δ 7.48–7.25 (m, 5H), 6.60–6.40 (br, 1H), 5.52 (s, 1H), 5.32–5.22 (m, 1H), 5.20–5.05 (m, 3H), 4.28–4.13 (m, 1H), 3.89 and 3.88 (each s, totally 6H), 1.80–1.42 (m, 6H), 1.10–0.85 (m, 12H).

EXAMPLE 10 (83)

(2S)-N-[(2S)-3-ethoxy-1-oxo-1-(3-(2-methylpropyl)-2-oxo-1,3,4-oxadiazolin-5-yl)-2-propyl]-2-benzyloxycarbonylamino-4-methylpentanamide

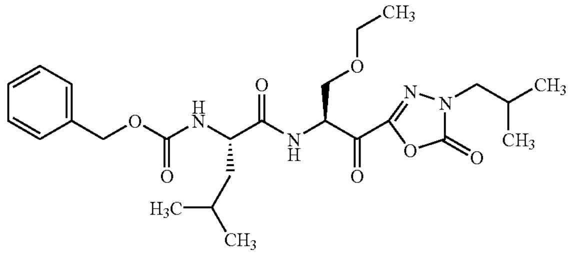

TLC: Rf 0.55 (n-hexane:ethyl acetate=1:1);

NMR ($CDCl_3$): δ 7.35 (s, 5H), 7.00 and 6.82 (each brd, J=7.8 Hz, totally 1H), 5.45–5.38 (m, 1H), 5.22–5.10 (m, 3H), 4.35–4.20 (m, 1H), 4.03 and 3.72 (each m, each 1H), 3.65 (d, J=7.2 Hz, 2H), 3.50–3.38 (m, 2H), 2.30–2.10 (m, 1H), 1.80–1.50 (m, 3H), 1.15 (t, J=6.8 Hz, 3H), 1.05–0.90 (m, 12H).

EXAMPLE 10 (84)

1-[(1R,2S)-2-benzoylaminocyclohexyl]-N-[(2S)-3-ethoxy-1-oxo-1-(3-(2-methylpropyl)-2-oxo-1,3,4-oxadiazolin-5-yl)-2-propyl]carboxamide

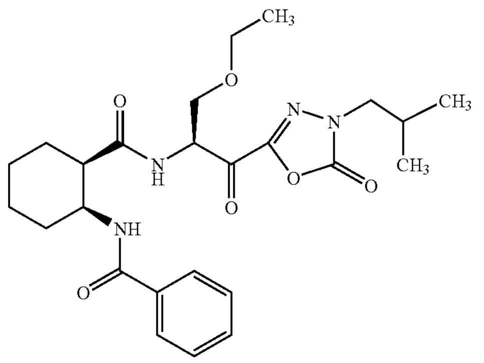

TLC: Rf 0.56 (n-hexane:ethyl acetate=2:3);

NMR ($CDCl_3$): δ 7.82 and 7.78 (each d, J=6.6 Hz, totally 2H), 7.50–7.30 (m, 4H), 6.59 and 6.54 (each brd, J=6.6 Hz, totally 1H), 5.42–5.30 (m, 1H), 4.42–4.30 (m, 1H), 3.98 and 3.70 (each m, each 1H), 3.65 (d, J=7.2 Hz, 2H), 3.45–3.35 (m, 2H), 2.92–2.84 (m, 1H), 2.30–1.40 (m, 9H), 1.15 (t, J=7.2 Hz, 3H), 1.05–0.90 (m, 6H).

EXAMPLE 10 (85)

1-[(2S)-2-phenylaminocarbonylpiperidino]-N-[(2S)-4-methyl-1-oxo-1-(3-(2-methylpropyl)-2-oxo-1,3,4-oxadiazolin-5-yl)-2-pentyl]carboxamide

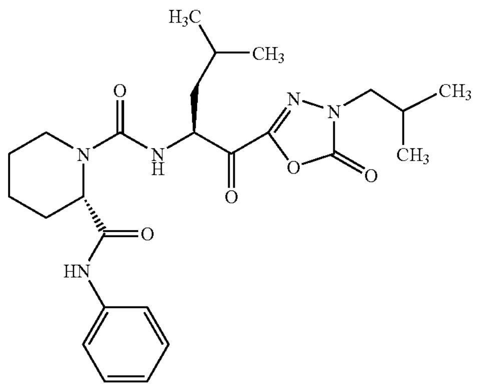

TLC: Rf 0.51 (n-hexane:ethyl acetate=1:1);

NMR ($CDCl_3$): δ 8.51 (brs, 1H), 7.57–7.48 (m, 2H), 7.36–7.24 (m, 2H), 7.13–7.05 (m, 1H), 5.28 (ddd, J=9.9, 8.1 and 4.2 Hz, 1H), 5.08 (d, J=8.1 Hz, 1H), 4.88–4.77 (m, 1H), 3.70–3.56 (m, 3H), 3.12 (td, J=13.2 and 2.7 Hz, 1H), 2.38–2.09 (m, 2H), 1.94–1.42 (m, 8H), 1.10–0.91 (m, 12H).

EXAMPLE 10 (86)

1-[(1R,2S)-2-t-butoxycarbonylaminocyclohexyl]-N-[(2S)-4-methyl-1-oxo-1-(3-((1R,2S)-2-t-butoxycarbonylaminocyclohexylcarbonyl)-2-oxo-1,3,4-oxadiazolin-5-yl)-2-pentyl]carboxamide

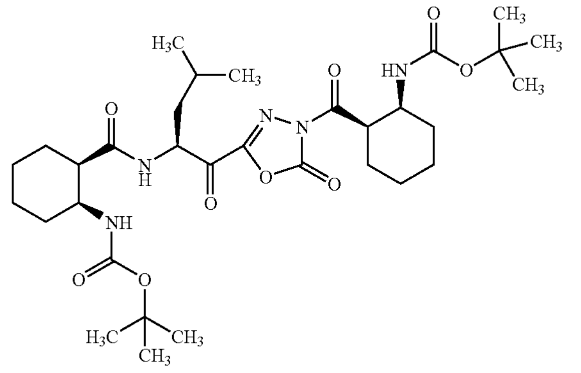

TLC: Rf 0.50 (n-hexane:ethyl acetate=3:2);

NMR ($CDCl_3$): δ 6.21 (d, J=6.9 Hz, 1H), 5.40–5.25 (m, 1H), 5.15 (d, J=7.5 Hz, 1H), 4.90 (d, J=9.3 Hz, 1H), 4.40–4.25 (m, 1H), 3.90–3.80 (m, 1H), 3.50–3.40 (m, 1H), 2.69 (q, J=5.1 Hz, 1H), 1.95–1.30 (m, 19H), 1.43 (s, 9H), 1.41 (s, 9H), 1.02 (d, J=6.0 Hz, 6H), 0.98 (d, J=6.3 Hz, 6H).

EXAMPLE 10 (87)

(2S)-N-[4-methyl-1-oxo-1-(3-(2-dimethylaminoethyl)-2-oxo-1,3,4-oxadiazolin-5-yl)-2-pentyl]-2-benzyloxycarbonylamino-4-methylpentanamide

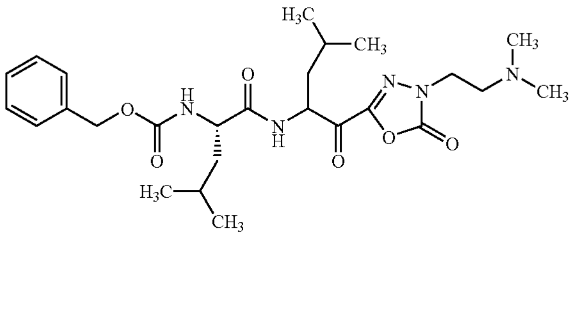

TLC: Rf0.47 (chloroform:methanol=9:1);

NMR ($CDCl_3$): δ 7.35 (s, 5H), 6.63 and 6.48 (each br, totally 1H), 5.38 (m, 1H), 5.22–5.00 (m, 3H), 4.30–4.18 (m, 1H), 4.02–3.80 (m, 2H), 2.80–2.60 (m, 2H), 2.27 (s, 6H), 2.05–1.40 (m, 6H), 1.02–0.80 (m, 12H).

EXAMPLE 10 (88)

1-[(1R,2S)-2-benzoylaminocyclohexyl]-N-[4-methyl-1-oxo-1-(3-(2-dimethylamino)ethyl-2-oxo-1,3,4-oxadiazolin-5-yl)-2-pentyl]carboxamide

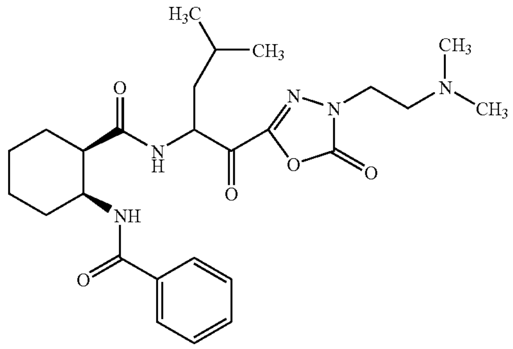

TLC: Rf 0.40 (chloroform:methanol=9:1);

NMR ($CDCl_3$): δ 7.83–7.71 (m, 2H), 7.50–7.38 (m, 3H), 7.20–7.10 (m, 1H), 6.25 and 6.19 (each d, J=6.6 Hz, totally 1H), 5.40–5.24 (m, 1H), 4.42–4.30 (m, 1H), 4.02–3.80 (m, 2H), 2.82 (m, 1H), 2.80–2.60 (m, 2H), 2.28 (s, 6H), 2.25–1.40 (m, 11H), 0.98, 0.94, 0.88, and 0.82 (each d, J=6.3 Hz, totally 6H).

EXAMPLE 10 (89)

(2S)-N-[(2S)-4-methoxy-1-oxo-1-(3-(2-methylpropyl)-2-oxo-1,3,4-oxadiazolin-5-yl)-2-butyl]-2-benzyloxycarbonylamino-4-methylpentanamide

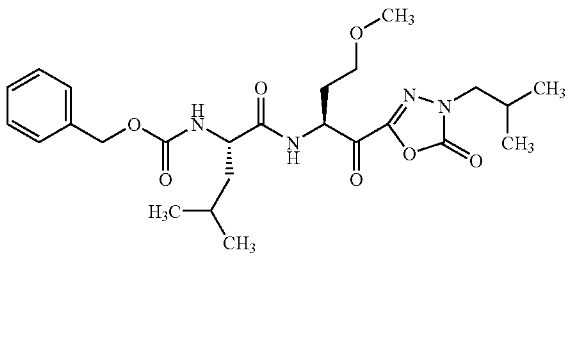

TLC: Rf 0.54 (n-hexane:ethyl acetate=1:1);

NMR ($CDCl_3$): δ 7.40–7.25 (m, 5H), 7.11 (d, J=6.3 Hz, 1H), 5.26 (q, J=6.3 Hz, 1H), 5.20–5.05 (m, 3H), 4.30–4.15 (m, 1H), 3.63 (d, J=7.2 Hz, 2H), 3.50–3.30 (m, 2H), 3.18 (s, 3H), 2.25–2.10 (m, 3H), 1.80–1.40 (m, 3H), 1.00–0.85 (m, 12H).

EXAMPLE 10 (90)

1-[(1R,2S)-2-benzoylaminocyclohexyl]-N-[(2S)-4-methoxy-1-oxo-1-(3-(2-methylpropyl)-2-oxo-1,3,4-oxadiazolin-5-yl)-2-butyl]carboxamide

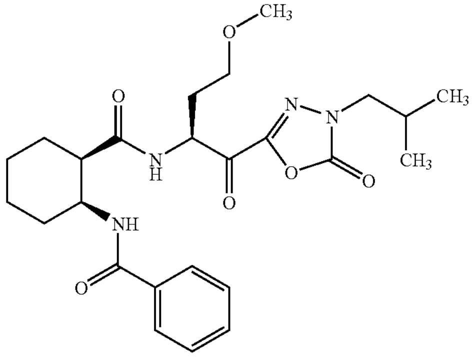

TLC: Rf 0.22 (n-hexane:ethyl acetate=1:1);

NMR ($CDCl_3$) δ 7.80–7.75 (m, 2H), 7.50–7.35 (m, 4H), 7.09 (d, J=5.7 Hz, 1H), 5.26 (q, J=5.7 Hz, 1H), 4.40–4.25 (m, 1H), 3.63 (d, J=6.9 Hz, 2H), 3.45–3.30 (m, 2H), 3.19 (s, 3H), 2.81 (q, J=5.1 Hz, 1H), 2.25–1.40 (m, 11H), 0.98 (d, J=6.9 Hz, 6H).

EXAMPLE 10 (91)

1-[(1R,2S)-2-benzoylaminocyclohexyl]-N-[2-oxo-2-(3-(2-methylpropyl)-2-oxo-1,3,4-oxadiazolin-5-yl)ethyl]carboxamide

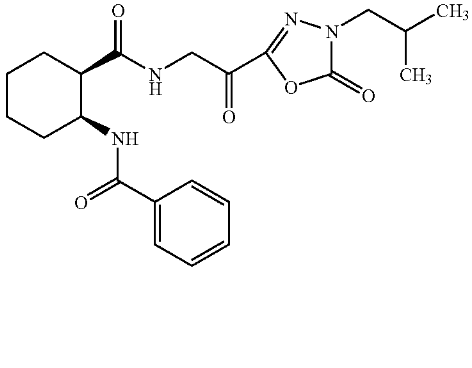

TLC: Rf 0.51 (chloroform:methanol=9:1);

NMR ($CDCl_3$): δ 7.82–7.75 (m, 2H), 7.52–7.37 (m, 3H), 7.27 (brd, J=7.8 Hz, 1H), 6.56–6.46 (br, 1H), 4.56 (d, J=5.1 Hz), 4.43–4.32 (m, 1H), 3.63 (d, J=7.2 Hz, 2H), 2.92–2.84 (m, 1H), 2.23–1.45 (m, 9H), 0.97 (d, J=6.6 Hz, 6H).

EXAMPLE 10 (92)

1-[(1R,2S)-2-benzoylaminocyclohexyl]-N-[2-oxo-2-(3-cyclopropylmethyl-2-oxo-1,3,4-oxadiazolin-5-yl)ethyl]carboxamide

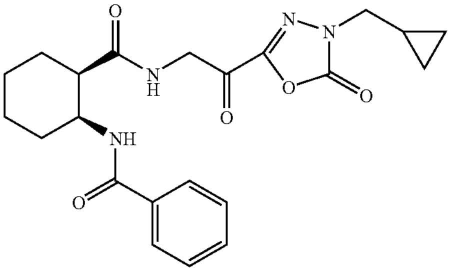

TLC: Rf 0.47 (chloroform:methanol=9:1);

NMR ($CDCl_3$): δ 7.83–7.75 (m, 2H), 7.55–7.38 (m, 3H), 7.28 (brd, J=9.0 Hz, 1H), 6.46 (brs, 1H), 4.61 (dd, J=19.5, 5.1 Hz, 1H), 4.58 (dd, J=19.5, 5.1 Hz, 1H), 4.44–4.31 (m, 1H), 3.68 (d, J=7.5 Hz, 2H), 2.92–2.84 (m, 1H), 2.13–1.13 (m, 9H), 0.68–0.59 and 0.47–0.38 (each m, totally 4H).

EXAMPLE 10 (93)

(2S)-N-[2-(3-(2-methylpropyl)-2-oxo-1,3,4-oxadiazolin-5-yl)-2-oxoethyl]-2-benzyloxycarbonylamino-4-methylpentanamide

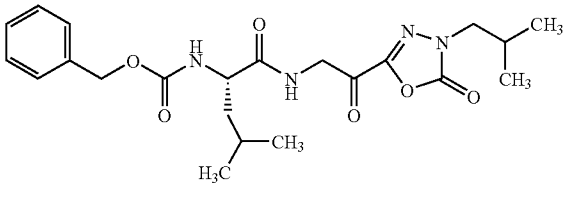

TLC: Rf 0.68 (chloroform:methanol=9:1);

NMR ($CDCl_3$): δ 7.44–7.24 (m, 5H), 6.94–6.78 (br, 1H), 5.31–5.19 (m, 1H), 5.12 (s, 2H), 4.59 (brd, J=4.2 Hz, 2H), 4.35–4.23 (m, 1H), 3.64 (d, J=7.2 Hz, 2H), 2.26–2.10 (m, 1H), 1.90–1.47 (m, 3H), 1.03–0.82 (m, 12H).

EXAMPLE 10 (94)

(2S)-N-[3-cyclopropyl-1-oxo-1-(3-(2-methylpropyl)-2-oxo-1,3,4-oxadiazolin-5-yl)-2-propyl]-2-benzyloxycarbonylamino-4-methylpentanamide

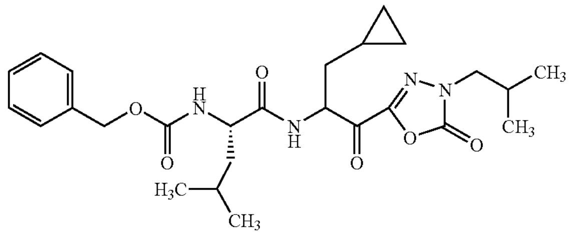

TLC: Rf 0.45 (n-hexane:ethyl acetate=2:1);

NMR ($CDCl_3$): δ 7.40–7.30 (m, 5H), 6.94 and 6.74 (br and d, J=6.6 Hz, totally 1H), 5.38 (q, J=6.6 Hz, 1H), 5.20–5.00 (m, 3H), 4.30–4.15 (m, 1H), 3.65 and 3.64 (each d, J=7.0 Hz, totally 2H), 2.18 (septet, J=7.0 Hz, 1H), 1.90–1.40 (m, 5H), 1.00–0.85 (m, 12H), 0.75–0.55 (m, 1H), 0.55–0.40 (m, 2H), 0.10–0.00 (m, 2H).

EXAMPLE 10 (95)

1-[(1R,2S)-2-benzoylaminocyclohexyl]-N-[3-cyclopropyl-1-oxo-1-(3-(2-methylpropyl)-2-oxo-1,3,4-oxadiazolin-5-yl)-2-propyl]carboxamide

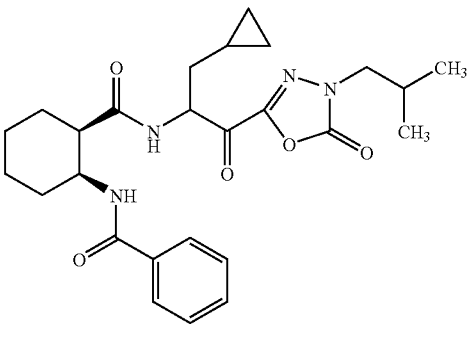

TLC: Rf 0.43 (n-hexane:ethyl acetate=1:1);

NMR ($CDCl_3$): δ 7.85–7.70 (m, 2H), 7.50–7.30 (m, 3H), 7.30–7.20 (m, 1H), 6.45 (d, J=6.6 Hz, 1H), 5.35 and 5.32 (each q, J=6.6 Hz, totally 1H), 4.40–4.30 (m, 1H), 3.70–3.55 (m, 2H), 2.90–2.80 (m, 1H), 2.25–2.10 (m, 1H), 2.10–1.40 (m, 10H), 0.97 and 0.96 (each d, J=6.6 Hz, totally 6H), 0.70–0.55 (m, 1H), 0.50–0.30 (m, 2H), 0.10–0.10 (m, 2H).

EXAMPLE 10 (96)

1-[(1R,2S)-2-benzoylaminocyclohexyl]-N-[(2S)-4-methyl-1-oxo-1-(3-t-butoxycarbonylmethyl-2-oxo-1,3,4-oxadiazolin-5-yl)-2-pentyl]carboxamide

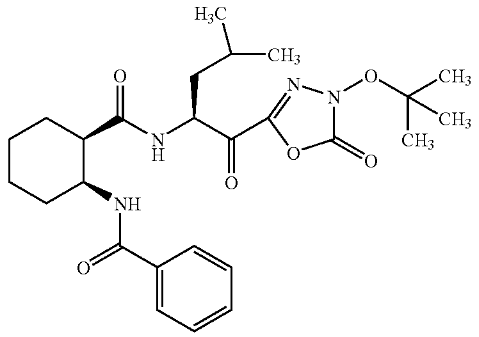

TLC: Rf 0.39 (n-hexane:ethyl acetate=1:1);

NMR ($CDCl_3$): δ 7.76 (d, J=6.9 Hz, 2H), 7.53–7.37 (m, 3H), 7.14 (brd, J=7.8 Hz, 1H), 6.18 (d, J=7.5 Hz, 1H), 5.36–5.26 (m, 1H), 4.53 (d, J=17.4 Hz, 1H), 4.44.(d, J=17.4 Hz, 1H), 4.39–4.27 (m, 1H), 2.84 (q, J=5.1 Hz, 1H), 2.15–1.38 (m, 11H), 1.49 (s, 9H), 0.87 and 0.83 (each d, J=6.0 Hz, totally 6H).

EXAMPLE 10 (97)

(2S)-N-[(2S)-4-methyl-1-oxo-1-(3-t-butoxycarbonylmethyl-2-oxo-1,3,4-oxadiazolin-5-yl)-2-pentyl]-2-benzyloxycarbonylamino-4-methylpentanamide

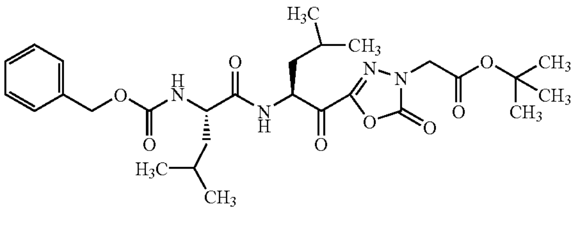

TLC: Rf 0.58 (n-hexane:ethyl acetate=1:1);

NMR ($CDCl_3$): δ 7.43–7.24 (m, 5H), 6.50 (brd, J=7.5 Hz, 1H), 5.34–5.24 (m, 1H), 5.20–5.00 (m, 1H), 5.12 (s, 2H), 4.53 (d, J=17.4 Hz, 1H), 4.44 (d, J=17.4 Hz, 1H), 4.26–4.08 (m, 1H), 1.80–1.30 (m, 6H), 1.49 (s, 9H), 1.05–0.80 (m, 12H).

EXAMPLE 10 (98)

1-[(1R,2S)-2-(2-pyrrolidinomethylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide Hydrochloride

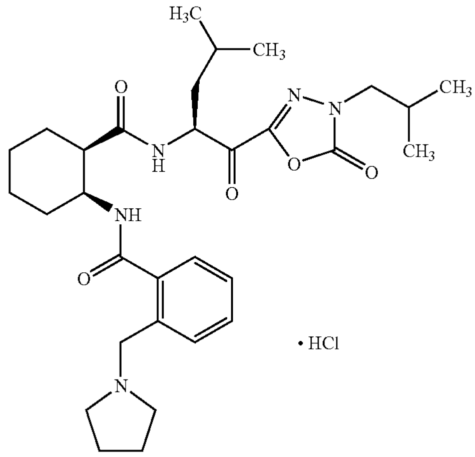

TLC: Rf 0.64 and 0.56(dichloromethane:methanol=7:1);

NMR (DMSO-$d_6$): δ 8.54 and 8.46 (each d, J=6.0 Hz, totally 1H), 8.40 and 8.25 (each d, J=8.4 Hz, totally 1H), 7.77–7.73 (m, 1H), 7.57–7.49 (m, 3H), 4.91–4.84 (m, 1H), 4.47–4.32 (m, 3H), 3.65–3.49 (m, 2H), 3.41–3.01 (m, 4H), 2.77–2.68 (m, 1H), 2.05–1.80 (m, 7H), 1.70–1.22 (m, 9H), 0.91 (d, J=6.6 Hz, 3H), 0.90 (d, J=6.6 Hz, 3H), 0.87, 0.81, and 0.78 (each d, J=6.3 Hz, totally 6H).

EXAMPLE 10 (99)

1-[(1R,2S)-2-(3-pyrrolidinomethylbenzoylamino)cyclohexyl]-N-[(2S)-4-methyl-1-oxo-1-(3-cyclopropylmethyl-2-oxo-1,3,4-oxadiazolin-5-yl)-2-pentyl]carboxamide Hydrochloride

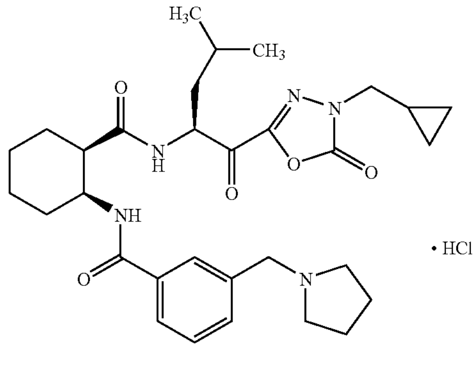

TLC: Rf 0.47 and 0.40 (chloroform:methanol=9:1);

NMR (DMSO-$d_6$): δ 8.54 and 8.47 (each d, J=6.3 Hz, totally 1H), 8.42 and 8.25 (each d, J=8.1 Hz, totally 1H), 7.74–7.72 (m, 1H), 7.56–7.52 (m, 3H), 4.92–4.85 (m, 1H), 4.47–4.27 (m, 3H), 3.73–3.55 (m, 2H), 3.41–3.00 (m, 4H), 2.78–2.70 (m, 1H), 2.11–1.78 (m, 6H), 1.72–1.23 (m, 9H), 1.18–1.06 (m, 1H), 0.89, 0.87, 0.83, and 0.79 (each d, J=6.0 Hz, totally 6H), 0.57–0.46 (m, 2H), 0.37–0.32 (m, 2H).

EXAMPLE 10 (100)

1-[(1R,2S)-2-(2-aminopyridin-5-ylcarbonylamino)cyclohexyl]-N-[(2S)-4-methyl-1-oxo-1-(3-cyclopropylmethyl-2-oxo-1,3,4-oxadiazolin-5-yl)-2-pentyl]carboxamide

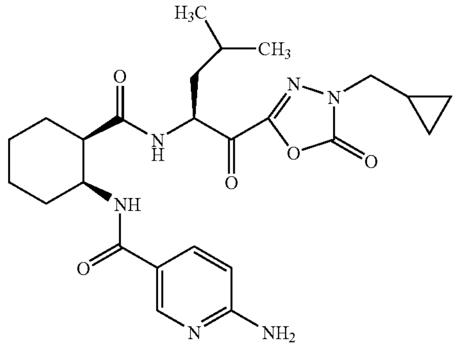

TLC: Rf0.37 (chloroform:methanol=9:1);

NMR ($CDCl_3$): δ 8.50 (d, J=2.2 Hz, 1H), 7.84 (dd, J=8.8, 2.2 Hz, 1H), 7.02 (d, J=7.6 Hz, 1H), 6.49 (d, J=8.8 Hz, 1H), 6.26 (d, J=7.8 Hz, 1H), 5.40–5.20 (m, 1H), 4.84 (br, 2H), 4.40–4.20 (m, 1H), 3.77 (dd, J=14.5, 7.1 Hz, 1H), 3.64 (dd, J=14.5, 7.5 Hz, 1H), 2.82 (q, J=5.1 Hz, 1H), 2.20–1.35 (m, 11H), 1.35–1.10 (m, 1H), 0.91 (d, J=5.8 Hz, 3H), 0.87 (d, J=6.2 Hz, 3H), 0.70–0.30 (m, 4H).

EXAMPLE 10 (101)

1-[(1R,2S)-2-(2-dimethylaminomethylbenzoylamino)cyclohexyl]-N-[(2S)-4-methyl-1-oxo-1-(3-(2-methylpropyl)-2-oxo-1,3,4-oxadiazolin-5-yl)-2-pentyl]carboxamide Hydrochloride

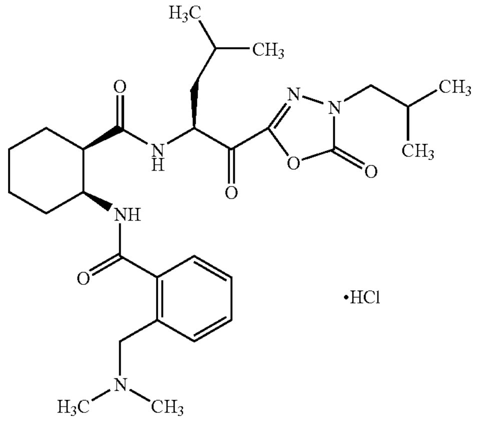

TLC: Rf 0.32 (chloroform:methanol=9:1);

NMR (DMSO-$d_6$): δ 9.82 (brs, 1H), 8.52–8.42 (m, 2H), 7.67 (d, J=7.5 Hz, 1H), 7.62–7.47 (m, 3H), 4.93–4.84 (m, 1H), 4.45–4.20 (m, 3H), 3.60 and 3.53 (each dd, J=15.1, 6.9

Hz, totally 2H), 2.85–2.62 (m, 7H), 2.08–1.10 (m, 12H), 0.91 and 0.90 (each d, J=6.9 Hz, totally 6H), 0.80 and 0.75 (each d, J=6.3 Hz).

EXAMPLE 10 (102)

1-[(1R,2S)-2-(2-butynoylamino)cyclohexyl]-N-[4-methyl-1-oxo-1-(3-(2-methylpropyl)-2-oxo-1,3,4-oxadiazolin-5-yl)-2-pentyl]carboxamide

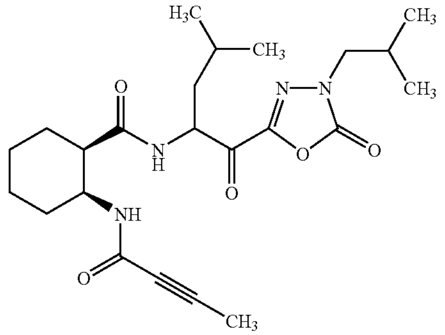

TLC: Rf 0.45 (n-hexane:ethyl acetate=1:1);

NMR ($CDCl_3$): δ 6.70 and 6.61 (each brd, J=9.0 Hz, 1H), 6.23 and 6.13 (each brd, J=7.5 Hz, 1H), 5.33 and 5.27 (each m, 1H), 4.20–4.08 (m, 1H), 3.70 (dd, J=14, 7.2 Hz, 1H), 3.63 (dd, J=14, 7.2 Hz, 1H), 2.79–2.71 (m, 1H), 2.18 (septet J=6.9 Hz, 1H), 2.00–1.35 (m, 11H), 1.93 (s, 3H), 1.01 (d, J=6.3 Hz, 3H), 1.00 (d, J=6.9 Hz, 6H), 0.97 (d, J=6.0 Hz, 3H).

EXAMPLE 10 (103)

1-[(1R,2S)-2-(4-(dimethylamino)but-2-ynoylamino) cyclohexyl]-N-[4-methyl-1-(3-(2-methylpropyl)-2-oxo-1,3,4-oxadiazolin-5-yl)-1-oxo-2-pentyl]carboxamide

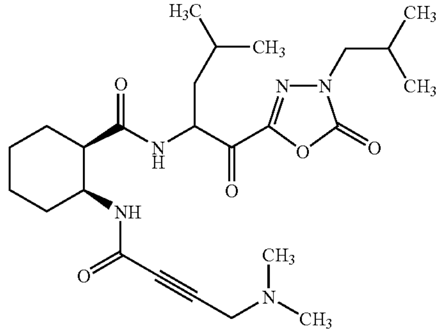

TLC: Rf 0.46 (chloroform:methanol=9:1);

NMR ($CDCl_3$): δ 6.79 and 6.73 (each brd, J=9.0 Hz, 1H), 6.20 and 6.14 (each brd, J=7.5 Hz, 1H), 5.38–5.24 (each m, 1H), 4.22–4.10 (m, 1H), 3.70 (dd, J=14, 7.2 Hz, 1H), 3.63 (dd, J=14, 7.2 Hz, 1H), 3.36 (s, 2H), 2.80–2.72 (m, 1H), 2.32 (s, 6H), 2.19 (septet J=6.9 Hz, 1H), 2.00–1.35 (m, 11H), 1.01 (d, J=6.0 Hz, 3H), 1.00 (d, J=6.6 Hz, 6H), 0.98 (d, J=6.0 Hz, 3H).

EXAMPLE 10 (104)

1-[(1R,2S)-2-(4-morpholinobut-2-ynoylamino)cyclohexyl]-N-[4-methyl-1-(3-(2-methylpropyl)-2-oxo-1,3,4-oxadiazolin-5-yl)-1-oxo-2-pentyl]carboxamide

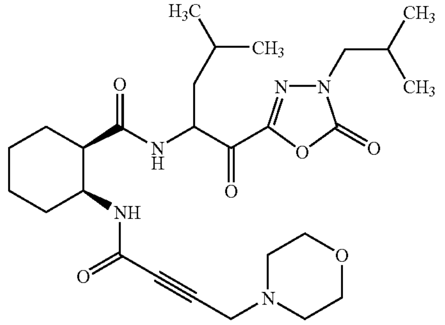

TLC: Rf 0.50 and 0.53 (chloroform:methanol=9:1);

NMR ($CDCl_3$): δ 6.80 and 6.77 (each brd, J=9.0 Hz, 1H), 6.11 and 6.08 (each brd, J=7.5 Hz, 1H), 5.34 and 5.28 (each m, 1H), 4.22–4.10 (m, 1H), 3.76–3.70 (m, 4H), 3.70 (dd, J=14, 6.9 Hz, 1H), 3.63 (dd, J=14, 6.9 Hz, 1H), 3.40 and 3.38 (each s, 2H), 2.79–2.70 (m, 1H), 2.57 (t, J=4.5 Hz, 4H), 2.19 and 2.18 (each septet, J=6.9 Hz, 1H), 2.00–1.35 (m, 11H), 1.01 (d, J=6.0 Hz, 3H), 1.00 (d, J=6.9 Hz, 6H), 0.98 and 0.97 (each d, J=6.0 Hz, 3H).

REFERENCE EXAMPLE 19

((4S)-2,2-dimethyl-3-t-butoxycarbonyl-4-(2-methylpropyl)-1,3-oxazolidin-5-yl)carboxylic Acid Methyl Ester

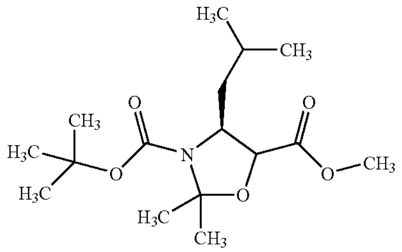

To a solution of (3S)-3-(N-t-butoxycarbonylamino)-5-methyl-2-hydroxyheptanoic acid methyl ester (4.40 g) in N,N-dimethylformamide (16 ml) was added methyl-2-propenyl ether (4.60 ml) and further was added dl-camphor sulfonic acid (186 mg) and the mixture was stirred overnight at room temperature. The residue was purified by column chromatography on silica gel (n-hexane:ethyl acetate=10:1 to 4:1) to give the title compound (3.90 g) having the following physical data.

TLC: Rf 0.52 and 0.48 (n-hexane:ethyl acetate=2:1);

NMR ($CDCl_3$): δ 4.61 and 4.44–4.12 (d and m, J=5.1 Hz, totally 2H), 3.78 (s, 3H), 1.70–1.30 (m, 9H), 1.48 and 1.47 (each s, totally 9H), 1.05–0.87 (m, 6H).

REFERENCE EXAMPLE 20

((4S)-2,2-dimethyl-3-t-butoxycarbonyl-4-(2-methylpropyl)-1,3-oxazolidin-5-yl)carboxylic Acid

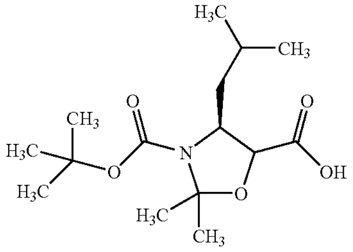

To a solution of the compound prepared in Reference Example 19 (3.84 g) in ethanol (12 ml)-water (6 ml) was added lithium hydroxide monohydrate (559 mg) and the mixture was stirred for 2 hours at room temperature. To the mixture was added n-hexane and the aqueous layer was collected. To the aqueous layer was added 1N hydrochloric acid and was extracted with ethyl acetate. The extract was washed with saturated aqueous solution of sodium chloride, dried over anhydrous magnesium sulfate and was concentrated to give a crude product of the title compound (3.82 g) having the following physical data.

NMR ($CDCl_3$): δ 4.45–4.22 (m, 2H), 1.85–1.30 (m, 3H), 1.66 and 1.58 (each s, totally 6H), 1.48 (s, 9H), 1.04–0.85 (m, 6H).

REFERENCE EXAMPLE 21

N-[(4S)-3-t-butoxycarbonyl-2,2-dimethyl-4-(2-methylpropyl)-1,3-oxazolidin-5-ylcarbonyl]-N'-phenylhydrazide

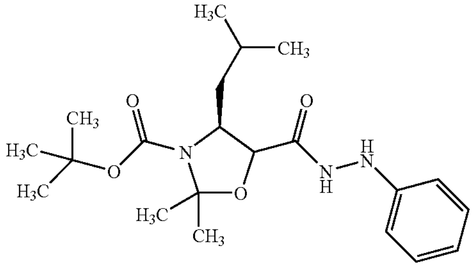

To a solution of the compound prepared in Reference Example 20 (3.81 g) in N,N-dimethylformamide (60 ml) were added 1-hydroxybenzotriazole (2.22 g), phenylhydrazine (1.79 ml) and 1-ethyl-3-[3-(dimethylamino)propyl]carbodiimide hydrochloride (2.78 g) successively at 0° C. and the mixture was stirred for 3 hours. The reaction mixture was poured into 0.5N hydrochloric acid and was extracted with ethyl acetate. The extract was washed with a saturated aqueous solution of sodium bicarbonate and saturated aqueous solution of sodium chloride successively, dried over anhydrous magnesium sulfate and concentrated to give a crude product of the title compound (4.39 g) having the following physical data.

TLC: Rf 0.44, 0.29 (n-hexane:ethyl acetate=2:1);

NMR ($CDCl_3$): δ 8.28–8.16 (m, 1H), 7.28–7.19 (m, 2H), 6.97–6.81 (m, 3H), 4.63 and 4.39 (each d, J=5.1 and 2.4 Hz), 4.42–4.30 (m, 1H), 1.76–1.30 (m, 9H), 1.48 and 1.47 (each s, totally 9H), 1.01–0.85 (m, 6H).

REFERENCE EXAMPLE 22

2-(3-t-butoxycarbonyl-2,2-dimethyl-4-(2-methylpropyl)-1,3-oxazolidin-5-yl)$_3$-phenyl-2-oxo-(1,3,4-oxadiazoline)

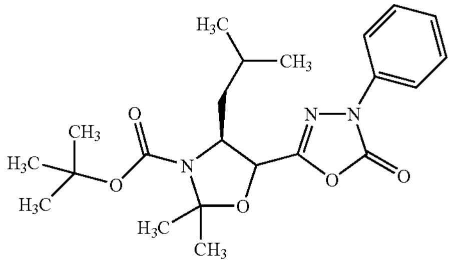

To a solution of the compound prepared in Reference Example 21 (4.36 g) in tetrahydrofuran (110 ml) were added triethylamine (4.64 ml) and 1,1-carbonyldiimidazole (9.00 g) successively and the mixture was refluxed overnight. The reaction mixture was concentrated and the residue was diluted with ethyl acetate. The solution was poured into 0.5N hydrochloric acid and was extracted with ethyl acetate. The extract was washed with a saturated aqueous solution of sodium bicarbonate and saturated aqueous solution of sodium chloride successively, dried over anhydrous magnesium sulfate and was concentrated to give a crude product of the title compound (3.32 g) having the following physical data.

TLC: Rf 0.45, 0.39 (n-hexane:ethyl acetate=4:1);

NMR ($CDCl_3$): δ 7.89–7.81 (m, 2H), 7.49–7.41 (m, 2H), 7.32–7.24 (m, 1H), 5.05 (d, J=8.7 Hz, 0.5H), 4.81 (d, J=2.1 Hz, 0.5H), 4.60–4.15 (br, 1H), 1.90–1.30 (m, 9H), 1.50 (s, 9H), 0.99, 0.93 and 0.86 (each d, J=6.0 Hz, totally 6H).

REFERENCE EXAMPLE 23

(2S)-2-amino-4-methyl-1-(2-oxo-3-phenyl-1,3,4-oxadiazolin-5-yl)pentanol Tosylate

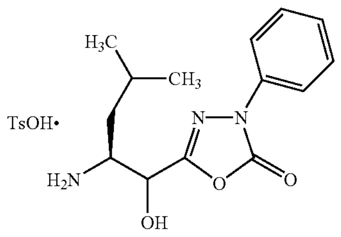

To a solution of the compound prepared in Reference Example 22 (1.26 g) in ethanol (30 ml) was added p-toluene tosyl acid monohydrate (800 mg) and the mixture was refluxed for 3 hours. The reaction mixture was concentrated. The residue was washed with diethyl ether to give a crude product of the title compound (1.24 g) having the following physical data.

TLC: Rf 0.22 (chloroform:methanol=9:1);

NMR ($CDCl_3$): δ 8.12–7.87 (br, 3H), 7.81–7.73 (m, 2H), 7.56–7.44 (m, 4H), 7.36–7.29 (m, 1H), 7.10 (d, J=8.7 Hz, 2H), 4.85 and 4.79 (each d, J=4.2 Hz, totally 1H), 3.54–3.35 (br, 1H), 2.27 (s, 3H), 1.84–1.68 (m, 1H), 1.64–1.44 (m, 2H), 1.00–0.82 (m, 6H).

EXAMPLE 11 TO EXAMPLE 11 (1)

By the same procedure as described in Reference Example 11→Example 1, using the compound prepared in Reference Example 23 and N-benzyloxycarbonyl-(L)-leucine or (1R,2S)-2-benzoylaminocyclohexylcarboxylic acid in place of the compound prepared in Reference Example 10, the compounds of the present invention having the following physical data were obtained.

EXAMPLE 11

1-[(1R,2S)-2-benzoylaminocyclohexyl]-N-[(2S)-4-methyl-1-oxo-1-(3-phenyl-2-oxo-1,3,4-oxadiazolin-5-yl)-2-pentyl]carboxamide

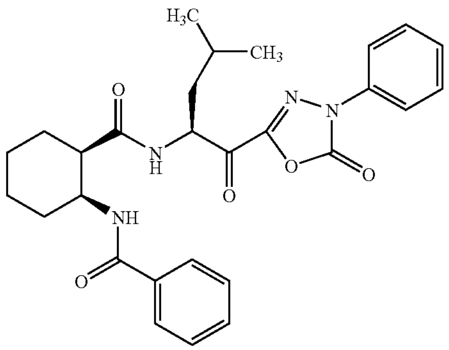

TLC: Rf 0.27 (n-hexane:ethyl acetate=1:1);

NMR ($CDCl_3$): δ 7.90–7.84 (m, 2H), 7.82–7.73 (m, 2H), 7.53–7.31 (m, 6H), 7.12 (d, J=8.1 Hz, 1H), 6.35–6.15 (m, 1H), 5.50–5.32 (m, 1H), 4.44–4.28 (m, 1H), 2.92–2.82 (m, 1H), 2.17–1.36 (m, 1H), 0.94 and 0.87 (each d, J=6.0 Hz, totally 6H).

EXAMPLE 11 (1)

(2S)-N-[(2S)-4-methyl-1-oxo-1-(3-phenyl-2-oxo-1,3,4-oxadiazolin-5-yl)-2-pentyl]-2-benzyloxycarbonylamino-4-methylpentanamide

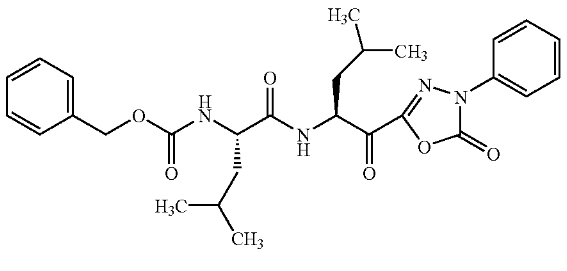

TLC: Rf 0.62 (n-hexane:ethyl acetate=1:1);

NMR ($CDCl_3$): δ 7.88 (d, J=8.1 Hz, 2H), 7.50 (t, J=8.1 Hz, 2H), 7.44–7.20 (m, 6H), 6.80–6.48 (m, 1H), 5.49–5.37 (m, 1H), 5.25–4.95 (m, 1H), 5.12 (s, 2H), 4.32–4.11 (m, 1H), 1.85–1.35 (m, 6H), 1.10–0.85 (m, 12H).

EXAMPLE 12

1-[(1R,2S)-2-benzoylaminocyclohexyl]-N-[(2S)-4-methyl-1-oxo-1-(3-carboxymethyl-2-oxo-1,3,4-oxadiazolin-5-yl)-2-pentyl]carboxamide

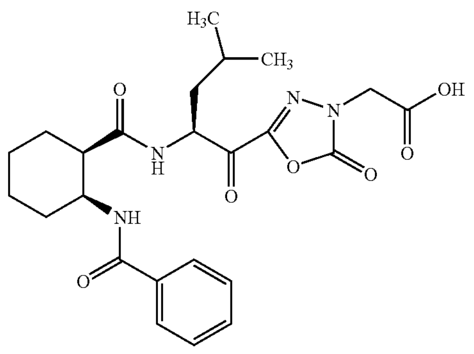

To the compound prepared in Example 10 (96) was added a 90% aqueous solution of trifluoroacetic acid and the mixture was stirred for 1 hour at room temperature. The reaction mixture was concentrated to give the compound of the present invention having the following physical data.

TLC: Rf 0.61 (chloroform:methanol:acetic acid=8:2:1);

NMR (DMSO-$d_6$): δ 8.39 (d, J=6.6 Hz, 1H), 7.79 (d, J=7.8 Hz, 1H), 7.75 (d, J=8.1 Hz, 2H), 7.53–7.37 (m, 3H), 4.89 (q, J=6.9 Hz, 1H), 4.62 (s, 2H), 4.29–4.16 (m, 1H), 2.81–2.69 (m, 1H), 2.09–1.81 (m, 2H), 1.70–1.21 (m, 9H), 0.73 and 0.66 (each d, J=6.0 Hz, totally 6H).

EXAMPLE 12 (1)

(2S)-N-[(2S)-4-methyl-1-oxo-1-(3-carboxymethyl-2-oxo-1,3,4-oxadiazolin-5-yl)-2-pentyl]-2-benzyloxycarbonylamino-4-methylpentanamide

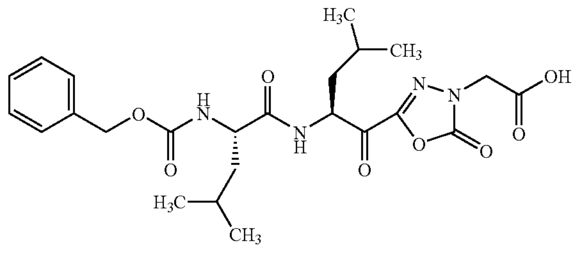

By the same procedure as described in Example 12 using the compound prepared in Example 10 (97) in place of the compound prepared in Example 10 (96), the compound of the present invention having the following physical data was obtained.

TLC: Rf 0.65 (chloroform:methanol:acetic acid=8:2:1 );

NMR (DMSO-$d_6$): δ 8.49 (d, J=6.6 Hz, 1H), 7.45–7.23 (m, 5H), 7.39 (d, J=8.1 Hz, 1H), 5.00 (s, 2H), 4.96–4.85 (m, 1H), 4.68 (s, 2H), 4.12–4.00 (m, 1H), 1.77–1.29 (m, 6H), 1.00–0.72 (m, 12H).

EXAMPLE 13 TO EXAMPLE 13 (121)

By the same procedure as described in Reference Example 15→Example 3 using the compound prepared in Reference Example 14 or a corresponding amino derivative and N-benzyloxycarbonyl-(L)-leucine or a corresponding carboxylic acid derivative and optionally converted into corresponding salts by known methods, the compounds of the present invention having the following physical data were obtained.

EXAMPLE 13

1-[(1R,2S)-2-(quinoxalin-2-ylcarbonylamino)cyclohexyl]-N-[(2S)-4-methyl-1-(5-methylthio-1,3,4-oxadiazol-2-yl)-1-oxo-2-pentyl]carboxamide

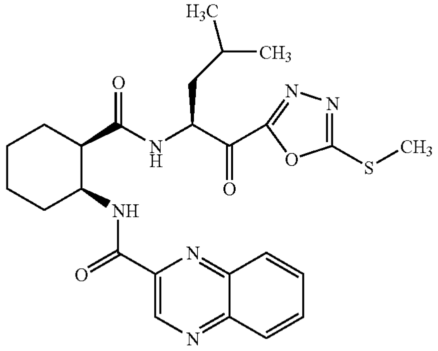

TLC: Rf 0.23 (n-hexane:ethyl acetate=1:1);

NMR ($CDCl_3$): δ 9.65 (s, 1H), 8.62 (d, J=9.2 Hz, 1H), 8.25–8.10 (m, 2H), 7.90–7.80 (m, 2H), 6.30 (d, J=7.8 Hz, 1H), 5.50–5.30 (m, 1H), 4.55–4.35 (m, 1H), 2.92 (q, J=5.0 Hz, 1H), 2.77 (s, 3H), 2.30–1.40 (m, 11H), 0.79 (d, J=6.6 Hz, 3H), 0.71 (d, J=6.2 Hz, 3H).

EXAMPLE 13 (1)

1-[(1R,2S)-2-(naphthalen-2-ylcarbonylamino)cyclohexyl]-N-[(2S)-4-methyl-1-(5-methylthio-1,3,4-oxadiazol-2-yl)-1-oxo-2-pentyl]carboxamide

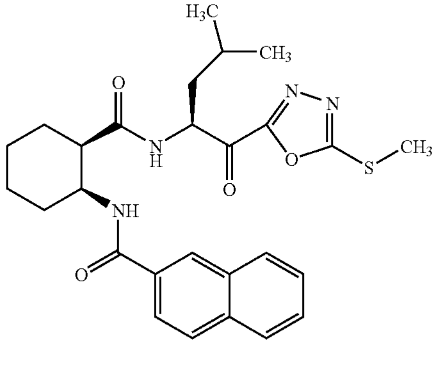

TLC: Rf 0.33 (n-hexane:ethyl acetate=1:1);

NMR ($CDCl_3$): δ 8.29 (s, 1H), 8.00–7.80 (m, 4H), 7.65–7.50 (m, 2H), 7.34 (d, J=8.0 Hz, 1H), 6.33 (d, J=7.6 Hz, 1H), 5.50–5.35 (m, 1H), 4.50–4.35 (m, 1H), 2.92 (q, J=4.9 Hz, 1H), 2.78 (s, 3H), 2.25–1.40 (m, 11H), 0.88 (d, J=6.2 Hz, 3H), 0.81 (d, J=6.2 Hz, 3H).

EXAMPLE 13 (2)

1-[(1R,2S)-2-(benzo[b]thiophen-2-ylcarbonylamino)cyclohexyl]-N-[(2S)-4-methyl-1-(5-methylthio-1,3,4-oxadiazol-2-yl)-1-oxo-2-pentyl]carboxamide

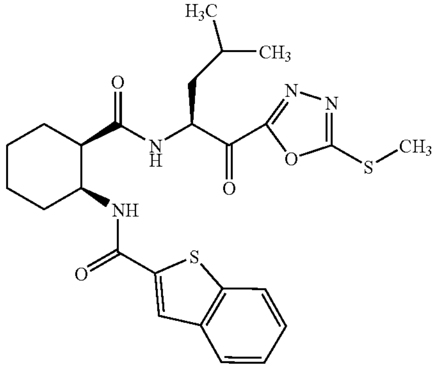

TLC: Rf 0.40 (n-hexane:ethyl acetate=1:1);

NMR ($CDCl_3$): δ 7.90–7.75 (m, 2H), 7.73 (s, 1H), 7.50–7.35 (m, 2H), 7.32 (d, J=8.4 Hz, 1H), 6.30 (d, J=7.8 Hz, 1H), 5.50–5.35 (m, 1H), 4.40–4.20 (m, 1H), 2.88 (q, J=4.8 Hz, 1H), 2.79 (s, 3H), 2.20–1.40 (m, 11H), 0.92 (d, J=6.2 Hz, 3H), 0.85 (d, J=6.4 Hz, 3H).

EXAMPLE 13 (3)

1-[(1R,2S)-2-(4-methoxybenzoylamino)cyclohexyl]-N-[(2S)-4-methyl-1-(5-methylthio-1,3,4-oxadiazol-2-yl)-1-oxo-2-pentyl]carboxamide

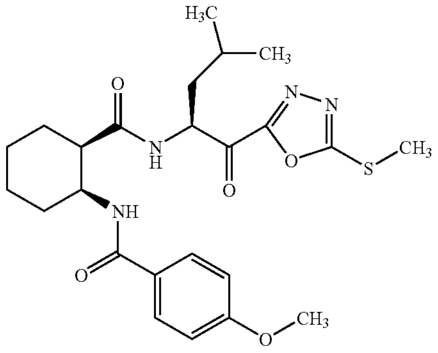

TLC: Rf 0.21 (n-hexane:ethyl acetate=1:1);

NMR ($CDCl_3$): δ 7.73 (d, J=8.8 Hz, 2H), 7.07 (d, J=8.4 Hz, 1H), 6.92 (d, J=8.8 Hz, 2H), 6.29 (d, J=7.6 Hz, 1H), 5.50–5.35 (m, 1H), 4.40–4.20 (m, 1H), 3.85 (s, 3H), 2.85 (q, J=5.0 Hz, 1H), 2.79 (s, 3H), 2.20–1.40 (m, 1H), 0.91 (d, J=6.2 Hz, 3H), 0.85 (d, J=6.4 Hz, 3H).

EXAMPLE 13 (4)

1-[(1R,2S)-2-(4-nitrobenzoylamino)cyclohexyl]-N-[(2S)-4-methyl-1-(5-methylthio-1,3,4-oxadiazol-2-yl)-1-oxo-2-pentyl]carboxamide

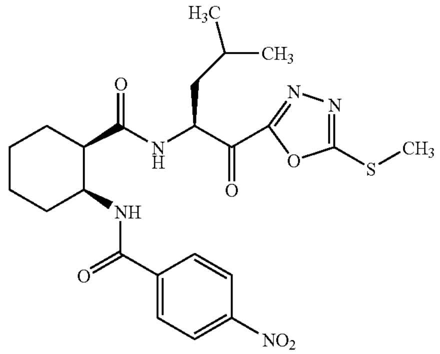

TLC: Rf 0.33 (n-hexane ethyl acetate=1:1);

NMR ($CDCl_3$): δ 8.28 (d, J=9.0 Hz, 2H), 7.94 (d, J=9.0 Hz, 2H), 7.67 (d, J=7.6 Hz, 1H), 6.25 (d, J=7.6 Hz, 1H), 5.50–5.35 (m, 1H), 4.40–4.20 (m, 1H), 2.85 (q, J=4.8 Hz, 1H), 2.81 (s, 3H), 2.10–1.40 (m, 11H), 0.96 (d, J=6.4 Hz, 3H), 0.91 (d, J=6.0 Hz, 3H).

EXAMPLE 13 (5)

1-[(1R,2S)-2-(4-chlorobenzoylamino)cyclohexyl]-N-[(2S)-4-methyl-1-(5-methylthio-1,3,4-oxadiazol-2-yl)-1-oxo-2-pentyl]carboxamide

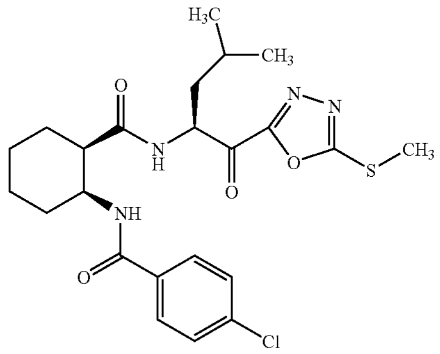

TLC: Rf 0.36 (n-hexane:ethyl acetate=1:1);

NMR ($CDCl_3$): δ 7.71 (d, J=8.6 Hz, 2H), 7.40 (d, J=8.6 Hz, 2H), 7.30 (d, J=8.0 Hz, 1H), 6.25 (d, J=7.6 Hz, 1H), 5.50–5.35 (m, 1H), 4.35–4.20 (m, 1H), 2.84 (q, J=5.0 Hz, 1H), 2.80 (s, 3H), 2.10–1.40 (m, 11H), 0.93 (d, J=6.2 Hz, 3H), 0.88 (d, J=6.2 Hz, 3H).

EXAMPLE 13 (6)

1-[(1R,2S)-2-(4-phenylbenzoylamino)cyclohexyl]-N-[(2S)-4-methyl-1-(5-methylthio-1,3,4-oxadiazol-2-yl)-1-oxo-2-pentyl]carboxamide

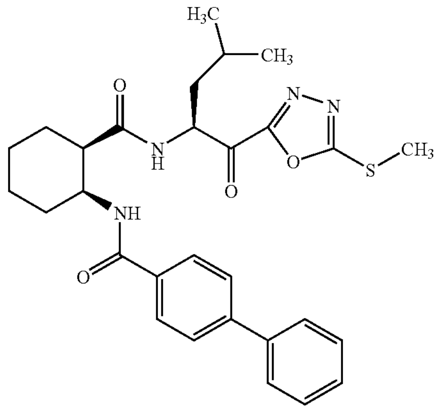

TLC: Rf 0.30 (n-hexane:ethyl acetate=1:1);

NMR ($CDCl_3$): δ 7.84 (d, J=8.7 Hz, 2H), 7.70–7.55 (m, 4H), 7.50–7.30 (m, 3H), 7.30–7.20 (m, 1H), 6.27 (d, J=7.5 Hz, 1H), 5.50–5.30 (m, 1H), 4.40–4.25 (m, 1H), 2.88 (q, J=4.9 Hz, 1H), 2.79 (s, 3H), 2.15–1.40 (m, 11H), 0.93 (d, J=6.3 Hz, 3H), 0.86 (d, J=6.3 Hz, 3H).

EXAMPLE 13 (7)

1-[(1R,2S)-2-(4-fluorobenzoylamino)cyclohexyl]-N-[(2S)-4-methyl-1-(5-methylthio-1,3,4-oxadiazol-2-yl)-1-oxo-2-pentyl]carboxamide

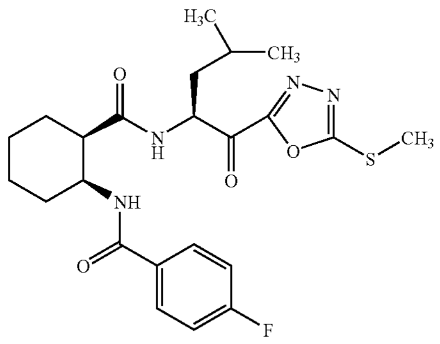

TLC: Rf 0.32 (n-hexane:ethyl acetate=1:1);

NMR ($CDCl_3$): δ 7.78 (dd, J=8.8, 5.0 Hz, 2H), 7.30–7.15 (m, 1H), 7.10 (t, J=8.8 Hz, 2H), 6.27 (d, J=7.4 Hz, 1H), 5.50–5.35 (m, 1H), 4.40–4.20 (m, 1H), 2.85 (q, J=4.8 Hz, 1H), 2.80 (s, 3H), 2.15–1.40 (m, 11H), 0.93 (d, J=6.6 Hz, 3H), 0.87 (d, J=6.4 Hz, 3H).

EXAMPLE 13 (8)

1-[(1R,2S)-2-(pyridin-2-ylcarbonylamino)cyclohexyl]-N-[(2S)-4-methyl-1-(5-methylthio-1,3,4-oxadiazol-2-yl)-1-oxo-2-pentyl]carboxamide

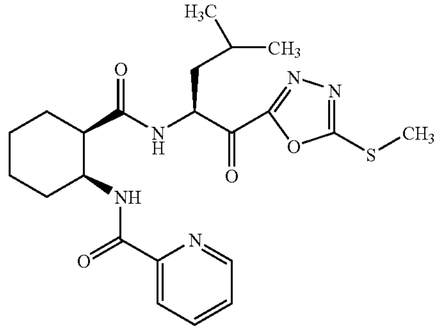

TLC: Rf 0.21 (n-hexane:ethyl acetate=1:1);

NMR ($CDCl_3$): δ 8.70–8.55 (m, 2H), 8.16 (d, J=8.8 Hz, 1H), 7.84 (dt, J=1.4, 8.8 Hz, 1H), 7.43 (ddd, J=8.8, 4.8, 1.4 Hz, 1H), 6.42 (d, J=7.0 Hz, 1H), 5.45–5.30 (m, 1H), 4.55–4.35 (m, 1H), 2.83 (q, J=5.3 Hz, 1H), 2.78 (s, 3H), 2.20–1.40 (m, 11H), 0.82 (d, J=6.4 Hz, 3H), 0.75 (d, J=6.2 Hz, 3H).

EXAMPLE 13 (9)

1-[(1R,2S)-2-(4-t-butylbenzoylamino)cyclohexyl]-N-[(2S)-4-methyl-1-(5-methylthio-1,3,4-oxadiazol-2-yl)-1-oxo-2-pentyl]carboxamide

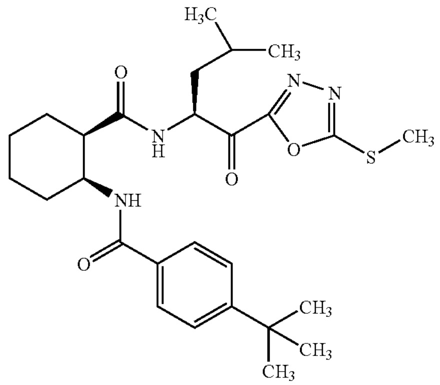

TLC: Rf 0.36 (n-hexane:ethyl acetate=1:1);

NMR ($CDCl_3$): δ 7.70 (d, J=8.8 Hz, 2H), 7.44 (d, J=8.8 Hz, 2H), 7.12 (d, J=8.0 Hz, 1H), 6.28 (d, J=7.6 Hz, 1H), 5.50–5.35 (m, 1H), 4.40–4.25 (m, 1H), 2.86 (q, J=4.9 Hz, 1H), 2.79 (s, 3H), 2.20–1.40 (m, 11H), 1.33 (s, 9H), 0.90 (d, J=6.2 Hz, 3H), 0.84 (d, J=6.0 Hz, 3H).

EXAMPLE 13 (10)

1-[(1R,2S)-2-(2-methylthiopyridin-3-ylcarbonylamino)cyclohexyl]-N-[(2S)-4-methyl-1-(5-methylthio-1,3,4-oxadiazol-2-yl)-1-oxo-2-pentyl]carboxamide

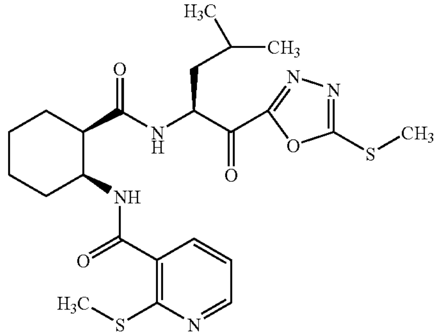

TLC: Rf 0.23 (n-hexane:ethyl acetate=1:1);

NMR ($CDCl_3$): δ 8.50 (dd, J=8.2, 1.8 Hz, 1H), 7.73 (dd, J=5.3, 1.8 Hz, 1H), 7.17 (d, J=8.0 Hz, 1H), 7.04 (dd, J=8.2, 5.3 Hz, 1H), 6.28 (d, J=7.2 Hz, 1H), 5.45–5.30 (m, 1H), 4.45–4.30 (m, 1H), 2.86 (q, J=5.0 Hz, 1H), 2.79 (s, 3H), 2.56 (s, 3H), 2.20–1.40 (m, 11H), 0.94 (d, J=6.2 Hz, 3H), 0.90 (d, J=6.2 Hz, 3H).

EXAMPLE 13 (11)

1-[(1R,2S)-2-(2-fluorobenzoylamino)cyclohexyl]-N-[(2S)-4-methyl-1-(5-methylthio-1,3,4-oxadiazol-2-yl)-1-oxo-2-pentyl]carboxamide

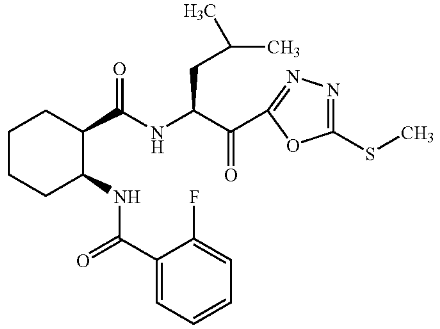

TLC: Rf 0.37 (n-hexane:ethyl acetate=1:1);

NMR ($CDCl_3$): δ 8.04 (dt, J=2.0, 7.6 Hz, 1H), 7.55–7.40 (m, 2H), 7.24 (dt, J=1.1, 7.6 Hz, 1H), 7.11 (ddd, J=12.0, 8.4, 1.1 Hz, 1H), 6.32 (d, J=7.4 Hz, 1H), 5.50–5.30 (m, 1H), 4.55–4.35 (m, 1H), 2.85 (q, J=4.9 Hz, 1H), 2.79 (s, 3H), 2.20–1.40 (m, 11H), 0.90 (d, J=6.4 Hz, 3H), 0.82 (d, J=6.4 Hz, 3H).

EXAMPLE 13 (12)

1-[(1R,2S)-2-(2-chloropyridin-5-ylcarbonylamino)cyclohexyl]-N-[(2S)-4-methyl-1-(5-methylthio-1,3,4-oxadiazol-2-yl)-1-oxo-2-pentyl]carboxamide

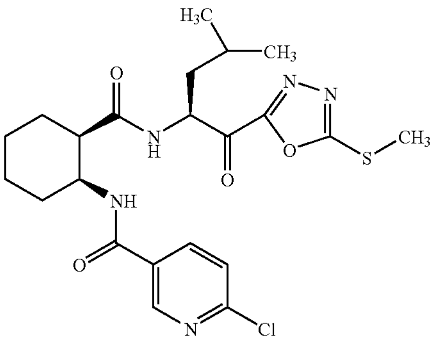

TLC: Rf 0.26 (n-hexane:ethyl acetate=1:1);

NMR ($CDCl_3$): δ 8.78 (d, J=2.2 Hz, 1H), 8.02 (dd, J=8.4, 2.2 Hz, 1H), 7.58 (d, J=8.0 Hz, 1H), 7.39 (d, J=8.4 Hz, 1H), 6.24 (d, J=7.4 Hz, 1H), 5.50–5.35 (m, 1H), 4.35–4.20 (m, 1H), 2.83 (q, J=4.9 Hz, 1H), 2.80 (s, 3H), 2.10–1.40 (m, 11H), 0.96 (d, J=6.2 Hz, 3H), 0.92 (d, J=6.2 Hz, 3H).

EXAMPLE 13 (13)

1-[(1R,2S)-2-(naphthalen-1-ylmethylcarbonylamino)cyclohexyl]-N-[(2S)-4-methyl-1-(5-methylthio-1,3,4-oxadiazol-2-yl)-1-oxo-2-pentyl]carboxamide

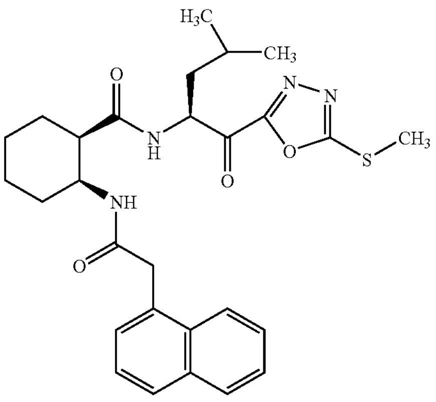

TLC: Rf 0.22 (n-hexane:ethyl acetate=1:1);

NMR ($CDCl_3$): δ 8.00–7.75 (m, 3H), 7.60–7.35 (m, 4H), 6.30 (d, J=8.4 Hz, 1H), 6.15 (d, J=6.6 Hz, 1H), 5.25–5.10 (m, 1H), 4.25–4.05 (m, 1H), 4.01 (d, J=16.4 Hz, 1H), 3.95 (d, J=16.4 Hz, 1H), 2.80 (s, 3H), 2.51 (dt, J=6.6, 4.4 Hz, 1H), 1.80–1.10 (m, 11H), 1.00 (d, J=6.0 Hz, 3H), 0.98 (d, J=6.0 Hz, 3H).

EXAMPLE 13 (14)

1-[(1R,2S)-2-benzylcarbonylaminocyclohexyl]-N-[(2S)-4-methyl-1-(5-methylthio-1,3,4-oxadiazol-2-yl)-1-oxo-2-pentyl]carboxamide

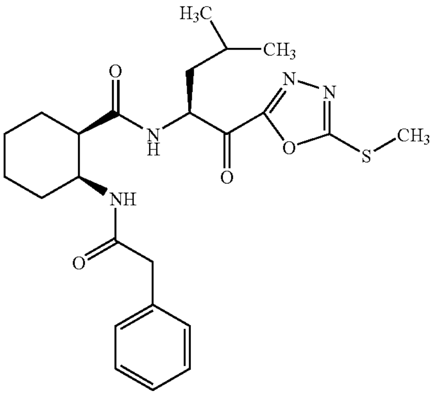

TLC: Rf 0.22 (n-hexane:ethyl acetate=1:1);

NMR ($CDCl_3$): δ 7.40–7.20 (m, 5H), 6.34 (d, J=8.8 Hz, 1H), 6.23 (d, J=7.2 Hz, 1H), 5.40–5.25 (m, 1H), 4.20–4.05 (m, 1H), 3.52 (s, 2H), 2.80 (s, 3H), 2.65 (q, J=5.0 Hz, 1H), 1.95–1.30 (m, 11H), 1.02 (d, J=6.2 Hz, 3H), 0.98 (d, J=6.0 Hz, 3H).

EXAMPLE 13 (15)

1-[(1R,2S)-2-phenethylcarbonylaminocyclohexyl]-N-[(2S)-4-methyl-1-(5-methylthio-1,3,4-oxadiazol-2-yl)-1-oxo-2-pentyl]carboxamide

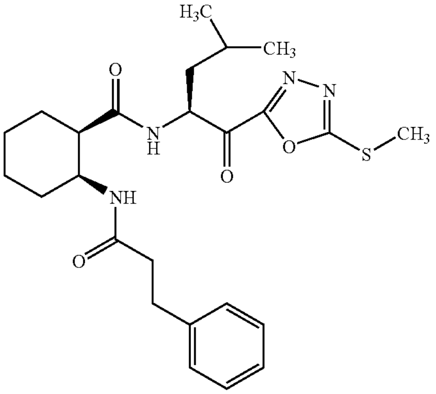

TLC: Rf 0.24 (n-hexane:ethyl acetate=1:1);

NMR ($CDCl_3$): δ 7.35–7.10 (m, 5H), 6.30 (d, J=8.0 Hz, 1H), 6.21 (d, J=7.0 Hz, 1H), 5.45–5.30 (m, 1H), 4.20–4.05 (m, 1H), 2.93 (t, J=7.5 Hz, 2H), 2.79 (s, 3H), 2.65 (q, J=5.0 Hz, 1H), 2.50–2.40 (m, 2H), 1.90–1.30 (m, 11H), 1.01 (d, J=6.4 Hz, 3H), 0.97 (d, J=6.2 Hz, 3H).

EXAMPLE 13 (16)

1-[(1R,2S)-2-acetylaminocyclohexyl]-N-[(2S)-4-methyl-1-(5-methylthio-1,3,4-oxadiazol-2-yl)-1-oxo-2-pentyl]carboxamide

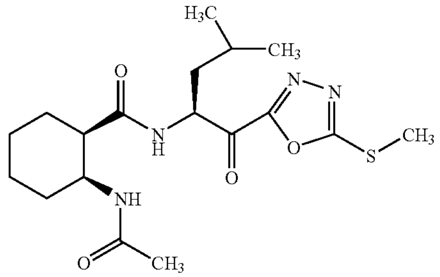

TLC: Rf 0.61 (chloroform:methanol=9:1);

NMR ($CDCl_3$) δ 6.37 (d, J=8.8 Hz, 1H), 6.25 (d, J=7.0 Hz, 1H), 5.50–5.30 (m, 1H), 4.20–4.05 (m, 1H), 2.80 (s, 3H), 2.74 (q, J=5.1 Hz, 1H), 2.00–1.30 (m, 11H), 1.95 (s, 3H), 1.03 (d, J=6.2 Hz, 3H), 0.98 (d, J=6.2 Hz, 3H).

EXAMPLE 13 (17)

1-[(2S)-N-phenethylpiperidin-2-yl]-N-[(2S)-4-methyl-1-(5-methylthio-1,3,4-oxadiazol-2-yl)-1-oxo-2-pentyl]carboxamide

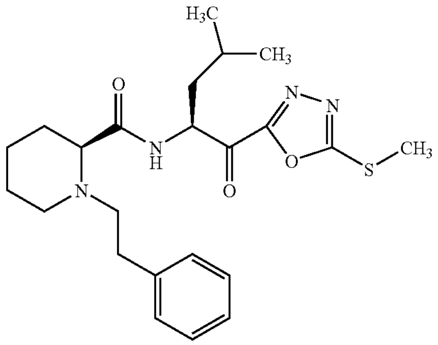

TLC: Rf 0.44 (chloroform:methanol=49:1);

NMR ($CDCl_3$): δ 7.30–7.10 (m, 5H), 6.75 (d, J=7.0 Hz, 1H), 5.40–5.20 (m, 1H), 3.35 (br-d, J=11.6 Hz, 1H), 3.15–2.65 (m, 4H), 2.79 (s, 3H), 2.60–1.10 (m, 11H), 0.97 (d, J=6.6 Hz, 3H), 0.93 (d, J=6.4 Hz, 3H).

EXAMPLE 13 (18)

1-[(2S)-N-(3-phenylpropyl)piperidin-2-yl]-N-[(2S)-4-methyl-1-(5-methylthio-1,3,4-oxadiazol-2-yl)-1-oxo-2-pentyl]carboxamide

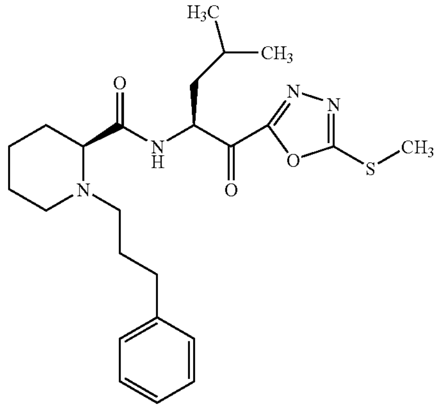

TLC: Rf 0.40 (chloroform:methanol=49:1);

NMR ($CDCl_3$): δ 7.35–7.10 (m, 6H), 5.55–5.35 (m, 1H), 3.14 (br-d, J=11.4 Hz, 1H), 2.85–2.45 (m, 4H), 2.79 (s, 3H), 2.35–1.10 (m, 13H), 1.05 (d, J=6.2 Hz, 3H), 0.98 (d, J=6.2 Hz, 3H).

EXAMPLE 13 (19)

1-[(2S)-N-(4-phenylbutyl)piperidin-2-yl]-N-[(2S)-4-methyl-1-(5-methylthio-1,3,4-oxadiazol-2-yl)-1-oxo-2-pentyl]carboxamide

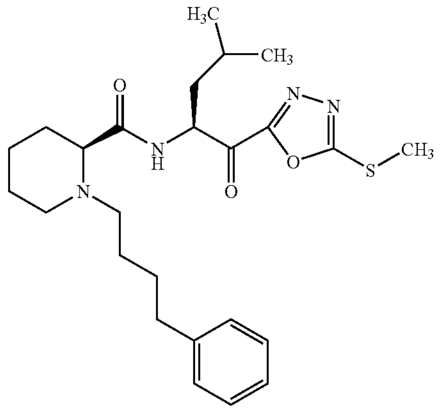

TLC: Rf 0.38 (chloroform methanol=49:1);

NMR ($CDCl_3$) δ 7.35–7.10 (m, 6H), 5.50–5.35 (m, 1H), 3.11 (br-d, J=11.6 Hz, 1H), 2.85–2.45 (m, 4H), 2.78 (s, 3H), 2.35–1.15 (m, 15H), 1.05–0.80 (m, 6H).

EXAMPLE 13 (20)

1-[(2S)-N-phenethylpiperidin-2-yl]-N-[(2S)-4-methyl-1-(5-(1-methylethylthio)-1,3,4-oxadiazol-2-yl)-1-oxo-2-pentyl]carboxamide

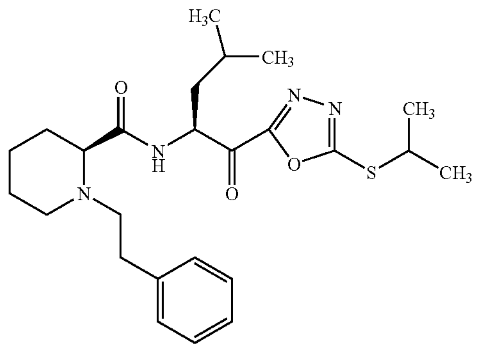

TLC: Rf 0.51 (chloroform:methanol=49:1);

NMR ($CDCl_3$): δ 7.35–7.10 (m, 5H), 6.74 (d, J=7.5 Hz, 1H), 5.40–5.25 (m, 1H), 4.03 (septet, J=6.9 Hz, 1H), 3.40–3.20 (m, 1H), 3.10–2.70 (m, 4H), 2.60–1.10 (m, 11H), 1.53 (d, J=6.9 Hz, 6H), 0.97 (d, J=6.3 Hz, 3H), 0.92 (d, J=6.3 Hz, 3H).

EXAMPLE 13 (21)

1-[(2S)-N-(3-phenylpropyl)piperidin-2-yl]-N-[(2S)-4-methyl-1-(5-(1-methylethylthio)-1,3,4-oxadiazol-2-yl)-1-oxo-2-pentyl]carboxamide

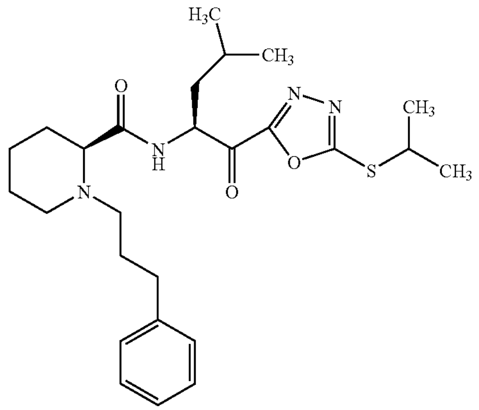

TLC: Rf 0.41 (chloroform:methanol=49:1);

NMR ($CDCl_3$): δ 7.35–7.10 (m, 6H), 5.55–5.40 (m, 1H), 4.04 (septet, J=6.7 Hz, 1H), 3.14 (br-d, J=11.4 Hz, 1H), 2.80–2.50 (m, 4H), 2.30–1.00 (m, 13H), 1.54 (d, J=6.7 Hz, 6H), 1.05 (d, J=6.3 Hz, 3H), 0.98 (d, J=6.3 Hz, 3H).

EXAMPLE 13 (22)

1-[(1R,2S)-2-(4-cyanobenzoylamino)cyclohexyl]-N-[(2S)-4-methyl-1-(5-methylthio-1,3,4-oxadiazol-2-yl)-1-oxo-2-pentyl]carboxamide

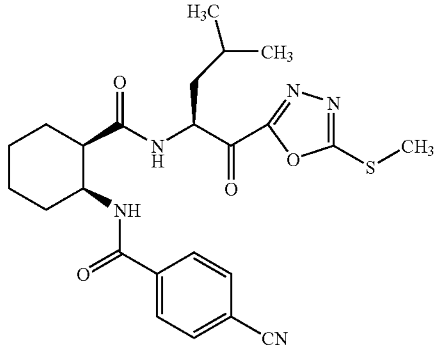

TLC: Rf 0.30 (n-hexane:ethyl acetate=1:1);

NMR ($CDCl_3$) δ 7.87 (d, J=8.0 Hz, 2H), 7.73 (d, J=8.0 Hz, 2H), 7.60 (d, J=8.4 Hz, 1H), 6.25 (d, J=7.8 Hz, 1H), 5.50–5.35 (m, 1H), 4.35–4.20 (m, 1H), 2.85 (q, J=5.0 Hz, 1H), 2.80 (s, 3H), 2.10–1.40 (m, 11H), 0.95 (d, J=6.3 Hz, 3H), 0.91 (d, J=6.6 Hz, 3H).

EXAMPLE 13 (23)

1-[(1R,2S)-2-(4-dimethylaminobenzoylamino)cyclohexyl]-N-[(2S)-4-methyl-1-(5-methylthio-1,3,4-oxadiazol-2-yl)-1-oxo-2-pentyl]carboxamide

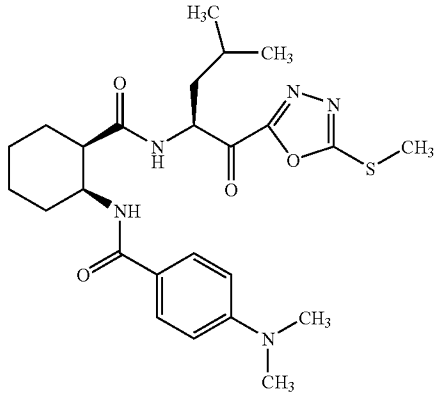

Free Compound

TLC: RF 0.62 (chloroform:methanol=9:1);

NMR ($CDCl_3$): δ 7.66 (d, J=8.8 Hz, 2H), 6.88 (d, J=8.0 Hz, 1H), 6.67 (d, J=8.8 Hz, 2H), 6.41 (d, J=7.4 Hz, 1H), 5.50–5.30 (m, 1H), 4.40–4.25 (m, 1H), 3.02 (s, 6H), 2.90–2.75 (m, 1H), 2.79 (s, 3H), 2.15–1.35 (m, 11H), 0.90 (d, J=6.4 Hz, 3H), 0.84 (d, J=6.0 Hz, 3H).

Hydrochloride

TLC: Rf 0.62 (chloroform:methanol=9:1);

NMR ($CDCl_3$): δ 7.89 (d, J=8.4 Hz, 2H), 7.66 (d, J=8.4 Hz, 2H), 7.50 (d, J=7.8 Hz, 1H), 6.35 (d, J=7.4 Hz, 1H), 5.50–5.30 (m, 1H), 4.40–4.20 (m, 1H), 3.16 (s, 6H), 2.90–2.75 (m, 1H), 2.80 (s, 3H), 2.10–1.30 (m, 11H), 0.94 (d, J=6.2 Hz, 3H), 0.90 (d, J=6.2 Hz, 3H).

EXAMPLE 13 (24)

1-[(1R,2S)-2-(4-fluorobenzoylamino)cyclohexyl]-N-[(2S)-4-methyl-1-(5-(1-methylethylthio)-1,3,4-oxadiazol-2-yl)-1-oxo-2-pentyl]carboxamide

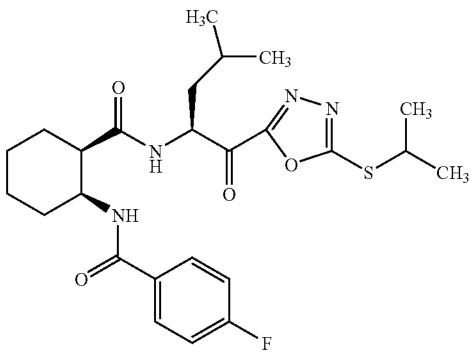

TLC: Rf 0.48 (n-hexane:ethyl acetate=1:1);

NMR ($CDCl_3$): δ 7.78 (dd, J=8.8, 5.0 Hz, 2H), 7.30–7.20 (m, 1H), 7.10 (t, J=8.8 Hz, 2H), 6.28 (d, J=7.6 Hz, 1H), 5.50–5.35 (m, 1H), 4.35–4.20 (m, 1H), 4.05 (septet, J=6.8 Hz, 1H), 2.85 (q, J=5.0 Hz, 1H), 2.20–1.30 (m, 11H), 1.54 (d, J=6.8 Hz, 6H), 0.93 (d, J=6.2 Hz, 3H), 0.87 (d, J=6.2 Hz, 3H).

EXAMPLE 13 (25)

1-[(1R,2S)-2-(4-chlorobenzoylamino)cyclohexyl]-N-[(2S)-4-methyl-1-(5-(1-methylethylthio)-1,3,4-oxadiazol-2-yl)-1-oxo-2-pentyl]carboxamide

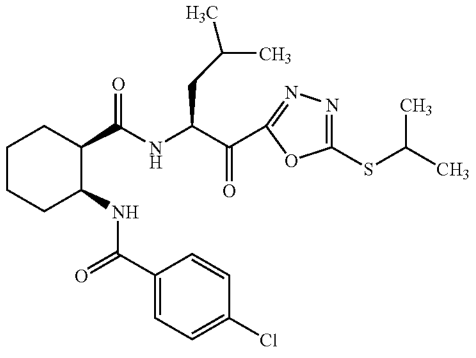

TLC: Rf 0.56 (n-hexane:ethyl acetate=1:1);

NMR ($CDCl_3$): δ 7.71 (d, J=8.4 Hz, 2H), 7.40 (d, J=8.4 Hz, 2H), 7.31 (d, J=6.8 Hz, 1H), 6.23 (d, J=7.8 Hz, 1H), 5.50–5.35 (m, 1H), 4.35–4.20 (m, 1H), 4.05 (septet, J=6.8 Hz, 1H), 2.84 (q, J=4.9 Hz, 1H), 2.15–1.30 (m, 11H), 1.55 (d, J=6.8 Hz, 6H), 0.94 (d, J=6.4 Hz, 3H), 0.88 (d, J=6.2 Hz, 3H).

EXAMPLE 13 (26)

1-[(1R,2S)-2-(4-methoxybenzoylamino)cyclohexyl]-N-[(2S)-4-methyl-1-(5-(1-methylethylthio)-1,3,4-oxadiazol-2-yl)-1-oxo-2-pentyl]carboxamide

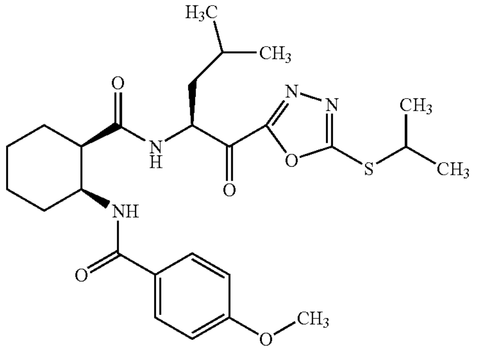

TLC: Rf0.35 (n-hexane:ethyl acetate=1:1);

NMR ($CDCl_3$): δ 7.73 (d, J=8.8 Hz, 2H), 7.08 (d, J=8.0 Hz, 1H), 6.92 (d, J=8.8 Hz, 2H), 6.28 (d, J=7.8 Hz, 1H), 5.50–5.35 (m, 1H), 4.40–4.20 (m, 1H), 4.04 (septet, J=7.0 Hz, 1H), 3.85 (s, 3H), 2.85 (q, J=4.9 Hz, 1H), 2.20–1.35 (m, 11H), 1.54 (d, J=7.0 Hz, 1H), 0.91 (d, J=6.2 Hz, 3H), 0.85 (d, J=6.4 Hz, 3H).

EXAMPLE 13 (27)

1-[(1R,2S)-2-(4-cyanobenzoylamino)cyclohexyl]-N-[(2S)-4-methyl-1-(5-(1-methylethylthio)-1,3,4-oxadiazol-2-yl)-1-oxo-2-pentyl]carboxamide

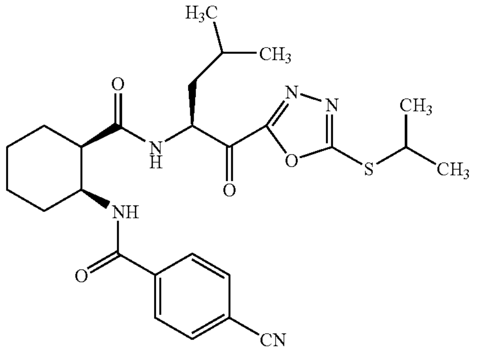

TLC: Rf 0.48 (n-hexane:ethyl acetate=1:1);

NMR ($CDCl_3$): δ 7.88 (d, J=8.5 Hz, 2H), 7.73 (d, J=8.5 Hz, 2H), 7.61 (d, J=7.8 Hz, 1H), 6.23 (d, J=7.8 Hz, 1H), 5.55–5.35 (m, 1H), 4.35–4.20 (m, 1H), 4.05 (septet, J=6.8 Hz, 1H), 2.84 (q, J=4.9 Hz, 1H), 2.10–1.30 (m, 11H), 1.55 (d, J=6.8 Hz, 6H), 0.95 (d, J=6.2 Hz, 3H), 0.91 (d, J=6.2 Hz, 3H).

EXAMPLE 13 (28)

1-[(1R,2S)-2-(4-dimethylaminobenzoylamino)cyclohexyl]-N-[(2S)-4-methyl-1-(5-(1-methylethylthio)-1,3,4-oxadiazol-2-yl)-1-oxo-2-pentyl]carboxamide

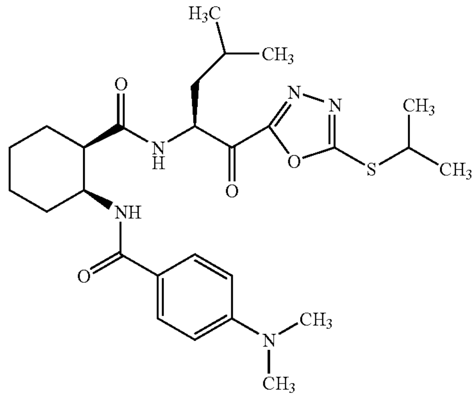

Free Compound

TLC: Rf 0.25 (n-hexane:ethyl acetate=1:1);

NMR ($CDCl_3$): δ 7.66 (d, J=9.2 Hz, 2H), 6.88 (d, J=8.0 Hz, 1H), 6.66 (d, J=9.2 Hz, 2H), 6.36 (d, J=7.4 Hz, 1H), 5.50–5.35 (m, 1H), 4.45–4.25 (m, 1H), 4.04 (septet, J=6.6 Hz, 1H), 3.02 (s, 6H), 2.85 (q, J=5.1 Hz, 1H), 2.15–1.40 (m, 11H), 1.54 (d, J=6.6 Hz, 6H), 0.90 (d, J=6.2 Hz, 3H), 0.84 (d, J=6.2 Hz, 3H).

Hydrochloride

TLC: Rf 0.25 (n-hexane:ethyl acetate=1:1);

NMR ($CDCl_3$) δ 7.92 (d, J=8.8 Hz, 2H), 7.77 (d, J=8.8 Hz, 2H), 7.56 (d, J=8.0 Hz, 1H), 6.31 (d, J=7.8 Hz, 1H), 5.50–5.35 (m, 1H), 4.35–4.20 (m, 1H), 4.05 (septet, J=6.8 Hz, 1H), 3.18 (s, 6H), 2.84 (q, J=4.9 Hz, 1H), 2.10–1.40 (m, 11H), 1.55 (d, J=6.8 Hz, 6H), 0.95 (d, J=6.2 Hz, 3H), 0.91 (d, J=6.2 Hz, 3H).

EXAMPLE 13 (29)

1-[(1R,2S)-2-(N-benzoyl-N-methylamino)cyclohexyl]-N-[(2S)-4-methyl-1-(5-methylthio-1,3,4-oxadiazol-2-yl)-1-oxo-2-pentyl]carboxamide

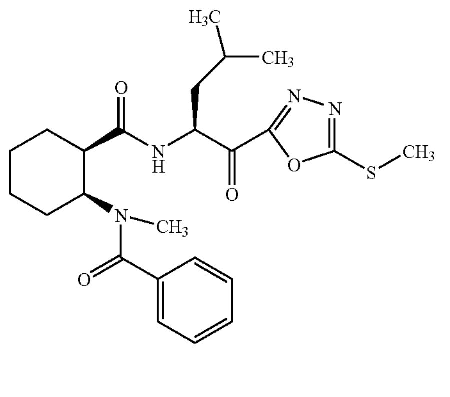

TLC: Rf 0.33 (n-hexane:ethyl acetate=1:1);

NMR ($CDCl_3$): δ 7.45–7.29 (m, 5H), 6.50–6.27 (br, 1H), 5.43–5.31 (m, 1H), 4.61–4.30 (br, 1H), 3.36–3.00 (br, 1H), 2.87 (s, 3H), 2.78 (s, 3H), 2.60–2.36 (m, 1H), 2.02–1.23 (m, 10H), 0.94 and 0.90 (each d, J=6.2 Hz, each 3H).

EXAMPLE 13 (30)

1-[(1R, 2S)-2-(4-dimethylaminomethylbenzoylamino)cyclohexyl]-N-[4-methyl-1-(5-(1-methylethylthio)-1,3,4-oxadiazol-2-yl)-1-oxo-2-pentyl]carboxamide

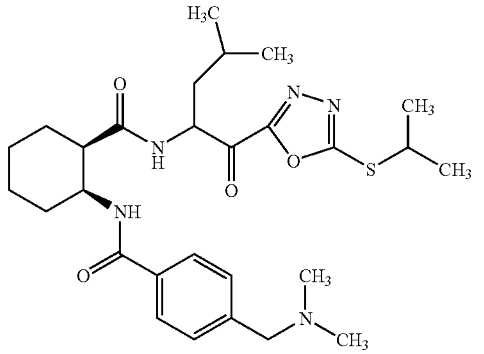

Free Compound

TLC: Rf 0.44 (chloroform:methanol=9:1);

NMR ($CDCl_3$): δ 7.66 and 7.72 (each d, J=8.4 Hz, totally 2H), 7.37 and 7.35 (each d, J=8.4 Hz, totally 2H), 7.24 and 7.16 (each d, J=8.0 Hz, totally 1H), 6.33 and 6.29 (each d, J=8.0 Hz, totally 1H), 5.50–5.30 (m, 1H), 4.40–4.25 (m, 1H), 4.05 and 4.03 (each septet, J=6.8 Hz, totally 1H), 3.47 and 3.46 (each s, totally 2H), 2.90–2.80 (m, 1H), 2.24 and 2.23 (each s, totally 6H), 2.20–1.40 (m, 11H), 1.54 and 1.53 (each d, J=6.8 Hz, totally 6H), 1.02, 0.94, 0.91 and 0.85 (each d, J=5.8, 5.8, 6.2 and 6.2 Hz, totally 6H).

Hydrochloride

TLC: Rf 0.44 (chloroform:methanol=9:1);

NMR ($CDCl_3$): δ 7.85 and 7.84 (each d, J=8.2 Hz, totally 2H), 7.68 and 7.64 (each d, J=8.2 Hz, totally 2H), 7.47 and 7.35 (each d, J=8.0 and 8.8 Hz, totally 1H), 6.78 and 6.37 (each d, J=7.0 and 7.8 Hz, totally 1H), 5.50–5.30 (m, 1H), 4.31 (br, 1H), 4.23 and 4.20 (each s, totally 2H), 4.05 (septet, J=6.8 Hz, 1H), 3.00–2.85 (m, 1H), 2.75 and 2.74 (each s, totally 6H), 2.10–1.40 (m, 1H), 1.54 (d, J=6.8 Hz, 6H), 1.04, 0.97, 0.94 and 0.90 (each d, J=6.0, 6.0, 6.2 and 6.2 Hz, totally 6H).

EXAMPLE 13 (31)

1-[(1R,2S)-2-(2-aminopyridin-5-ylcarbonylamino) cyclohexyl]-N-[4-methyl-1-(5-(1-methylethylthio)-1,3,4-oxadiazol-2-yl)-1-oxo-2-pentyl]carboxamide

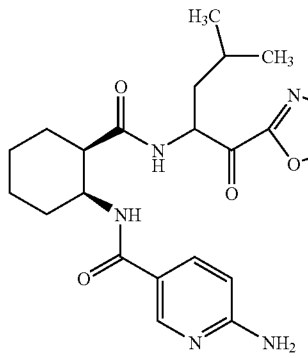

TLC: Rf 0.37 (chloroform:methanol=9:1);

NMR ($CDCl_3$): δ 8.56 and 8.52 (each d, J=2.2 Hz, totally 1H), 7.84 and 7.81 (each dd, J=8.6, 2.2 Hz, totally 1H), 7.15–7.00 (m, 1H), 6.48 (d, J=8.6 Hz, 1H), 6.45–6.30 (m, 1H), 5.50–5.30 (m, 1H), 4.84 (br, 2H), 4.40–4.20 (m, 1H), 4.04 (septet, J=6.6 Hz, 1H), 2.90–2.75 (m, 1H), 2.20–1.30 (m, 11H), 1.54 (d, J=6.6 Hz, 6H), 1.02, 0.95, 0.93 and 0.87 (each d, J=5.8, 6.0, 6.2 and 6.2 Hz, totally 6H).

EXAMPLE 13 (32)

1-[(1R,2S)-2-(2-aminopyridin-5-ylcarbonylamino) cyclohexyl]-N-[4-methyl-1-(5-methylthio-1,3,4-oxadiazol-2-yl)-1-oxo-2-pentyl]carboxamide

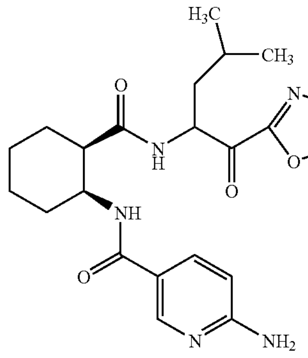

TLC: Rf 0.42 (chloroform methanol=9:1);

NMR ($CDCl_3$): δ 8.55 and 8.52 (each d, J=2.4 Hz, totally 1H), 7.85 and 7.81 (each dd, J=8.8, 2.4 Hz, totally 1H), 7.07 (d, J=7.4 Hz, 1H), 6.55–6.35 (m, 2H), 5.50–5.30 (m, 1H), 4.88 (br, 2H), 4.40–4.20 (m, 1H), 2.90–2.75 (m, 1H), 2.79 and 2.78 (each s, totally 3H), 2.10–1.30 (m, 11H), 1.02, 0.95, 0.92 and 0.87 (each d, J=6.0, 6.2, 6.2 and 6.2 Hz, totally 6H).

EXAMPLE 13 (33)

1-[(1R,2S)-2-benzoylaminocyclohexyl]-N-[(2S)-4-methyl-1-(5-t-butoxycarbonylmethylthio-1,3,4-oxadiazol-2-yl)-1-oxo-2-pentyl]carboxamide

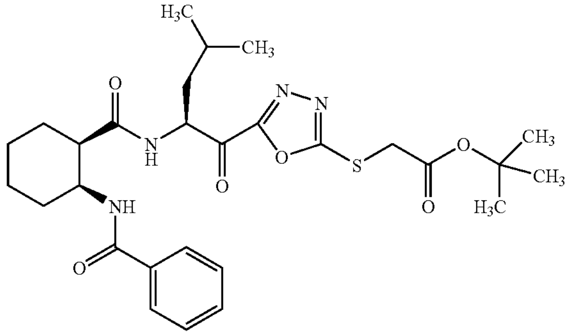

TLC: Rf 0.54 (n-hexane:ethyl acetate=1:2);

NMR ($CDCl_3$): δ 7.80–7.73 (m, 2H), 7.53–7.38 (m, 3H), 7.20 (brd, J=8.4 Hz, 1H), 6.26 (d, J=7.8 Hz, 1H), 5.46–5.36 (m, 1H), 4.37–4.27 (m, 1H), 4.06 (s, 2H), 2.86 (q, J=4.8 Hz, 1H), 2.15–1.30 (m, 11H), 1.49 (s, 9H), 0.90 and 0.85 (each d, J=6.3 Hz, totally 6H).

EXAMPLE 13 (34)

(2S)-N-[(2S)-4-methyl-1-(5-t-butoxycarbonylmethylthio-1,3,4-oxadiazol-2-yl)-1-oxo-2-pentyl]-4-methyl-2-benzyloxycarbonylaminopentanamide

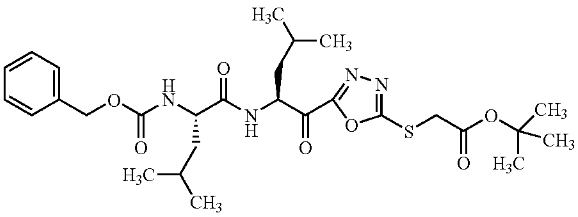

TLC: Rf 0.53 (n-hexane:ethyl acetate=1:1);

NMR ($CDCl_3$): δ 7.45–7.24 (m, 5H), 6.64 (brd, J=6.6 Hz, 1H), 5.46–5.35 (m, 1H), 5.23–5.06 (m, 3H), 4.32–4.18 (m, 1H), 4.06 (s, 2H), 1.86–1.41 (m, 6H), 1.48 (s, 9H), 1.03–0.85 (m, 12H).

EXAMPLE 13 (35)

1-[(1R,2S)-2-(4-dimethylaminomethylbenzoylamino)cyclohexyl]-N-[(2S)-4-methyl-1-(5-(1-methylethylthio)-1,3,4-oxadiazol-2-yl)-1-oxo-2-pentyl]carboxamide

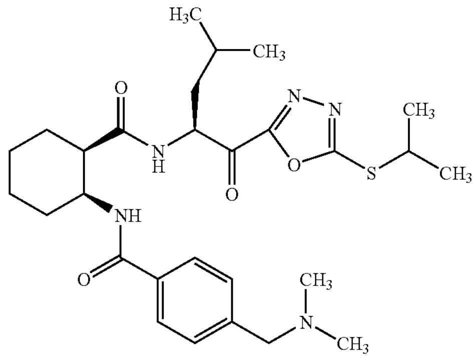

TLC: Rf 0.44 (chloroform:methanol=9:1);

NMR ($CDCl_3$): δ 7.72 (d, J=8.4 Hz, 2H), 7.37 (d, J=8.4 Hz, 2H), 7.16 (d, J=8.1 Hz, 1H), 6.25 (d, J=7.8 Hz, 1H), 5.48–5.41 (m, 1H), 4.36–4.30 (m, 1H), 4.09–4.00 (m, 1H), 3.48 (s, 2H), 2.89–2.84 (m, 1H), 2.25 (s, 6H), 2.14–1.43 (m, 17H), 0.91 (d, J=6.6 Hz, 3H), 0.85 (d, J=6.6 Hz, 3H).

EXAMPLE 13 (36)

1-[(1R,2S)-2-(4-dimethylaminomethylbenzoylamino)cyclohexyl]-N-[4-methyl-1-(5-methylthio-1,3,4-oxadiazol-2-yl)-1-oxo-2-pentyl]carboxamide

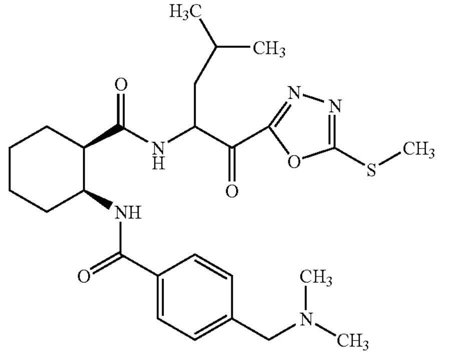

TLC: Rf 0.35 (chloroform:methanol=9:1);

NMR ($CDCl_3$): δ 7.76 and 7.72 (each d, J=8.0 and 8.4 Hz, totally 2H), 7.37 and 7.35 (each d, J=8.0 and 8.4 Hz, totally 2H), 7.22 and 7.16 (each d, J=8.4 and 8.0 Hz, totally 1H), 6.39 and 6.33 (each d, J=7.0 and 7.6 Hz, totally 1H), 5.50–5.30 (m, 1H), 4.40–4.25 (m, 1H), 3.48 and 3.47 (each s, totally 2H), 2.90–2.80 (m, 1H), 2.79 and 2.78 (each s, totally 3H), 2.25 and 2.24 (each s, totally 6H), 2.20–1.40 (m, 11H), 1.01, 0.94, 0.91 and 0.84 (each d, J=6.0, 6.0, 6.2 and 6.2 Hz, totally 6H).

EXAMPLE 13 (37)

1-[(1R,2S)-2-benzoylaminocyclohexyl]-N-[(2S)-4-methyl-1-(5-bis(methoxycarbonyl)methylthio-1,3,4-oxadiazol-2-yl)-1-oxo-2-pentyl]carboxamide

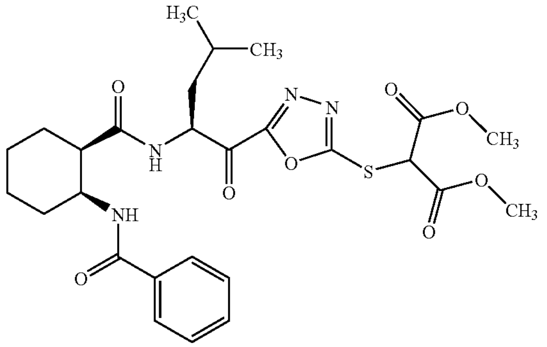

TLC: Rf 0.26 (n-hexane:ethyl acetate=1:2);

NMR ($CDCl_3$): δ 7.80–7.72 (m, 2H), 7.53–7.38 (m, 3H), 7.15 (brd, J=7.8 Hz, 1H), 6.24 (d, J=7.5 Hz, 1H), 5.46–5.35 (m, 1H), 5.39 (s, 1H), 4.39–4.27 (m, 1H), 3.87 (s, 6H), 2.86 (q, J=5.4 Hz, 1H), 2.14–1.40 (m, 11H), 0.90 and 0.85 (each d, J=6.3 Hz, totally 6H).

EXAMPLE 13 (38)

(2S)-N-[(2S)-4-methyl-1-(5-bis(methoxycarbonyl)methylthio-1,3,4-oxadiazol-2-yl)-1-oxo-2-pentyl]-4-methyl-2-benzyloxycarbonylaminopentanamide

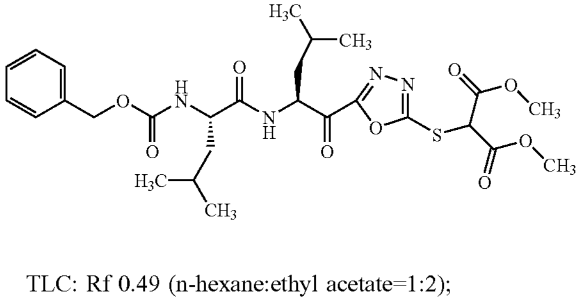

TLC: Rf 0.49 (n-hexane:ethyl acetate=1:2);

NMR ($CDCl_3$): δ 7.45–7.26 (m, 5H), 6.74–6.56 (br, 1H), 5.44–5.34 (m, 1H), 5.39 (s, 1H), 5.20–5.04 (m, 3H), 4.30–4.15 (m, 1H), 3.87 (s, 6H), 1.87–1.40 (m, 6H), 1.04–0.83 (m, 12H).

EXAMPLE 13 (39)

1-[(1R,2S)-2-(4-dimethylaminomethyl-2-fluorobenzoylamino)cyclohexyl]-N-[4-methyl-1-(5-(1-methylethylthio)-1,3,4-oxadiazol-2-yl)-1-oxo-2-pentyl]carboxamide

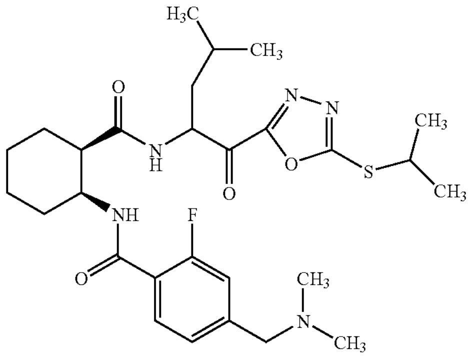

TLC: Rf 0.57 (chloroform:methanol=9:1);

NMR ($CDCl_3$): δ 8.02–7.90 (m, 1H), 7.50–7.38 (m, 1H), 7.22–7.05 (m, 2H), 6.50 and 6.30 (each brd, J=7.5 Hz, totally 1H), 5.48–5.32 (m, 1H), 4.52–4.39 (m, 1H), 4.10–3.93 (m, 1H), 3.43 (m, 2H), 2.88–2.75 (m, 1H), 2.25 (s, 6H), 2.20–1.40 (m, 17H), 1.01, 0.95, 0.89, and 0.81 (each d, J=6.3 Hz, totally 6H).

EXAMPLE 13 (40)

1-[(1R,2S)-2-(4-dimethylaminomethyl-2-fluorobenzoylamino)cyclohexyl]-N-[4-methyl-1-(5-methylthio-1,3,4-oxadiazol-2-yl)-1-oxo-2-pentyl]carboxamide

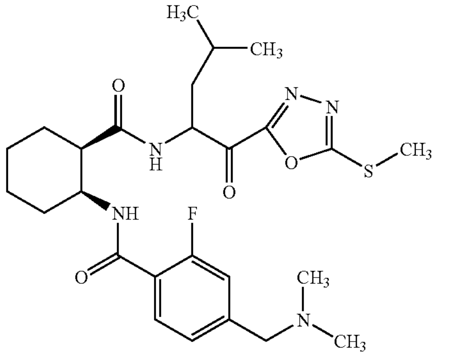

TLC: Rf 0.37 (chloroform:methanol=9:1);

NMR ($CDCl_3$) δ 8.01–7.90 (m, 1H), 7.50–7.35 (m, 1H), 7.20–7.05 (m, 2H), 6.55 and 6.35 (each brd, J=6.3 Hz, totally 1H), 5.48–5.30 (m, 1H), 4.60–4.38 (m, 1H), 3.45 (m, 2H), 2.85 (m, 1H), 2.78 and 2.76 (each s, totally 3H), 2.25 (s, 6H), 2.20–1.40 (m, 11H), 1.05–0.80 (m, 6H).

EXAMPLE 13 (41)

1-[(1R,2S)-2-benzoylaminocyclopentyl]-N-[(2S)-4-methyl-1-(5-(1-methylethylthio)-1,3,4-oxadiazol-2-yl)-1-oxo-2-pentyl]carboxamide

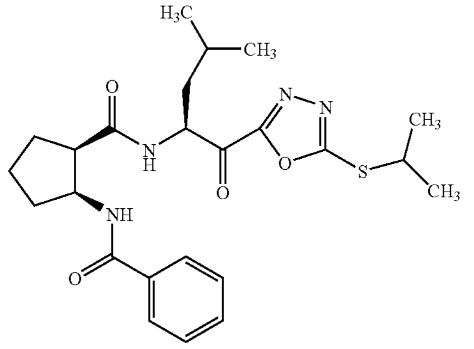

TLC: Rf 0.35 (n-hexane:ethyl acetate=1:1);

NMR ($CDCl_3$): δ 7.83–7.75 (m, 2H), 7.54–7.39 (m, 3H), 6.95 (brd, J=7.8 Hz, 1H), 6.23 (brd, J=7.5 Hz, 1H), 5.43–5.33 (m, 1H), 4.71–4.58 (m, 1H), 4.10–3.96 (m, 1H), 3.07 (q, J=7.5 Hz, 1H), 2.16–1.38 (m, 9H), 1.54 (d, J=6.9 Hz, 6H), 0.73 and 0.72 (each d, J=6.3 Hz, totally 6H).

EXAMPLE 13 (42)

1-[(1R,2S)-2-benzoylaminocyclopentyl]-N-[(2S)-4-methyl-1-(5-methylthio-1,3,4-oxadiazol-2-yl)-1-oxo-2-pentyl]carboxamide

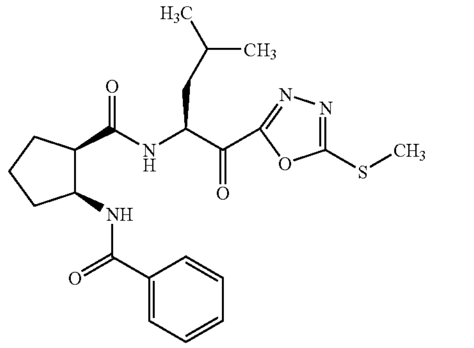

TLC: Rf 0.20 (n-hexane:ethyl acetate=1:1);

NMR ($CDCl_3$): δ 7.82–7.72 (m, 2H), 7.54–7.39 (m, 3H), 6.94 (brd, J=7.5 Hz, 1H), 6.23 (brd, J=7.5 Hz, 1H), 5.42–5.33 (m, 1H), 4.72–4.58 (m, 1H), 3.07 (q, J=7.5 Hz, 1H), 2.79 (s, 3H), 2.15–1.37 (m, 9H), 0.73 and 0.72 (each d, J=6.3 Hz, totally 6H).

EXAMPLE 13 (43)

1-[(1R,2S)-2-(4-morpholinomethylbenzoylamino)cyclohexyl]-N-[(2S)-4-methyl-1-(5-(1-methylethylthio)-1,3,4-oxadiazol-2-yl)-1-oxo-2-pentyl]carboxamide Hydrochloride

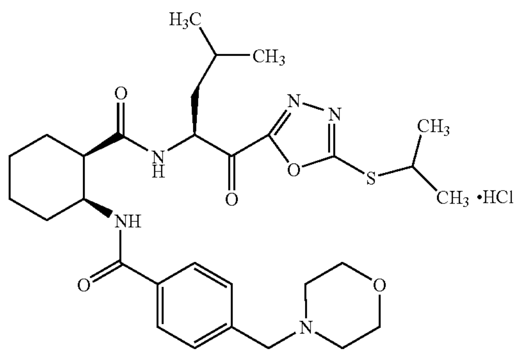

TLC: Rf 0.63 (chloroform:methanol=9:1);

NMR (DMSO-$d_6$): δ 8.47 (d, J=6.3 Hz, 1H), 7.88–7.82 (m, 3H), 7.66 (d, J=7.5 Hz, 2H), 5.07–5.00 (m, 1H), 4.39 (br-s, 2H), 4.27 (m, 1H), 4.00–3.87 (m, 3H), 3.79–3.82 (m, 2H), 3.24–3.02 (m, 4H), 2.78–2.75 (m, 1H), 2.04–1.84 (m, 2H), 1.67–1.22 (m, 9H), 1.45 (d, J=6.9 Hz, 6H), 0.77 (d, J=6.0 Hz, 3H), 0.72 (d, J=6.0 Hz, 3H).

EXAMPLE 13 (44)

1-[(1R,2S)-2-(4-pyrrolidinomethylbenzoylamino)cyclohexyl]-N-[(2S)-4-methyl-1-(5-(1-methylethylthio)-1,3,4-oxadiazol-2-yl)-1-oxo-2-pentyl]carboxamide Hydrochloride

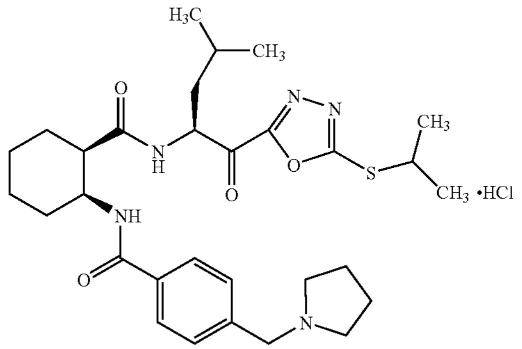

TLC: Rf 0.48 (chloroform:methanol=9:1);

NMR (DMSO-$d_6$): δ 8.63 and 8.46 (each d, J=6.6 Hz, totally 1H), 7.90–7.74 (m, 3H), 7.67–7.63 (m, 2H), 5.04–4.88 (m, 1H), 4.38 (m, 2H), 4.30–4.11 (m, 1H), 3.98–3.86 (m, 1H), 3.41–3.24 (m, 2H), 3.03 (m, 2H), 2.80–2.73 (m, 1H), 2.00–1.88 (m, 6H), 1.68–1.22 (m, 15H), 0.86, 0.82, 0.76, and 0.71 (each d, J=5.7 Hz, totally 6H).

EXAMPLE 13 (45)

1-[(1R,2S)-2-(2-dimethylaminomethylbenzoylamino)cyclohexyl]-N-[4-methyl-1-(5-methylthio-1,3,4-oxadiazol-2-yl)-1-oxo-2-pentyl]carboxamide

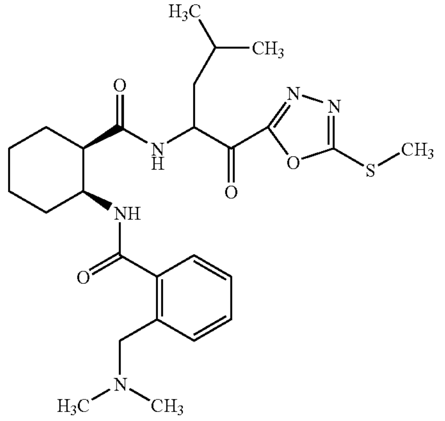

TLC: Rf 0.41 and 0.34 (chloroform:methanol=9:1);

NMR ($CDCl_3$): δ 10.65–10.40 (m, 1H), 8.05–7.90 (m, 1H), 7.50–7.30 (m, 2H), 7.25–7.10 (m, 1H), 7.05 and 6.36 (each d, J=6.6 Hz, totally 1H), 5.35–5.20 (m, 1H), 4.53 and 4.34 (each br, totally 1H), 3.71, 3.53, 3.44 and 3.40 (each d, J=12.0, 11.8, 11.8 and 12.0 Hz, totally 2H), 3.15–2.80 (m, 1H), 2.77 and 2.74 (each s, totally 3H), 2.22 and 2.20 (each s, totally 6H), 2.20–1.30 (m, 11H), 0.97, 0.94, 0.72 and 0.70 (each d, J=6.2 Hz, totally 6H).

EXAMPLE 13 (46)

1-[(1R,2S)-2-(2-dimethylaminomethylbenzoylamino)cyclohexyl]-N-[4-methyl-1-(5-(1-methylethylthio)-1,3,4-oxadiazol-2-yl)-1-oxo-2-pentyl]carboxamide

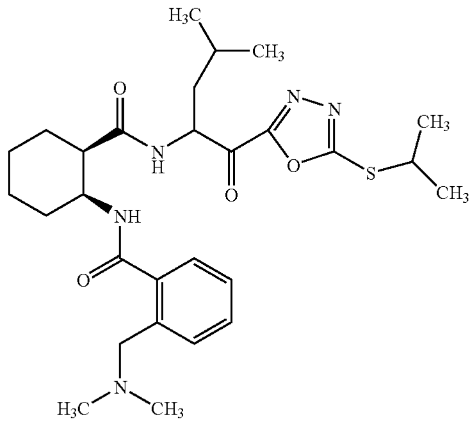

TLC: Rf 0.43 and 0.36 (chloroform:methanol=9:1);

NMR ($CDCl_3$): δ 10.65–10.40 (m, 1H), 8.05–7.90 (m, 1H), 7.45–7.30 (m, 2H), 7.25–7.10 (m, 1H), 7.04 and 6.36 (each d, J=6.2 and 7.4 Hz, totally 1H), 5.40–5.20 (m, 1H), 4.53 and 4.33 (each br, totally 1H), 4.02 and 3.99 (each septet, J=6.8 Hz, totally 1H), 3.72, 3.53, 3.44 and 3.41 (each d, J=12.2, 11.7, 11.7 and 12.2 Hz, totally 2H), 3.15–2.85 (m, 1H), 2.22 and 2.21 (each s, totally 6H), 2.20–1.20 (m, 11H), 1.53 and 1.51 (each d, J=6.8 Hz, totally 6H), 0.98, 0.94, 0.72 and 0.71 (each d, J=6.4 Hz, totally 6H).

EXAMPLE 13 (47)

1-[(1R,2S)-2-(3-dimethylaminomethylbenzoylamino)cyclohexyl]-N-[4-methyl-1-(5-methylthio-1,3,4-oxadiazol-2-yl)-1-oxo-2-pentyl]carboxamide

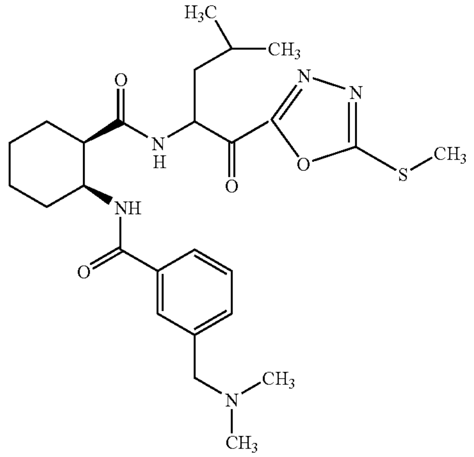

TLC: Rf 0.44 (chloroform:methanol=9:1);

NMR ($CDCl_3$): δ 7.75–7.60 (m, 2H), 7.50–7.30 (m, 2H), 7.21 and 7.16 (each d, J=8.8 and 7.6 Hz, totally 1H), 6.42 and 6.35 (each d, J=7.8 and 7.4 Hz, totally 1H), 5.50–5.30 (m, 1H), 4.40–4.25 (m, 1H), 3.47 (s, 2H), 2.90–2.80 (m, 1H), 2.79 and 2.77 (each s, totally 3H), 2.25 and 2.23 (each s, totally 6H), 2.20–1.35 (m, 11H), 1.01, 0.94, 0.89 and 0.84 (each d, J=6.2 Hz, totally 6H).

EXAMPLE 13 (48)

1-[(1R, 2S)-2-(3-dimethylaminomethylbenzoylamino)cyclohexyl]-N-[4-methyl-1-(5-(1-methylethylthio)-1,3,4-oxadiazol-2-yl)-1-oxo-2-pentyl]carboxamide

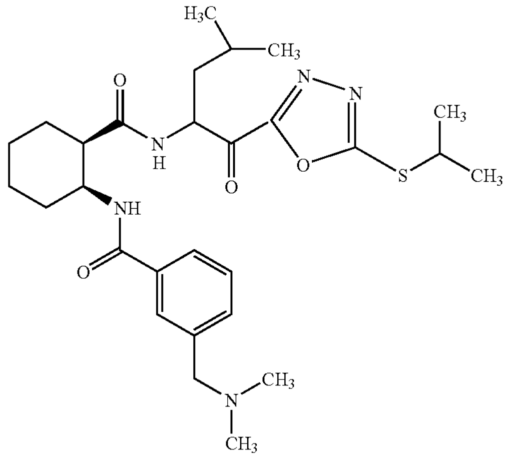

TLC: Rf 0.40 (chloroform methanol=9:1);

NMR ($CDCl_3$): δ 7.75–7.60 (m, 2H), 7.50–7.30 (m, 2H), 7.21 and 7.17 (each d, J=9.6 Hz, totally 1H), 6.43 and 6.35 (each d, J=7.0 and 7.4 Hz, totally 1H), 5.50–5.30 (m, 1H), 4.40–4.25 (m, 1H), 4.04 and 4.03 (each septet, J=6.7 Hz, totally 1H), 3.47 (s, 2H), 2.90–2.80 (m, 1H), 2.25 and 2.24 (each s, totally 6H), 2.20–1.30 (m, 11H), 1.54 and 1.53 (each d, J=6.7 Hz, totally 6H), 1.02, 0.94, 0.90 and 0.84 (each d, J=6.2 Hz, totally 6H).

EXAMPLE 13 (49)

1-[(1R,2S)-2-benzoylaminocyclohexyl]-N-[1-(5-(2-dimethylaminoethylthio)-1,3,4-oxadiazol-2-yl)-4-methyl-1-oxo-2-pentyl]carboxamide

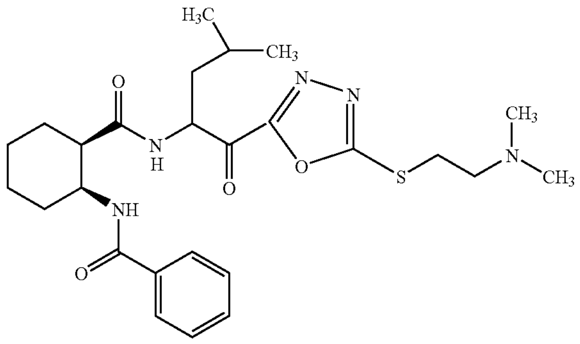

TLC: Rf 0.24 (chloroform:methanol=9:1);

NMR ($CDCl_3$): δ 7.82–7.71 (m, 2H), 7.51–7.38 (m, 3H), 7.24–7.18 (m, 1H), 6.29 and 6.25 (each brd, J=7.5 Hz, totally 1H), 5.50–5.30 (m, 1H), 4.42–4.30 (m, 1H), 3.51–3.40 (m, 2H), 2.90–2.82 (m, 1H), 2.80–2.70 (m, 2H), 2.32 (s, 6H), 2.10–1.40 (m, 11H), 1.01, 0.94, 0.90 and 0.84 (each d, J=6.3 Hz, totally 6H).

EXAMPLE 13 (50)

1-[(1R,2S)-2-(4-morpholinomethylbenzoylamino)cyclohexyl]-N-[(2S)-4-methyl-1-(5-methylthio-1,3,4-oxadiazol-2-yl)-1-oxo-2-pentyl]carboxamide Hydrochloride

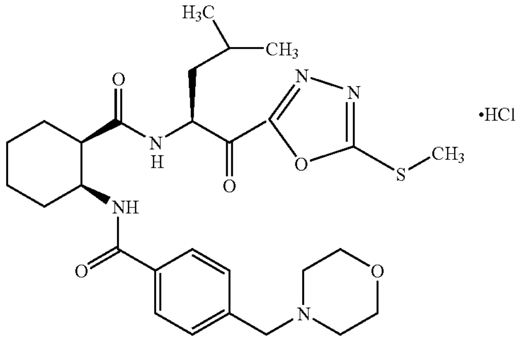

TLC: Rf 0.66 (chloroform:methanol=9:1);

NMR (DMSO-$d_6$): δ 8.61 and 8.47 (each d, J=6.9 Hz, totally 1H), 7.87–7.81 (m, 3H), 7.65 (d, J=7.8 Hz, 2H), 5.06–4.91 (m, 1H), 4.37 (br-s, 2H), 4.30–4.12 (m, 1H), 3.95–3.91 (m, 2H), 3.81–3.73 (m, 2H), 3.26–3.00 (m, 4H), 2.82–2.66 (m, 4H), 2.07–1.82 (m, 2H), 1.65–1.22 (m, 9H), 0.86, 0.83, 0.77, and 0.72 (each d, J=6.3 Hz, totally 6H).

EXAMPLE 13 (51)

1-[(1R,2S)-2-(4-pyrrolidinomethylbenzoylamino)cyclohexyl]-N-[4-methyl-1-(5-methylthio-1,3,4-oxadiazol-2-yl)-1-oxo-2-pentyl]carboxamide

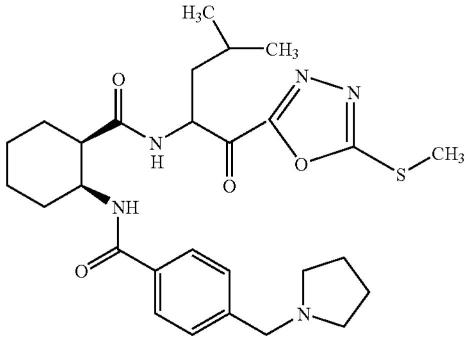

TLC: Rf 0.41 (chloroform:methanol=9:1);

NMR ($CDCl_3$): δ 7.79 and 7.75 (each d, J=8.1 Hz, totally 2H), 7.51 (d, J=8.1 Hz, 2H), 7.29–7.23 (m, 1H), 6.39 and 6.28 (each d, J=7.5 Hz, totally 1H), 5.45–5.34 (m, 1H), 4.38–4.37 (m, 1H), 3.89 and 3.88 (each s, totally 2H), 2.85–2.70 (m, 8H), 2.05–1.42 (m, 15H), 1.02, 0.95, 0.92, and 0.87 (each d, J=6.3 Hz, totally 6H).

EXAMPLE 13 (52)

(2S)-N-[1-(5-(2-dimethylaminoethylthio)-1,3,4-oxadiazol-2-yl)-4-methyl-1-oxo-2-pentyl]-4-methyl-2-benzyloxycarbonylaminopentanamide

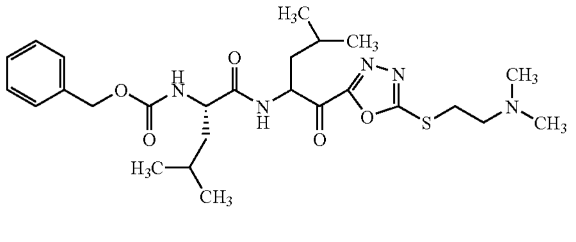

TLC: Rf 0.41 (chloroform:methanol=9:1);

NMR ($CDCl_3$): δ 7.42–7.30 (m, 5H), 6.72 and 6.59 (each m, totally 1H), 5.45–5.35 (m, 1H), 5.21–5.02 (m, 3H), 4.32–4.19 (m, 1H), 3.49 (t, J=5.7 Hz, 2H), 2.75 (t, J=5.7 Hz, 2H), 2.31 (s, 6H), 1.90–1.41 (m, 6H), 1.05–0.90 (m, 12H).

EXAMPLE 13 (53)

1-[(1R,2S)-2-(2-dimethylaminomethyl-4-fluorobenzoylamino)cyclohexyl]-N-[4-methyl-1-(5-(1-methylethylthio)-1,3,4-oxadiazol-2-yl)-1-oxo-2-pentyl]carboxamide

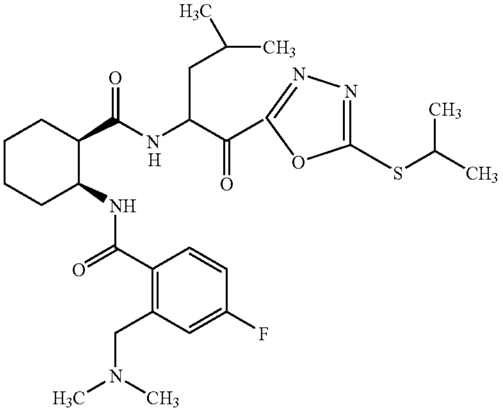

TLC: Rf0.43 and 0.37 (chloroform:methanol=9:1);

NMR ($CDCl_3$): δ 10.52–10.31 (m, 1H), 8.05–7.92 (m, 1H), 7.10–7.02 (m, 1H), 6.90 (m, 1H), 6.90 and 6.28 (each br, totally 1H), 5.38–5.27 (m, 1H), 4.50 and 4.30 (each m, totally 1H), 4.01 (septet, J=6.9 Hz, 1H), 3.70–3.30 (m, 2H), 3.08 and 2.92 (each m, totally 1H), 2.30–2.20 (m, 6H), 2.10–1.40 (m, 17H), 1.05–0.70 (m, 6H).

EXAMPLE 13 (54)

(2S)-N-[3-cyclopropyl-1-(5-methylthio-1,3,4-oxadiazol-2-yl)-1-oxo-2-propyl]-4-methyl-2-benzyloxycarbonylaminopentanamide

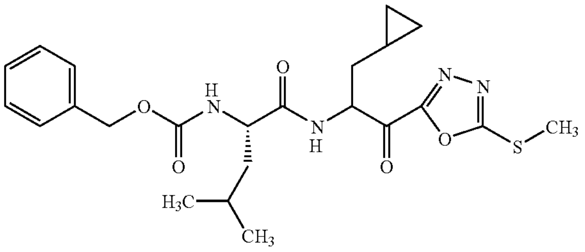

TLC: Rf 0.27 (n-hexane:ethyl acetate=2:1);

NMR ($CDCl_3$): δ 7.40–7.25 (m, 5H), 7.01 and 6.87 (br and d, J=6.6 Hz, totally 1H), 5.55–5.40 (m, 1H), 5.20–5.05 (m, 3H), 4.30–4.20 (m, 1H), 2.79 and 2.78 (each s, totally 3H), 2.00–1.40 (m, 5H), 1.00–0.85 (m, 6H), 0.80–0.60 (m, 1H), 0.50–0.35 (m, 2H), 0.15–0.05 (m, 2H).

EXAMPLE 13 (55)

1-[(1R,2S)-2-benzoylaminocyclohexyl]-N-[3-cyclopropyl-1-(5-methylthio-1,3,4-oxadiazol-2-yl)-1-oxo-2-propyl]carboxamide

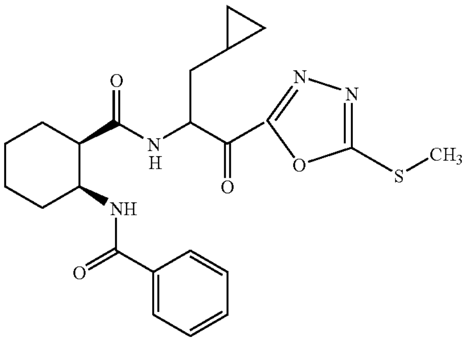

TLC: Rf 0.43 (n-hexane:ethyl acetate=1:1);

NMR ($CDCl_3$): δ 7.85–7.70 (m, 2H), 7.50–7.25 (m, 4H), 6.54 (d, J=6.6 Hz, 1H), 5.55–5.40 (m, 1H), 4.40–4.25 (m, 1H), 2.87 (q, J=5.1 Hz, 1H), 2.79 and 2.78 (each s, totally 3H), 2.10–1.40 (m, 10H), 0.70–0.55 (m, 1H), 0.50–0.30 (m, 2H), 0.10–0.10 (m, 2H).

EXAMPLE 13 (56)

1-[(1R,2S)-2-(2-dimethylaminomethyl-4-fluorobenzoylamino)cyclohexyl]-N-[4-methyl-1-(5-methylthio-1,3,4-oxadiazol-2-yl)-1-oxo-2-pentyl]carboxamide

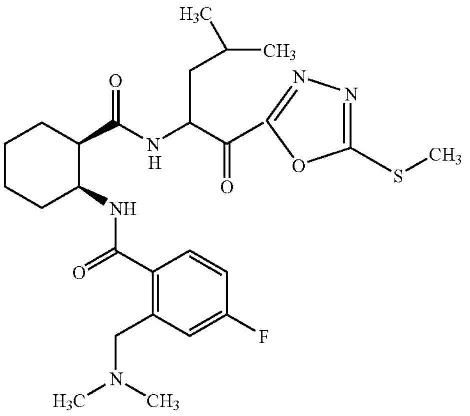

TLC: Rf 0.28 (chloroform:methanol=9:1);

NMR ($CDCl_3$): δ 7.58–7.20 (m, 4H), 6.29 and 6.25 (each brd, J=7.8 Hz, totally 1H), 5.51–5.35 (m, 1H), 4.38–4.25 (m, 1H), 3.60–3.40 (m, 2H), 2.90–2.70 (m, 4H), 2.32–1.39 (m, 11H), 1.05, 0.99, 0.97, and 0.88 (each d, J=6.3 Hz, totally 6H).

EXAMPLE 13 (57)

1-benzoylaminocyclohexyl-N-[(2S)-4-methyl-1-(5-(1-methylethylthio)-1,3,4-oxadiazol-2-yl)-1-oxo-2-pentyl]carboxamide

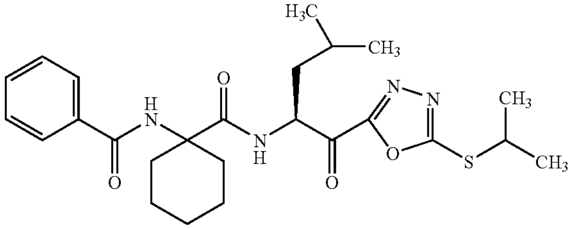

TLC: Rf 0.70 (n-hexane:ethyl acetate=1:1);

NMR ($CDCl_3$): δ 8.02 (d, J=6.6 Hz, 1H), 7.77 (d, J=6.9 Hz, 2H), 7.55 (t, J=6.9 Hz, 1H), 7.47 (t, J=6.9 Hz, 2H), 6.04 (brs, 1H), 5.38 (m, 1H), 4.00 (septet, J=6.6 Hz, 1H), 2.28 (br, 2H), 2.00 (br, 2H), 1.90–1.21 (m, 15H), 1.01 and 0.97 (each d, J=5.7 Hz, each 3H).

EXAMPLE 13 (58)

1-[(1R,2S)-2-(3-morpholinomethylbenzoylamino) cyclohexyl]-N-[(2S)-4-methyl-1-(5-methylthio-1,3,4-oxadiazol-2-yl)-1-oxo-2-pentyl]carboxamide Hydrochloride

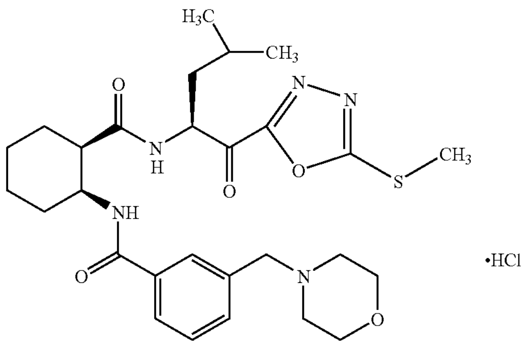

TLC: Rf 0.46 (chloroform:methanol=19:1);

NMR ($DMSO-d_6$): δ 8.46 (d, J=6.3 Hz, 1H), 8.01 (s, 1H), 7.82 (d, J=7.5 Hz, 2H), 7.72 (d, J=7.2 Hz, 1H), 7.53 (t-like, J=7.5 Hz, 1H), 5.06–4.98 (m, 1H), 4.39 (br-s, 2H), 4.29 (m, 1H), 3.95–3.91 (m, 2H), 3.77–3.69 (m, 2H), 3.38–3.03 (m, 4H), 2.75 (s, 4H), 1.98–1.90 (m, 2H), 1.70–1.23 (m, 9H), 0.77 (d, J=6.0 Hz, 3H), 0.72 (d, J=6.0 Hz, 3H).

EXAMPLE 13 (59)

1-[(1R,2S)-2-(3-morpholinomethylbenzoylamino) cyclohexyl]-N-[(2S)-4-methyl-1-(5-(1-methylethylthio)-1,3,4-oxadiazol-2-yl)-1-oxo-2-pentyl]carboxamide Hydrochloride

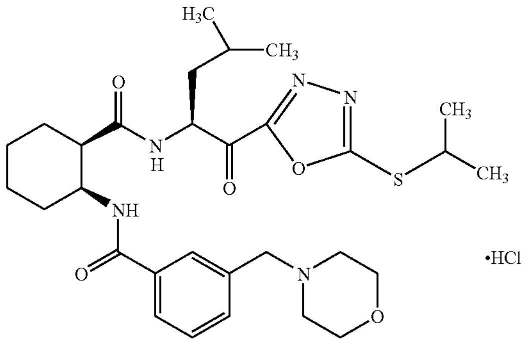

TLC: Rf 0.49 (chloroform:methanol=19:1);

NMR ($DMSO-d_6$) δ 8.46 (d, J=6.3 Hz, 1H), 8.02 (s, 1H), 7.81 (d, J=7.5 Hz, 2H), 7.73 (d, J=7.8 Hz, 1H), 7.53 (t-like, J=7.5 Hz, 1H), 5.06–4.99 (m, 1H), 4.39 (br-s, 2H), 4.30 (m, 1H), 3.98–3.87 (m, 3H), 3.79–3.71 (m, 2H), 3.41–3.03 (m, 4H), 2.76–2.73 (m, 1H), 2.02–1.90 (m, 2H), 1.67–1.22 (m, 9H), 1.45 (d, J=6.6 Hz, 6H), 0.77 (d, J=6.0 Hz, 3H), 0.72 (d, J=6.0 Hz, 3H).

EXAMPLE 13 (60)

1-[(1R,2S)-2-(3-pyrrolidinomethylbenzoylamino) cyclohexyl]-N-[(2S)-4-methyl-1-(5-methylthio-1,3,4-oxadiazol-2-yl)-1-oxo-2-pentyl]carboxamide Hydrochloride

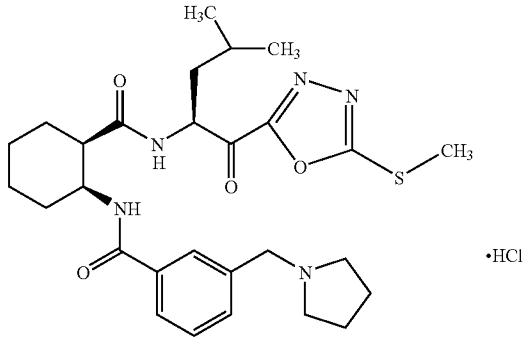

TLC: Rf 0.43 (chloroform:methanol=9:1);

NMR ($DMSO-d_6$): δ 8.58 and 8.46 (each d, J=6.3 Hz, totally 1H), 7.99 and 7.94 (each s, totally 1H), 7.80 (d, J=7.5 Hz, 2H), 7.74 and 7.67 (each d, J=7.8 Hz, totally 1H), 7.52 (t-like, J=7.5 Hz, 1H), 5.06–4.98 (m, 1H), 4.39 and 4.37 (each s, totally 2H), 4.29 (m, 1H), 3.41–3.26 (m, 2H), 3.11–2.98 (m, 2H), 2.81–2.70 (m, 1H), 2.74 (s, 3H), 2.01–1.85 (m, 7H), 1.61–1.22 (m, 8H), 0.86, 0.83, 0.77, and 0.71 (each d, J=6.3 Hz, totally 6H).

EXAMPLE 13 (61)

1-[(1R,2S)-2-(3-pyrrolidinomethylbenzoylamino) cyclohexyl]-N-[4-methyl-1-(5-(1-methylethylthio)-1,3,4-oxadiazol-2-yl)-1-oxo-2-pentyl]carboxamide Hydrochloride

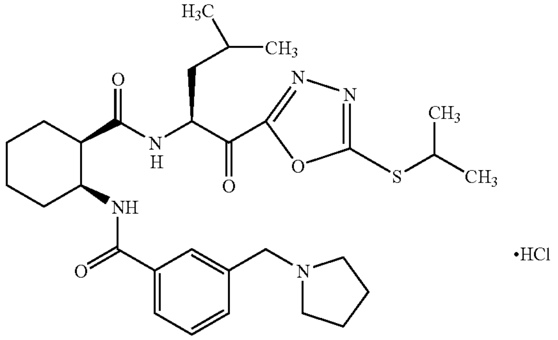

TLC: Rf 0.39 (chloroform:methanol=9:1);

NMR ($DMSO-d_6$): δ 8.46 (each d, J=6.6 Hz, 1H), 7.98 (s, 1H), 7.81 (d, J=7.5 Hz, 2H), 7.72 (d, J=6.9 Hz, 1H), 7.52 (t-like, J=7.5 Hz, 1H), 5.08–5.00 (m, 1H), 4.40 and 4.38 (each s, totally 2H), 4.29 (m, 1H), 4.00–3.87 (m, 1H), 3.41–3.32 (m, 2H), 3.12–3.00 (m, 2H), 2.77–2.73 (m, 1H), 2.01–1.85 (m, 7H), 1.68–1.23 (m, 8H), 1.45 (d, J=6.9 Hz, 6H) 0.77 (d, J=5.1 Hz, 3H), 0.71 (d, J=5.1 Hz, 3H).

EXAMPLE 13 (62)

1-[(1R,2S)-2-benzoylaminocyclohexyl]-N-[2-(5-methylthio-1,3,4-oxadiazol-2-yl)-2-oxoethyl]carboxamide

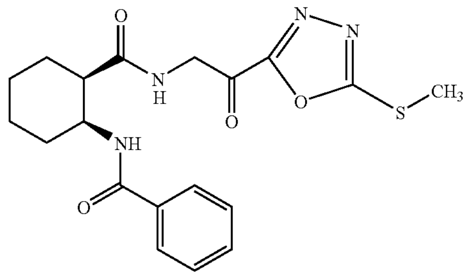

TLC: Rf 0.38 (chloroform:methanol=9:1);

NMR ($CDCl_3$): δ 7.82–7.74 (m, 2H), 7.51–7.38 (m, 3H), 7.31 (brd, J=8.7 Hz, 1H), 6.53 (brt, J=5.4 Hz, 1H), 4.78 (dd, J=19.5, 5.1 Hz, 1H), 4.75 (dd, J=19.5, 5.1 Hz, 1H), 4.42–4.31 (m, 1H), 2.93–2.87 (m, 1H), 2.79 (s, 3H), 2.13–1.40 (m, 8H).

EXAMPLE 13 (63)

(2S)-N-[2-(5-methylthio-1,3,4-oxadiazol-2-yl)-2-oxoethyl]-2-benzyloxycarbonylamino-4-methylpentanamide

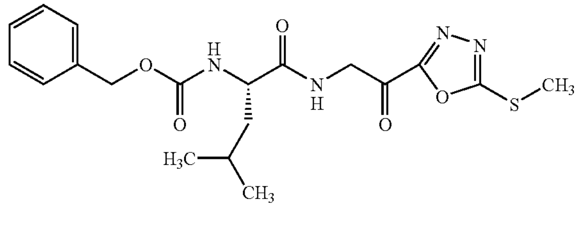

TLC: Rf 0.53 (chloroform:methanol=9:1);

NMR ($CDCl_3$): δ 7.45–7.26 (m, 5H), 6.82 (brs, 1H), 5.23–5.06 (m, 1H), 5.13 (s, 2H), 4.85–4.73 (m, 2H), 4.36–4.24 (m, 1H), 2.80 (s, 3H), 1.81–1.48 (m, 3H), 1.04–0.85 (m, 6H).

EXAMPLE 13 (64)

1-[(1R,2S)-2-(4-dimethylaminomethyl-3-fluorobenzoylamino) cyclohexyl]-N-[4-methyl-1-(5-(1-methylethylthio)-1,3,4-oxadiazol-2-yl)-1-oxo-2-pentyl] carboxamide Hydrochloride

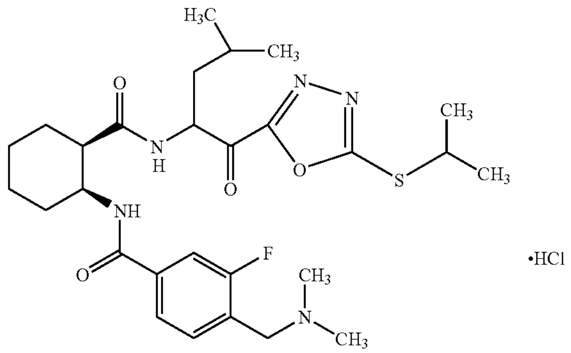

TLC: Rf 0.35 (chloroform:methanol=9:1);

NMR ($CDCl_3$): δ 8.03–7.88 (m, 1H), 7.68–7.54 (m, 2H), 7.59 and 7.41 (each brd, J=9.0 Hz, totally 1H), 6.55 and 6.32 (each brd, J=6.9 Hz, totally 1H), 5.50–5.38 (m, 1H), 4.38–4.20 (m, 3H), 4.13–3.90 (m, 1H), 2.90–2.70 (m, 7H), 2.10–1.40 (m, 17H), 1.04, 0.97, and 0.92 (each d, J=6.0 Hz, totally 6H).

EXAMPLE 13 (65)

(2S)-N-[(2S)-4-methoxy-1-(5-methylthio-1,3,4-oxadiazol-2-yl)-1-oxo-2-butyl]-4-methyl-2-benzyloxycarbonylaminopentanamide

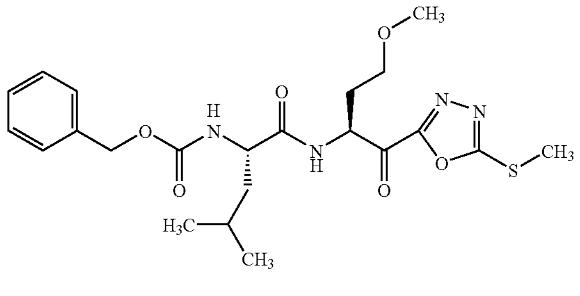

TLC: Rf 0.36 (n-hexane:ethyl acetate=1:1);

NMR ($CDCl_3$): δ 7.40–7.20 (m, 6H), 5.41 (q, J=5.5 Hz, 1H), 5.17 (d, J=8.4 Hz, 1H), 5.12 (s, 2H), 4.30–4.20 (m, 1H), 3.43 (t, J=5.1 Hz, 2H), 3.17 (s, 3H), 2.78 (s, 3H), 2.40–2.20 (m, 2H) 1.80–1.45 (m, 3H), 0.95 (d, J=6.0 Hz, 6H).

EXAMPLE 13 (66)

1-[(1R,2S)-2-benzoylaminocyclohexyl]-N-[(2S)-4-methoxy-1-(5-methylthio-1,3,4-oxadiazol-2-yl)-1-oxo-2-butyl]carboxamide

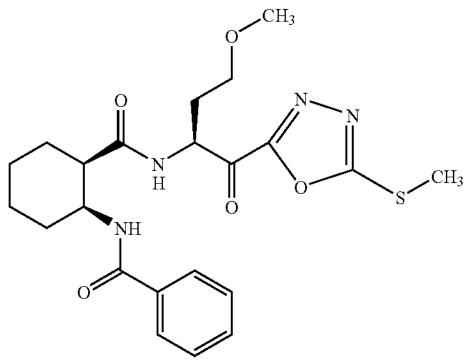

TLC: Rf 0.32 (n-hexane:ethyl acetate=1:2);

NMR ($CDCl_3$): δ 7.80–7.75 (m, 2H), 7.55 (d, J=8.1 Hz, 1H) 7.50–7.35 (m, 3H), 7.22 (d, J=5.7 Hz, 1H), 5.42 (q, J=5.7 Hz, 1H), 4.35–4.25 (m, 1H), 3.50–3.35 (m, 2H), 3.19 (s, 3H), 2.82 (q, J=4.8 Hz, 1H), 2.79 (s, 3H), 2.40–2.20 (m, 2H), 2.05–1.40 (m, 8H).

EXAMPLE 13 (67)

1-benzoylaminocyclohexyl-N-[(2S)-4-methyl-1-(5-methylthio-1,3,4-oxadiazol-2-yl)-1-oxo-2-pentyl] carboxamide

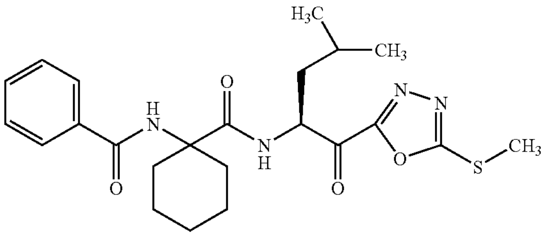

TLC: Rf 0.42 (n-hexane ethyl acetate=1:1);

NMR ($CDCl_3$): δ 8.02 (brd, J=6.6 Hz, 1H), 7.76 (d, J=7.8 Hz, 2H), 7.58–7.43 (m, 3H), 6.07 (brs, 1H), 5.36 (ddd, J=10.2, 6.9, 4.2 Hz, 1H), 2.76 (s, 3H), 2.37–2.20 (m, 2H), 2.06–1.90 (m, 2H), 1.90–1.30 (m, 9H), 1.00 and 0.96 (each d, J=6.0 Hz, each 3H).

EXAMPLE 13 (68)

1-[(1R,2S)-2-(4-dimethylaminomethyl-2-fluorobenzoylamino)cyclohexyl]-N-[(2S)-4-methyl-1-(5-(1-methylethylthio)-1,3,4-oxadiazol-2-yl)-1-oxo-2-pentyl]carboxamide

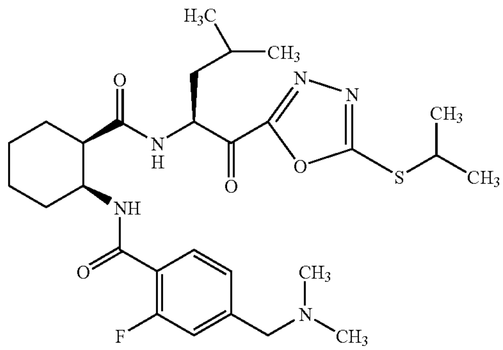

TLC: Rf 0.42 (chloroform:methanol=9:1);

NMR ($CDCl_3$): δ 8.09 (t, J=7.8 Hz, 1H), 7.71–7.42 (m, 3H), 6.28 (d, J=7.2 Hz, 1H), 5.50–5.33 (m, 1H), 4.52–4.31 (m, 1H), 4.17 (brs, 2H), 4.13–3.95 (m, 1H), 2.90–2.70 (m, 1H), 2.76 (brs, 6H), 2.15–1.38 (m, 11H), 1.54 (d, J=6.6 Hz, 6H), 0.94 and 0.89 (each d, J=6.3 Hz, each 3H).

EXAMPLE 13 (69)

1-[1-morpholinocarbonylaminocyclohexyl]-N-[(2S)-4-methyl-1-(5-(1-methylethylthio)-1,3,4-oxadiazol-2-yl)-1-oxo-2-pentyl]carboxamide

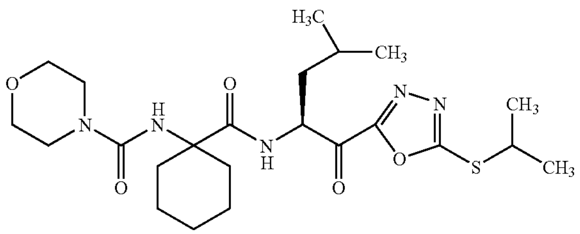

TLC: Rf 0.48 (chloroform:methanol=9:1);

NMR ($CDCl_3$): δ 8.17 (brd, J=6.6 Hz, 1H), 5.31 (ddd, J=9.9, 6.6, 3.9 Hz, 1H), 4.43 (brs, 1H), 4.02 (septet, J=6.9 Hz, 1H), 3.72 (t, J=5.1 Hz, 4H), 3.38 (t, J=5.1 Hz, 4H), 2.21–1.20 (m, 13H), 1.53 (d, J=6.9 Hz, 6H), 1.00 and 0.97 (each d, J=5.7 Hz, each 3H).

EXAMPLE 13 (70)

1-(1-morpholinocarbonylaminocyclohexyl)-N-[(2S)-4-methyl-1-(5-methylthio-1,3,4-oxadiazol-2-yl)-1-oxo-2-pentyl]carboxamide

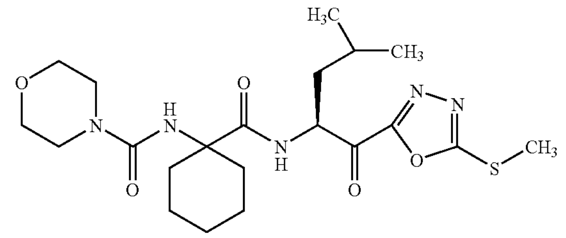

TLC: Rf 0.55 (ethyl acetate);

NMR ($CDCl_3$): δ 8.17 (brd, J=6.3 Hz, 1H), 5.29 (m, 1H), 4.41 (brs, 1H), 3.72 (t, J=4.5 Hz, 4H), 3.38 (t, J=4.5 Hz, 4H), 2.79 (s, 3H), 2.21–1.28 (m, 13H), 1.00 and 0.97 (each d, J=5.7 Hz, each 3H).

EXAMPLE 13 (71)

1-[1-t-butoxycarbonylaminocyclohexyl]-N-[(2S)-4-methyl-1-(5-methylthio-1,3,4-oxadiazol-2-yl)-1-oxo-2-pentyl]carboxamide

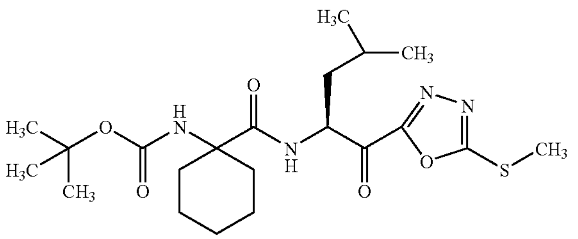

TLC: Rf 0.69 (n-hexane:ethyl acetate=1:1);

NMR ($CDCl_3$): δ 7.49 (br, 1H), 5.38 (m, 1H), 4.70 (brs, 1H), 2.78 (s, 3H), 2.11–1.20 (m, 22H), 1.01 and 0.97 (each d, J=6.0 Hz, each 3H).

EXAMPLE 13 (72)

(2S)-N-[(2S)-4-methoxy-1-(5-(1-methylethylthio)-1,3,4-oxadiazol-2-yl)-1-oxo-2-butyl]-4-methyl-2-benzyloxycarbonylaminopentanamide

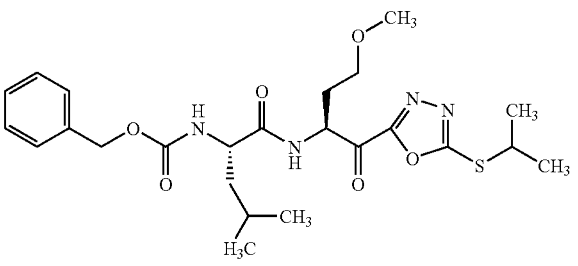

TLC: Rf 0.49 (n-hexane:ethyl acetate=1:1);

NMR ($CDCl_3$): δ 7.40–7.25 (m, 5H), 7.24 (d, J=6.0 Hz, 1H), 5.42 (q, J=6.0 Hz, 1H), 5.17 (d, J=7.8 Hz, 1H), 5.12 (s, 2H), 4.30–4.20 (m, 1H), 4.03 (septet, J=6.9 Hz, 1H), 3.43 (t, J 5.0 Hz, 2H), 3.17 (s, 3H), 2.40–2.20 (m, 2H), 1.80–1.40 (m, 3H), 1.53 (d, J=6.9 Hz, 6H), 0.95 (d, J=6.0 Hz, 6H).

EXAMPLE 13 (73)

1-[(1R,2S)-2-benzoylaminocyclohexyl]-N-[(2S)-4-methoxy-1-(5-(1-methylethylthio)-1,3,4-oxadiazol-2-yl)-1-oxo-2-butyl]carboxamide

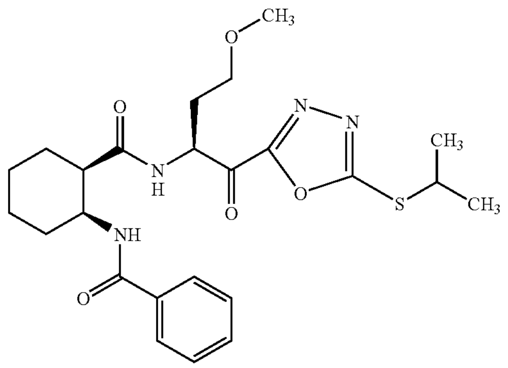

TLC: Rf 0.37 (n-hexane:ethyl acetate=2:3);

NMR ($CDCl_3$) δ 7.80–7.75 (m, 2H), 7.57 (d, J=6.0 Hz, 1H) 7.50–7.35 (m, 3H), 7.23 (d, J=6.0 Hz, 1H), 5.43 (q, J=6.0 Hz, 1H), 4.35–4.25 (m, 1H), 4.04 (septet, J=6.9 Hz, 1H), 3.45–3.35 (m, 2H), 3.20 (s, 3H), 2.83 (q, J=4.7 Hz, 1H), 2.40–2.20 (m, 2H), 2.05–1.40 (m, 8H), 1.53 (d, J=6.9 Hz, 6H).

EXAMPLE 13 (74)

1-[(1R,2S)-2-(2-morpholinomethylbenzoylamino)cyclohexyl]-N-[(2S)-4-methyl-1-(5-methylthio-1,3,4-oxadiazol-2-yl)-1-oxo-2-pentyl]carboxamide Hydrochloride

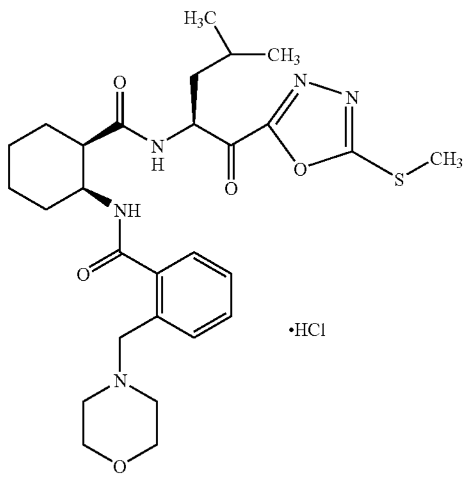

•HCl

TLC: Rf 0.66 (chloroform:methanol=19:1);

NMR (DMSO-$d_6$): δ 8.66 and 8.56 (each d, J=5.7 Hz, 1H), 8.45 and 8.31 (each d, J=5.4 Hz, 1H), 7.75–7.69 (m, 1H), 7.60–7.48 (m, 3H), 5.06–4.98 (m, 1H), 4.50–4.45 (m, 1H), 4.37–4.32 (m, 2H), 3.94–3.87 (m, 2H), 3.78–3.65 (m, 2H), 3.41–3.00 (m, 4H), 2.82–2.71 (m, 4H), 2.00–1.22 (m, 11H), 1.92–0.85, 0.83, and 0.79 (m, d, and d, J=6.3 Hz, totally 6H).

EXAMPLE 13 (75)

1-[1-morpholinocarbonylaminocyclohexyl]-N-[(2S)-1-(5-(1-methylethylthio)-1,3,4-oxadiazol-2-yl)-1-oxo-2-hexyl]carboxamide

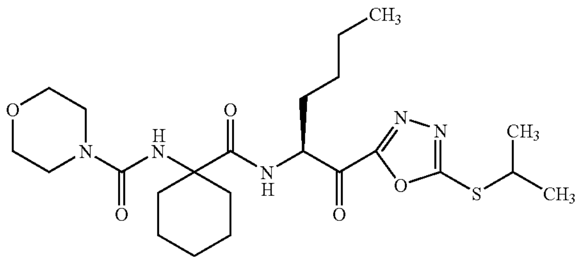

TLC: Rf 0.38 (n-hexane:ethyl acetate=1:2);

NMR ($CDCl_3$): δ 8.16 (brd, J=6.6 Hz, 1H), 5.29 (ddd, J=9.0, 6.6, 5.1 Hz, 1H), 4.43 (brs, 1H), 4.03 (septet, J=6.9 Hz, 1H), 3.72 (t, J=4.8 Hz, 4H), 3.38 (t, J=4.8 Hz, 4H), 2.20–1.20 (m, 16H), 1.53 (d, J=6.9 Hz, 6H), 0.89 (t, J=6.6 Hz, 3H).

EXAMPLE 13 (76)

1-(1-benzoylaminocyclohexyl)-N-[(2S)-1-(5-(1-methylethylthio)-1,3,4-oxadiazol-2-yl)-1-oxo-2-hexyl] carboxamide

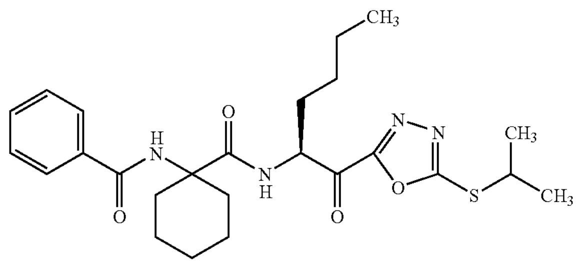

TLC: Rf 0.32 (n-hexane:ethyl acetate=2:1);

NMR ($CDCl_3$): δ 8.02 (brd, J=6.9 Hz, 1H), 7.78 (d, J=6.9 Hz, 2H), 7.59–7.44 (m, 3H), 6.09 (brs, 1H), 5.33 (ddd, J=9.0, 6.9, 5.1 Hz, 1H), 4.00 (septet, J=6.6 Hz, 1H), 2.40–1.30 (m, 16H), 1.52 (d, J=6.6 Hz, 6H), 0.87 (t, J=7.2 Hz, 3H).

EXAMPLE 13 (77)

1-[1-(4-dimethylaminomethylbenzoylamino)cyclohexyl]-N-[4-methyl-1-(5-(1-methylethylthio)-1,3,4-oxadiazol-2-yl)-1-oxo-2-pentyl]carboxamide

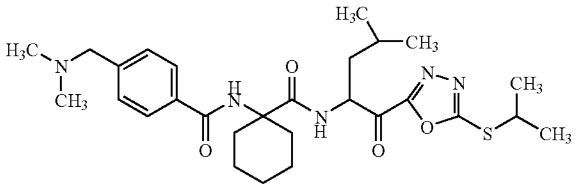

TLC: Rf 0.43 (chloroform:methanol=9:1);

NMR ($CDCl_3$): δ 8.02 (d, J=6.9 Hz, 1H), 7.73 (d, J=8.3 Hz, 2H), 7.43 (d, J=8.3 Hz, 2H), 6.05 (s, 1H), 5.45–5.30 (m, 1H), 4.01 (septet, J=6.9 Hz, 1H), 3.51 (s, 2H), 2.35–2.20 (m, 2H), 2.28 (s, 6H), 2.10–1.90 (m, 2H), 1.85–1.30 (m, 9H), 1.52 (d, J=6.9 Hz, 6H), 1.01 (d, J=6.0 Hz, 3H), 0.97 (d, J=6.0 Hz, 3H).

EXAMPLE 13 (78)

1-[(1R,2S)-2-(3-morpholinomethylbenzoylamino) cyclohexyl]-N-[(2S)-4-methyl-1-(5-(1-methylethylthio)-1,3,4-oxadiazol-2-yl)-1-oxo-2-pentyl]carboxamide Hydrochloride

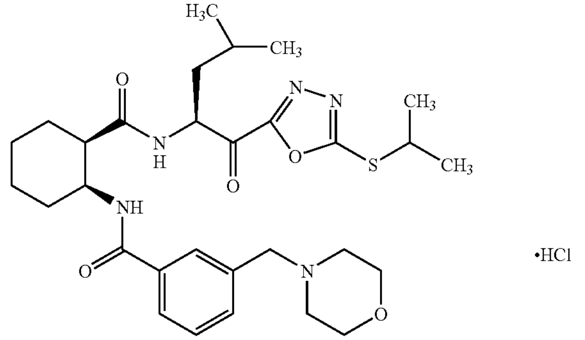

TLC: Rf 0.30 (n-hexane ethyl acetate=1:1);

NMR (DMSO-$d_6$): δ 8.68 and 8.57 (each d, J=5.4 Hz, totally 1H), 8.43 and 8.30 (each d, J=8.1 Hz, totally 1H), 7.78–7.75 (m, 1H), 7.55–7.46 (m, 3H), 5.07–4.99 (m, 1H), 4.50–4.24 (m, 3H), 4.00–3.66 (m, 5H), 3.41–3.00 (m, 4H), 2.80–2.71 (m, 1H), 2.00–1.23 (m, 11H), 1.46 (d, J=6.6 Hz, 3H), 1.43 (d, J=6.6 Hz, 3H), 0.90, 0.86, 0.85, and 0.82 (each d, J=6.6 Hz, totally 6H).

EXAMPLE 13 (79)

1-[1-(3-dimethylaminomethylbenzoylamino)cyclohexyl]-N-[4-methyl-1-(5-(1-methylethylthio)-1,3,4-oxadiazol-2-yl)-1-oxo-2-pentyl]carboxamide

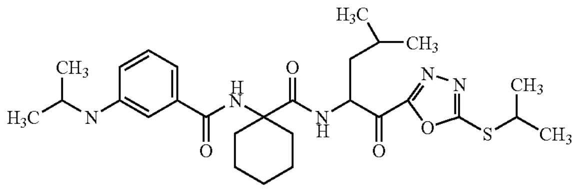

TLC: Rf 0.53 (chloroform:methanol=9:1);

NMR ($CDCl_3$): δ 7.97 (d, J=6.9 Hz, 1H), 7.76 (s, 1H), 7.69 (d, J=7.5 Hz, 1H), 7.50 (d, J=7.5 Hz, 1H), 7.43 (t, J=7.5 Hz, 1H), 6.22 (brs, 1H), 5.45–5.30 (m, 1H), 4.01 (septet, J=6.9 Hz, 1H), 3.52 (s, 2H), 2.40–2.15 (m, 2H), 2.29 (s, 6H), 2.10–1.90 (m, 2H), 1.85–1.30 (m, 9H), 1.52 (d, J=6.9 Hz, 6H), 1.01 (d, J=6.0 Hz, 3H), 0.97 (d, J=6.0 Hz, 3H).

EXAMPLE 13 (80)

1-[(1R,2S)-2-(2-pyrrolidin-1-ylmethylbenzoylamino)cyclohexyl]-N-[4-methyl-1-(5-methylthio-1,3,4-oxadiazol-2-yl)-1-oxo-2-pentyl]carboxamide hydrochloride

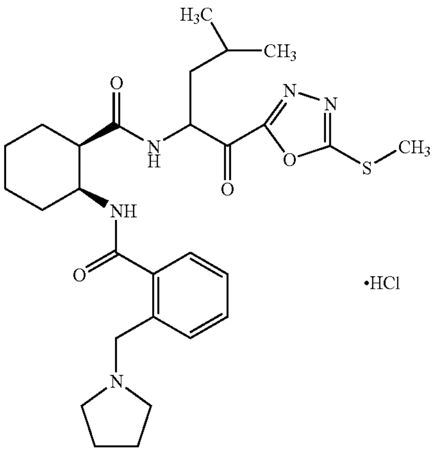

TLC: Rf 0.46 and 0.35 (chloroform:methanol=9:1);

NMR (DMSO-$d_6$): δ 8.65 and 8.55 (each d, J=6.6 Hz, totally 1H), 8.42 and 8.28 (each d, J=8.4 Hz, totally 1H), 7.74–7.67 (m, 1H), 7.56–7.46 (m, 3H), 5.05–4.97 (m, 1H), 4.46–4.22 (m, 3H), 3.26–3.00 (m, 4H), 2.81–2.67 (m, 1H), 2.76 and 2.73 (each s, totally 3H), 2.13–1.22 (m, 15H), 0.88, 0.87, 0.84, and 0.81 (each d, J=6.0 Hz, totally 6H).

EXAMPLE 13 (81)

1-[(1R,2S)-2-(2-pyrrolidin-1-ylmethylbenzoylamino)cyclohexyl]-N-[4-methyl-1-(5-(1-methylethylthio)-1,3,4-oxadiazol-2-yl)-1-oxo-2-pentyl]carboxamide Hydrochloride

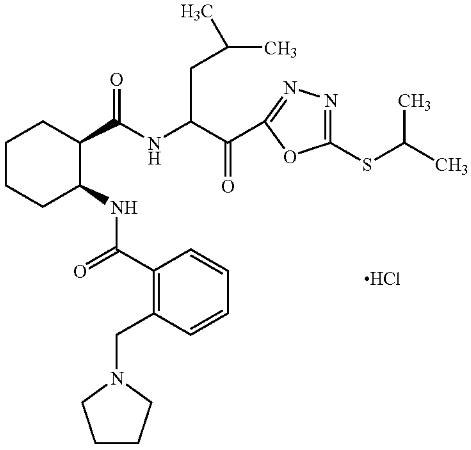

TLC: Rf 0.57 and 0.46 (chloroform:methanol=9:1);

NMR (DMSO-$d_6$): δ 8.67 and 8.56 (each d, J=6.6 Hz, totally 1H), 8.41 and 8.26 (each d, J=7.8 Hz, totally 1H), 7.74–7.70 (m, 1H), 7.60–7.45 (m, 3H), 5.05–4.96 (m, 1H), 4.46–4.23 (m, 3H), 4.00–3.86 (m, 1H), 3.21–3.01 (m, 4H), 2.80–2.70 (m, 1H), 2.07–1.01 (m, 21H), 0.89, 0.88, 0.85, and 0.81 (each d, J=6.6 Hz, totally 6H).

EXAMPLE 13 (82)

1-(1-benzoylaminocyclohexyl)-N-[1-(5-(2-dimethylaminoethylthio)-1,3,4-oxadiazol-2-yl)-4-methyl-1-oxo-2-pentyl]carboxamide

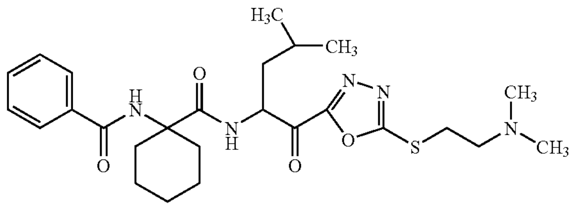

TLC: Rf 0.21 (chloroform:methanol:water=9:1:0.1);

NMR ($CDCl_3$): δ 8.01 (brd, J=6.9 Hz, 1H), 7.82–7.74 (m, 2H), 7.60–7.40 (m, 3H), 6.07 (brs, 1H), 5.42–5.31 (m, 1H), 3.52–3.40 (m, 2H), 2.78 (t, J=6.9 Hz, 2H), 2.34 (s, 6H), 2.05–1.30 (m, 13H), 1.01 and 0.97 (each d, J=6.0 Hz, each 3H).

EXAMPLE 13 (83)

1-[1-(4-dimethylaminomethylbenzoylamino)cyclohexyl]-N-[1-(5-(1-methylethylthio)-1,3,4-oxadiazol-2-yl)-1-oxo-2-hexyl]carboxamide

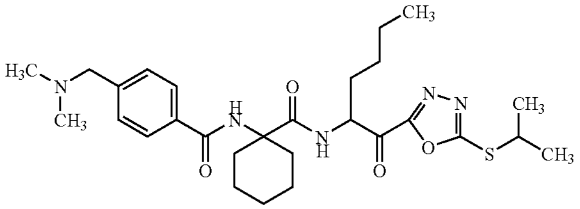

TLC: Rf 0.55 (chloroform methanol:acetic acid=10:2:1);

NMR ($CDCl_3$): δ 8.02 (brd, J=6.9 Hz, 1H), 7.74 (d, J=8.4 Hz, 2H), 7.43 (d, J=8.4 Hz, 2H), 6.09 (brs, 1H), 5.31 (m, 1H), 4.01 (m, 1H), 3.54 (brs, 2H), 2.60–1.20 (m, 28H), 0.87 (t, J=7.2 Hz, 3H).

EXAMPLE 13 (84)

1-(1-acetylaminocyclohexyl)-N-[(2S)-4-methyl-1-(5-(1-methylethylthio)-1,3,4-oxadiazol-2-yl)-1-oxo-2-pentyl]carboxamide

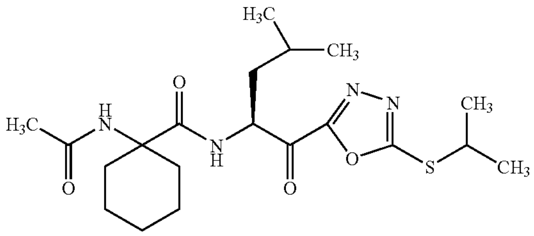

TLC: Rf 0.61 (chloroform:methanol=9:1);

NMR ($CDCl_3$) δ 7.91 (brd, J=6.9 Hz, 1H), 5.40 (brs, 1H), 5.31 (m, 1H), 4.02 (septet, J=6.9 Hz, 1H), 2.20–1.25 (m, 13H), 2.08 (s, 3H), 1.53 (d, J=6.6 Hz, 6H), 1.01 (d, J=6.0 Hz, 3H), 0.98 (d, J=6.6 Hz, 3H).

EXAMPLE 13 (85)

1-[1-(pyridin-3-ylcarbonylamino)cyclohexyl]-N-[(2S)-4-methyl-1-(5-(1-methylethylthio)-1,3,4-oxadiazol-2-yl)-1-oxo-2-pentyl]carboxamide

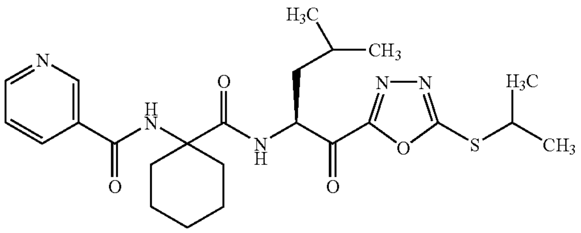

TLC: Rf 0.47 (chloroform:methanol=9:1);

NMR ($CDCl_3$): δ 9.01 (brs, 1H), 8.77 (brs, 1H), 8.12 (d, J=8.1 Hz, 1H), 7.79 (d, J=6.9 Hz, 1H), 7.48–7.38 (m, 1H), 6.20 (brs, 1H), 5.43–5.32 (m, 1H), 4.08–3.95 (m, 1H), 2.37–1.28 (m, 13H), 1.52 (d, J=6.9 Hz, 6H), 1.02 and 0.98 (each d, J=6.0 Hz, totally 6H).

EXAMPLE 13 (86)

1-[1-(pyridin-4-ylcarbonylamino)cyclohexyl]-N-[(2S)-4-methyl-1-(5-(1-methylethylthio)-1,3,4-oxadiazol-2-yl)-1-oxo-2-pentyl]carboxamide

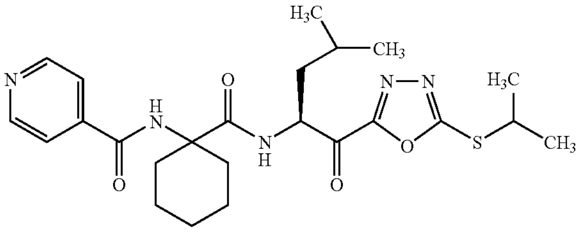

TLC: Rf 0.46 (chloroform:methanol=9:1);

NMR ($CDCl_3$): δ 8.78 (brd, J=5.7 Hz, 2H), 7.71 (d, J=7.2 Hz, 1H), 7.62 (d, J=5.7 Hz, 2H), 6.17 (brs, 1H), 5.43–5.33 (m, 1H), 4.08–3.93 (m, 1H), 2.35–1.30 (m, 13H), 1.52 (d, J=6.9 Hz, 6H), 1.02 and 0.98 (each d, J=6.0 Hz, totally 6H).

EXAMPLE 13 (87)

1-[1-(2-dimethylaminomethylbenzoylamino)cyclohexyl]-N-[4-methyl-1-(5-(1-methylethylthio)-1,3,4-oxadiazol-2-yl)-1-oxo-2-pentyl]carboxamide

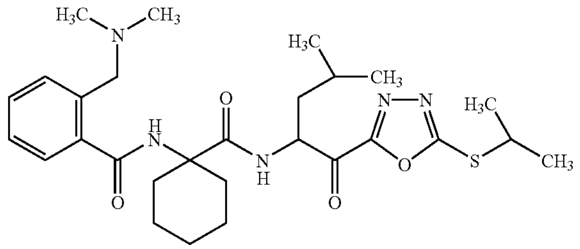

TLC: Rf 0.66 (chloroform:methanol=9:1);

NMR ($CDCl_3$): δ 10.7 (brs, 1H), 8.50 (brd, J=6.6 Hz, 1H), 7.87 (m, 1H), 7.45–7.36 (m, 2H), 7.19 (m, 1H), 5.37 (m, 1H), 4.01 (septet, J=6.9 Hz, 1H), 3.84 (brd, J=12 Hz, 1H), 3.32 (brd, J=12 Hz, 1H), 2.57 (m, 1H), 2.30–1.25 (m, 12H), 2.23 (s, 6H), 1.52 (d, J=6.6 Hz, 3H), 1.51 (d, J=6.6 Hz, 3H), 1.02 (d, J=6.0 Hz, 3H), 0.97 (d, J=6.3 Hz, 3H).

EXAMPLE 13 (88)

1-[1-(4-morpholinomethylbenzoylamino)cyclohexyl]-N-[(2S)-4-methyl-1-(5-(1-methylethylthio)-1,3,4-oxadiazol-2-yl)-1-oxo-2-pentyl]carboxamide

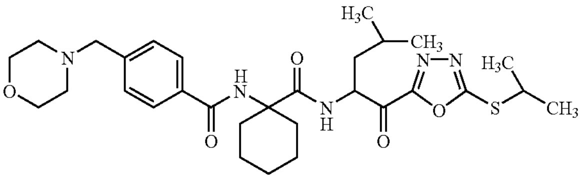

TLC: Rf 0.66 (chloroform:methanol=9:1);

NMR ($CDCl_3$): δ 8.03 (brd, J=6.6 Hz, 1H), 7.73 (d, J=8.4 Hz, 2H), 7.44 (d, J=8.4 Hz, 2H), 6.05 (brs, 1H), 5.37 (m, 1H), 4.01 (septet, J=6.6 Hz, 1H), 3.72 (brt, J=4.5 Hz, 4H), 3.56 (s, 2H), 2.46 (brt, J=4.5 Hz, 4H), 2.27 (m, 2H), 1.98 (m, 2H), 1.85–1.30 (m, 9H), 1.52 (d, J=6.6 Hz, 6H), 1.01 (d, J=6.0 Hz, 3H), 0.97 (d, J=6.3 Hz, 3H).

EXAMPLE 13 (89)

1-(4-benzoylamino-1-t-butoxycarbonylpiperidin-4-yl)-N-[(2S)-4-methyl-1-(5-(1-methylethylthio)-1,3,4-oxadiazol-2-yl)-1-oxo-2-pentyl]carboxamide

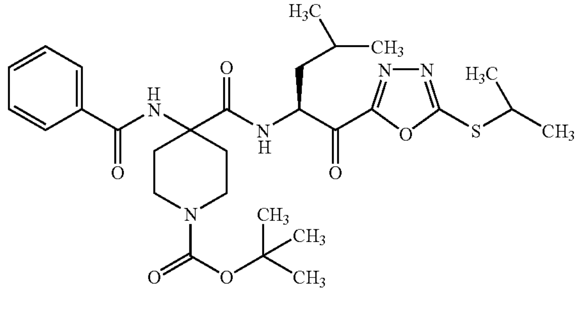

TLC: Rf 0.71 (n-hexane:ethyl acetate=1:2);

NMR ($CDCl_3$): δ 8.06 (br, 1H), 7.76 (d, J=6.9 Hz, 2H), 7.60–7.42 (m, 3H), 6.13 (brs, 1H), 5.37 (ddd, J=9.9, 6.6, 3.6 Hz, 1H), 4.00 (septet, J=6.6 Hz, 1H), 3.90–3.70 (m, 2H), 3.35–3.20 (m, 2H), 2.40–2.10 (m, 4H), 1.90–1.40 (m, 18H), 1.01 and 0.97 (each d, J=6.3 Hz, each 3H).

EXAMPLE 13 (90)

1-(1-benzoylaminocyclopentyl)-N-[(2S)-4-methyl-1-(5-(1-methylethylthio)-1,3,4-oxadiazol-2-yl)-1-oxo-2-pentyl]carboxamide

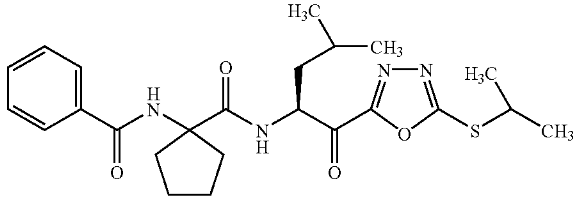

TLC: Rf 0.60 (n-hexane:ethyl acetate=1:1);

NMR ($CDCl_3$): δ 7.89 (brd, J=6.9 Hz, 1H), 7.75 (m, 2H), 7.54 (m, 1H), 7.46 (m, 2H), 6.37 (brs, 1H), 5.38 (m, 1H), 4.00 (septet, J=6.9 Hz, 1H), 2.43 (m, 2H), 2.12 (m, 2H), 1.88–1.58 (m, 7H), 1.52 (d, J=6.9 Hz, 6H), 1.01 (d, J=6.3 Hz, 3H), 0.96 (d, J=6.3 Hz, 3H).

EXAMPLE 13 (91)

1-[1-(4-dimethylaminomethylbenzoylamino)cyclopentyl]-N-[4-methyl-1-(5-(1-methylethylthio)-1-oxo-1,3,4-oxadiazol-2-yl)-2-pentyl]carboxamide

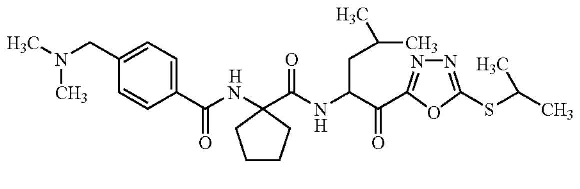

TLC: Rf 0.40 (chloroform methanol=9:1);

NMR ($CDCl_3$): δ 7.90 (brd, J=6.6 Hz, 1H), 7.71 (d, J=8.4 Hz, 2H), 7.41 (d, J=8.4 Hz, 2H), 6.36 (brs, 1H), 5.38 (m, 1H), 4.01 (septet, J=6.9 Hz, 1H), 3.50 (s, 2H), 2.43 (m, 2H), 2.26 (s, 6H), 2.12 (m, 2H), 1.88–1.60 (m, 7H), 1.52 (d, J=6.9 Hz, 6H), 1.01 (d, J=6.0 Hz, 3H), 0.96 (d, J=6.3 Hz, 3H).

EXAMPLE 13 (92)

1-[1-(4-morpholinomethylbenzoylamino)cyclopentyl]-N-[4-methyl-1-(5-(i-methylethylthio)-1-oxo-1,3,4-oxadiazol-2-yl)-2-pentyl]carboxamide

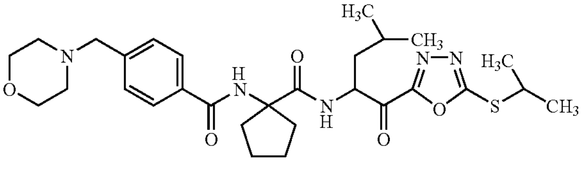

TLC: Rf 0.65 (chloroform:methanol=9:1);

NMR ($CDCl_3$): δ 7.89 (brd, J=6.9 Hz, 1H), 7.70 (d, J=8.4 Hz, 2H), 7.43 (d, J=8.4 Hz, 2H), 6.34 (brs, 1H), 5.38 (m, 1H), 4.01 (septet, J=6.9 Hz, 1H), 3.72 (brt, J=4.5 Hz, 4H), 3.55 (s, 2H), 2.45 (brt, J=4.5 Hz, 4H), 2.43 (m, 2H), 2.11 (m, 2H), 1.88–1.60 (m, 7H), 1.52 (d, J=6.9 Hz, 6H), 1.01 (d, J=6.0 Hz, 3H), 0.96 (d, J=6.3 Hz, 3H).

EXAMPLE 13 (93)

1-(4-benzoylamino-1-methoxycarbonylpiperidin-4-yl)-N-[(2S)-4-methyl-1-(5-(1-methylethylthio)-1-oxo-1,3,4-oxadiazol-2-yl)-2-pentyl]carboxamide

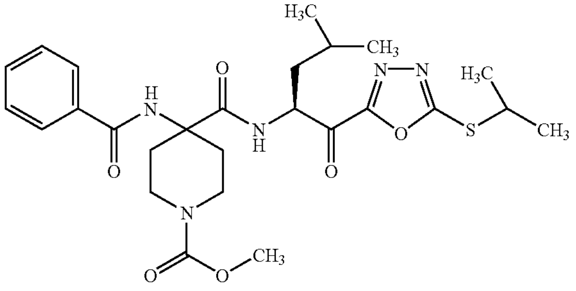

TLC: Rf 0.50 (chloroform methanol 9:1);

NMR ($CDCl_3$): δ 8.06 (br, 1H), 7.75 (d, J=6.9 Hz, 1H), 7.61–7.42 (m, 3H), 6.10 (brs, 1H), 5.38 (ddd, J=9.9, 6.6, 3.6 Hz, 1H), 4.05 (septet, J=6.6 Hz, 1H), 3.90–3.70 (m, 2H), 3.35–3.20 (m, 2H), 3.70 (s, 3H), 3.43–3.31 (m, 2H), 2.40–2.11 (m, 4H), 1.90–1.50 (m, 9H), 1.01 and 0.97 (each d, J=6.0 Hz, each 3H).

EXAMPLE 13 (94)

1-[1-(pyridin-2-ylcarbonylamino)cyclohexyl]-N-[(2S)-4-methyl-1-(5-(1-methylethylthio)-1,3,4-oxadiazol-2-yl)-1-oxo-2-pentyl]carboxamide

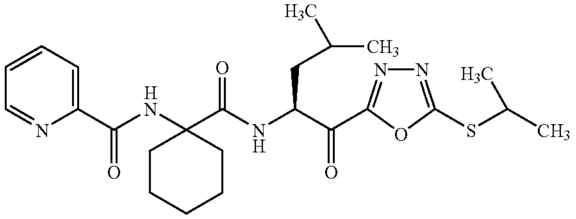

TLC: Rf 0.62 (n-hexane:ethyl acetate=1:1);

NMR ($CDCl_3$): δ 8.62–8.57 (m, 1H), 8.31 (brs, 1H), 8.18 (d, J=7.8 Hz, 1H), 7.95 (brd, J=6.6 Hz, 1H), 7.88 (dt, J=1.5, 7.8 Hz, 1H), 7.48 (ddd, J=7.8, 4.5, 1.5 Hz, 1H), 5.41–5.32 (m, 1H), 4.08–3.92 (m, 1H), 2.40–1.23 (m, 13H), 1.52 (d, J=6.9 Hz, 6H), 0.99 and 0.94 (each d, J=6.0 Hz, each 3H).

EXAMPLE 13 (95)

1-[1-(4-(N-t-butoxycarbonyl)piperazin-1-ylcarbonylamino)cyclohexyl]-N-[(2S)-4-methyl-1-(5-(1-methylethylthio)-1,3,4-oxadiazol-2-yl)-1-oxo-2-pentyl]carboxamide

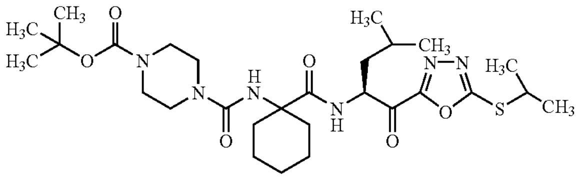

TLC: Rf 0.38 (n-hexane:ethyl acetate=1:1);

NMR ($CDCl_3$): δ 8.16 (brd, J=6.3 Hz, 1H), 5.30 (ddd, J=9.9, 6.6, 4.2 Hz, 1H), 4.42 (brs, 1H), 4.01 (septet, J=6.6 Hz, 1H), 3.51–3.38 (m, 8H), 2.21–1.30 (m, 28H), 0.98 and 0.96 (each d, J=6.3 Hz, each 3H).

EXAMPLE 13 (96)

1-[1-(t-butoxycarbonylamino)cyclohexyl]-N-[(2S)-4-methyl-1-(5-(1-methylethylthio)-1,3,4-oxadiazol-2-yl)-1-oxo-2-pentyl]carboxamide

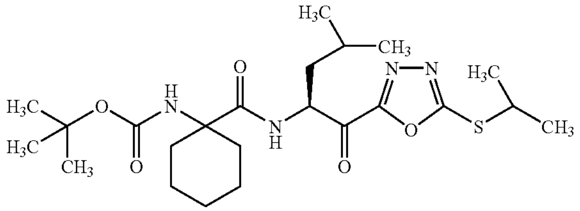

TLC: Rf 0.75 (n-hexane:ethyl acetate=1:1);

NMR ($CDCl_3$): 7.43 (br, 1H), 5.39 (ddd, J=10.5, 7.2, 3.0 Hz, 1H), 4.69 (brs, 1H), 4.03 (septet, J=6.6 Hz, 1H), 2.11–1.21 (m, 28H), 1.02 and 0.95 (each d, J=6.0 Hz, each 3H).

EXAMPLE 13 (97)

1-cyclohexyl-N-[(2S)-4-methyl-1-(5-(1-methylethylthio)-1,3,4-oxadiazol-2-yl)-1-oxo-2-pentyl]carboxamide

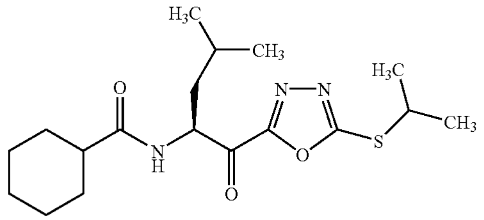

TLC: Rf 0.35 (n-hexane ethyl acetate=3:1);

NMR ($CDCl_3$): δ 6.02 (d, J=8.0 Hz, 1H), 5.43 (ddd, J=10.1, 8.0 and 3.9 Hz, 1H), 4.13–3.96 (m, 1H), 2.24–2.10

(m, 1H), 1.94–1.15 (m, 13H), 1.54 (d, J=6.9 Hz, 6H), 1.03 and 0.97 (each d, J=6.3 Hz, each 3H).

EXAMPLE 13 (98)

1-(1-(2-butynoylamino)cyclohexyl)-N-[(2S)-4-methyl-1-(5-(1-methylethylthio)-1,3,4-oxadiazol-2-yl)-1-oxo-2-pentyl]carboxamide

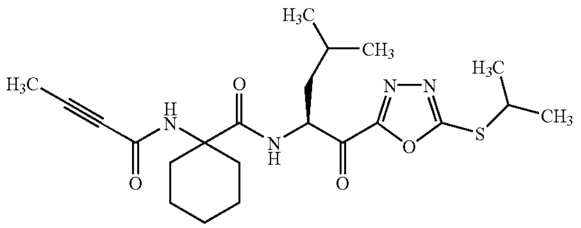

TLC: Rf 0.41 (chloroform:methanol=9:1);

NMR ($CDCl_3$): δ 9.00 (d, J=1.8 Hz, 1H), 8.77 (dd, J=4.8, 1.8 Hz, 1H), 8.12 (dt, J=7.8, 1.8 Hz, 1H), 7.70 (d, J=7.2 Hz, 1H), 7.43 (dd, J=7.8, 4.8 Hz, 1H), 6.16 (s, 1H), 5.41–5.34 (m, 1H,), 4.06–3.97 (m, 1H), 2.34–2.19 (m, 2H), 2.08–1.98 (m, 2H), 1.81–1.26 (m, 9H), 1.51 (d, J=6.6 Hz, 6H), 1.01 (d, J=6.0 Hz, 3H), 0.98 (d, J=6.0 Hz, 3H).

EXAMPLE 13 (99)

1-(1-cyclohexyl)-N-[4-methyl-1-(2-(2-dimethylethylthio)-1,3,4-oxadiazol-5-yl)-1-oxo-2-pentyl]carboxamide Hydrochloride

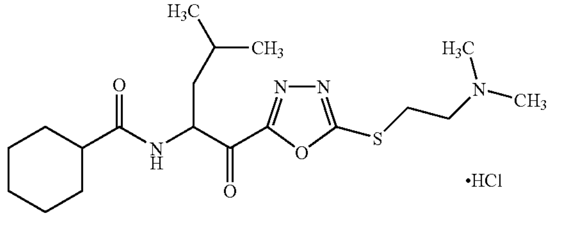

TLC: Rf 0.54 (chloroform:methanol:ammonia water=190:10:1);

NMR ($CDCl_3$): δ 13.08 (brs, 1H), 5.98 (d, J=6.9 Hz, 1H), 5.47–5.37 (m, 1H), 3.97–3.84 (m, 2H), 3.62–3.44 (m, 2H), 2.93 (brs, 6H), 2.24–2.11 (m, 1H), 2.02–1.11 (m, 13H), 1.03 and 0.99 (each d, J=6.0 Hz, each 3H).

EXAMPLE 13 (100)

1-[(1R,2S)-2-(2-butynoylamino)cyclohexyl]-N-[4-methyl-1-(2-(1-methylethylthio)-1,3,4-oxadiazol-5-yl)-1-oxo-2-pentyl]carboxamide

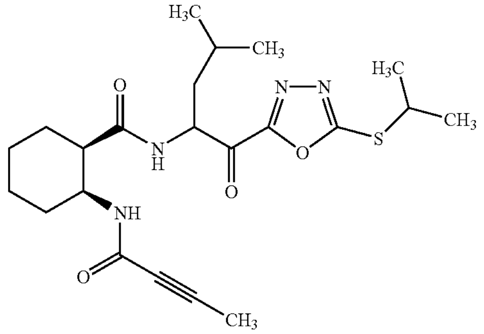

TLC: Rf 0.35 (n-hexane:ethyl acetate=1:1);

NMR ($CDCl_3$): δ 6.82 and 6.67 (each brd, J=9.0 Hz, 1H), 6.27 and 6.17 (each brd, J=7.5 Hz, 1H), 5.45 and 5.41 (each m, 1H), 4.20–4.08 (m, 1H), 4.06 and 4.05 (each septet, J=6.9 Hz, 1H), 2.77 and 2.74 (each m, 1H), 2.00–1.35 (m, 11H), 1.93 and 1.92 (each s, 3H), 1.55 and 1.54 (each d, J=6.9 Hz, 6H), 1.04 (d, J=6.3 Hz, 3H), 0.99 and 0.98 (each d, J=6.6 Hz, 3H).

EXAMPLE 13 (101)

1-(4-benzoylamino-1,1-dimethylpiperidinium-4-yl)-N-[(2S)-4-methyl-1-(5-(1-methylethylthio)-1-oxo-1,3,4-oxadiazol-2-yl)-2-pentyl]carboxamide Iodide

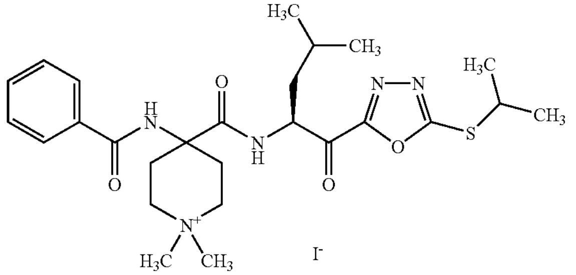

TLC: Rf 0.22 (chloroform:methanol:acetic acid=10:2:1);

NMR ($CDCl_3$): δ 8.98 (brs, 1H), 8.17 (d, J=7.2 Hz, 2H), 7.88 (d, J=7.2 Hz, 1H), 7.50–7.35 (m, 3H), 5.31–5.25 (m, 1H), 4.10–3.10 (m, 11H), 2.90–2.50 (m, 4H), 2.20–1.20 (m, 9H), 0.93 and 0.82 (each d, J=5.7 Hz, each 3H).

EXAMPLE 13 (102)

1-[(1R,2S)-2-(4-(2-dimethylaminoethyl)benzoylamino)cyclohexyl]-N-[4-methyl-1-(2-(1-methylethylthio)-1,3,4-oxadiazol-5-yl)-1-oxo-2-pentyl]carboxamide

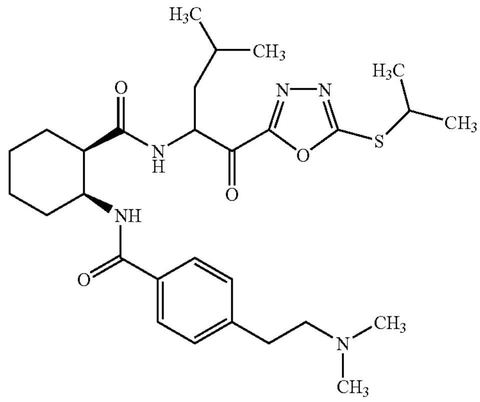

TLC: Rf 0.38 (chloroform:methanol=9:1);

NMR ($CDCl_3$): δ 7.72 and 7.68 (each d, J=8.1 Hz, 2H), 7.26 and 7.24 (each d, J=8.1 Hz, 2H), 7.21 and 7.15 (each brd, J=9.0 Hz, 1H), 6.33 and 6.27 (each brd, J=7.5 Hz, 1H), 5.43 and 5.38 (each m, 1H), 4.38–4.25 (m, 1H), 4.05 and 4.03 (each septet, J=6.9 Hz, 1H), 2.88–2.77 (m, 3H), 2.58–2.50 (m, 2H), 2.30 (s, 6H), 2.10–1.40 (m, 11H), 1.54 and 1.53 (each d, J=6.9 Hz, 6H), 1.02 and 0.94 (each d, J=6.0 Hz, 3H), 0.91 and 0.85 (each d, J=6.3 Hz, 3H).

EXAMPLE 13 (103)

1-[(1R,2S)-2-benzoylaminocyclohexyl]-N-[(2S)-4-methyl-1-(2-(2-morpholinoethylthio)-1,3,4-oxadiazol-5-yl)-1-oxo-2-pentyl]carboxamide

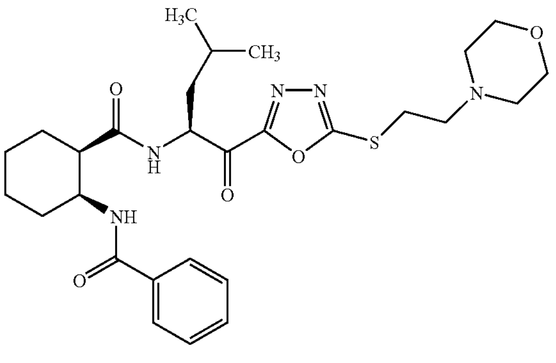

TLC: Rf 0.49 (chloroform:methanol=9:1);

NMR ($CDCl_3$): δ 7.77–7.75 (m, 2H), 7.49–7.40 (m, 3H), 7.19 (d, J=8.1 Hz, 1H), 6.36 and 6.27 (each d, J=7.5 Hz, total 1H), 5.47–5.41 (m, 1H), 4.38–4.28 (m, 1H), 3.70 (t, J=4.5

Hz, 4H), 3.51 (t, J=6.9 Hz, 2H), 2.87–2.78 (m, 3H), 2.53 (t, J=4.5 Hz, 4H), 2.13–1.41 (m, 1H), 1.01, 0.95, 0.91, and 0.85 (each d, J=6.3 Hz, total 6H).

EXAMPLE 13 (104)

1-[1-(4-(2-dimethylaminoethyl)benzoylamino)cyclohexyl]-N-[4-methyl-1-(5-(1-methylethylthio)-1,3,4-oxadiazol-2-yl)-1-oxo-2-pentyl]carboxamide

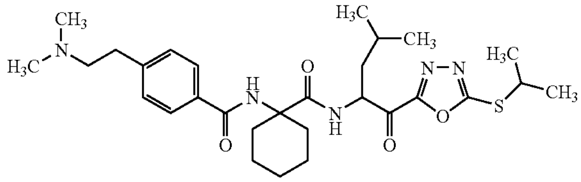

TLC: Rf0.31 (chloroform:methanol=9:1);

NMR ($CDCl_3$): δ 8.05 (brd, J=6.9 Hz, 1H), 7.70 (d, J=8.1 Hz, 2H), 7.31 (d, J=8.1 Hz, 2H), 6.03 (brs, 1H), 5.37 (m, 1H), 4.01 (septet, J=6.9 Hz, 1H), 2.85 (t, J=8.0 Hz, 2H), 2.56 (t, J=8.0 Hz, 2H), 2.30 (s, 6H), 2.25 (m, 2H), 1.98 (m, 2H), 1.85–1.30 (m, 9H), 1.52 (d, J=6.6 Hz, 6H), 1.01 (d, J=5.7 Hz, 3H), 0.97 (d, J=6.0 Hz, 3H).

EXAMPLE 13 (105)

1-[(1R,2S)-2-benzoylaminocyclohexyl]-N-[4-methyl-1-(2-(2-pyrrolidinoethylthio)-1,3,4-oxadiazol-5-yl)-1-oxo-2-pentyl]carboxamide

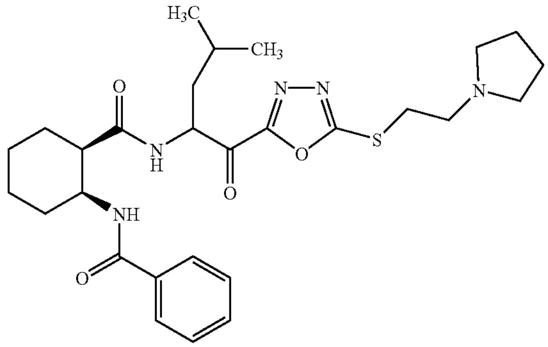

TLC: Rf 0.59 (chloroform:methanol:water=40:10:1);

NMR ($CDCl_3$): δ 7.80–7.75 (m, 2H), 7.52–7.39 (m, 3H), 7.26 and 7.20 (each d, J=8.4 Hz, total 1H), 6.30 and 6.25 (each d, J 8.1 Hz, total 1H), 5.47–5.34 (m, 1H), 4.36–4.29 (m, 1H), 3.53–3.47 (m, 2H), 2.95–2.91 (m, 2H), 2.88–2.84 (m, 1H), 2.61 (br-s, 4H), 2.08–1.46 (m, 15H), 1.01, 0.97, 0.93, and 0.85 (each d, J=6.6 Hz, total 6H).

EXAMPLE 13 (106)

1-[(1R,2S)-2-benzoylaminocyclohexyl]-N-[(2S)-1-(2-cyclohexylthio-1,3,4-oxadiazol-5-yl)-4-methyl-1-oxo-2-pentyl]carboxamide

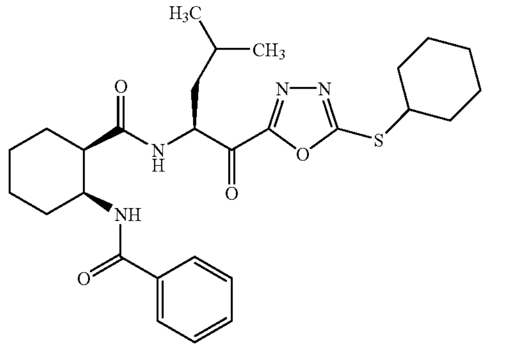

TLC: Rf 0.28 (n-hexane:ethyl acetate=2:1);

NMR ($CDCl_3$): δ 7.82–7.74 (m, 2H), 7.53–7.38 (m, 3H), 7.20 (brd, J=8.4 Hz, 1H), 6.35–6.22 (m, 1H), 5.50–5.40 (m, 1H), 4.38–4.26 (m, 1H), 3.95–3.84 (m, 1H), 2.91–2.83 (m, 1H), 2.27–1.25 (m, 21H), 0.91 and 0.85 (each d, J=6.3 Hz, each 3H).

EXAMPLE 13 (107)

1-cyclohexyl-N-[(2S)-1-(2-cyclohexylthio-1,3,4-oxadiazol-5-yl)-4-methyl-1-oxo-2-pentyl]carboxamide

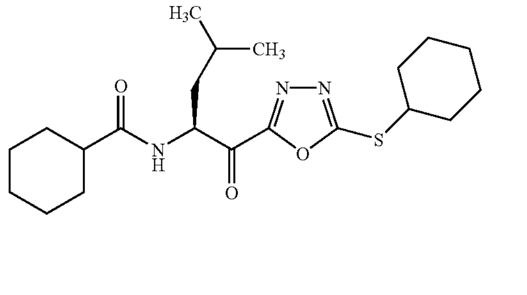

TLC: Rf 0.70 (n-hexane:ethyl acetate=2:1);

NMR ($CDCl_3$): δ 6.03 (brd, J=7.8 Hz, 1H), 5.48–5.38 (m, 1H), 3.95–3.83 (m, 1H), 2.27–2.11 and 1.93–1.17 (each m, total 24H), 1.02 and 0.97 (each d, J=6.3 Hz, each 3H).

EXAMPLE 13 (108)

1-[(1R,2S)-2-benzoylaminocyclohexyl]-N-[1-(2-(3-dimethylaminopropylthio)-1,3,4-oxadiazol-5-yl)-4-methyl-1-oxo-2-pentyl]carboxamide

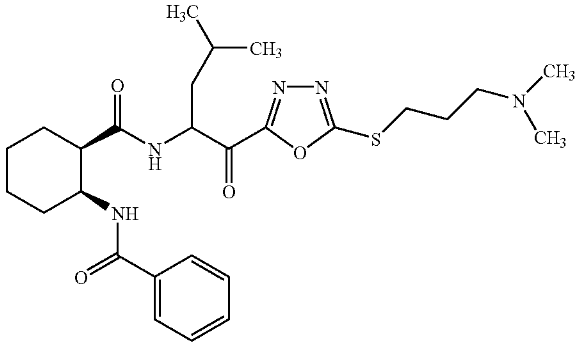

TLC: Rf 0.55 (chloroform:methanol=4:1);

NMR ($CDCl_3$): δ 7.83–7.75 (m, 2H), 7.53–7.39 (m, 3H), 7.30–7.20 (m, 1H), 6.27 and 6.23 (each brd, J=6.6 Hz, totally 1H) 5.50–5.38 (m, 1H), 4.40–4.30 (m, 1H), 3.43–3.33 (m, 2H), 2.89 (m, 1H), 2.42 (t, J=6.9 Hz, 2H), 2.24 (s, 6H), 2.10–1.40 (m, 13H), 1.01, 0.94, 0.90 and 0.84 (each d, J=6.3 Hz, totally 6H).

EXAMPLE 13 (109)

1-cyclohexyl-N-[4-methyl-1-(2-(3-dimethylaminopropylthio)-1,3,4-oxadiazol-5-yl)-1-oxo-2-pentyl]carboxamide

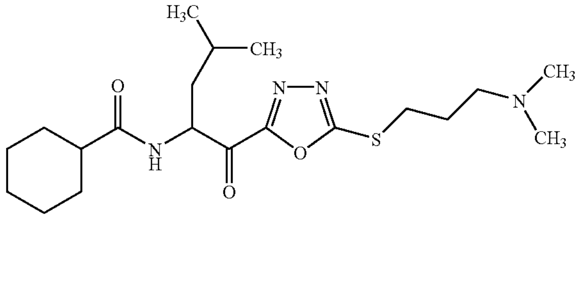

TLC: Rf 0.42 (chloroform:methanol=4:1);

NMR ($CDCl_3$): δ 6.04 (brd, J=7.5 Hz, 1H), 5.42 (ddd, J=9.9, 7.8, 3.9 Hz, 1H), 3.37 (dt, J=1.2, 6.9 Hz, 2H), 2.41 (t, J=6.9 Hz, 2H), 2.23 (s, 6H), 2.22–1.19 (m, 14H), 1.02 and 0.97 (each d, J=6.3 Hz, each 3H).

EXAMPLE 13 (110)

1-[(1R,2S)-2-(4-(dimethylamino)but-2-ynoylamino)cyclohexyl]-N-[4-methyl-1-(2-(1-methylethylthio)-1,3,4-oxadiazol-5-yl)-1-oxo-2-pentyl]carboxamide

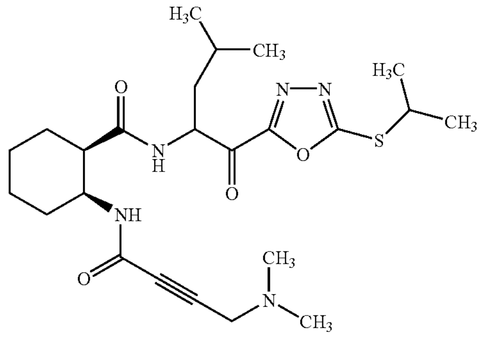

TLC: Rf 0.54 (chloroform:methanol=9:1);

NMR ($CDCl_3$): δ 6.90 and 6.80 (each brd, J=9.0 Hz, 1H), 6.24 and 6.19 (each brd, J=7.2 Hz, 1H), 5.45 and 5.42 (each m, 1H), 4.20–4.10 (m, 1H), 4.05 (septet, J=6.9 Hz, 1H), 3.37 (s, 2H), 2.82–2.75 (m, 1H), 2.32 and 2.31 (each s, 6H), 2.00–1.35 (m, 11H), 1.55 (d, J=6.6 Hz, 6H), 1.05 and 1.04 (each d, J=6.0 Hz, 3H), 0.99 and 0.98 (each d, J=6.3 Hz, 3H).

EXAMPLE 13 (111)

1-[1-(4-(dimethylamino)but-2-ynoylaminocyclohexyl)]-N-[4-methyl-1-(5-(1-methylethylthio)-1,3,4-oxadiazol-2-yl)-1-oxo-2-pentyl]carboxamide

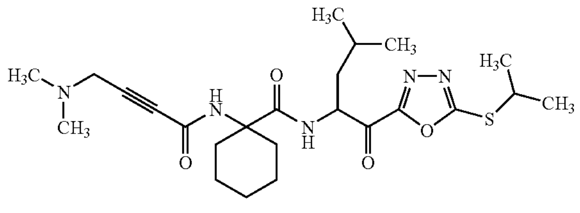

TLC: Rf 0.51 (chloroform:methanol=9:1);

NMR ($CDCl_3$): δ 7.48 (brd, J=6.9 Hz, 1H), 5.81 (brs, 1H), 5.35 (m, 1H), 4.03 (septet, J=6.9 Hz, 1H), 3.40 (s, 2H), 2.36 (s, 6H), 2.12 (m, 2H), 1.92 (m, 2H), 1.85–1.30 (m, 9H), 1.53 (d, J=6.6 Hz, 6H), 1.01 (d, J=6.0 Hz, 3H), 0.97 (d, J=6.3 Hz, 3H).

EXAMPLE 13 (112)

1-[(1R,2S)-2-dimethylaminocyclohexyl]-N-[(2S)-4-methyl-1-(2-(1-methylethylthio)-1,3,4-oxadiazol-5-yl)-1-oxo-2-pentyl]carboxamide Hydrochloride

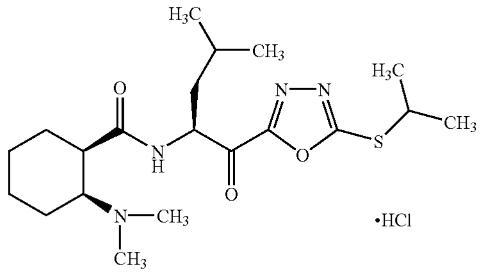

TLC: Rf 0.47 (chloroform:methanol=9:1);

NMR (DMSO-$d_6$): δ 9.24–8.87 (m, 2H), 5.13–4.99 (m, 1H), 4.08–3.88 (m, 1H), 3.30–3.00 (m, 2H), 2.85–2.53 (m, 6H), 2.29–2.10 and 2.05–1.01 (each m, total 11H), 1.47 (d, J=6.9 Hz, 6H), 0.93 (d, J=6.0 Hz, 6H).

EXAMPLE 13 (113)

1-cyclohexyl-N-[4-methyl-1-(2-(2-morpholinoethylthio)-1,3,4-oxadiazol-5-yl)-1-oxo-2-pentyl]carboxamide

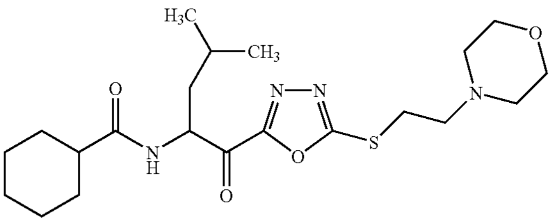

TLC: Rf 0.57 (chloroform:methanol=9:1);

NMR ($CDCl_3$): δ 6.00 (d, J=8.1 Hz, 1H), 5.45–5.38 (m, 1H), 3.71 (t, J=4.5 Hz, 4H), 3.51 and 3.50 (each t, J=6.6 Hz, total 2H), 2.81 (t, J=6.6 Hz, 2H), 2.54 (t, J=4.5 Hz, 4H), 2.20–2.13 (m, 1H) 1.89–1.23 (m, 13H), 1.03 (d, J=6.3 Hz, 3H), 0.97 (d, J=6.3 Hz, 3H).

EXAMPLE 13 (114)

1-cyclohexyl-N-[4-methyl-1-oxo-1-(2-(2-pyrrolidinoethylthio)-1,3,4-oxadiazol-5-yl)-2-pentyl]carboxamide

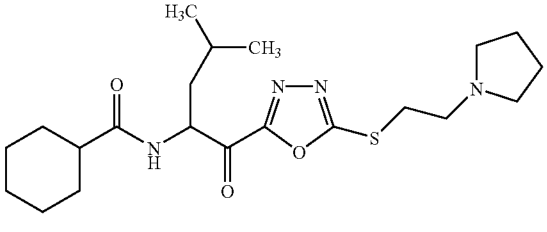

TLC: Rf 0.53 (chloroform:methanol=9:1);

NMR ($CDCl_3$): δ 6.02 (d, J=7.8 Hz, 1H), 5.46–5.39 (m, 1H), 3.51 and 3.50 (each t, J=6.6 Hz, total 2H), 2.93 (t, J=6.6 Hz, 2H), 2.61 (br-s, 4H), 2.20–2.11 (m, 1H), 1.89–1.12 (m, 17H), 1.03 (d, J=6.3 Hz, 3H), 0.97 (d, J=6.3 Hz, 3H).

EXAMPLE 13 (115)

1-(1-benzoylaminocyclohexyl)-N-[4-methyl-1-(2-(3-dimethylaminopropylthio)-1,3,4-oxadiazol-5-yl)-1-oxo-2-pentyl]carboxamide

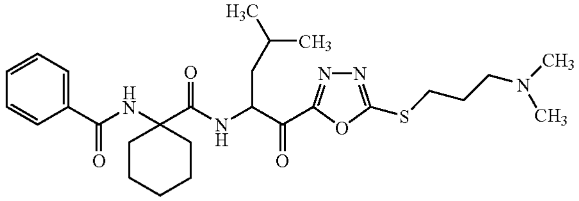

TLC: Rf 0.50 (chloroform:methanol:water=4:1:0.1);

NMR ($CDCl_3$): δ 8.02 (brd, J=6.6 Hz, 1H), 7.78 (d, J=8.1 Hz, 2H), 7.58–7.40 (m, 3H), 6.08 (brs, 1H), 5.36.(ddd, J=10.2, 6.6, 3.9 Hz, 1H), 3.36 (m, 2H), 2.49 (t, J=6.9 Hz, 2H), 2.29 (s, 6H), 2.20–1.30 (m, 15H), 1.01 and 0.97 (each d, J=6.0 Hz, each 3H).

EXAMPLE 13 (116)

1-cyclohexyl-N-[(2S)-4-methyl-1-(2-benzylthio-1,3,4-oxadiazol-5-yl)-1-oxo-2-pentyl]carboxamide

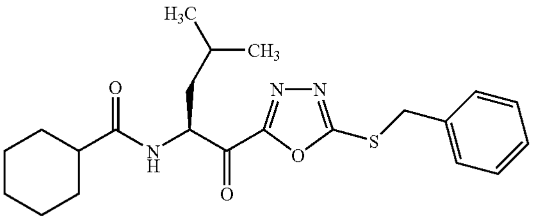

TLC: Rf 0.71 (n-hexane:ethyl acetate=1:1);

NMR ($CDCl_3$): δ 7.48–7.40 (m, 2H), 7.40–7.26 (m, 3H), 6.01 (brd, J=7.5 Hz, 1H), 5.46–5.36 (m, 1H), 4.56 (d, J=13.2 Hz, 1H), 4.54 (d, J=13.2 Hz, 1H), 2.23–2.08 (m, 1H), 1.93–1.12 (m, 13H), 1.03 and 0.97 (each d, J=6.3 Hz, each 3H).

EXAMPLE 13 (117)

1-(1-benzoylaminocyclohexyl)-N-[(2S)-1-(2-cyclohexylthio-1,3,4-oxadiazol-5-yl)-4-methyl-1-oxo-2-pentyl]carboxamide

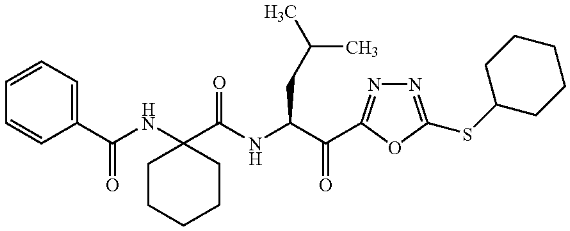

TLC: Rf0.66 (n-hexane:ethyl acetate=1:1);

NMR ($CDCl_3$): δ 8.01 (brd, J=6.9 Hz, 1H), 7.81–7.74 (m, 2H), 7.60–7.43 (m, 3H), 6.07 (brs, 1H), 5.43–5.33 (m, 1H), 3.91–3.78 (m, 1H), 2.37–1.25 (m, 23H), 1.01 and 0.97 (each d, J=6.3 Hz, each 3H).

EXAMPLE 13 (118)

1-(1-benzoylaminocyclohexyl)-N-[(2S)-1-(2-benzylthio-1,3,4-oxadiazol-5-yl)-4-methyl-1-oxo-2-pentyl]carboxamide

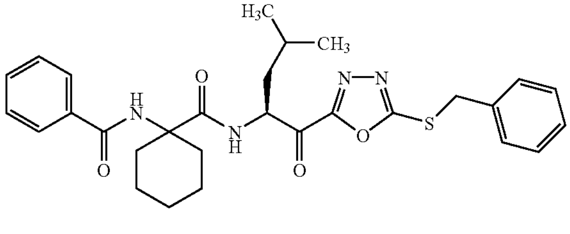

TLC: Rf 0.56 (n-hexane:ethyl acetate=1:1);

NMR ($CDCl_3$): δ 8.03 (brd, J=6.6 Hz, 1H), 7.81–7.74 (m, 2H), 7.61–7.26 (m, 8H), 6.08 (brs, 1H), 5.40–5.31 (m, 1H), 4.53 (d, J=12.9 Hz, 1H), 4.51 (d, J=12.9 Hz, 1H), 2.35–1.28 (m, 13H), 1.01 and 0.97 (each d, J=6.0 Hz, each 3H).

EXAMPLE 13 (119)

1-[(1R,2S)-2-(t-butoxycarbonylamino)cyclohexyl]-N-[(2S)-4-methyl-1-(2-(1-methylethylthio)-1,3,4-oxadiazol-5-yl)-1-oxo-2-pentyl]carboxamide

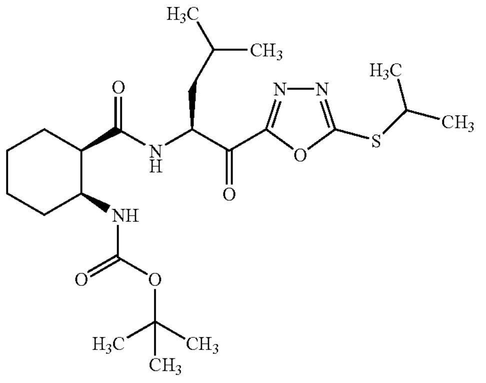

TLC: Rf 0.45 (n-hexane:ethyl acetate=2:1);

NMR (DMSO-$d_6$): δ 8.37 (d, J=6.0 Hz, 1H), 6.25 (d, J=8.4 Hz, 1H), 5.11–5.00 (m, 1H), 4.06–3.74 (m, 2H), 2.64–2.51 (m, 1H), 1.87–1.11 (m, 11H), 1.48 (d, J=6.6 Hz, 6H), 1.37 (s, 9H), 0.91 (d, J=6.3 Hz, 6H).

EXAMPLE 13 (120)

1-(1-benzoylaminocyclohexyl)-N-[4-methyl-1-(2-(2-morpholinoethylthio)-1,3,4-oxadiazol-5-yl)-1-oxo-2-pentyl]carboxamide

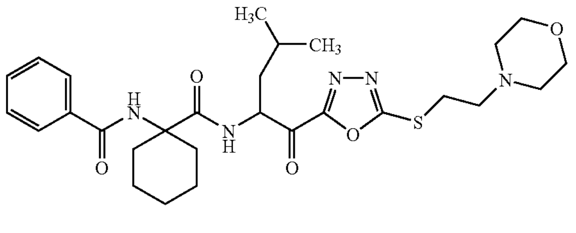

TLC: Rf 0.72 (chloroform:methanol=9:1);

NMR ($CDCl_3$): δ 8.03 (d, J=6.6 Hz, 1H), 7.77 (d, J=7.8 Hz, 2H), 7.58–7.45 (m, 3H), 6.06 (s, 1H), 5.39–5.30 (m, 1H), 3.69 (t, J=4.5 Hz, 4H), 3.48 and 3.47 (each t, J=6.6 Hz, total 2H), 2.79 (t, J=6.6 Hz, 2H), 2.52 (t, J=4.5 Hz, 4H), 2.32–2.23 (m, 2H), 2.03–1.95 (m, 2H), 1.85–1.25 (m, 9H), 1.01 (d, J=6.0 Hz, 3H), 0.97 (d, J=6.0 Hz, 3H).

EXAMPLE 13 (121)

1-[(1R,2S)-2-(4-morpholinobut-2-ynoylamino)cyclohexyl]-N-[4-methyl-1-(2-(1-methylethylthio)-1,3,4-oxadiazol-5-yl)-1-oxo-2-pentyl]carboxamide

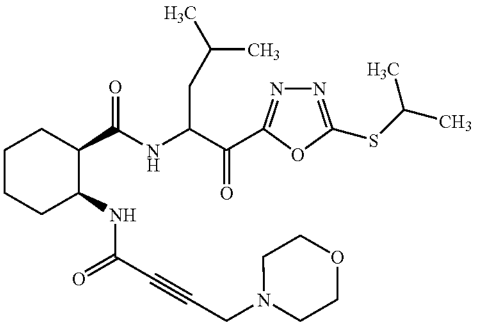

TLC: Rf 0.53 (chloroform:methanol=9:1);

NMR ($CDCl_3$): δ 6.91 and 6.83 (each brd, J=9.0 Hz, 1H), 6.19 and 6.16 (each brd, J=7.5 Hz, 1H), 5.44 and 5.43 (each m, 1H), 4.20–4.08 (m, 1H), 4.06 and 4.05 (each septet, J=6.9 Hz, 1H), 3.75–3.70 (m, 4H), 3.38 (s, 2H), 2.80–2.73 (m, 1H), 2.57 (t, J=4.5 Hz, 4H), 2.00–1.35 (m, 11H), 1.55 and 1.54 (each d, J=6.6 Hz, 6H), 1.05 and 1.04 (each d, J=6.3 Hz, 3H), 0.99 and 0.98 (each d, J=6.3 Hz, 3H).

EXAMPLE 14 TO EXAMPLE 14(3)

By the same procedure as described in Reference Example 10, using the compound prepared in Example 13 (71), 13(89), 13(96) or 13 (119) in place of the compound prepared in Reference Example 9, the compounds of the present invention having the following physical data ware obtained.

EXAMPLE 14

1-(1-aminocyclohexyl)-N-[(2S)-4-methyl-1-(5-methylthio-1,3,4-oxadiazol-2-yl)-1-oxo-2-pentyl]carboxamide hydrochloride

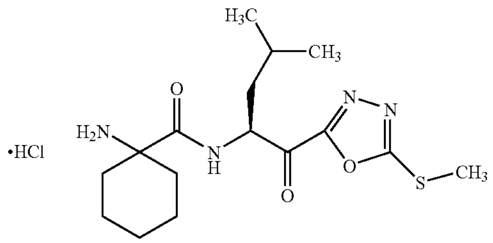

TLC: Rf 0.58 (n-hexane:ethyl acetate=1:2);

NMR ($CDCl_3$): δ 8.79 (br, 3H), 7.90 (br, 1H), 5.42–5.30 (m, 1H), 2.78 (s, 3H), 2.30–1.40 (m, 13H), 1.12–0.90 (m, 6H).

EXAMPLE 14 (1)

1-(4-benzoylaminopiperidin-4-yl)-N-[(2S)-4-methyl-1-(5-(1-methylethylthio)-1,3,4-oxadiazol-2-yl)-1-oxo-2-pentyl]carboxamide Hydrochloride

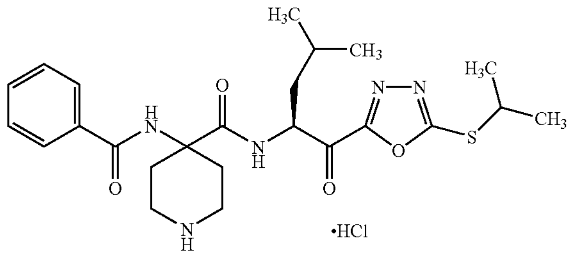

TLC: Rf 0.46 (chloroform:methanol:acetic acid=10:2:1);

NMR (DMSO-$d_6$): δ 8.72 (br, 1H), 8.37 (d, J=6.9 Hz, 1H), 8.30 (brs, 1H), 7.89 (d, J=8.4 Hz, 2H), 7.60–7.43 (m, 3H), 5.01 (m, 1H), 3.95 (septet, J=6.9 Hz, 1H), 3.40–3.05 (m, 4H), 2.75–2.01 (m, 4H), 1.70–1.31 (m, 3H), 1.46 (d, J=6.9 Hz, 6H) 0.84 and 0.81 (each d, J=5.4 Hz, each 3H).

EXAMPLE 14 (2)

1-(1-aminocyclohexyl)-N-[(2S)-4-methyl-1-(5-(1-methylethylthio)-1,3,4-oxadiazol-2-yl)-1-oxo-2-pentyl]carboxamide Hydrochloride

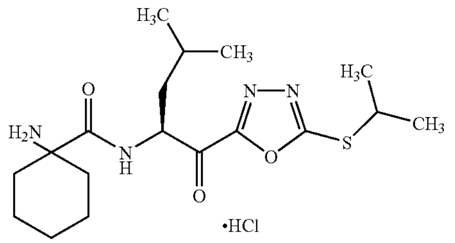

TLC: Rf 0.28 (chloroform:methanol=9:1);

NMR ($CDCl_3$): δ 8.80 (brs, 3H), 7.87 (brd, J=6.0 Hz, 1H), 5.39 (m, 1H), 4.02 (septet, J=6.6 Hz, 1H), 2.28–1.40 (m, 19H), 1.03–0.92 (m, 6H).

EXAMPLE 14 (3)

1-[(1R,2S)-2-aminocyclohexyl]-N-[(2S)-4-methyl-1-(2-(1-methylethylthio)-1,3,4-oxadiazol-5-yl)-1-oxo-2-pentyl]carboxamide Hydrochloride

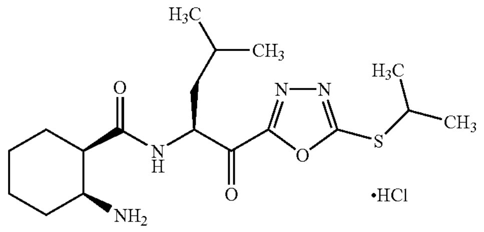

TLC: Rf 0.49 (chloroform:methanol:acetic acid=10:1:1); NMR (DMSO-$d_6$): δ 8.81 (d, J=5.4 Hz, 1H), 8.17–7.48 (br, 3H), 5.15–5.02 (m, 1H), 4.04–3.89 (m, 1H), 3.40–3.21 (m, 1H), 2.85–2.73 (m, 1H), 1.97–1.20 (m, 11H), 1.47 (d, J=6.6 Hz, 6H), 0.93 (d, J=6.3 Hz, 6H).

EXAMPLE 15

1-[(1R,2S)-2-benzylaminocyclohexyl]-N-[(2S)-4-methyl-1-(5-methylthio-1,3,4-oxadiazol-2-yl)-1-oxo-2-pentyl]carboxamide hydrochloride

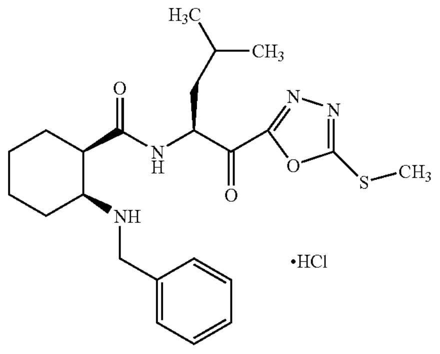

By the same procedure as described in Reference Example 15→Example 3→Reference Example 18 using (2S)-2-amino-4-methyl-1-(5-methylthio-1,3,4-oxadiazol-2-yl)pentanol hydrochloride in place of the compound prepared in Reference Example 14 and 2-N-benzyl-N-t-butoxycarbonylaminocyclohexanecarboxylic acid in place of the N-benzyloxycarbonyl-(L)-leucine, the compound of the present invention having the following physical data was obtained.

TLC: Rf 0.31 (ethyl acetate);

NMR (DMSO-$d_6$): δ 9.10–8.60 (m, 3H), 7.62–7.30 (m, 5H), 5.18–5.04 (m, 1H), 4.30–3.97 (m, 2H), 3.31–3.10 and 3.10–2.93 (each br, each 1H), 2.78 (s, 3H), 2.21–1.16 (m, 11H), 0.95 and 0.94 (each d, J=6.2 Hz, each 3H).

REFERENCE EXAMPLE 24

(3S)-3-(t-butoxycarbonylamino)-5-methylhexanenitrile

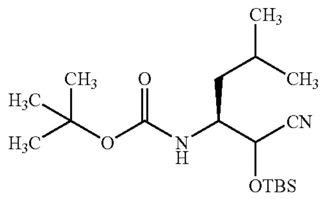

To a solution of the compound prepared in Reference Example 3 (2.04 g) in N,N-dimethylformamide (15 ml) were added imidazole (1.26 g) and t-butyldimethylsilylchloride (2.79 g) and the mixture was stirred for 3 hours at room temperature. To the reaction mixture was added water and was extracted with ethyl acetate. The organic layer was washed with water, saturated aqueous solution of sodium chloride and dried and concentrated. The residue was purified by column chromatography on silica gel (n-hexane: ethyl acetate=19:1) to give the title compound (3.06 g) having the following physical data.

TLC: Rf 0.51, 0.47 (hexane:ethyl acetate=5:1).

NMR ($CDCl_3$): δ 4.64–4.40 (m, 2H), 3.82 (m, 1H), 1.80–1.40 (m, 12H), 1.05–0.84 (m, 15H), 0.25–0.10 (m, 6H).

REFERENCE EXAMPLE 25

3-(t-butoxycarbonylamino)-2-(t-butyldimethylsilyloxy)-5-methyl-N'-hydroxyhexanimidamide

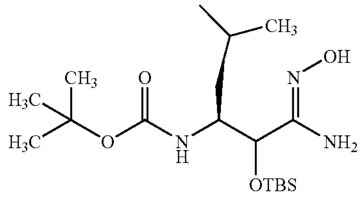

To a solution of the compound prepared in Reference Example 24 (4.27 g) in methanol (36 ml) were added hydroxylamine hydrochloride (2.50 g) and triethylamine (5.02 ml) at room temperature and the mixture was stirred at 50° C. The reaction mixture was concentrated and to the residue were added water and ethyl acetate. The organic layer was washed with saturated aqueous solution of sodium chloride, dried over anhydrous magnesium sulfate and was concentrated. The residue was purified by column chromatography on silica gel (chloroform:methanol=20:1) to give the title compound (4.44 g) having the following physical data.

TLC: Rf 0.44 (chloroform:methanol=9:1);

NMR ($CDCl_3$): δ 6.60–6.00 and 4.86–4.42 (each m, totally 3H), 4.08–4.00 (m, 1H), 3.90–3.70 (m, 1H), 1.44 (s, 9H), 1.42–1.15 (m, 3H), 1.00–0.85 (m, 15H), 0.16–0.08 (m, 6H).

REFERENCE EXAMPLE 26

(2S)-2-(t-butoxycarbonylamino)-4-methyl-1-(5-thioxo-1,2,4-oxadiazolin)-1-(t-butyldimethylsilyloxy)-2-pentylamide

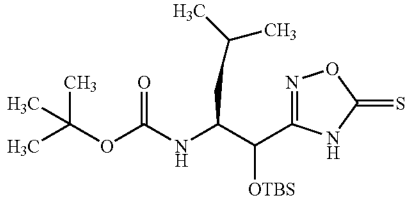

To a solution of the compound prepared in Reference Example 25 (4.43 g) in acetonitrile (114 ml) was added DBU (1,8-diazabicyclo[4.3.0]non-5-one (6.81 ml) and further was added thiocarbonyldiimidazole (TCDI) (2.23 g) at 0° C. and the mixture was stirred for 13 hours at room temperature. The reaction mixture was poured into 1N hydrochloric chloride (100 ml) and the mixture was extracted with ethyl acetate and was concentrated. The residue was diluted by 1N aqueous solution of sodium hydroxide, washed with diethyl ether and the solution was adjusted to pH 2 by adding 1N hydrochloric acid. The solution was extracted with ethyl acetate and the organic layer was washed with saturated aqueous solution of sodium chloride and dried over anhydrous magnesium sulfate and was concentrated. The residue was purified by column chromatography on silica gel (n-hexane:ethyl acetate=4:1) to give the title compound (4.22 g) having the following physical data.

TLC: Rf 0.44 (n-hexane:ethyl acetate=2:1);

NMR ($CDCl_3$): δ 6.73–5.70 (m, 1H), 4.82–3.75 (m, 2H), 1.83–1.15 (m, 3H), 1.43 and 1.39 (each s, totally 9H), 1.01–0.82 (m, 15H), 0.23–0.02 (m, 6H).

REFERENCE EXAMPLE 27

(2S)-4-methyl-1-(5-thioxo-1,2,4-oxadiazolin-3-yl)-1-(t-butyldimethylsilyloxy)-2-pentylamine Hydrochloride

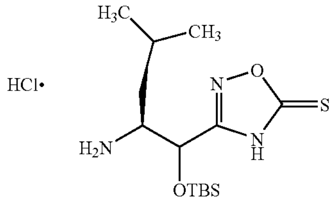

By the same procedure as described in Reference Example 10 using the compound prepared in Reference Example 26 (2.155 g) in place of the compound prepared in Reference Example 9, the title compound (1.234 g) having the following physical data was obtained.

TLC: Rf 0.41 (chloroform:methanol=9:1);

NMR (DMSO-$d_6$): δ 8.30–8.00 (br, 3H), 5.06–4.87 (m, 1H), 3.47–3.34 (m, 1H), 1.88–1.32 (m, 3H), 0.96–0.78 (m, 15H), 0.11 and 0.03 (each s, totally 6H).

REFERENCE EXAMPLE 28

(2S)-N-[(2S)-4-methyl-1-(5-thioxo-1,2,4-oxadiazolin-3-yl)-1-(t-butyldimethylsilyloxy)-2-pentyl]-2-benzyloxycarbonylamino-4-methylpentanamide

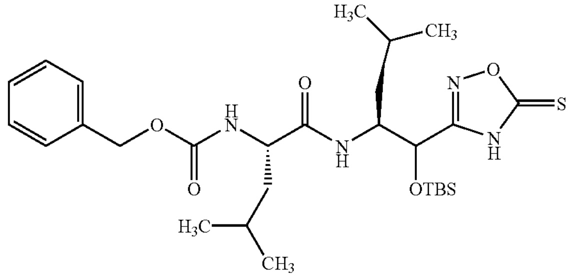

By the same procedure as described in Reference Example 11 using the compound prepared in Reference Example 27 (1.10 g) in place of the compound prepared in Reference Example 10, the title compound (1.10 g) having the following physical data was obtained.

TLC: Rf 0.27 and 0.37 (n-hexane:ethyl acetate=1:1);

NMR ($CDCl_3$): δ 7.47–7.23 (m, 5H), 6.41 and 6.22 (each brd, J=10.2 Hz, totally 1H), 5.68–5.50 and 5.23–5.00 (each m, totally 1H), 5.36 and 5.07 (each d, J=12.0 Hz, totally 2H), 5.16 (s, 1H), 4.88–4.64 (m, 1H), 4.45–4.28 (m, 1H), 4.14–4.02 (m, 1H), 1.85–1.30 (m, 6H), 1.03–0.78 (m, 21H), 0.15, 0.13, 0.05and 0.03 (each s, total 6H)

REFERENCE EXAMPLE 29

(2S)-N-[(2S)-4-methyl-1-(5-methylthio-1,2,4-oxadiazol-3-yl)-1-(t-butyldimethylsilyloxy)-2-pentyl]-2-benzyloxycarbonylamino-4-methylpentanamide

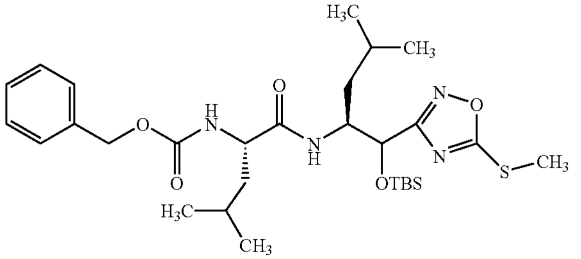

To a solution of the compound prepared in Reference Example 28 (347 mg) in N,N-dimethylformamide (3 ml) was added methyl iodide (45 μl) and the mixture was stirred for 1 hour at room temperature. The reaction mixture was poured into water and was extracted with ethyl acetate, washed with saturated aqueous solution of sodium chloride, dried over anhydrous magnesium sulfate and was concentrated. The residue was purified by column chromatography on silica gel (n-hexane: ethyl acetate=4:1) to give the title compound having the following physical data.

TLC: Rf 0.61 (n-hexane:ethyl acetate=2:1);

NMR ($CDCl_3$): δ 7.43–7.25 (m, 5H), 6.57 and 6.21 (each brd, J=8.7 Hz, totally 1H), 5.25 and 5.17 (each brd, J=8.4 Hz, totally 1H), 5.09 (s, 2H), 4.90–4.81 (m, 1H), 4.51–4.25 (m, 1H), 4.24–4.06 (m, 1H), 2.73 and 2.69 (each s, totally 3H), 1.80–1.30 (m, 6H), 1.20–1.10 and 1.05–0.88 (each m, totally 21H), 0.15–0.00 (m, 6H).

REFERENCE EXAMPLE 30

(2S)-N-[(2S)-4-methyl-1-(5-methylthio-1,2,4-oxadiazol-3-yl)-1-hydroxy-2-pentyl]-2-benzyloxycarbonylamino-4-methylpentanamide

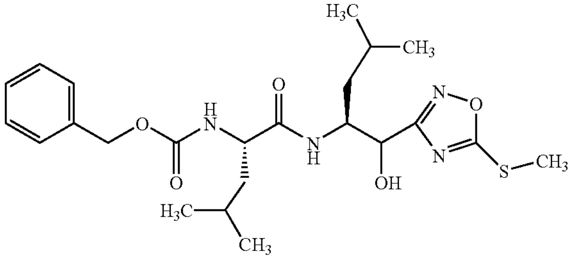

To a solution of the compound prepared in Reference Example 29 (310 mg) in tetrahydrofuran (1 ml) was added t-butyl ammonium fluoride (1.0M tetrahydrofuran solution, 0.79 ml) at room temperature and the mixture was stirred for 30 minutes. The reaction mixture was concentrated. The residue was purified by column chromatography on silica gel (n-hexane:ethyl acetate=1:1) to give the title compound (242 mg) having the following physical data.

TLC: Rf 0.16 (n-hexane:ethyl acetate=2:1);

NMR ($CDCl_3$): δ 7.42–7.24 (m, 5H), 6.65 and 6.31 (each brd, J=9.3 Hz, totally 1H), 5.20–5.00 (m, 1H), 5.09 (s, 2H), 4.83 (brs, 1H), 4.63–4.50 and 4.43–4.32 (each m, totally 1H), 4.17–4.03 (m, 1H), 2.71 and 2.70 (each s, totally 3H), 2.48–2.39 (m, 1H), 1.80–1.36 (m, 6H), 1.02–0.80 (m, 12H).

EXAMPLE 16

(2S)-N-[(2S)-4-methyl-1-(5-methylthio-1,2,4-oxadiazol-3-yl)-1-oxo-2-pentyl]-2-benzyloxycarbonylamino-4-methylpentanamide

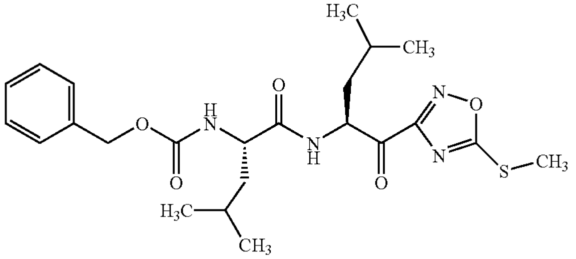

By the same procedure as described in Example 1 using the compound prepared in Reference Example 30 in place of the compound prepared in Reference Example 11, the compound of the present invention having the following physical data was obtained.

TLC: Rf 0.34 (n-hexane:ethyl acetate=2:1);

NMR ($CDCl_3$): δ 7.45–7.24 (m, 5H), 6.53 (brd, J=6.3 Hz, 1H), 5.46–5.35 (m, 1H), 5.26–5.03 (m, 1H), 5.12 (s, 2H), 4.31–4.10 (m, 1H), 2.79 (s, 3H), 1.82–1.42 (m, 6H), 1.09–0.84 (m, 12H).

EXAMPLE 16 (1) TO EXAMPLE 16 (9)

By the same procedure as described in Example 16 using the compound corresponding to the compound prepared in Reference Example 30, the compounds of the present invention having the following physical data were obtained.

EXAMPLE 16 (1)

1-[(1R,2S)-2-benzoylaminocyclohexyl]-N-[4-methyl-1-(5-methylthio-1,2,4-oxadiazol-3-yl)-1-oxo-2-pentyl]carboxamide

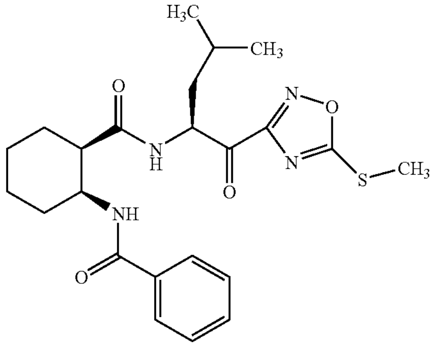

TLC: Rf 0.29 (chloroform:methanol=9:1);

NMR ($CDCl_3$): δ 7.73 (d, J=6.6 Hz, 2H), 7.53–7.38 (m, 3H), 7.23 (brd, J=7.8 Hz, 1H), 6.21 (brd, J=7.5 Hz, 1H), 5.42 (m, 1H), 4.31 (m, 1H), 2.88 (m, 1H), 2.78 (s, 3H), 2.20–1.40 (m, 1H), 0.90 and 0.83 (each d, J=6.3 Hz, each 3H).

EXAMPLE 16 (2)

1-[(1R,2S)-2-benzoylaminocyclohexyl]-N-[4-methyl-1-(5-(1-methylethylthio)-1,2,4-oxadiazol-3-yl)-1-oxo-2-pentyl]carboxamide

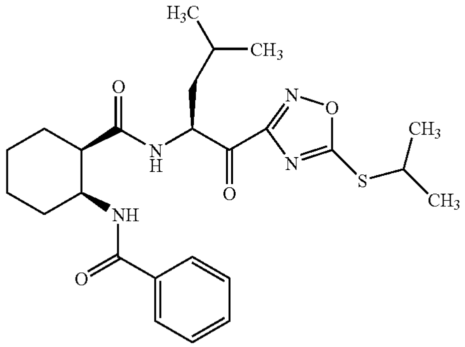

TLC: Rf 0.20 (n-hexane:ethyl acetate=2:1);

NMR ($CDCl_3$) δ 7.81–7.74 (m, 2H), 7.53–7.38 (m, 3H), 7.23 (brd, J=7.8 Hz, 1H), 6.21 (d, J=8.1 Hz, 1H), 5.50–5.39 (m, 1H), 4.37–4.26 (m, 1H), 4.11–3.95 (m, 1H), 2.86 (q, J=5.1 Hz, 1H), 2.17–1.40 (m, 11H), 1.52 (d, J=6.6 Hz, 6H), 0.90 and 0.85 (each d, J=6.3 Hz, totally 6H).

EXAMPLE 16 (3)

(2S)-N-[(2S)-4-methyl-1-(5-(1-methylethylthio)-1,2,4-oxadiazol-3-yl)-1-oxo-2-pentyl]-2-benzyloxycarbonylamino-4-methylpentanamide

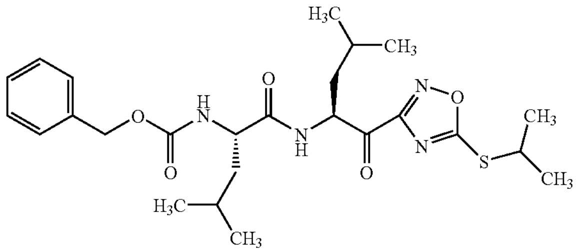

TLC: Rf 0.49 (n-hexane:ethyl acetate=2:1);

NMR ($CDCl_3$): δ 7.45–7.27 (m, 5H), 6.53 (brd, J=7.5 Hz, 1H), 5.47–5.38 (m, 1H), 5.22–5.04 (m, 1H), 5.12 (s, 2H), 4.29–4.17 (m, 1H), 4.10–3.95 (m, 1H), 1.82–1.42 (m, 6H), 1.52 (d, J=6.9 Hz, 6H), 1.03–0.86 (m, 12H).

EXAMPLE 16 (4)

1-[1-(4-dimethylaminomethylbenzoylamino)cyclohexyl]-N-[4-methyl-1-(5-(1-methylethylthio)-1,2,4-oxadiazol-3-yl)-1-oxo-2-pentyl]carboxamide

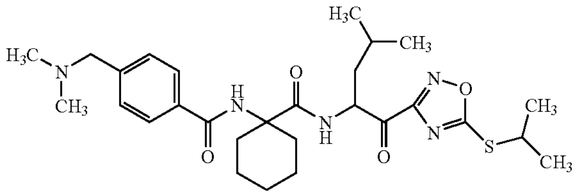

TLC: Rf 0.38 (chloroform:methanol=9:1);

NMR ($CDCl_3$): δ 7.93 (d, J=6.9 Hz, 1H), 7.74 (d, J=8.4 Hz, 2H), 7.43 (d, J=8.4 Hz, 2H), 6.06 (s, 1H), 5.39–5.32 (m, 1H), 4.06–3.97 (m, 1H), 3.52 (s, 2H), 2.37–2.18 (m, 2H), 2.28 (s, 6H), 2.06–1.95 (m, 2H), 1.86–1.32 (m, 9H), 1.51 (d, J=6.9 Hz, 6H), 1.00 (d, J=6.0 Hz, 3H), 0.95 (d, J=6.0 Hz, 3H).

EXAMPLE 16 (5)

1-[1-(4-morpholinomethylbenzoylamino)cyclohexyl]-N-[4-methyl-1-(5-(1-methylethylthio)-1,2,4-oxadiazol-3-yl)-1-oxo-2-pentyl]carboxamide

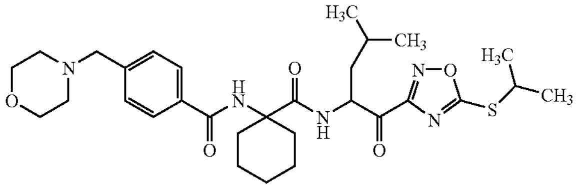

TLC: Rf 0.55 (chloroform:methanol=9:1);

NMR ($CDCl_3$): δ 7.93 (d, J=7.2 Hz, 1H), 7.73 (d, J=8.4 Hz, 2H), 7.44 (d, J=8.4 Hz, 2H), 6.04 (s, 1H), 5.39–5.32 (m, 1H), 4.06–3.97 (m, 1H), 3.72 (t, J=4.5 Hz, 4H), 3.55 (s, 2H), 2.45 (t, J=4.5 Hz, 4H), 2.36–2.18 (m, 2H), 2.04–1.96 (m, 2H), 1.77–1.26 (m, 9H), 1.51 (d, J=6.6 Hz, 6H), 1.00 (d, J=6.0 Hz, 3H), 0.95 (d, J=6.0 Hz, 3H).

EXAMPLE 16 (6)

1-[1-(pyridin-3-ylcarbonylamino)cyclohexyl]-N-[(2S)-4-methyl-1-(5-(1-methylethylthio)-1,2,4-oxadiazol-3-yl)-1-oxo-2-pentyl]carboxamide

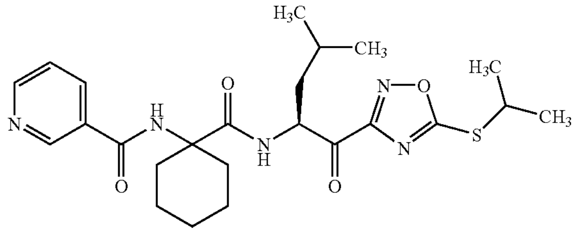

TLC: Rf 0.41 (chloroform:methanol=9:1);

NMR ($CDCl_3$): δ 9.00 (d, J=1.8 Hz, 1H), 8.77 (dd, J=4.8, 1.8 Hz, 1H), 8.12 (dt, J=7.8, 1.8 Hz, 1H), 7.70 (d, J=7.2 Hz, 1H), 7.43 (dd, J=7.8, 4.8 Hz, 1H), 6.16 (s, 1H), 5.41–5.34 (m, 1H), 4.06–3.97 (m, 1H), 2.34–2.19 (m, 2H), 2.08–1.98 (m, 2H), 1.81–1.26 (m, 9H), 1.51 (d, J=6.6 Hz, 6H), 1.01 (d, J=6.0 Hz, 3H), 0.98 (d, J=6.0 Hz, 3H).

EXAMPLE 16 (7)

1-(1-morpholinocarbonylaminocyclohexyl)-N-[(2S)-4-methyl-1-(5-(1-methylethylthio)-1,2,4-oxadiazol-3-yl)-1-oxo-2-pentyl]carboxamide

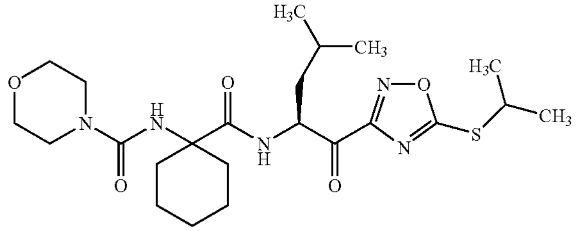

TLC: Rf 0.43 (n-hexane:ethyl acetate=1:3);

NMR ($CDCl_3$): δ 8.04 (d, J=6.9 Hz, 1H), 5.36–5.30 (m, 1H), 4.45 (s, 1H), 4.07–3.98 (m, 1H), 3.72 (t, J=4.8 Hz, 4H), 3.39 (t, J=4.8 Hz, 4H), 2.18–1.26 (m, 13H), 1.52 (d, J=6.6 Hz, 6H), 1.00 (d, J=6.0 Hz, 3H), 0.95 (d, J=6.0 Hz, 3H).

EXAMPLE 16 (8)

1-[1-(pyridin-4-ylcarbonylamino)cyclohexyl]-N-[(2S)-4-methyl-1-(5-(1-methylethylthio)-1,2,4-oxadiazol-3-yl)-1-oxo-2-pentyl]carboxamide

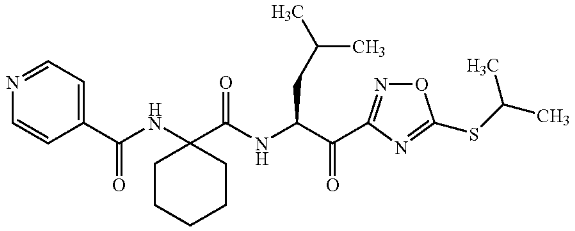

TLC: Rf 0.51 (chloroform:methanol=9:1);

NMR ($CDCl_3$): δ 8.78 (dd, J=4.5, 1.5 Hz, 2H), 7.62–7.60 (m, 1H), 7.61 (dd, J=4.5, 1.5 Hz, 2H), 6.14 (s, 1H), 5.41–5.34 (m, 1H), 4.06–3.97 (m, 1H), 2.33–2.29 (m, 1H), 2.22–2.17 (m, 1H), 2.07–1.99 (m, 2H), 1.82–1.24 (m, 9H), 1.51 (d, J=6.6 Hz, 6H), 1.01 (d, J=6.0 Hz, 3H), 0.96 (d, J=6.0 Hz, 3H).

EXAMPLE 16 (9)

1-cyclohexyl-N-[(2S)-4-methyl-1-(5-(1-methylethylthio)-1,2,4-oxadiazol-3-yl)-1-oxo-2-pentyl]carboxamide

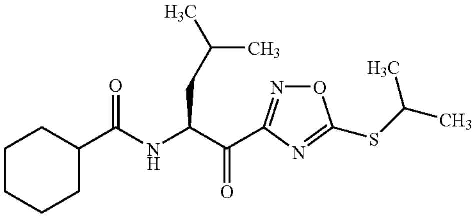

TLC: Rf 0.66 (n-hexane:ethyl acetate=2:1);

NMR ($CDCl_3$): δ 6.00 (d, J=7.8 Hz, 1H), 5.51–5.44 (m, 1H), 4.08–3.99 (m, 1H), 2.22–2.12 (m, 1H), 1.89–1.19 (m, 13H), 1.53 (d, J=6.9 Hz, 3H), 1.52 (d, J=6.9 Hz, 3H), 1.03 (d, J=6.0 Hz, 3H), 0.95 (d, J=6.0 Hz, 3H).

FORMULATION EXAMPLE

FORMULATION EXAMPLE 1

The following components were admixed in a conventional method and punched out to give 100 tablets each containing 50 mg of active ingredient.

| | |
|---|---|
| (2S)-N-[(2S)-4-methyl-1-(5-(1-methylethylthio)-1,3,4-oxadiazol-2-yl)]-1-oxo-2-pentyl]-2-benzyloxycarbonylamino-4-methylpentanamide | 5.0 g |
| carboxymethylcellulose calcium (disintegrating agent) | 0.2 g |
| magnesium stearate (lubricant) | 0.1 g |
| microcrystalline cellulose | 4.7 g |

FORMULATION EXAMPLE 2

The following components were admixed in a conventional method. The solution was sterilized in conventional method, placed 5 ml portions into ampoules and freeze-dried to give 100 ampoules each containing 20 mg of the active ingredient.

| | |
|---|---|
| (2S)-N-[(2S)-4-methyl-1-(5-(1-methylethylthio)-1,3,4-oxadiazol-2-yl)]-1-oxo-2-pentyl]-2-benzyloxycarbonylamino-4-methylpentanamide | 2.0 g |
| mannitol | 20 g |
| distilled water | 500 ml |

What is claimed is:

1. An oxadiazole compound of formula (I), (I)

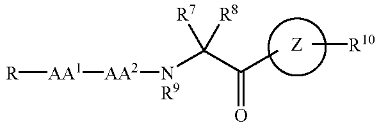

wherein R is (v)

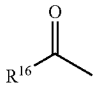

$R^{16}$ is

CycA wherein CycA is mono-, bi- or tri-cyclic C3–15 carboring $AA^1$ is a single bond $AA^2$ is (iv)

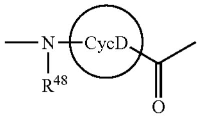, wherein $R^{48}$ is hydrogen, C1–4 alkyl, phenyl or C1–4 alkyl substituted with phenyl CycD is a C3–14 mono- or bi-cyclic carboring, $R^7$ and $R^8$ are the same or different to represent (i) hydrogen, (ii) C1–8 alkyl, or (iii) C1–8 alkyl substituted with 1–5 of groups selected from the following (1)~(7):

(1) —$NR^{61}R^{62}$, (2) —$OR^{63}$, (3) —$SR^{64}$, (4) —$COR^{65}$, (5)-$NR^{66}CONR^{61}R^{62}$, (6) CycA, (7)-$NR^{66}SO_2R^{61}$, $R^{61}$, $R^{62}$, $R^{63}$, $R^{64}$ and $R^{66}$ are the same or different to represent hydrogen, C1–4 alkyl, phenyl or C1–4 alkyl substituted with phenyl, $R^{65}$ is C1–4 alkyl, phenyl, —$NR^{61}R^{62}$, wherein all symbols are the same meanings as above, —$OR^{63}$, wherein $R^{63}$ is the same meaning as above, or C1–4 alkyl substituted with phenyl, $R^9$ is hydrogen, C1–8 alkyl, phenyl or C1–8 alkyl substituted with phenyl

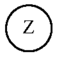 is 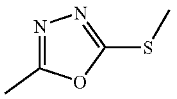 or $R^{10}$ is (i) C1–8 alkyl, (ii) C2–8 alkenyl, (iii) CycA, (iv) —$COR^{71}$ or (v) C1–8 alkyl substituted with 1–3 of group selected from CycA, —$COR^{71}$, —$NR^{72}R^{73}$, —$OR^{74}$, cyano or —$P(O)(OR^{78})_2$, wherein $R^{71}$ is (1) C1–4 alkyl, (2) C1–4 alkoxy, (3) CycA, (4) —O-CycA, (5) —$NR^{72}R^{73}$, (6) C1–4 alkyl substituted with CycA, (7) C1–4 alkoxy substituted with CycA, or (8) hydroxy, $R^{72}$ and $R^{73}$ are the same or different to represent hydrogen, C1–8 alkyl, CycA or C1–8 alkyl substituted with CycA, $R^{74}$ is (1) hydrogen, (2) C1–8 alkyl, (3) CycA, (4) C1–8 alkyl substituted with —$SiR^{75}R^{76}R^{77}$, wherein $R^{75}$, $R^{76}$ and $R^{77}$ are the same or different to represent C1–8 alkyl, phenyl or C1–8 alkyl substituted with phenyl, or (5) C1–8 alkyl substituted with CycA, $R^{78}$ is C1–8 alkyl, phenyl, or C1–8 alkyl substituted with phenyl;

and, CycA's included in $R^{10}$ and $R^{16}$ are the same or different and CycA and CycD, independently, may be substituted with 1–5 of $R^{27}$:

$R^{27}$ is (1) C1–8 alkyl, (2) halogen, (3) —$NR^{11}R^{12}$, (4) —$OR^3$, (5) a C5–10 mono- or bi-cyclic carboring, (6) nitro, (7) $CF_3$, (8) cyano, (9) —$SR^{14}$,

(10) —$COR^{15}$,

(11) oxo,

(12) —$SO_2R^{15}$,

(13) —$OCF_3$, or

(14) C1–8 alkyl substituted with 1–5 of group selected from the following (a)~(k):

(a) halogen, (b) —$NR^{11}R^{12}$, (c) —$OR^{13}$, (d) a C5–10 mono- or bi-cyclic carboring, (e) nitro, (f) $CF_3$, (g) cyano, (h) —$SR^{14}$, (i) —$COR^{15}$, (j) —$SO_2R^{15}$, or (k) —$OCF^3$, wherein $R^{11}$ and $R^{12}$ are the same or different to represent hydrogen, C1–4 alkyl, —COO-(C1–4 alkyl), phenyl or C1–4 alkyl substituted with phenyl, $R^{13}$ and $R^{14}$ are the same or different to represent hydrogen, C1–4 alkyl, phenyl or C1–4 alkyl substituted with phenyl, $R^{15}$ is C1–4 alkyl, phenyl, —$NR^{11}R^{12}$, wherein all symbols are the same meanings as above, —$OR^{13}$ wherein $R^{13}$ is the same meaning as above, or C1–4 alkyl substituted with phenyl or a non-toxic salt thereof.

2. The compound according to claim 1, wherein $AA^2$ is (vi)

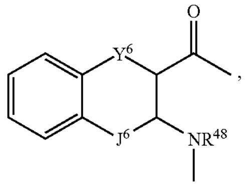

(vii)

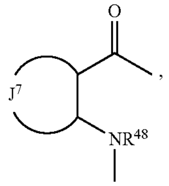

(viii)

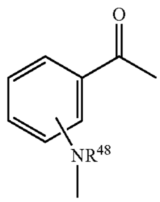

or (ix)

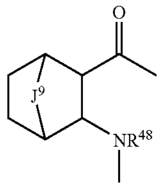

$J^6$ and $Y^6$ are the same or different to represent a single bond or C1–3 alkylene (with proviso that $J^6$ and $Y^6$ do not represent a single bond at the same time), $J^7$ is C1–6 alkylene, $J^9$ is C1–3 alkylene, and each ring may be substituted with 1–5 of $R^{27}$, and $R^{27}$ in CycA is (1) C1–8 alkyl, (2) halogen, (3) —$NR^{11}R^{12}$, (4) —$OR^{13}$, (5) phenyl, (6) nitro, (7) $CF_3$, (8) cyano, (9) —$SR^{14}$,

(10) —$COR^{15}$,

(11) oxo, or

(12) C1–8 alkyl substituted with 1–5 group selected from the following (a)~(i):

(a) halogen, (b) —$NR^{11}R^{12}$, (c) —$OR^{13}$, (d) phenyl, (e) nitro, (f) $CF_3$, (g) cyano, (h) —$SR^{14}$, or (i) —$COR^{15}$, wherein all symbols are the same meanings as above, and $R^{10}$ is (i) C1–8 alkyl, (ii) CycA, (iii) —$COR^{71}$ or (iv) C1–8 alkyl substituted with CycA, —$COR^{71}$, —$NR^{72}R^{73}$ or —$OR^{74}$ wherein all symbols are the same meanings as defined in claim 1, or a non-toxic salt thereof.

3. The compound according to claim 1, wherein $R^{10}$ is C1–8 alkenyl, or C1–8 alkyl substituted with 1–3 group selected from CycA, $COR^{71}$, $NR^{72}R^{73}$, $OR^{74}$, cyano or $P(O)(OR^{78})_2$ (with proviso that the substituent is one, then it is not CycA, $COR^{71}$, $NR^{72}R^{73}$, or $OR^{74}$), or a non-toxic salt thereof.

4. The compound according to claim 1, which is (1) 1-[(1R,2S)-2-benzoylaminocyclohexyl]-N-[(2S)-4-methyl-1-(5-(1-methylethylthio)-1,3,4-oxadiazol-2-yl)-1-oxo-2-pentyl]carboxamide, (2) 1-[(1R,2S)-2-benzoylaminocyclohexyl]-N-[(2S)-4-methyl-1-(5-methylthio-1,3,4-oxadiazol-2-yl)-1-oxo-2-pentyl]carboxamide, (3) 1-[(1R,2S)-2-benzoylaminocyclohexyl]-N-[(2S)-1-(5-benzylthio-1,3,4-oxadiazol-2-yl-4-methyl-1-oxo-2-pentyl] carboxamide, (4) 1-[(1R,2S)-2-benzoylaminocyclohexyl]-N-[(2S)-1-(5-methylthio-1,3,4-oxadiazol-2-yl)-1-oxo-2-hexyl]carboxamide, (5) 1-[(1R,2S)-2-benzoylaminocyclohexyl]-N-[2S)-1-(5-methylthio-1,3,4-oxadiazol-2-yl)-1-oxo-4-phenyl-2-butyl] carboxamide, (6) 1-[(1R,2S)-2-(naphthalen-2-ylcarbonylamino)cyclohexyl]-N-[2S)-4-methyl-1-(5-methylthio-1,3,4-oxadiazol-2-yl)-1-oxo-2-pentyl], (7) 1-[(1R,2S)-2-(4-methoxybenzoylamino)cyclohexyl]-N-[(2S)-4-methyl-1-(5-methylthio -1,3,4-oxadiazol-2-yl)-1-oxo-2-pentyl]carboxamide, (8) 1-[(1R,2S)-2-(4-nitrobenzoylamino)cyclohexyl]-N-[(2S)-4-methyl-1-(5-methylthio-1,3,4-oxadiazol-2-yl)-1-oxo-2-pentyl]carboxamide, (9) 1-[(1R,2S)-2-(4-chlorobenzoylamino)cyclohexyl]-N-[(2S)-4-methyl-1-(5-methylthio -1,3,4-oxadiazol-2-yl)-1-oxo-2-pentyl]carboxamide,

(10) 1-[(1R,2S)-2-(4-phenylbenzoylamino)cyclohexyl]-N-[(2S)-4-methyl-1-(5-methylthio -1,3,4-oxadiazol-2-yl)-1-oxo-2-pentyl]carboxamide,

(11) 1-[(1R,2S)-2-(4-fluorobenzoylamino)cyclohexyl]-N-[(2S)-4-methyl-1-(5-methylthio-1,3,4-oxadiazol-2-yl)-1-oxo-2-pentyl]carboxamide,

(12) 1-[(1R,2S)-2-(4-t-butylbenzoylamino)cyclohexyl]-N-[(2S)-4-methyl-1-(5-methylthio -1,3,4-oxadiazol-2-yl)-1-oxo-2-pentyl]carboxamide,

(13) 1-[(1R,2S)-2-(2-fluorobenzoylamino)cyclohexyl]-N-[(2S)-4-methyl-1-(5-methylthio-1,3,4-oxadiazol-2-yl)-1-oxo-2-pentyl]carboxamide,

(14) 1-[(1R,2S)-2-(4-cyanobenzoylamino)cyclohexyl]-N-[(2S)-4-methyl-1-(5-methylthio-1,3,4-oxadiazol-2-yl)-1-oxo-2-pentyl]carboxamide,

(15) 1-[(1R,2S)-2-(4-dimethylaminobenzoylamino)cyclohexyl]-N-[(2S)-4-methyl-1-(5-methylthio-1,3,4-oxadiazol-2-yl)-1-oxo-2-pentyl]carboxamide,

(16) 1-[(1R,2S)-2-(4-fluorobenzoylamino)cyclohexyl]-N-[(2S)-4-methyl-1-(5-(1-methylethylthio)-1,3,4-oxadiazol-2-yl)-1-oxo-2-pentyl]carboxamide,

(17) 1-[(1R,2S)-2-(4-chlorobenzoylamino)cyclohexyl]-N-[(2S)-4-methyl-1-(5-(1-methylethylthio)-1,3,4-oxadiazol-2-yl)-1-oxo-2-pentyl]carboxamide,

(18) 1-[(1R,2S)-2-(4-methoxybenzoylamino)cyclohexyl]-N-[(2S)-4-methyl-1-(5-(1-methylethylthio)-1,3,4-oxadiazol-2-yl)-1-oxo-2-pentyl]carboxamide,

(19) 1-[(1R,2S)-2-(4-cyanobenzoylamino)cyclohexyl]-N-[(2S)-4-methyl-1-(5-(1-methylethylthio)-1,3,4-oxadiazol-2-yl)-1-oxo-2-pentyl]carboxamide,

(20) 1-[(1R,2S)-2-(4-dimethylaminobenzoylamino)cyclohexyl]-N-[2S)-4-methyl-1-(5-(1-methylethylthio)-1,3,4-oxadiazol-2-yl)-1-oxo-2-pentyl]carboxamide,

(21) 1-[(1R,2S)-2-(N-benzoyl-N-methylamino)cyclohexyl]-N-[(2S)-4-methyl-1-(5-methylthio -1,3,4-oxadiazol-2-yl)-1-oxo-2-pentyl]carboxamide,

(22) 1-[(1R,2S)-2-(4-dimethylaminomethylbenzoylamino)cyclohexyl]-N-[4-methyl-1-(5-(1-methylethylthio)-1,3,4-oxadiazol-2-yl)-1-oxo-2-pentyl]carboxamide,

(23) 1-[(1R,2S)-2-benzoylaminocyclohexyl]-N-[(2S)-4-methyl-1-(5-t -butoxycarbonylmethylthio-1,3,4-oxadiazol-2-yl)-1-oxo-2-pentyl]carboxamide,

(24) 1-[(1R,2S)-2-(4-dimethylaminomethylbenzoylamino)cyclohexyl]-N-[(2S)-4-methyl-1-(5-(1-methylethylthio)-1,3,4-oxadiazol-2-yl)-1-oxo-2-pentyl]carboxamide,

(25) 1-[(1R,2S)-2-(4-dimethylaminomethylbenzoylamino)cyclohexyl]-N-[4-methyl-1-(5-methylthio-1,3,4-oxadiazol-2-yl)-1-oxo-2-pentyl]carboxamide,

(26) 1-[(1R,2S)-2-(4-dimethylaminomethyl-2-fluorobenzoylamino)cyclohexyl]-N-[4-methyl-1-(5-(1-methylethylthio)-1,3,4-oxadiazol-2-yl)-1-oxo-2-pentyl]carboxamide,

(27) 1-[(1R,2S)-2-(4-dimethylaminomethyl-2-fluorobenzoylamino)cyclohexyl]-N-[4-methyl-1-(5-methylthio-1,3,4-oxadiazol-2-yl)-1-oxo-2-pentyl]carboxamide,

(28) 1-[(1R,2S)-2-benzoylaminocyclopentyl]-N-[(2S)-4-methyl-1-(5-(1-methylethylthio)-1,3,4-oxadiazol-2-yl)-1-oxo-2-pentyl]carboxamide,

(29) 1-[(1R,2S)-2-benzoylaminocyclopentyl]-N-[(2S)-4-methyl-1-(5-methylthio-1,3,4-oxadiazol-2-yl)-1-oxo-2-pentyl]carboxamide,

(30) 1-[(1R,2S)-2-(2-dimethylaminomethylbenzoylamino)cyclohexyl]-N-[4-methyl-1-(5-methylthio-1,3,4-oxadiazol-2-yl)-1-oxo-2-pentyl]carboxamide,

(31) 1-[(1R,2S)-2-(2-dimethylaminomethylbenzoylamino)cyclohexyl]-N-[4-methyl-1-(5-(1-methylethylthio)-1,3,4-oxadiazol-2-yl)-1-oxo-2-pentyl]carboxamide,

(32) 1-[(1R,2S)-2-(3-dimethylaminomethylbenzoylamino)cyclohexyl]-N-[4-methyl-1-(5-methylthio-1,3,4-oxadiazol-2-yl)-1-oxo-2-pentyl]carboxamide,

(33) 1-[(1R,2S)-2-(3-dimethylaminomethylbenzoylamino)cyclohexyl]-N-[4-methyl-1-(5-(1-methylethylthio)-1,3,4-oxadiazol-2-yl)-1-oxo-2-pentyl]carboxamide,

(34) 1-[(1R,2S)-2-benzoylaminocyclohexyl]-N-[1-(5-(2-dimethylaminoethylthio)-1,3,4-oxadiazol-2-yl)-4-methyl-1-oxo-2-pentyl]carboxamide,

(35) 1-[(1R,2S)-2-(2-dimethylaminomethyl-4-fluorobenzoylamino)cyclohexyl]-N-[4-methyl-1-(5-(1-methylethylthio)-1,3,4-oxadiazol-2-yl)-1-oxo-2-pentyl]carboxamide,

(36) 1-[(1R,2S)-2-benzoylaminocyclohexyl]-N-[3-cyclopropyl-1-(5-methylthio-1,3,4-oxadiazol -2-yl)-1-oxo-2-propyl]carboxamide,

(37) 1-[(1R,2S)-2-(2-dimethylaminomethyl-4-fluorobenzoylamino)Cyclohexyl]-N-[4-methyl-1-(5-methylthio-1,3,4-oxadiazol-2-yl)-1-oxo-2-pentyl]carboxamide,

(38) 1-benzoylaminocyclohexyl-N-[(2S)-4-methyl-1-(5-(1-methylethylthio)-1,3,4-oxadiazol-2-yl)-1-oxo-2-pentyl] carboxamide,

(39) 1-[(1R,2S)-2-benzoylaminocyclohexyl]-N-[2-(5-methylthio-1,3,4-oxadiazol-2-yl)-2-oxoethyl]carboxamide,

(40) 1-[(1R,2S)-2-(4-dimethylaminomethyl-3-fluorobenzoylamino)cyclohexyl]-N-[4-methyl-1-(5-(1-methylethylthio)-1,3,4-oxadiazol-2-yl)-1-oxo-2-pentyl]carboxamide,

(41) 1-[(1R,2S)-2-benzoylaminocyclohexyl]-N-[2S)-4-methoxy-1-(5-methylthio-1,3,4-oxadiazol-2-yl)-1-oxo-2-butyl]carboxamide,

(42) 1-benzoylaminocyclohexyl-N-[(2S)-4-methyl-1-(5-methylthio-1,3,4-oxadiazol-2-yl)-1-oxo -2-pentyl]carboxamide,

(43) 1-[(1R,2S)-2-(4-dimethylaminomethyl-2-fluorobenzoylamino)cyclohexyl]-N-[(2S)-4-methyl-1-(5-(1-methylethylthio)-1,3,4-oxadiazol-2-yl)-1-oxo-2-pentyl]carboxamide,

(44) 1-[(1R,2S)-2-benzoylaminocyclohexyl]N-[2S)-4-methoxy-1-(5-(1-methylethylthio) -1,3,4-oxadiazol-2-yl)-1-oxo-2-butyl]carboxamide,

(45) 1-(1-benzoylaminocyclohexyl)-N-[(2S)-1-(5-(1-methylethylthio)-1,3,4-oxadiazol-2-yl)-1-oxo-2-hexyl]carboxamide,

(46) 1-[1-(4-dimethylaminomethylbenzoylamino)cyclohexyl]-N-[4-methyl-1-(5-(1-methylethylthio)-1,3,4-oxadiazol-2-yl)-1-oxo-2-pentyl]carboxamide,

(47) 1-[1-(3-dimethylaminomethylbenzoylamino)cyclohexyl]-N-[4-methyl-1-(5-(1-methylethylthio)-1,3,4-oxadiazol-2-yl)-1-oxo-2-pentyl]carboxamide,

(48) 1-(1-benzoylaminocyclohexyl)-N-[1-(5-(2-dimethylaminoethylthio)-1,3,4-oxadiazol-2-yl) -4-methyl-1-oxo-2-pentyl]carboxamide,

(49) 1-[1-(4-dimethylaminomethylbenzoylamino)cyclohexyl]-N-[1-(5-(1-methylethylthio) -1,3,4-oxadiazol-2-yl)-1-oxo-2-hexyl]carboxamide,

(50) 1-[1-(2-dimethylaminomethylbenzoylamino)cyclohexyl]-N-[4-methyl-1-(5-(1-methylethylthio)-1,3,4-oxadiazol-2-yl)-1-oxo-2-pentyl]carboxamide,

(51) 1-(1-benzoylaminocyclopentyl)-N-[(2S)-4-methyl-1-(5-(1-methylethylthio)-1,3,4-oxadiazol-2-yl)-1-oxo-2-pentyl]carboxamide,

(52) 1-[1-(4-dimethylaminomethylbenzoylamino)cyclopentyl]-N-[4-methyl-1-(5-(1-methylethylthio)-1-oxo-1,3,4-oxadiazol-2-yl)-2-pentyl]carboxamide,

(53) 1-[(1R,2S)-2-(4-(2-dimethylaminoethyl)benzoylamino)cyclohexyl]-N-[4-methyl-1-(2-(1-methylethylthio)-1,3,4-oxadiazol-5-yl)-1-oxo-2-pentyl]carboxamide,

(54) 1-[1-(4-(2-dimethylaminoethyl)benzoylamino)cyclohexyl]-N-[4-methyl-1-(5-(1-methylethylthio)-1,3,4-oxadiazol-2-yl)-1-oxo-2-pentyl]carboxamide,

(55) 1-[(1R,2S)-2-benzoylaminocyclohexyl]-N-[(2S)-1-(2-cyclohexylthio-1,3,4-oxadiazol-5-yl) -4-methyl-1-oxo-2-pentyl]carboxamide,

(56) 1-[(1R,2S)-2-benzoylaminocyclohexyl]-N-[1-(2-(3-dimethylaminopropylthio)-1,3,4-oxadiazol-5-yl)-4-methyl-1-oxo-2-pentyl]carboxamide,

(57) 1-(1-benzoylaminocyclohexyl)-N-[4-methyl-1-(2-(3-dimethylaminopropylthio)-1,3,4-oxadiazol-5-yl)-1-oxo-2-pentyl]carboxamide,

(58) 1-(1-benzoylaminocyclohexyl)-N-[(2S)-1-(2-cyclohexylthio-1,3,4-oxadiazol-5-yl)-4-methyl-1-oxo-2-pentyl] carboxamide or

(59) 1-(1-benzoylaminocyclohexyl)-N-[(2S)-1-(2-benzylthio-1,3,4-oxadiazol-5-yl)-4-methyl-1-oxo-2-pentyl]carboxamide, or a non-toxic salt thereof.

5. The compound according to claim 1, which is 1-[(1R,2S)-2-benzoylaminocyclohexyl]-N-[(2S)-4-methyl-1-(5-bis(methoxycarbonyl)methylthio -1,3,4-oxadiazol-2-yl)-1-oxo-2-pentyl]carboxamide, or a non-toxic salt thereof.

6. A pharmaceutical composition comprising an oxadiazole compound of formula (I) according to claim 1 or a non-toxic salt thereof and a pharmaceutically acceptable vehicle.

* * * * *